US010117932B2

(12) United States Patent
Schulz et al.

(10) Patent No.: US 10,117,932 B2
(45) Date of Patent: Nov. 6, 2018

(54) USES OF IMMUNOCONJUGATES TARGETING CD138

(71) Applicants: Biotest AG, Dreieich (DE); ImmunoGen, Inc., Waltham, MA (US)

(72) Inventors: Gregor Schulz, Umkirch (DE); Frank Osterroth, Dietzenbach (DE); Thomas Haeder, Dreieich (DE); Christoph Bruecher, Eschborn (DE); Gabriele Niemann, Walzbachtal (DE); Andre Engling, Bad Homburg (DE); Christoph Uherek, Seligenstadt (DE); Benjamin Daelken, Frankfurt am Main (DE); Andrea Wartenberg-Demand, Schrecksbach (DE); Chantal Zuber, Ulm (DE); Marcus Gutscher, Langen (DE); Katrin Bernoester, Wiesbaden (DE); Martin Koenig, Wiesbaden (DE)

(73) Assignees: BIOTEST AG (DE); IMMUNOGEN INC., Waltham, MA (US)

( * ) Notice: Subject to any disclaimer, the term of this patent is extended or adjusted under 35 U.S.C. 154(b) by 318 days.

(21) Appl. No.: 13/708,014

(22) Filed: Dec. 7, 2012

(65) Prior Publication Data
US 2014/0010828 A1 Jan. 9, 2014

Related U.S. Application Data

(60) Provisional application No. 61/722,367, filed on Nov. 5, 2012, provisional application No. 61/568,640, filed on Dec. 8, 2011.

(51) Int. Cl.
A61K 49/00 (2006.01)
A61K 39/00 (2006.01)
A61K 39/395 (2006.01)
A61K 47/68 (2017.01)

(52) U.S. Cl.
CPC .... *A61K 39/39558* (2013.01); *A61K 47/6809* (2017.08); *A61K 47/6851* (2017.08)

(58) Field of Classification Search
CPC ........ A61K 47/48384; A61K 47/48407; A61K 47/48569; A61K 47/48561; A61K 49/00; A61K 39/395; A61K 39/00
USPC ..... 424/9.1, 9.2, 130.1, 134.1, 138.1, 141.1, 424/152.1
See application file for complete search history.

(56) References Cited

U.S. PATENT DOCUMENTS

| | | | |
|---|---|---|---|
| 3,896,111 A | 7/1975 | Kupchan et al. | |
| 4,137,230 A | 1/1979 | Hashimoto et al. | |
| 4,151,042 A | 4/1979 | Higashide et al. | |
| 4,169,888 A | 10/1979 | Hanka et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,317,821 A | 3/1982 | Miyashita et al. | |
| 4,322,348 A | 3/1982 | Asai et al. | |
| 4,331,598 A | 5/1982 | Hasegawa et al. | |
| 4,361,650 A | 11/1982 | Asai et al. | |
| 4,315,929 A | 12/1982 | Freedman et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,418,064 A | 11/1983 | Powell et al. | |
| 4,424,219 A | 1/1984 | Hashimoto et al. | |
| 4,444,887 A | 4/1984 | Hoffmann | |
| 4,761,111 A | 8/1988 | Brown | |
| 5,034,223 A | 7/1991 | Abrams | |

(Continued)

FOREIGN PATENT DOCUMENTS

EP 0239400 A2 9/1987
EP 0519596 A1 12/1992

(Continued)

OTHER PUBLICATIONS

Chanan-Khan, A.A., et al. Phase I study of BT062 given as repeated single dose once every 3 weeks in patients with relapsed or relapsed/refractory multiple myeloma. Blood, vol. 114, Issue 22, Abstract 1862, 2009.*

Palaiologou, M. et al. CD138 (syndecan-1) expression in health and disease. Histology and Histopathology, vol. 29, No. 2, pp. 177-189, 2014.*

Chanan-Khan et al., Blood, vol. 114, Issue 22, Abstract 1862, 2009.*

Abdelkefi et al.; "Single autologous stem-cell transplantation followed by maintenance therapy with thalidomide is superior to double autologous transplantaion in multiple myeloma: results of a multicenter randomized clinical trial;" Blood; 111; 2008; pp. 1805-1810.

(Continued)

*Primary Examiner* — Rodney P Swartz
(74) *Attorney, Agent, or Firm* — Agris & von Natzmer LLP; Joyce von Natzmer

(57) ABSTRACT

Disclosed is a method and composition for treating a disease associated with target cells expressing CD138 in a multiple dose regimen. An immunoconjugate comprising an engineered targeting antibody targeting CD138 expressing cells and an effector molecule is administered in a multiple dose regimen. The multiple dose regimen comprises at least two doses and the aggregate dose administered within an active treatment cycle is an aggregate maximum tolerable dose (AMTD) or a fraction of the AMTD. The AMTD and/or said fraction exceeds the dose resulting in dose limiting toxicity (DLT) and/or exceeds the maximum tolerable dose (MTD) when the immunoconjugate is administered as a single dose, including as part of a multiple single dose regimen within said active treatment cycle.

46 Claims, 41 Drawing Sheets

Specification includes a Sequence Listing.

(56) References Cited

U.S. PATENT DOCUMENTS

| | | | |
|---|---|---|---|
| 5,053,394 | A | 10/1991 | Ellestad et al. |
| 5,208,020 | A | 5/1993 | Chari et al. |
| 5,367,086 | A | 11/1994 | Rao |
| 5,475,092 | A | 12/1995 | Chari et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,585,089 | A | 12/1996 | Queen et al. |
| 5,585,499 | A | 12/1996 | Chari et al. |
| 5,612,016 | A | 3/1997 | Griffiths et al. |
| 5,639,641 | A | 6/1997 | Pedersen et al. |
| 5,703,247 | A | 12/1997 | Kingston et al. |
| 5,705,508 | A | 1/1998 | Ojima et al. |
| 5,712,374 | A | 1/1998 | Kuntsmann et al. |
| 5,714,586 | A | 2/1998 | Kunstmann et al. |
| 5,739,350 | A | 4/1998 | Kelly et al. |
| 5,763,477 | A | 6/1998 | Duvvuri et al. |
| 5,773,001 | A | 6/1998 | Hamann et al. |
| 5,814,318 | A | 9/1998 | Lonberg et al. |
| 5,831,012 | A | 11/1998 | Nilsson et al. |
| 5,846,545 | A | 12/1998 | Chari et al. |
| 5,877,296 | A | 3/1999 | Hamann et al. |
| 5,892,063 | A | 4/1999 | Zheng et al. |
| 5,998,656 | A | 12/1999 | Holton et al. |
| 6,001,358 | A | 12/1999 | Black et al. |
| 6,002,023 | A | 12/1999 | Kingston et al. |
| 6,005,079 | A | 12/1999 | Casterman et al. |
| 6,080,777 | A | 6/2000 | Schiff |
| 6,087,362 | A | 7/2000 | El-Rashidy |
| 6,333,410 | B1 | 12/2001 | Chari et al. |
| 6,340,701 | B1 | 1/2002 | Chari et al. |
| 6,436,931 | B1 | 8/2002 | Chari et al. |
| 6,534,628 | B1 | 3/2003 | Nilsson et al. |
| 6,534,660 | B1 | 3/2003 | Yongxin et al. |
| 6,596,757 | B1 | 7/2003 | Chari et al. |
| 6,706,708 | B2 | 3/2004 | Chari et al. |
| 6,716,821 | B2 | 4/2004 | Zhao et al. |
| 6,740,734 | B1 | 5/2004 | Nilsson et al. |
| 6,756,397 | B2 | 6/2004 | Zhao et al. |
| 7,601,354 | B2 | 10/2009 | Chari |
| 7,612,178 | B2 | 11/2009 | Hariharan et al. |
| 2002/0006379 | A1 | 1/2002 | Hansen et al. |
| 2002/0131967 | A1 | 9/2002 | Nakamura et al. |
| 2003/0004210 | A1 | 1/2003 | Chari et al. |
| 2003/0055226 | A1 | 3/2003 | Chari et al. |
| 2003/0105000 | A1 | 6/2003 | Pero et al. |
| 2003/0109682 | A1 | 6/2003 | Santi et al. |
| 2004/0002587 | A1 | 1/2004 | Watkins et al. |
| 2004/0126379 | A1 | 1/2004 | Adolf et al. |
| 2004/0024049 | A1 | 2/2004 | Baloglu et al. |
| 2004/0082764 | A1 | 4/2004 | Kunz et al. |
| 2004/0087649 | A1 | 5/2004 | Chari et al. |
| 2004/0235840 | A1 | 11/2004 | Chari et al. |
| 2004/0241817 | A1 | 12/2004 | Umana et al. |
| 2005/0123549 | A1 | 6/2005 | Payne et al. |
| 2005/0169933 | A1 | 8/2005 | Steeves et al. |
| 2005/0271653 | A1 | 12/2005 | Strahilevitz |
| 2005/0272128 | A1 | 12/2005 | Umana et al. |
| 2006/0045877 | A1 | 3/2006 | Goldmakher |
| 2006/0233814 | A1 | 10/2006 | Goldmakher et al. |
| 2007/0183971 | A1 | 8/2007 | Goldmakher |
| 2008/0171040 | A1 | 7/2008 | Ebens et al. |
| 2009/0169570 | A1 | 7/2009 | Daelken et al. |
| 2009/0175863 | A1 | 7/2009 | Kraus et al. |
| 2009/0181038 | A1 | 7/2009 | Schulz et al. |
| 2009/0232810 | A1 | 9/2009 | Kraus et al. |
| 2010/0028346 | A1 | 2/2010 | Lutz et al. |
| 2011/0123554 | A1 | 5/2011 | Osterroth et al. |

FOREIGN PATENT DOCUMENTS

| | | | |
|---|---|---|---|
| EP | 0592106 | A1 | 4/1994 |
| WO | 91/09967 | A1 | 7/1991 |
| WO | 91/10741 | A1 | 7/1991 |
| WO | 96/33735 | A1 | 10/1996 |
| WO | 96/34096 | A1 | 10/1996 |
| WO | 97/11971 | A1 | 4/1997 |
| WO | 98/16654 | A1 | 4/1998 |
| WO | 98/24893 | A1 | 6/1998 |
| WO | 98/46645 | A2 | 10/1998 |
| WO | 98/50433 | A2 | 11/1998 |
| WO | 03/070234 | A1 | 8/2003 |
| WO | 2004/099379 | A1 | 9/2006 |
| WO | 2006099875 | | 9/2006 |
| WO | 2007066109 | | 6/2007 |
| WO | 2007/144046 | A2 | 12/2007 |
| WO | 2009/080829 | A1 | 7/2009 |
| WO | 2009/080830 | A1 | 7/2009 |
| WO | 2009/080831 | A1 | 7/2009 |
| WO | 2009/080832 | A1 | 7/2009 |
| WO | 2010/008726 | A1 | 1/2010 |
| WO | 2010128087 | A2 | 11/2010 |

OTHER PUBLICATIONS

Armour et al.; "Recombinant human IgG molecules lacking Fcgamma receptor I binding and monocyte triggering activities;" Eur J Immunol; 29(8); 1999; pp. 2613-2624.

Anderson et al.; Multiple Myeloma: New Insights and Therapeutic Approaches; Hematology; 2000; pp. 147-165.

Anderson et al.; Multiple Myeloma; Hematology Am Soc Hematol Educ Program; 2002; pp. 214-240.

Anttonen et al.: "Syndecan-1 expression has prognostic significance in head and neck carcinoma;" Br J of Cancer 79 (3/4), 1999, pp. 558-564.

Anttonen et al.: "High syndecan-1 expression is associated with favourable outcome in squamous cell lung carcinoma treated with radical surgery;" Lung Cancer; 32(3); Jun. 2001; pp. 297-305.

Aref et al.: "Syndecan-1 in multiple myeloma: relationship to conventional prognostic factors;" Hematology; 8; 2003; pp. 221-228.

Bataille et al:, "The phenotype of normal, reactive and malignant plasma cells. Identification of "many and multiple myelomas" and of new targets for myeloma therapy," Haematologica 91(9); Sep. 2006; pp. 1234-1240.

Bayer-Garner et al.; "Syndecan-1 (CD138) immunoreactivity in bone marrow biopsies of multiple myeloma: shed syndecan-1 accumulates in fibrotic regions;" Mod Pathol.; 14(10); Oct. 2001; pp. 1052-1058.

Beeram et al. "A phase I study of trastuzumab-DM1 (T-DM1), a first-in-class HER2 antibody-drug conjugate (ADC), in patients (pts) with advanced HER2+ breast cancer (BC);" ASCO Meeting; Abstracts; May 20, 2008; pp. 1028.

Berenson et al.; "New drugs in multiple myeloma;" Curr Opin Support Palliat Care; 2(3); Sep. 2008; pp. 204-210.

Bisping et al., "Targeting receptor kinases by a novel indolinone derivative in multiple myeloma: abrogation of stroma-derived interleukin-6 secretion and induction of apoptosis in cytogenetically defined subgroups;" Blood; 107(5); Mar. 1, 2006, pp. 2079-2089.

Bissery et al., "Experimental Antitumor Activity of Taxotere (RP 56976, NSC 628503), a Taxol Analogue", Cancer Research 51, 1991, pp. 4845-4852.

Bladé et al.; "Advances in therapy of multiple myeloma;" Curr Opin Oncol; 20(6); Nov. 2008; pp. 697-704.

Blum et al.: "Maytansine: A Phase I study of an ansa macrolide with antitumor activity;" Cancer Treat Rep; 62; 1978; pp. 435-438.

Brand et al.; "Management of high risk metastatic prostate cancer: the case for novel therapies;" J Urol Dec; 176 (6Pt 2); 2006; pp. S76-S80.

Carlsson et al., "Protein thiolation and reversible protein-protein conjugation. N-succinimidyl-3-(2-pyridyldithio) propionate, a new heterobifunctional reagent;" Biochem J; 173; 1978; pp. 723-737.

Carter and Senter, "Antibody-Drug Conjugates", The Cancer Journal, vol. 14(3), 2008, pp. 154-169.

Chabner et al.; "Initial clinical trials of maytansine, an antitumor plant alkaloid;" Cancer Treat Rep; 62; 1973; pp. 429-433.

Chanan-Khan et al.; "Phase I Study of huN901-DM1 (BB-10901) in Patients with Relapsed and Relapsed/Refractory CD56-Positive Multiple Myeloma;" Blood; 108(11); Abstract #1174 (ASH Meeting); Nov. 16, 2007.

(56) References Cited

OTHER PUBLICATIONS

Chanan-Khan et al.; "Phase I Study of IMGN901 in Patients with Relapsed and Relapsed/Refractory CD56-Positive Multiple Myeloma;" Blood (ASH Annual Meeting Abstracts); 112; Nov. 2008; pp. 3689.

Chari et al.; "Immunoconjugates containing novel maytansinoids: promising anticancer drugs;" Cancer Res; 52; 1992; pp. 127-131.

Choi et al.; "Syndecan-1, a key regulator of cell viability in endometrial cancer;" Int J Cancer 121(4); 2007; pp. 741-750.

Chou and Talalay; "Quantitative analysis of dose-effect relationships: the combined effects of multiple drugs on enzyme inhibitors;" Adv. Enzyme Regul, 22; 1984, pp. 27-55.

Conejo et al.; "Syndecan-1 expression is up-regulated in pancreatic but not in other gastrointestinal cancers;" Int J Cancer; 88(1); Oct. 1, 2000; pp. 12-20.

DeGeorge et al.; "Regulatory considerations for preclinical development of anticancer drugs;" Cancer Chemother Pharmacol; 41(3); 1998; p. 173-185.

Dmoszyńska A.; "Diagnosis and the current trends in multiple myeloma therapy;" Pol Arch Med Wewn; 118(10); Oct. 2008; pp. 563-566.

Dimopoulos et al.; "The role of novel drugs in multiple myeloma;" Annals of Oncology19 (Supplement 7); 2008; pp. vii121-vii127.

Durie et al.; "Myeloma management guidelines: a consensus report from the Scientific Advisors of the International Myeloma Foundation;" Hematol J, 4(6), 2003, pp. 379-398.

Durie et al.; "International unform response criteria four multiple myeloma;" Leukemia; 20(12); Dec. 2006; pp. 2220.

Eagan et al.; "Early clinical study of an intermittent schedule for maytansine (NSC-153858): brief communication;" J Natl Cancer Insti (Bethesda); 60; 1978; pp. 93-96.

Facon et al.; "Superiority of melphalan-prednisone (MP) + thalidomide (THAL) over MP and autologous stem cell transplantation in the treatment of newly diagnosed elderly patients with multiple myeloma," J. Clin. Oncol.; 24(Suppl. 18); Abstract 1; 2006.

Fossella et al., "Phase II Trial of BB-10901 (huN901-DM1) given weekly for four consecutive weeks every 6 weeks in patents with relapsed SCLC and CD56-positive small cell carcinoma;" J Clin Onco, ASCO Annual Meeting Proceedings; 23(16S), Part I of II; Jun. 1, 2005; 7159; Supplement.

Galsky et al., "Phase I Trial of the Prostate-Specific Membrane Antigen-Directed Immunoconjugate MLN2704 in Patients With Progressive Metastatic Castration-Resistant Prostate Cancer:" Journal of Clinical Oncology; May 1, 2008; pp: 2147-2154.

Ghobrial et al.; "Emerging drugs in multiple myeloma;" Expert Opin Emerg Drugs; 12(1); Mar. 2007; pp. 155-163.

Giles et al.: "Phase l study of AVE9633, an AntiCD33-Maytansinoid Immunoconjugate, Administered as an Intravenous Infusion in Patients with Refractory/Relapsed CD33-Positive Acute Myeloid Leukemia (AML);" Blood; 108(11); Nov. 16, 2006.

Greipp at al.; "International staging system for multiple myeloma," J Clin Oncol; 23(15); May 20, 2005; pp. 3412-3420.

Gunaratnum et al.; "G-quadruplex compounds and cis-platin act synergistically to inhibit cancer cell growth in vitro and in vivo;" Biochemical Pharmacology; 78; 2009; pp. 115-122.

Hashimoto et al.; "Colorectal Association of loss of epithelial syndecan-1 with stage and local metastasis of colorectal adenocarcinomas: an immunohistochemical study of clinically annotated tumors;"BMC Cancer 8; 2008; p. 185.

Helft et al.; "A phase I study of cantuzumab mertansine administered as a single intravenous infusion once weekly in patients with advanced solid tumors;" Clin Cancer Res; 10(13); Jul. 1, 2004; pp. 4363-4368.

Hideshima et al.:, "Perifosine, an oral bioactive novel alkylphospholipid, inhibits Akt and induces in vitro and in vivo cytotoxicity in human multiple myeloma cells;" Blood; 107(10); 2006, pp. 4053-4062.

Hideshima et al.; "Understanding multiple myeloma pathogenesis in the bone marrow to dentify new therapeutic targets;" Nat Rev Cancer; 7(8); 2007; pp. 585-598.

Hiroshi et al.; "The Monoclonal Antibody nBT062 Conjugated to Cytotoxic Maytansinoids Has Potent and Selective Cytotoxicity against CD138 Positive Multiple Myeloma Cells in Vitro and in Vivo;" Blood; (ASH Annual Meeting Abstracts), 112; Nov. 2008; p. 1716.

Holden et al,; "A phase I study of weekly dosing of trastuzumab-DM1 (T-DM1) in patients (pts) with advanced HER2+ breast cancer (BC)," ASCO Meeting Abstracts, May 20, 2008, p. 1029.

Horvathova et al.: In: al. SFSe, ed. Leucocyte Typing V.; Oxford: Oxford University Press; 1995: pp. 713-714.

Huang et al.; "Validation and reduction of FACT/GOG-Ntx subscale for platinum/paclitaxel-induced neurologic symptoms: a gynecologic oncology group study;" Int J Gynecol Cancer; 17; 2007; pp. 387-393.

Hwang et al.; "New Frontiers in the Treatment of Multiple Myeloma;" Scientific World Journal; 6; Dec. 6, 2006; pp. 1475-1503.

Ikeda et at; "The monoclonal antibody nBT062 conjugated to maytansinoids has potent and selective cytotoxicity against CD138 positive multiple myeloma cells in vitro and in vivo;" Clin. Cancer Research; 15(12): 2009; available at http://precedings.nature.com/documents/2374/version/1.

Ishitsuka et al.; "Targeting CD53 by the maytansinoid immunoconjugate IMGN901 (huN901-DM1): a potential therapeutic modality implication against natural killer/T cell malignancy;" Br. J. Haematol; 141(1); Apr. 2008; pp. 129-131.

Issell et al.; "Maytansine;"Cancer Treat Rev; 5; 1978; pp. 199-207.

Jemal et al.; "Cancer statistics:" CA Cancer J Clin; 58; 2008; pp. 71-96.

Kovtun et al.; "Antibody-drug conjugates designed to eradicate tumors with homogeneous and heterogeneous expression of the target antigen;" Cancer Res; 66(6); 2006; pp. 3214-3221.

Kuesters et al.; Correlation of ErbB2 Gene Status, mRNA and Protein Expression in a Panel of <100 Human Tumor Xenografts of Different Origin; Onkologie; 29; 2006; pp. 249-256.

Krebs et al.; "High-throughput generation and engineering of recombinant human antibodies;" J. Immunol, Methods; 254; 2001; pp. 67-84.

Krop et al.: "A Phase I Study of Trastuzumab-DM1, a First-in-Class HER2 Antibody-Drug Conjugate (ADC), in patients with HER2+ Metastatic Breast Cancer;" 14th European Cancer Conference (ECCO 14); Poster #2118; 2007.

Kyle et al.; "Multiple myeloma;" N. Engl J Med; 351(18); Oct. 28, 2004; pp. 1860-1873.

Kyle et al.; "Criteria for diagnosis, staging, risk stratification dn response assessment of multiple myeloma;" Leukemia; 23; 2009; pp. 3-9.

Kyoizumi et al.; "Implantation and maintenance of functional human bone marrow in SCID-hu mice;" Blood; 79; 1992; pp. 1704-1711.

Lambert JM; "Drug-conjugated monoclonal antibodies for the treatment of cancer;" Current Opinion in Pharmacology; 5; 2005; pp. 543-549.

Langford et al.; "Multiple heparan sulfate chains are required for optimal syndecan-1 function;" J Biol Chem; 273(45); Nov. 6, 1998; pp. 29965-29971.

Legrand et al.; "An open label, dose escalation study of AVE9633 administered as a single agent by intravenous (IV) infusion weekly for 2 weeks in a 4-week cycle to patients with relapsed or refractory CD33-positive Acute Myeloid Leukemia (AML);" Blood; 118(11); Nov. 16, 2007.

Li et al ; "Clinicopathological significance of expression of paxillin, syndecan-1 and EMMPRIN in hepatocellular carcinoma;" World J Gastroenterol. 11(10); 2005; pp. 1445-1451.

Loussouam et al.; "Prognostic impact of syndecan-1 expression in invasive ductal breast carcinomas;" Br J Cancer; 28; 2008; pp. 1993-1998.

Lorigan et al.; "Phase I trial of BB-10901 (huN901-DM1) given daily by IV infusion for three consecutive days every three weeks in patients with SCLC and other CD56-positive solid tumors;" European Journal of Cancer Supplements; 4(12); 2006; pp. 195.

Ludwig et al.: "Supportive care in multiple myeloma;" Best Practice & Research Clinical Haematology; 20; Issue 4; 2007; pp. 817-835.

McCann et al.; "Phase II trial of huN901-DM1 in patients with relapsed small cell lung cancer (SCLC) and CD56-positive small

(56) References Cited

OTHER PUBLICATIONS cell carcinoma;" J Clin Onco; ASCO Annual Meeting Proceedings Part 1; 25(185); Jun. 20, 2007; Supplement; p. 18084.
Mateos et al.; "Bortezomib plus melphalan and prednisone in elderly untreated patients with multiple myeloma: results of a multicenter phase 1/2 study;" Blood; 108; 2006; pp. 2165-2172.
Milowsky et al.; "Phase I/II trial of the prostate-specific membrane antigen (PSMA)-targeted immunoconjugate MLN2704 in patients (pts) with progressive metastatic castration resistant prostate cancer (CRPC);" J Olin Onco; ASCO Annual Meeting Proceedings Part I; 24(18S); 2006 p. 4500.
Mita et al.; "A phase I study of a CanAg-targeted immunocongugate, huC242-DM4, in subjects with CanAg-expressing solid tumors;" J Olin Onco; ASCO Annual Meeting Proceedings Part 1; 25(185); Jun. 20, 2007; Supplement; p. 3062, 2007.
Mitsogiannis et al; "Plasmacytoid transitional cell carcinoma of the urinary bladder;" Urology66(1); 2005; p. 194.
NCCN Guidelines; "NCCN Clinical Practice Guidelines in Oncology;" Multiple Myeloma V.2.2009; National Comprehensive Cancer Network; Nov. 9, 2008; available at www.nccn.org.
Ning et al.; "Liposomal doxorubicin in combination with bortezomib for relapsed or refractory multiple myeloma;" Oncology (Williston Park); 21(12); Nov. 277; pp. 1503-1508, 2004.
Numa et al.;Syndecan-1 expression in cancer of the uterine cervix: association with lymph node metastasis; Int J Oncol. 20(1); Abstract, 2002.
Ocio et al., "New drugs in multiple myeloma: mechanisms of action and phase I/II clinical findings;" Lancet Oncol: 9(12); Dec. 2008; pp. 1157-1165.
Palumbo et al.; "Oral revlimid plus melphalan and prednisone (R-MP) for newly diagnosed multiple myeloma: results of a multicenter Phase I/II study;" Blood; 108; (ASH Annual Meeting Abstracts); Abstract 800; 2006.
Palumbo et al.; "Treatment of newly diagnosed myeloma;" Leukemia; 23; Nov. 13, 2009; pp. 449-456.
Patriarca et al.; "Considerations in the treatment of multipte myeloma: a consensus tatement from Italian experts;" Eur J Haematol; 82(2); Feb. 2009; pp. 93-105.
Podar et al.; "Bone marrow microenvironment and the identification of new targets far myeloma therapy;" Leukemia 23(1); Jan. 2009; pp. 10-24.
Qin et al.: "The pharmacokinetics and pharmacodynamics of IMGN242 (huC242-DM4) in patients with CanAg-expressing solid tumors:" Journal of Clinical Oncology, 2008 ASCO Annual Meeting Proceedings (Post-Meeting Edition); 26(15S); May 20, 2008; Supplement; p. 3066.
Quach et al.; "Mechanism of action of immunomodulatory drugs (ImiDS) in multiple myeloma," Leukemia; 24; 2010; pp. 22-32.
Raje et al.; "Therapeutic use of immunomodulatory drugs in the treatment of multiple myeloma;" Expert Rev Anticancer Ther; 6(9); Sep. 2006, pp. 1239-1247.
Rajkumar et al.; "Combination therapy with lenalidomide plus dexamethasone (Rev/Dex) for newly diagnosed myeloma;" Blood; Dec. 15, 2005; 106(13); pp. 4050-4053.
Rajkumar et al.; "Phase III clinical trial of thalidomide plus dexamethasone compared with dexamethasone alone in newly diagnosed multiple myeloma: a clinical trial coordinated by the Eastern cooperative Oncology Group;" J Clin Oncol 2006; 24; pp. 431-436.
Rajkumar et al.; "A Randomized Trial of Lenalidomide Plus High-Dose Dexamethasone (RD) Versus Lenalidomide Plus Low-Dose Dexamethasone (Rd) in Newly Diagnosed Multiple Myeloma (E4A03): A Trial Coordinated by the Eastern Cooperative Oncology Group;" Blood; 110; 2007; p: 74.
Richardson et al.; "New treatments for multiple myeloma;" Oncology (Williston Park); 19(14); Dec. 2005; pp. 1781-1792.
Richardson et al.; "Lenalidomide in multiple myeloma;" Expert Rev Anticancer Ther, 6(8); Aug. 2006; pp. 1165-1173.
Richardson et al.; "New Drugs for Myeloma;" Oncologist Jun; 12(6); 2007; pp. 664-689.

Richardson et al.: "Lenalodomide, bortezomib, and dexamethasone as front-line-therapy for patients with multiple myeloma (MM): preliminary results of a phase I/II study;" Blood; 110: 2007: p. 63a.
Riechelmann et al.: "Phase I trial with the CD44v6-targeting immunoconjugate bivatuzumab mertansine in head and neck squamous cell carcinoma;" Oral Oncol; 44(9); Sep. 2008; pp. 823-829.
Roh et al.; "Syndecan-1 expression in gallbladder cancer and its prognostic significance;" Eur Surg Res. 41(2): 2008; pp. 245-250.
Roguska et al.; "Humanization of murine monoclonal antibodies through variable domain resurfacing;" Proc Natl Acad Sci U S A; 91; 1994; pp. 969-973.
Rowinsky et al.; "SB-408075, a tumor-activated immunoconjugate targeting the C242 CanAg antigen with a potent maytansinoid payload: phase I, pharmacokinetic (PK), and biological studies;" Proc Am Soc Clin Oncol 21: Abstract #118; 2002.
Rupp et al.; "Safety and pharmacokinetics of bivatuzumab mertansine in patients with CD44v6-positive metastatic breast cancer: final results of a phase I study;" Anticancer Drugs; 18(4); Apr. 2007; pp. 477-485.
Salfeld, "Isotype selection in antibody engineering", Nat. Biotechnol, 25 (12), 2007, pp. 1369-1372.
Sankhala et al.; "A phase I and pharmacokinetic study of a CanAg-targeted immunoconjugate, HuC242-DM4, in patients with CanAg-expressing solid tumors;" AACR-NCI-EORTC "Molecular Targets and Cancer Therapeutics" International Conference; Abstract #B70; 2007.
Sauter et al.; „Pharmacokinetics, immunogenicity and safety of bivatuzumab mertansine, a novel CD44v6-targeting immunoconjugate, in patients with squamous cell carcinoma of the head and neck; Int J Oncol.; 30(4); Apr. 2007; pp. 927-935.
Schuurman, et al.; "Normal human immunoglobulin G4 is bispecific: it has two different antigen-combining sites;" Immunology; 97; 1999; pp. 693-698.
Shah et al.; "Expression of syndecan-1 and expression of epidermal growth factor receptor are associated with survival in patients with nonsmall cell lung carcinoma," Cancer 101(7); 2004 ; pp. 1632-1638.
Shields et al.; "High resolution mapping of the binding site on human IgG1 for Fc gamma RI, Fc gamma RII, Fc gamma RIII, and FcRn and design of IgG1 variants with improved binding to the Fc gamma R.;" J Biol Chem; 276(9); 2001; pp. 6591-6604.
Strobeck M; "Multiple Myeloma therapies," Nature Reviews Drug Discovery; 6(3); Mar. 2007; pp. 181-182.
Tai et al; "Immunomodulatory drug lenalidomide (CC-5013, IMiD3) augments anti-CD40 SGN-40-induced cytotoxicity in human multiple myeloma: clinical implications;" Cancer Res. Dec. 15, 2005; 65(24):11712-20.
Takimoto et al.; "Principles of oncologic pharmacotherapy;" Cancer Management: A multidisciptnary Approach; 11th Edition; Chapter 3; 2008; Apr. 15, 2009; available at http://www.cancernetwork.com/display/article/10165/1402628.
Yang et al.; "The syndecan-1 heparan sulfate proteoglycan is a viable target for myeloma therapy;" Blood; 110(6); Sep. 15, 2007 pp. 2041-2048.
Terpos et al.; "The use of bisphosphonates in multiple myeloma, recommendations of an expert panel on behalf of the European Myeloma Network;" Ann Oncol. 20(8); 2009; pp. 1303-1317.
Tijink et al.; "A phase I dose escalation study with anti-CD44v6 bivatuzumab mertansine in patients with incurable squamous cell carcinoma of the head and neck or esophagus;" Clin Cancer Res; 12(20 Pt 1); Oct. 15, 2008; pp. 6064-6072.
Tolcher et al.; "A Phase I study at huC242-DM4 to assess the safety and pharmacokinetics of huC242-DM4 administered as a single intravenous infusion once every three weeks to subjects with solid tumors;" European Journal of Cancer Supplements;4(12); 2006 p. 66.
Tomayko et al., "Determination of subcutaneous tumor size in athymic (nude) mice;" Cancer Chemother. Pharmacol, 24; 1989; pp. 148.
Toyoshima et al., "Expression of syndecan-1 is common in human lung cancers independent of expression of epidermal growth factor receptor;" Lung Cancer 31(2-3); 2001; pp. 193-202.

(56) References Cited

OTHER PUBLICATIONS

Weber et al.; "Lenalidomide plus high-dose dexamethasone provides improved overall survival compared to high-dose dexamethasone alone for relapsed or refractory multiple myeloma (MM): results of 2 Phase III studies (MM-009, MM-010) and subgroup analysis of patients with impaired renal function," Blood; 108; (ASH Annual Meeting Abstracts); Abstract 3547; 2006.
Yasui et al.; "Recent advances in the treatment Multiple Myeloma;" Curr Pharm Biotechnol; 7(5); Oct. 2006; pp. 381-393.
Yoshitake, et al.; "Conjugation of glucose oxidase from Aspergillus niger and rabbit antibodies using N-hydroxysuccinimide ester of N-(4-carboxycyclohexylmethyl)-maleimide;" Eur J Biochem; 101; 1979; pp. 395-399.
Yu et al ; "Antitumor synergy of CV787, a prostate cancer-specific adenovirus, and paclitaxel and docetaxel;" Cancer Research; 61; Jan. 15, 2001; pp. 517-525.
Zellweger et al.: "Tissue microarray analysis reveals prognostic significance of syndecan-1 expression in prostate cancer;" Prostate 55(1); 2003; pp. 20-29.
Alyanakian et al.; "Pharmacokinetics of total immunoglobulin G and immunoglobulin G subclasses in patients undergoing replacement therapy for primary immunodeficiency syndromes;" Vox Sang; 84(3); Apr. 2003; pp. 188-192.
Rajkumar et al.; "Lenalidomide plus high-dose dexamethasone versus lenalidomide plus low-dose dexamethasone as initial therapy for newly diagnosed multiple myeloma: and open-label randomized controlled trial;" Lancet Oncol.; 11(1); Jan. 2010; pp. 29-37.
Inki et al.; "1994 Association between syndecan-1 expression and clinical outcome in squamous cell carcinoma of the head and neck;" Br J Cancer; 7092); Aug. 1994; pp. 319-323.
Chen et al.; "2004 Syndecan-1 expression in locally invasive and metastatic prostate cancer;" Urology; 63(2): Feb. 2004; pp. 402-407.
Takimoto et al., "Chapter 3: Principles of Oncologic Pharmacotherapy in Cancer Management: A Multidisciplinary Approach;" 11th Edition (2008), edited by: Pazdur et al.; available at http://www.cancernetwork.com/cancer-management-11.
Chou TC: "Theoretical basis, experimental design, and computerized simulation of synergism and antagonism in drug combination studies;" Pharmacol Rev; 58(3); Sep. 2006; pp. 621-681. Review.
Fundamental Immunology, William E. Paul M.D., ed., 3rd Ed., pp. 292-295, 1993.
Rudikoff et al., "Single amino acid substitution altering antigen-binding specificity," in Proc. Natl. Acad. Sci. USA, vol. 79, pp. 1979-1983, Mar. 1982.
Colman, "Effects of amino acid sequence changes in antibody-antigen interactions," in Research in Immunology, vol. 145, pp. 33-36. 1994.
Buchsbaum, "Experimental approaches to increase radiolabeled antibody localization in tumors," in Cancer Res. Suppl., vol. 55, pp. 5729s-5732s, Dec. 1, 1995.
Chanan-Khan et al., "3689 Phase 1 Study of IMGN901 in Patients with Relapsed and Relapsed/Refractory CD56-Postiive Multiple Myeloma," in 50th ASH Annual Meeting and Exposition: Online Program and Abstracts, American Society of Hematology, Dec. 6-9, 2008.
Post J., Inter J Cancer, vol. 83, p. 571-576 . . . 1999, IOS, XXX, filed on Jan. 31, 2005.
Allum et al., J. Clin. Pathol., 1986, 39:610-614.
MacCallum et al. J. Mol. Biol., 262, 732-745, 1996.
Fundamental Immunology, (William E. Paul, M.D.ed.,3d ed. 1993), p. 242.
Casset et al. Biochemical and Biophysical Research Communications, 307:198-205, 2003.
Bendig. M. M., Methods: A Campanion to Methods in Enzymology, 1995; 8:83-93.
Reichert (Nature, vol. 19, 2001, p. 819-822).
Pascalis et al The Journal of Immunology vol. 169, 3076-3084, 2002.
Chari et al ,Cancer Res. 52:127-131, 1992.
Lynch et al. (Pain, 2004, 110: 56-63).
Cabanillas et al., "Phase I study of maytansine using a 3 day schedule," Cancer Treat Rep., vol. 62, 1976, pp. 425-428.
Wiesenthal (http://weisenthal.org/feedback.html, Feb. 4, 2002).
Krontiris and Capizzi (Internal Medicine, 4th Edition, Editor-in-chief Jay Stein, Elsevier Science, 1994 Chapters 71-72, pp. 699-729).
Carter, S. K. et al. (Chemotherapy of Cancer; Second edition: John Wiley & Sons: New York, 1981; appendix C).
Berenbaum (Clin. Exp Immunol. 28:1-18, 1977).
Abaza et al, (Journal of Protein Chemistry, vol. 11, No. 5, 1992, pp. 433-444).
Burgess et al (J of Gell Bio. 111 :2129-2138, 1990).
Cohen (Int J Radial Oncol Biol Phys, 1987, 13:251-8).
Gussow et al. (1991, Methods in Enzymology 203:99-121).
Gura (Science, 1997, 278:1 041-1 042).
Rawstron AC, Owen RG, Davies FE, Johnson RJ, Jones RA, Richards SJ, Evans PA, Child JA, Smith GM, Jack AS, Morgan GJ. Circulating plasma cells in multiple myeloma: characterization and correlation with disease stage. Br J Haematol. 1997,97:46-55.
Remillard S, Rebhun LI, Howie GA, Kupchan SM. Antimitotic activity of the potent tumor inhibitor maytansine. Science. 1975;189:1002-1005.
Rintala M, Inki P, Klemi P, Jalkanen M. Grenman S. Association of syndecan-1 with tumor grade and histology in primary invasive cervical carcinoma. Gynecol Oncol. Dec. 1999;75(3):372-8.
Roguska MA, Pedersen JT, Keddy CA, Henry AH, Searle SJ, Lambert JM, Goldmacher VS, Blättler WA, Rees AR, Guild BC. Humanization of murine monoclonal antibodies through variable domain resurfacing. Proc Natl Acad Sei U S A. 1994;91:969-973.
Ross JS, Gray K, Gray G, Worland PJ, Rolfe M. Anticancer Antibodies, Am J Clin Path. (Apr. 17, 2003).
Ross S, Spencer SD, Holcomb I, Tan C, Hongo J, Devaux B, Rangell L, Keller GA, Schow P, Steeves PM, Lutz RJ, Frantz G, Hillan K, Peale F, Tobin P, Eberhard D, Rubin MA, Lasky LA, Koeppen H. Prostate stem cell antigen as therapy target: tissue expression and in vivo efficacy of an immunoconjugate. Cancer Res, May 1, 2002 ;62(9)2546-53.
Sanderson RD, Lalor P, Bernfield M. B lymphocytes express and lose syndecan at specific stages of differentiation. Cell Regul. 1989;1:27-35.
Sandhu JS, Clark BR, Boynton EL, Atkins H, Messner H, Keating A, Hozumi N. Human hematopoiesis in SCID mice implanted with human adult cancellous bone. Blood. 1996;88:1973-1982.
Sasaki A, Boyce BF, Story B, Wright KR, Chapman M, Boyce R, Mundy GR, Yoneda T. Bisphosphonate risedronate reduces metastatic human breast cancer burden in bone in nude mice. Cancer Res 1995;55:3551-3557.
Schneider U, van Lessen A, Huhn D, Serke S. Two subsets of peripheral blood plasma cells defined by differential expression of CD45 antigen. Br J Haematol. 1997;97:56-64.
Sebestyen A, Berczi L, Mihalik R, Paku S, Matolcsy A, Kopper L. Syndecan-1 (CD138) expression in human non-Hodgkin lymphomas. Br J Haematol. 1999; 104(2):412-9.
Seftalioglu A, Karakus S. Syndecan-1/CD138 expression in normal myeloid, acute lymphoblastic and myeloblastic leukemia cells, Acta Histochem. 2003;105:213-221.
Seftalioglu A, Karakus S, Dundar S, Can B, Erdemli E, Irmak MK, Oztas E, Korkmaz C, Yazar F, Cavusoglu I. Syndecan-1 (CD 138) expression in acute myeloblastic leukemia cells—an immuno electron microscopic study. Acta Oncol. 2003;42:71-74.
Senter PD, Doronina S, Cerveny C, Chace D, Francisco J, Kinsman K, Mendelsohn B, Meyer D, Siegall CB, Thompson J et al. Cures and regressions of established tumors with monoclonal antibody auristatin conjugates. Abstract #2062, Proc. Am. Assoc. Can. Res. (San Francisco, CA: American Association for Cancer Res.) 2002; Mar. 43: 414-15.
Sievers EL, Larson R.A.,. Stadtmauer, E.A., Estey, E., Lowenberg, B., Dombret, H., Karanes, C., Theobald, M., Bennett, J.M., Sherman M.L. et al. Efficacy and safety of gemtuzumab ozogamicin in patients with CD33-positive acute myeloid leukemia in first relapse. 2001. J. Clin. Oncol. 19, pp. 3244-3254.

(56) References Cited

OTHER PUBLICATIONS

Sievers EL and Linenberger M. Mylotarg: antibody-targeted chemotherapy comes of age. 2001, Curr. Opin. Oncol. 13, pp. 522-527.
Smith R., Sinale chain antibody variable region fragments; www.stanford.edu/ -smithr/science/scfv.html (last updated on May 2001).
Stanley MJ, Stanley MW, Sanderson RD, Zera R. Syndecan-1 expression is induced in the stroma of infiltrating breast carcinoma. Am J Clin Pathol. Sep. 1999;112(3):377-83.
Studnicka GM, Soares S, Better M, Williams RE, Nadell R, Horwitz AH. Human-engineered monoclonal antibodies retain full specific binding activity by preserving non-CDR complementarily-modulating residues. Protein Eng. 1994: 7(6): 805-814.
Sun RC, Lu ZY, Wijdenes J, Brochier J, Hertog C, Rossi JF, Klein B. Large scale and clinical grade purification of syndecan-1 + malignant plasma cells. J Immunol Methods, Jun. 23, 1997;205(1):73-9.
Tolcher AW, Ochoa L, Hammond LA, Patnaik A, Edwards T, Takimoto C, Smith L, de Bono J, Schwartz G, Mays T, Jonak ZL, Johnson R, DeWitte M, Martino H, Audette C, Maes K, Chari RV, Lambert JM, Rowinsky EK. Cantuzumab mertansine, a maytansinoid immunoconjugate directed to the CanAg antigen: a phase I, pharmacokinetic, and biologic correlative study. J Clin Oncol. 2003;21:211-222.
Urashima M, Chen BP, Chen S, Pinkus GS, Bronson RT, Dedera DA, Hoshi Y, Teoh G, Ogata A, Treon SP, Chauhan D, Anderson KC. The development of a model for the homing of multiple myeloma cells to human bone marrow. Blood. 1997;90:754-765.
Vogel CW. Preparation of immunoconjugates using antibody oligosaccharide moieties. Methods in Molecular Biology: Bioconjugation protocols strategies and methods. 2004;283:087-108.
Vooijs WC, Post J. Wijdenes J, Schuurman HJ, Bolognesi A, Polito L, Stirpe F, Bast EJ, de Gast GC. Efficacy and toxicity of plasma-cell-reactive monoclonal antibodies B-B2 and B-B4 and their immunotoxins. Cancer Immunol Immunother. 1996,42:319-328.
Ward, E.S., D. Gussow, A.D. Griffiths, P.T. Jones, and G. Winter. Binding activities of a repertoire of single immunoglobin variable domains secreted from *Escherchia coli*. Nature. 1989. 341:544-546.
Wargalla UC, Reisfeld RA. Rate of internalization of an immunotoxin correlates with cytotoxic activity against human tumor cells. Proc. Natl. Acad. Sei. USA. 1989;86:5146-5150.
Wijdenes J, Vooijs WC, Clement C, Post J, Morard F, Vita N, Laurent P, Sun RX, Klein B, Dore JM. A plasmocyte selective monoclonal antibody (B-B4) recognizes syndecan-1. Br J Haematol. 1996;94:318-323.
Wijdenes J, Dore JM, Clement C, Vermot-Desroches C. CD138, J Biol Regul Homeost Agents. Apr.-Jun. 2002;16(2):152-5.
Wiksten JP, Lundin J, Nordling S, Lundin M, Kokkola A, von Boguslawski K, Haglund C. Epithelial and stromal syndecan-1 expression as predictor of outcome in patients with gastric cancer. Int J Cancer. Jan. 20, 2001:95(1):1-6.
Witzig TE, Kimlinger TK, Ahmann GJ. Katzman JA, Greipp PR. Detection of myeioma cells in the peripheral blood by flow cytometry. Cytometry. 1996;26:113-120.
Xie H, Audette C, Hoffee M, Lambert JM, Blättler W. Pharmacokinetics and biodistribution of the antitumor immunoconjugate, cantuzumab mertansine (huC242-DM1), and its two components in mice.J Pharmacol Exp Ther. Mar. 2004,308(3):1073-82.
Yang M, Jiang P, An Z, Baranov E, Li L, Hasegawa S, Al-Tuwaijri M, Chishima T, Shimada H, Moossa AR, Hoffman RM. Genetic-ally fluorescent melanoma bone and organ metastasis models. Clin Cancer Res 1999;5:3549-3559.
Yang M, Baranov E, Jiang P, Sun FX, Li XM, Li L, Hasegawa S, Bouvet M, Al-Tuwaijri M, Chishima T, Shimada H, Moossa AR, Penman S, Hoffman RM. Whole-body optical imaging of green fluorescent protein-expressing tumors and metastases. Proc Natl Acad Sei USA. 2000;97:1206-1211.
Tassone et al., "Cytotoxic activity of the maytansinoid immunoconjugate B-B4-DM1 against CD138+ multiple myeloma cells," Blood First Edition Paper, prepublished online Aug. 3, 2004; vol. 104, No. 12, Dec. 1, 2004, pp. 3688-3696.

Supiot et al., "Compariosn of the Biologic Effects of MA5 and B-B4 Monoclonal Antibody Labeled with Iodine-131 and Bismuth-213 on Multiple Myeloma," Cancer, vol. 94, No. 54, pp. 1202-1209.
Cavallaro et al.; "α2-macroglobulin receptor mediates binding and cytotoxicity of plant ribosome-inactivating proteins;" in Eur. J. Biochem.; vol. 232; 1995; pp. 165-171, 2002.
Casellas et al., Chapter 19, "Immunotoxin Enhancers," in Cancer Treatment and Research, William L. McGuire, series editor, Kluwer Academic Publishers, Boston/Dordrecht/Lancaster, vol. 37, 1988, pp. 351-369.
Thrush et al., "Immunotoxins: An Update," in Ann. Rev. Immunol., vol. 14, 1996, pp. 49-71.
Shih et al., "Internalization and Intracellular Processing of an Anti-B-Cell Lymphoma Monoclonal Antibody, LL2," in Int. J. Cancer, vol. 56, 1994, pp. 538-545.
Austin et al., "Oxidizing Potential of Endosomes and Lysosornes Limits Intracellular Cleavage of Disulfide-Based Antibody-Drug Conjugates," in PNAS, vol. 102(50), Dec. 13, 2005, pp. 17987-17992.
Chari, "Targeted Delivery of Chemotherapeutics: Tumor-Activated Prodrug Therapy," in Advanced Drug Delivery Reviews, vol. 31, 1998, pp. 89-104.
Goldmacher et al., "Cytotoxicity of Gelonin and Its Conjugates With Antibodies Is Deteremined by the Extent of Their Endocytosis," in Journal of Cellular Physiology, vol. 141, 1989, pp. 222-234.
Sharkey Robert M et al: "Targeted therapy of Cancer: new prospects for antibodies and immunoconjugates." in CA: A Cancer Journal For Clinicians Jul.-Aug. 2006, vol. 56, No. 4, Jul. 2006, pp. 226-243.
Turner et al.. "1311-Anti CD20 radioimmunotherapy of relapsed or refractory non-Hodgkins lymphoma: a phase II clim'cal trial of a nonmyeloablative dose regimen of chimeric rituximab radiolabeled in a hospital," in Cancer Biotherapy & Radiopharmaceuticals Aug. 2003, vol. 18, No. 4, Aug. 2003, pp. 513-524.
Israel et al.: "Plasmapheresis and immunological control of cancer," in Lancet Sep. 18, 1976, vol. 2, No. 7986, Sep. 18, 1976, pp. 642-643.
Cortesini: "Pancreas cancer and the role of soluble immunoglobulin-like transcript 3 (ILT3)," in JOP: Journal of the Pancreas 2007, vol. 8. No. 6, Nov. 1, 2007, pp. 697-703.
Tassone et al., "In vitro and in vivo activity of the maytansinoid immunoconiugate huN901-N2'-Deacetyl-N2'-(3-Mercapto-1-Oxopropyl)-Maytansine against CD56+ Multiple Myeloma Cells," Cancer Research, vol. 64, Jul. 1, 2004, pp. 4629-4636.
Tassone et al, Blood, Nov. 16, 2003, vol. 102, 45th ASH meeting abstract 449s-450a (abstract).
Tassone et al., Proc Amer Assoc Cancer Res vol. 45, abstract #1425, Mar. 2004, abstract.
Aalberse et al., "The Apparent Monovalency of Human IgG4 is Due to Bispecificity," in Int Arch Allergy Immunol, vol. 118, 1999, pp. 187-189.
Akkina RK, Rosenblatt JD, Campbell AG, Chen IS, Zack JA. Modeling human lymphoid precursor cell gene therapy in the SCID-hu mouse. Blood. 1994;84:1393-1398.
Anttonen A, Heikkila P, Kajanti M, Jalkanen M, Joensuu H. High syndecan-1 expression is associated with favourable outcome in squamous cell lung carcinoma treated with radical surgery. Lung Cancer. Jun. 2001; 32(3):297-305.
Barbareschi M, Maisonneuve P, Aldovini D, Cangi MG, Pecciarini L, Angelo Mauri F, Veronese S, Caffo 0, Lucenti A, Palma PD, Galligioni L, Dogiloni C. High syndecan-1 expression in breast carcinoma is related to an aggressive phenotype and to poorer prognosis. Cancer. Aug. 1, 2003 ;98(3):474-83.
Bernfield M, Kokenyesi R, Kato M, Hinkes MT, Spring J, Gallo RI, Lose EJ. Biology of the syndecans: a family of transmembrane heparan sulfate proteoglycans. Annu Rev Cell Biol. 1992;8:365-393.
Beste G, Schmidt FS, Stibora T, Skerra A. Small antibody-like proteins with prescribed ligand specificities derived from the lipocalin fold. Proc. Natl. Acad. Sci. USA. 1999: 96, 1898-1903.
Bhattacharyya B, Wolff J. Maytansine binding to the vinblastine sites of tubulin. FEBS Lett. 1977;75:159-162.

(56) References Cited

OTHER PUBLICATIONS

Blaettler WA and Chari RVJ. Drugs to Enhance the Therapeutic Potency of Anticancer Antibodies: Antibody-Drug Conjugates as Tumor-Activated Prodrugs. In: Ojima, I., Vite, G.D. And Altmann, K.-H., Editors, 2001. Anticancer Agents—Frontiers in Cancer Chemotherapy, American Chemical Society, Washington, DC, pp. 317-338.

Bross PF, Reitz J, Chen G, Chen XH, Duffy E, Kieffer L, Roy S, Sridhara R, Rahman A, Williams G, Pazdur R. Approval summary: gemtuzumab ozogamicin in relapsed acute myeloid leukemia. Clin Cancer Res. 2001 ;7:1490-1496.

Carbone A, Gaidano G, Gloghini A, Ferlito A, Rinaldo A, Stein H. AIDS-related plasma-blastic lymphomas of the oral cavity and jaws: a diagnostic dilemma.Ann. Otol. Rhinol. Laryngol. 1999; 108: 95-99.

Carbone A et al. Reed-Sternberg cells of classical Hodgkin's disease react with the plasma cell-specific monoclonal antibody B-B4 and express human syndecan-1. Blood. 1997; 89:3787-94.

Carter P., "Improving the efficacy of antibody-based Cancer therapies," Nat Rev Cancer, 2001, 1, pp. 118-129.

Chari RV, Martell BA, Gross JL, Cook SB, Shah SA, Blättler WW, McKenzie SJ, Goldmtacher VS. Immunoconjugates containing novel maytanisnoids: promising anticancer drugs. Cancer Res. 1992;52:127-131.

Chari RV, Jackel KA, Bourret LA, Derr SM, Tadayoni BM, Mattocks KM, Shah SA, Liu C, Blattler WA and Goldmacher VS. Enhancement of the selectivity and antitumor efficacy of a CC-1065 analogue through immunoconjugate formation. Cancer Res. 1995; 55: 4079-4084.

Charnaux N, Brule S, Chaigneau T, Saffar L, Sutton A, Hamon M, Prost C, Lievre N, Vita C, Gattegno L. RANTES (CCL5) induces a CCCR5-dependent accelerated shedding of syndecan-1 (Cd138) and syndecan-4 from HeLa cells and forms complexes with the shed ectodomains of these proteoglycans as well as with those of CD44. Glycobiology. 2005 5(2):119-130 (Sep. 8, 2004).

Chen BP, Galy A, Kyoizumi S, Namikawa R, Scarborough J, Webb S, Ford B, Cen DZ, Chen SC. Engraftment of human hematopoietic precursor cells with secondary transfer potential in SCID-hu mice. Blood. 1994;84:2497-2505.

Chilosi M, Adami F, Lestani M, Montagna L, Cimarosto L, Semenzato G, Pizzolo G, Menestrina F. CD138/syndecan-1: a useful immunohistochemical marker of normal and neoplastic plasma cells on routine trephine bone marrow biopsies. Mod Pathol 1999;12:1101-1106.

Clement C, Vooijs, W.C., Klein, B., and Wijdenes, J. B-B2 and B-B4: two new mAb against secreting plasma cells. In: al. SFSe, ed. J. Leukocyte Typing V. Oxford: Oxford University Press; 1995:714-715.

Couturier O, Faivre-Chauvet A ; Filippovich IV; Thedrez P, Sai'-Maurel C: Bardies M: Mishra AK; Gauvrit M; Blain G; Apostolidis C; Molinet R; Abbe JC, Bateille R; Wijdenes J, Chatal JF; Cherel M; Validation of 213Bi-alpha radioimmunotherapy for multiple myeloma. Clinical Cancer Research 5(10 Suppl.) (Oct. 1999) 3165s-3170s.

Davies EJ et al., Blackhall FH, Shanks JH, David G, McGown AT, Swindell R, Slade RJ, Martin-Hirsch P, Gallagher JT, Jayson GC. Distribution and Clinical Significance of Heparan Sulfate Proteoglycans in Ovarian Cancer Clin Cancer Res. 2004: 10(15):5178-86.

Dhodapkar KM, Krasovsky J, Williamson B, Dhodapkar MV. Antitumor monoclonal abs enhance cross-presentation of Cellular antigens and the generation of myeloma-specific killer T cells by dendritic cells. J Exp Med. Jan. 7, 2002;195(1 ):125-33.

Dhodapkar MV, Krasovsky J, Olson K. T cells from the tumor microenvironment of patients with progressive myeloma can generate strong, tumor-specific cytolytic responses to autologous, tumor-loaded dendritic cells. Proc Nati Acac Sei USA. Oct. 1, 2002;99(20):13009-13. Epub Sep. 16, 2002.

Dhodapkar MV, Abe E, Theus A, Lacy M, Langford JK, Barlogie B, Sanderson RD. Syndecan-1 is a multifunctional regulator of myeloma pathobiology: control of tumor cell survival, growth, and bone cell differentiation. Blood. 1998;91:2679-2688.

Dore JM, Morard F, Vita N, Wijderies J. Identification and location on syndecan-1 core protein of the epitopes of B-B2 and B-B4 monoclonal antibodies. FEBS Lett. 1998:426:67-70.

Dowell JA, Korth-Bradley J, Liu H, King SP, Berger MS. Pharmacokinetics of gemtuzumab ozogamicin, an antibody-targeted chemotherapy agent for the treatment of patients with acute myeloid leukemia in first relapse. J Clin Pharmacol. 2001;41:1206-1214.

Edinger M, Sweeney TJ, Tucker AA, Olomu AB, Negrin RS, Contag, CH. Noninvasive assessment of tumor cell proliferation in animal models. Neoplasia 1999;1:303-310.

Gattei V, Godeas C, Degan M, Rossi FM, Aldinucci B, Pinto A. Characterization of Anti-CD138 monoclonal antibodies as tools for investigating the molecular polymorphism of syndecan-1 in human lymphoma cells. Br J Haematol. 1999;104;152-162.

Hamann PP, Hinman LM, Beyer CF, Lindh D, Upeslacis J, Flowers DA, Bernstein I. An anti-CD33 antibody-calicheamicin conjugate for treatment of acute myeloid leukemia. Choice of linker. Bioconjug Chem. 2002;13:40-46.

Han I, Park H, Oh ES. New insights into syndecan-2 expression and tumourigenic activity in colon carcinoma cells. J Mol Histol. 2004: 35(3):319-26.

Horvathova M, Gaillard, J.-P., Liutard, J., Duperray, C., Lavabre-Bertrand T., Bourquard, P. et al. In: al. SFSe, ed. Leucocyte Typing V. Oxford: Oxford University Press; 1995:713-714.

Jokimaa V, Inki P, Kujari H, Hirvonen O, Ekholm E, Anttila L. Expression of syndecan-1 in human placenta and decidua . . . Placenta. Mar.-Apr. 1998;19(2-3):157-63.

Jokimaa VI, Kujan HP, Ekholm EM, Inki PL, Anttila L. Placental expression of syndecan 1 is diminished in preeclampsia. Am J Obstet Gynecol. Dec. 2000;183(6):1495-8.

Krebs B, Rauchenberger R, Reiffert S, Rothe C, Tesar M, Thomassen E, Cao M, Dreier T, Fischer D, Hoss A et al. High-throughput generation and engineering of recombinant human antibodies. 2001. J. Immunol. Methods 254, pp. 67-84.

Kupchan SM, Sneden AT, Branfman AR, Howie GA, Rebhun LI, Molvor WE, Wang RW, Schnaitman TC. Structural requirements for antileukemic activity among the naturally occurring and semisynthetic maytansinoids. J Med Chem. 1978;21:31-37.

Kyoizumi S, Baum CM, Kaneshima H, McCune JM, Yee EJ, Namikawa R. Implantation and maintenance of functional human bone marrow in SCID-hu mice. Blood. 1992,79:1704-1711.

Kyoizumi S, Murray LJ, Namikawa R. Preclinical analysis of cytokine therapy in the SCID-hu mouse. Blood. 1993;81: 1479-1488.

Liu C, Tadayoni BM, Bourret LA, Mattocks KM, Derr SM, Widdison WC, Kedersha NL, Ariniello PD, Goldmacher VS, Lambert JM, Blättler WA, Chari RV. Eradication of large colon tumor xenografts by targeted delivery of maytansinoids. Proc Natl Acad Sei USA. 1996;93:8618-8623.

McCune JM, Namikawa R, Kaneshima H, Shultz LD, Lieberman M, Weissman IL. The SCID-hu mouse: murine model for the analysis of human hematolymphoid differentiation and function. Science. 1988;241:1632-1639.

Mennerich D, Vogel A, Klarnan I, Dahl E, Lichtner RB, Rosenthal A, Pohlenz HD, Thierauch KH, Sommer A. Shift of syndecan-1 expression from epithelial to stromal cells during progression of solid tumours. Eur J Cancer, Jun. 2004; 40(9):1373-82.

Mosmann T. Rapid colorimetric assay for cellular growth and survival: application to Proliferation and cytotoxicity assays. J Immunol Methods. 1983;65:55-63.

Mukunyadzi P, Sanderson RD, Fan CY, Smoller BR. The level of syndecan-1 expression is a distinguishing feature in behavior between keratoacanthoma and invasive cutaneous squamous cell carcinoma. Mod Pathol. Jan. 2002;15(1):45-9.

Namikawa R, Ueda R, Kyoizumi S. Growth of human myeloid leukemias in the human narrow environment of SCID-hu mice. Blood. Oct. 15, 1993;82 (8)1526-36.

(56) References Cited

OTHER PUBLICATIONS

O'Connell FP, Pinkus JL, Pinkus GS. CD138 (Syndecan-1), a Plasma Cell Marker Immunohistochemical Profile in Hematopoietic and Nonhematopoietic Neoplasms. Am J Clin Pathol 2004; 121:254-263.

Ojima I, Gong X, Wu X, Qu C, Borella CP, Xie H, Wilhelm SD, Leece BA, Bartle LM, Goldmacher VS and Chari RV. Tumor-specific novel taxoid-monoclonal antibody conjugates. 2002. J. Med. Chem. 45, pp. 5620-5623.

Olafsen, T, Cheung, CC, Yazaki, PJ, Li L, Sundaresan G, Garnbhir SS, Sherman, MA, Williams, LE, Shively, JE, Raubitschek, AA, and Wu, AM. Covalent disulfide-linked anti-CEA diabody allows site-specific conjugation and radiolabeling for tumor targeting applications. 2004; Prot. Eng. Design & Selection 17:1: 21-27.

Orosz Z, Kopper L. Syndecan-1 expression in different soft tissue tumours. Anticancer Res. 2001: 21(1 B):733-7.

Padian, EA. A possible procedure for reducing the immunogenicity of antibody variable domains while preserving their ligand-binding properties. Mol. Immunol. 1991; 28: 489-98.

Palacios M, Perez MA, Scolnik MD. B-84 monoclonal antibody and identification of human bone arrow plasma cells (including response) Br J Haematol. 1997;96:654-657.

Payne G. Progress in immunoconjugate cancer therapeutics. Cancer Cell. 2003;3:207-212.

Pegram MD, Lipton A, Hayes DF, Weber BL, Baselga JM, Tripathy D, Baty D, Baughman SA, Twaddell T, Glaspy JA and Slamon DJ. Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. 1998. J. Clin. Oncol. 16, pp. 2659-2671.

Post J, Vooijs WC, Bast BJ, De Gast GC. Efficacy of an anti-CD138 immunotoxin and doxorubicin on drug-resistant and drug-sensitive myeloma cell. Int J Cancer. Nov. 12, 1999;83(4):571-6.

Chanan-Khan et al., "Phase I study of BT062 given as repeated single dose once every 3 weeks in patients with relapsed or relapsed/refractory multiple myeloma", Blood, vol. 114, issue 2, p. 1862 (2009).

Zuber Chantal et al: "BT062, aCD138-Specific Immunoconjugate, Demonstrates Superior In Vivo Anti-Myeloma Efficacy in Combination with Lenalidomideor Bortezomib", XP002693090,Database accession No. PREV2O11OO425551 abstract & Blo0d, vol. 115, No. 21, Nov. 2010 (Nov. 2010),pp. 1239-1240.

Jagannath Sundar et al: "BT062, An Antibody-Drug Conjugate Directed Against CD138, Shows Clinical Activity in a Phase I Study in Patients with Relapsed or Relapsed/Refractory Multiple Myeloma", XP002693088, Database accession No. PREV201100425603 abstract & Blood, vol. 115, No. 21, Nov. 2010 (Nov. 2010), p. 1252.

Jagannath Sundar et al: "BT062, An Antibody-Drug Conjugate Directed Against CD138, Shows Clinical Activity in Patients with Relapsed or Relapsed/Refractory Multiple Myeloma", XP0O2693087, Database accession No. PREV201200217590 abstract & Blood, vol. 118, No. 21, Nov. 2011 (Nov. 2011), pp. 142-143.

Zuber C et al: "226 High in vivo anti-tumor activity of the immunoconjugate BT-062 against CD138 positive solid tumors", European Journal of Cancer. Supplement, Pergamon, Oxford, GB, Nov. 2010 (Nov. 2010), p. 74.

Erickson et al., "Antibody-Maytansinoid Conjugates Are Activated in Targeted Cancer Cells by Lysosomal Degradation and Linker-Dependent Intracellular Processing", Cancer Research, 2006, vol. 66, No. 8, pp. 4426-4433.

* cited by examiner

FIG. 1
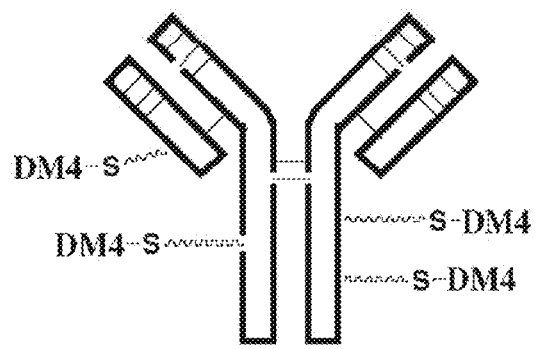
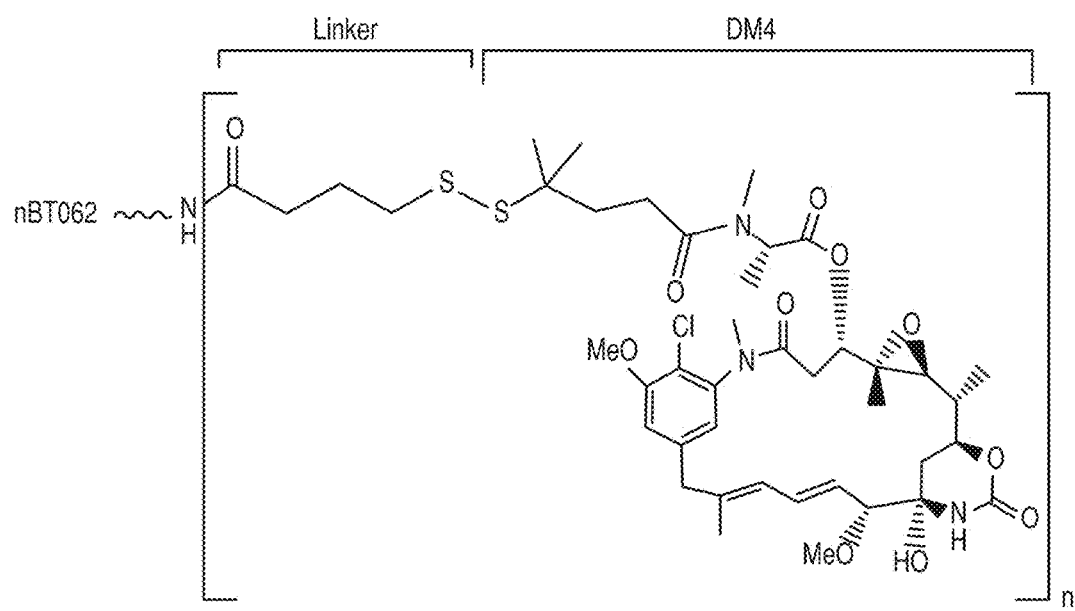
*n is approximately 3.5 drug linked per antibody molecule
FIG. 2

DCC: 1,3-dicyclohexylcarbodiimide
DTT: Dithiothreitol
DME: 1,2-Dimethoxyethane

Xenograft model: Mammary carcinoma:
Complete remission in all BT-062 treated mice

SEQUENCE LISTING

<160> NUMBER OF SEQ ID NOS: 13

<210> SEQ ID NO 1
<211> LENGTH: 448
<212> TYPE: PRT
<213> ORGANISM: Artificial Sequence
<220> FEATURE:
<223> OTHER INFORMATION: Amino Acid sequence (predicted) of heavy
      chain of chimeric human/mouse antibody
<220> FEATURE:
<221> NAME/KEY: CDR1
<222> LOCATION: (31)..(35)
<220> FEATURE:
<221> NAME/KEY: CDR2
<222> LOCATION: (51)..(68)
<220> FEATURE:
<221> NAME/KEY: CDR3
<222> LOCATION: (99)..(111)

<400> SEQUENCE: 1

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Thr Gly Arg Thr Ile Tyr Asn Glu Lys Phe
50                  55                  60

Lys Gly Lys Ala Thr Phe Thr Ala Asp Ile Ser Ser Asn Thr Val Gln
65                  70                  75                  80

Met Gln Leu Ser Ser Leu Thr Ser Glu Asp Ser Ala Val Tyr Tyr Cys
                85                  90                  95

Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

```
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Amino Acid sequence (predicted) of light
      chain of chimeric human/mouse antibody
<220> FEATURE:
<221> NAME/KEY: CDR1
<222> LOCATION: (24)..(34)
<220> FEATURE:
<221> NAME/KEY: CDR2
<222> LOCATION: (50)..(56)
<220> FEATURE:
<221> NAME/KEY: CDR3
<222> LOCATION: (89)..(97)

<400> SEQUENCE: 2

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
                20                  25                  30

Leu Asn Trp Tyr Gln Gln Lys Pro Asp Gly Thr Val Glu Leu Leu Ile
            35                  40                  45

Tyr Tyr Thr Ser Thr Leu Gln Ser Gly Val Pro Ser Arg Phe Ser Gly
        50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 31
<212> TYPE: DNA
<213> ORGANISM: Artificial Sequence
<220> FEATURE:
<223> OTHER INFORMATION: IgH primer MHV7

<400> SEQUENCE: 3
atgggcatca agatggagtc acagacccag g                              31

<210> SEQ ID NO 4
<211> LENGTH: 21
<212> TYPE: DNA
<213> ORGANISM: Artificial Sequence
<220> FEATURE:
<223> OTHER INFORMATION: IgG1 constant region primer MHCG1

<400> SEQUENCE: 4
cagtggatag acagatgggg g                                         21

<210> SEQ ID NO 5
<211> LENGTH: 30
<212> TYPE: DNA
<213> ORGANISM: Artificial Sequence
<220> FEATURE:
<223> OTHER INFORMATION: Ig kappa primer MKV2

<400> SEQUENCE: 5
atggagacag acacactcct gctatgggtg                                30

<210> SEQ ID NO 6
<211> LENGTH: 33
<212> TYPE: DNA
<213> ORGANISM: Artificial Sequence
<220> FEATURE:
<223> OTHER INFORMATION: Ig kappa primer MKV4

<400> SEQUENCE: 6
atgagggccc ctgctcagtt ttttggcttc ttg                            33

<210> SEQ ID NO 7
<211> LENGTH: 25
<212> TYPE: DNA
<213> ORGANISM: Artificial Sequence
<220> FEATURE:
<223> OTHER INFORMATION: Ig kappa primer MKV9

<400> SEQUENCE: 7
atggtatcca cacctcagtt ccttg                                     25

<210> SEQ ID NO 8
<211> LENGTH: 20
<212> TYPE: DNA
<213> ORGANISM: Artificial Sequence
<220> FEATURE:
<223> OTHER INFORMATION: primer MKC

<400> SEQUENCE: 8
```

```
actggatggt gggaagatgg                                              20

<210> SEQ ID NO 9
<211> LENGTH: 50
<212> TYPE: DNA
<213> ORGANISM: Artificial Sequence
<220> FEATURE:
<223> OTHER INFORMATION: forward (For) primer

<400> SEQUENCE: 9
agagaagctt gccgccacca tgattgcctc tgctcagttc cttggtctcc             50

<210> SEQ ID NO 10
<211> LENGTH: 35
<212> TYPE: DNA
<213> ORGANISM: Artificial Sequence
<220> FEATURE:
<223> OTHER INFORMATION: oligonucleotide primer BT03

<400> SEQUENCE: 10
caacagtata gtaagctccc tcggacgttc ggtgg                             35

<210> SEQ ID NO 11
<211> LENGTH: 35
<212> TYPE: DNA
<213> ORGANISM: Artificial Sequence
<220> FEATURE:
<223> OTHER INFORMATION: oligonucleotide primer BT04

<400> SEQUENCE: 11
ccaccgaacg tccgagggag cttactatac tgttg                             35

<210> SEQ ID NO 12
<211> LENGTH: 41
<212> TYPE: DNA
<213> ORGANISM: Artificial Sequence
<220> FEATURE:
<223> OTHER INFORMATION: primer g2258

<400> SEQUENCE: 12
cgcgggatcc actcacgttt gatttccagc ttggtgcctc c                      41

<210> SEQ ID NO 13
<211> LENGTH: 45
<212> TYPE: DNA
<213> ORGANISM: Artificial Sequence
<220> FEATURE:
<223> OTHER INFORMATION: Primer g22949

<400> SEQUENCE: 13
cgatgggccc ttggtggagg ctgaggagac ggtgactgag gttcc                  45
```

USES OF IMMUNOCONJUGATES TARGETING CD138

FIELD OF THE INVENTION

The present invention relates to methods and treatment regimens, in particular for human subjects, which include the administration of immunoconjugates that are designed to target cells that express CD138. The present invention is also directed at anticancer combinations, pharmaceutical compositions comprising the same, and uses thereof in the treatment of cancers that have target cells that express CD138. The present invention is in particular directed at anticancer combinations that show synergy or unexpected additive effects in the treatment relative to treatments involving less than all of the components of the combination.

BACKGROUND

CD138, which acts as a receptor for the extracellular matrix, is overexpressed on multiple myeloma (MM) cells and has been shown to influence MM cell development and/or proliferation. CD138 is also expressed on cells of ovarian carcinoma, cervical cancer (Numa et al., 2002), endometrial cancer (Choi et al., 2007), kidney carcinoma, gall bladder, transitional cell bladder carcinoma, gastric cancer (Wiksten et al. 2008), prostate adenocarcinoma (Zellweger et al., 2003), mammary carcinoma (Loussouarn et al., 2008), non small cell lung carcinoma (Shah et al., 2004), squamous cell lung carcinoma (Toyoshima et al., 2001), colon carcinoma cells and cells of Hodgkin's and non-Hodgkin's lymphomas, colorectal carcinoma (Hashimoto et al., 2008), hepato-carcinoma (Li et al., 2005), chronic lymphocytic leukemia (CLL), pancreatic (Conejo et al., 2000), and head and neck carcinoma (Anttonen et al., 1999) to name just a few.

The publications and other materials, including patents, used herein to illustrate the invention and, in particular, to provide additional details respecting the practice are incorporated herein by reference. For convenience, the publications are referenced in the following text by author and date and/or are listed alphabetically by author in the appended bibliography.

Tassone et al. (2004) reported excellent binding of the murine IgG1 antibody B-B4 to the CD138 antigen expressed on the surface of MM cells. Tassone also reported high cytotoxic activity of the immunoconjugate B-B4-DM1, which comprises the maytansinoid DM1 as an effector molecule, against multiple myeloma cells (see also US Patent Publ. 20070183971).

Ikeda et al. (2008 and 2009) reported promising in vitro results and results in xenograft models with the immunoconjugate BT062, which is based on B-B4.

While Tassone et al. and Ikeda et al. represent contributions to providing an effective treatment of MM and a composition of matter that may be employed in such a treatment, there remain a number of needs in the art.

While the use of immunoconjugates, in particular those which have highly toxic effector molecules which are functionally attached to a targeting agent that binds to, e.g., antigens that are not only expressed on target cells, such as tumor cells, but also on non-target cells which perform vital functions in the organism, have been shown to be effective in destroying the target cells, many failed due to their toxicity towards non-target cells. In fact, many immunoconjugates have to be discontinued during clinical trials because a balance between effectiveness and toxicity (therapeutic window) could not be found: at concentrations at which the immunoconjugate can confer benefits in terms of combating disease, its toxicity becomes unacceptable. Thus, especially with highly toxic effector molecules, the question often is not only whether the targeting agent of the immunoconjugate can in fact, bring the effector to the target and allow the effector to be released at the target, but also if, on its way to the target cells, the same immunoconjugate will destroy or attack an unacceptable number of cells or organs that are pivotal to the survival of the organism.

US Patent Publication 20110123554 discloses methods and treatment regimens that include the administration of immunoconjugates targeting CD138 to combat diseases, in particular in tolerable amounts. However, while these results showed that the immunoconjugate could be effective, while being tolerable, there is a need for further improved treatment regimens.

There remains in particular a need to provide suitable treatment regimens for diseases associated with CD138 expression, including plasmaproliferative disorders associated with CD138 expression, such as MM. There, more in particular, remains a need for treatment regimens that ensure that toxicities towards non tumor cells, which also express CD138 are kept to a clinically acceptable level, either by employing only certain tolerable amounts of immunoconjugate at levels that balance toxicities with effectiveness to combat diseases and/or by combining the immunoconjugate with cytotoxic agents known to be effective against the disorder in question. There is also a need for treatment regimens that reduce the need for medications that are used to alleviate other symptoms of the disease and for maintenance therapy to maintain a patient's health in a disease-free or limited-disease state after a certain grade of disease control was achieved with the most recent prior treatment.

This invention fulfills, in certain embodiments, one or more of these needs as well as other needs in the art which will become more apparent to the skilled artisan once given the following disclosure.

SUMMARY OF THE INVENTION

The invention is directed at a method for treating a disease associated with target cells expressing CD138, comprising:
administering to a patient in need thereof a pharmaceutical composition an immunoconjugate and a pharmaceutically acceptable carrier at least once a week for at least three weeks, wherein each three week period is optionally followed by a resting period, wherein the immunoconjugate comprises
at least one targeting agent targeting CD138 expressing cells, and
at least one effector molecule, wherein said targeting agent is functionally attached to said effector molecule to form said immunoconjugate, and wherein the dose of the immunoconjugate administered at least once a week is about 20 mg/m$^2$ to about 280 mg/m$^2$, e.g. once a week at a dose from about 40 mg/m$^2$ to about 140 mg/m$^2$, and the pharmaceutical composition is administered for at least three weeks alone or in combination with a cytotoxic agent.

The invention is also directed at a method for treating a disease associated with target cells expressing CD138 comprising:
administering to a subject, in particular a human subject, in need thereof an immunoconjugate comprising
at least one engineered targeting antibody targeting CD138 expressing cells, and at least one effector molecule, wherein said engineered targeting antibody is functionally attached to said effector molecule to form said immunoconjugate, wherein preferably at least a part of the engineered targeting antibody confers IgG4 isotype properties, wherein the immunoconjugate is administered in a multiple dose regimen comprising at least two doses, wherein the aggregate dose administered within an active treatment cycle, such as an active treatment cycle comprising 21 days, is an aggregate maximum tolerable dose (AMTD) or a fraction of the AMTD and wherein said AMTD and/or said fraction exceeds the dose resulting in dose limiting toxicity (DLT) when the immunoconjugate is administered once, preferably on day 1, within said active treatment cycle and/or exceeds the maximum tolerable dose (MTD) when the immunoconjugate is administered as a single dose, including a repeated single dose.

The AMTD may exceed the dose of said DLT by at least 20% and said MTD by at least 30%. The AMTD may be at least 240 mg/m$^2$, preferably 300 mg/m$^2$, more preferably 360 mg/m$^2$ or 420 mg/m$^2$ and the dose resulting in said DLT may be 180 mg/m$^2$ or 200 mg/m$^2$. The AMTD may be at least 240 mg/m$^2$, preferably 300 mg/m$^2$, more preferably 360 mg/m$^2$ or 420 mg/m$^2$ and said MTD may be at least 160 mg/m$^2$ or at least 180 mg/m$^2$.

The immunoconjugate may be administered at least three times within 21 days, preferably in equal doses.

Said multiple dose regimen may last 3 weeks and may be followed by a resting period. During this resting period progression free survival or stable disease may be maintained. A level of immunoconjugate in a body fluid of a subject, during said resting period may be at least or up to 0.5 µg/ml, 1 µg/ml or 2 µg/ml, 3 µg/ml, 4 µg/ml, 5 µg/ml or 6 µg/ml.

The "receptor occupancy" of target cells expressing CD138, in particular isolated target cells expressing CD138, preferably in target cells isolated from non-solid tumors, such as myleloma cells in bone marrow aspirates, e.g., within 24 hours, preferably within eighteen, twelf, eight or four hours after completition of administration of an immunconjugate according to the present invention is, in one embodiment, more than 60%, more than 70%, more than 75%, more than 80%, more than 85%, more than 90% or more than 95%. The "receptor occupancy" of target cells expressing CD138 prior to a subsequent administration or, respectively, more than 48 hours, more than 72 hours, more than 96 hours (4 days), more than 120 hours (5 days) or more than 144 hours (6 days) after completition of administration is less than 70%, less than 60%, less then 55%, less than 50%, less than 45% or less than 40%.

In one embodiment, the difference in "receptor occupancy" of target cells expressing CD138 twentyfour, eighteen, twelf, eight or four hours after completition of administration of the immunoconjugate and the "receptor occupancy" of said target cells more than 48 hours, more than 72 hours, more than 96 hours (4 days), more than 120 hours (5 days) or more than 144 hours (6 days) after completition of administration, is at least 5%, at least, 10%, at least 15%, at least 20%, at least 25%, at least 30%, at least 35%, at least 40%, at least 45% or at least 50%, preferably between 10% and 50% or 20% and 40%.

In a further embodiment, the "receptor occupancy" of target cells expressing CD138 24 hours, preferably within eighteen, twelf, eight or four hours after completition of administration of the immunoconjugate is high, that is, more than 60%, more than 70%, more than 75%, more than 80%, more than 85%, more than 90% or more than 95%, even when the immunoconjugate is administered at realitvely low concentrations, e.g., at concentrations that constitute less than 50%, less than 60%, less than 70%, less than 80%, but generally more than 10%, more than 20% or more an 30% of the determined DLT of the immunoconjugate when administered once in a 21 day treatment cycle. In yet a further embodiment, the "receptor occupancy" of target cells expressing CD138 prior to a subsequent administration or, respectively, more than 48 hours, more than 72 hours, more than 96 hours (4 days), more than 120 hours (5 days) or more than 144 hours (6 days) after completion of administration is less than 70%, less than 60%, less then 55%, less than 50%, less than 45% or less than 40%, even when the immunoconjugate is administered at realitvely high concentrations, e.g., at concentrations that constitute more than 50%, more than 60%, more than 70%, more than 80% of the determined DLT of the immunoconjugate when administered once in a 21 day treatment cycle.

The invention is also directed at administering a total amount of maytansinoid, in particular DM4 to a patient within 21 days of more than 2 mg/m$^2$, more than 3 mg/m$^2$, more than 4 mg/m$^2$, more than 5 mg/m$^2$, more than 6 mg/m$^2$, more than 7 mg/m$^2$, more than 8 mg/m$^2$, more than 9 mg/m$^2$ or more than 10 mg/m$^2$ preferably in accordance to any one of the methods referred to herein.

The administering may be performed at least once a week, at preferably equal doses for at least three weeks followed preferably by a resting period of, e.g., one week. "Resting period" means in this context a period after a point in time, at which, according to the treatment schedule established for a patient, the next dose should, but was not, administered. For example, in an administration scheme that involves weekly administrations on days 1, 8 and 15, the resting period defines the time after day 22, when there was no administration. In this example, this resting period result in a treatment free interval of two weeks. The at least three weeks followed by the resting period may define a treatment cycle of at least 28 days, and wherein, after two or more treatment cycles, at least stable disease may be achieved. The immunoconjugate may, e.g., be administered every 3$^{rd}$ day, every 4$^{th}$ day, every 5$^{th}$ day or every 6$^{th}$ day during said three weeks period. At least stable disease may be maintained during three, four, five, six, seven treatment cycles. After reaching at least stable disease, the immunoconjugate may be administered as a maintenance therapy less than three times or less than twice within said 21 days, preferably once in said 21 days, preferably as a repeated single dose of between 60 mg/m$^2$ and 200 mg/m$^2$, including about 70 mg/m$^2$, about 80 mg/m$^2$, about 90 mg/m$^2$, about 100 mg/m$^2$, about 110 mg/m$^2$, about 120 mg/m$^2$, about 130 mg/m$^2$, about 140 mg/m$^2$, 150 mg/m$^2$, about 160 mg/m$^2$, about 170 mg/m$^2$, about 180 mg/m$^2$, about 190 mg/m$^2$ and about 200 mg/m$^2$. At least progression free survival, stable disease and or a minor response may be obtained for more than 3 months during a maintenance therapy.

Administration of said immunoconjugate as a repeated multiple dose in treatment cycles lasting at least 21 days may result, after the last administration in each cycle, in an aggregate effective amount and a first level of the immunoconjugate in a body fluid of the subject and wherein, when an amount equivalent to said aggregate effective amount is administered as a single dose or repeated single dose in said treatment cycle, it may result in a second level of the immunoconjugate in a body fluid of said subject, wherein the first level may be equal or below the second level, e.g. more than 10%, more than 20% or more than 30% below the second level.

The treatment cycle may last 21 days and/or the repeated multiple dose may consist of 3 equal, preferably equidistant doses, more preferably administered on days 1, 8 and 15. The aggregate effective amount may be more than/up to 200 mg/m$^2$, about 220 mg/m$^2$, about 240 mg/m$^2$, about 260 mg/m$^2$, about 280 mg/m$^2$, about 300 mg/m$^2$, about 360 mg/m$^2$ or about 420 mg/m$^2$.

The immunoconjugate or pharmaceutical composition may be administered for at least two 21 day treatments cycles with a one week resting period between each treatment cycle. An administration may be followed, after at least two 21 day treatment cycles, each optionally followed by a resting period and/or by a further administration of the immunoconjugate or pharmaceutical composition as a maintenance therapy. The maintenance therapy may comprise administering the immunoconjugate or a pharmaceutical composition comprising the same (i) once every three to six weeks or (ii) at repeated multiple doses, wherein each individual dose of immunoconjugate is about 10 mg/m$^2$, about 20 mg/m$^2$, about 30 mg/m$^2$, about 40 mg/m$^2$, about 50 mg/m$^2$, about 60 mg/m$^2$, 70 mg/m$^2$, about 80 mg/m$^2$, about 90 mg/m$^2$, about 100 mg/m$^2$, about 110 mg/m$^2$ or about 120 mg/m$^2$ lower than the individual dose of a primary therapy and/or wherein individual doses may be administered in intervals exceeding the interval of the individual doses, e.g., by 1, 2, 3, 4, 5, 6, 7 days. Any administration of said immunoconjugate as a multiple dose regime may result, 0-2 hours after completion of administration, in a mean plasma level of at least 7 µg/ml, 8, 9, 10, 11, 12, 13, 14, 15, 16, 17, 18, 19, 20, 21, 22, 23, 24, 25, 26, 27, 28, 29, 30, 40, 50, 60, 70, 80, 90 or 100 µg/ml.

The methods of the invention may further include, determining 0-4 hours, including at about 1, 2, 3 or 4 hours, following an completion of administering said immunoconjugate or a pharmaceutical composition comprising the same, a reference level of an said immunoconjugate or of an efficacy blood parameter in a body fluid of a patient and determining in a subsequent administration of said immunoconjugate, at 0-4 hours following an completion of said subsequent administration, a subsequent level of said immunoconjugate or efficacy blood parameter, wherein, when the reference level is higher than the subsequent level, the aggregate dose in a treatment cycle following said subsequent administration may be increased by 5-100%, including 10-50% or 20-30% and/or when the reference level is lower than the subsequent level, the aggregate dose in a treatment cycle following said subsequent administration may be lowered by 5-100%, including 10-50% or 20-30%.

The methods of the present invention may also further comprise determining, 0-2 hours following an completion of administering an individual dose of said immunoconjugate or a pharmaceutical composition comprising the same, a level of said immunoconjugate in a body fluid, wherein, if said level is below 7 µg/ml, 8, 9, 10, 11, 12, 13, 14, 15, 16, 17, 18, 19, 20 µg/ml, the individual dose may be increased in the next treatment cycle by at least 10 mg/m$^2$, 20 mg/m$^2$, about 30 mg/m$^2$, about 40 mg/m$^2$, about 50 mg/m$^2$, about 60 mg/m$^2$, 70 mg/m$^2$, about 80 mg/m$^2$, about 90 mg/m$^2$ or about 100 mg/m$^2$.

The methods of the present invention may also further comprise determining, 0-2 hours following an completion of administering an individual dose of said immunoconjugate or a pharmaceutical composition comprising the same, a level of an said immunoconjugate in a body fluid, wherein, if said level is above 50 µg/ml, 60, 70, 80 or 100 µg/ml, the individual dose may be decreased in the next treatment cycle by at least 10 mg/m$^2$, 20 mg/m$^2$, about 30 mg/m$^2$, about 40 mg/m$^2$, about 50 mg/m$^2$, about 60 mg/m$^2$, 70 mg/m$^2$, about 80 mg/m$^2$, about 90 mg/m$^2$, about 100 mg/m$^2$, about 110 mg/m$^2$ or about 120 mg/m$^2$.

In any of the methods of the present invention at least one cytotoxic agent, including two or three, may be administered at least once a week or once in a treatment cycle. Said cytotoxic agent may be lenalidomide and/or dexamethasone. The said subject to which the drug combination is administered may or may not have previously been exposed to an immunoconjugate comprising an antibody targeting CD138 expressing cells, to lenalidomide and/or to dexamethasone. The subject may have responded to an exposure to an immunoconjugate comprising an antibody targeting CD138 expressing cells, lenalidomide and/or dexamethasone. Target cells expressing CD138 may be refractory to exposure to an immunoconjugate comprising an antibody targeting CD138 expressing cells, lenalidomide and/or dexamethasone. The subject may have relapsed after said previous exposure. Lenalidomide may be administered at a dose of 5 to 35 mg, preferably at about 25 mg, or at a dose of less than 25, 20, 15 or 10 mg, more preferably orally once a day in a treatment cycle of, e.g., 21 or 28 days and/or dexamethasone may be administered at a dose of 20 to 50 mg, preferably at about 40 mg, or at a dose of less than 40 or 30 mg, e.g., orally once a day in a treatment cycle of, e.g., of 21 or 28 days or, e.g., on days 1-4, 9-12, 17-20 within 28 days or e.g., on day 1, 8, 15 and 22.

The subject may suffer from a solid tumor comprising target cells which express CD138 and said solid tumor may be refractory to cancer hormone therapy or chemotherapy or the subject may have relapsed after hormone therapy or chemotherapy, wherein said administration may result in at least tumor growth delay or tumor stasis. Said immunoconjugate may be administered in a repeated multiple dose regime with individual doses of 20 mg/m$^2$ to 160 mg/m$^2$. The solid tumor may be estrogen receptor negative and/or progesterone receptor negative and/or Her2/neu negative, including triple negative with all of three, e.g., triple-negative breast cancer.

An administration of said immunoconjugate or pharmaceutical composition may also be preceded by an administration of different targeting agent, e.g., an unconjugated antibody targeting CD138 expressing cells, wherein said immunoconjugate is administered 1-6, preferably 2-4, hours after completion of the administration of said unconjugated antibody. The unconjugated antibody may be administered at a dose corresponding to a level of 10 to 30 µg/ml immunoconjugate in a body fluid of the subject, in particular a plasma level of the subject. This dose administered may correspond to about a difference between a theoretical and actual level of said immunoconjugate in a body fluid, 0-2 hours after completion of an administration of said immunoconjugate to said subject. The targeting agent may be administered at a dose of 10 to 40 mg/m$^2$, preferably 20-30 mg/m$^2$. As a result, the immunoconjugate may be administered at an individual dose that is up to 10 mg/m$^2$, up to 20 mg/m$^2$ or up to 30 mg/m$^2$ lower than the dose administered without said administration of said unconjugated antibody.

The invention is also directed at a kit comprising an antibody against the immunoconjugate and, in a separate container, instructions how to determine, a level of said immunoconjugate in a body fluid obtained from said subject by addition of said antibody to said body fluid. The kit may further comprise an immunoconjugate comprising at least one engineered targeting antibody targeting CD138 expressing cells, and at least one effector molecule, wherein said engineered targeting antibody is functionally attached to said effector molecule to form said immunoconjugate.

The engineered targeting antibody may comprise an antigen binding region (ABR) against CD138, and a further antibody region, wherein at least part of said further antibody region is of a human antibody and confers said IgG4 isotype properties.

The disease may be multiple myeloma, in particular relapsed or refractory multiple myeloma. Refractory multiple myeloma includes "primary refractory myeloma" and "relapsed and refractory myeloma."

Said disease expressing CD138 on target cells may be also selected from the group consisting of renal cell carcinoma, endometrial cancer, cervical cancer, prostate adenocarcinoma, pancreatic carcinoma, gastric cancer, bladder cancer, mammary carcinoma, hepato-carcinoma, colorectal carcinoma, colon carcinoma, squamous cell carcinoma, lung cancer in particular squamous cell lung carcinoma, non Hodgkin lymphoma, thymus, uterus, urinary or ovarian carcinoma.

In preferred embodiments, the immunoconjugate homogenously targets CD138 expressing target cells.

In certain embodiments, the engineered targeting antibody of the present invention may
(i) consist essentially of antigen binding region (ABR) against CD138 of a non-human antibody, or
(ii) comprise an antigen binding region (ABR) against CD138, wherein said antigen binding region is of a non-human antibody, and
a further antibody region, wherein at least part of said further antibody region is of a human antibody.

The ABR may comprise:
(a) heavy chain variable region CDR3 comprising amino acid residues 99 to 111 of SEQ ID NO: 1, and
(b) light chain variable region CDR3 comprising amino acid residues 89 to 97 of SEQ ID NO: 2, respectively.

The ABR may further comprise:
(a) heavy chain variable region CDR1 and CDR2 comprising amino acid residues 31 to 35 and 51 to 68 of SEQ ID NO: 1, and/or
(b) light chain variable region CDR1 and CDR 2 comprising amino acid residues 24 to 34 and 50 to 56 of SEQ ID NO: 2, respectively.

The further antibody region may comprise:
(a) amino acid residues 123 to 448 of SEQ ID NO: 1, and/or
(b) amino acid residues 108 to 214 of SEQ ID NO: 2, respectively and mutations thereof that
    (i) maintain or lower the antibody-dependent cytotoxicity and/or complement-dependent cytotoxicity of the engineered targeting antibody and/or
    (ii) stabilize the engineered targeting antibody.

The antibody may comprise a light chain having at least about 70%, more preferably 80%, 85% or 90%, sequence identity with SEQ ID No: 2 and a heavy chain having at least about 70%, more preferably 80%, 85% or 90%, sequence identity with SEQ ID No: 1, and comprising the antigen binding regions specified above.

The effector molecule may be attached to said engineered targeting antibody via a linker. The linker may comprise a disulfide bond. The effector molecule (e.g., DM4) may provide sterical hindrance between the targeting antibody and the effector molecule. The effector molecule may be at least one maytansinoid (e.g., DM1, DM3, or DM4), taxane, another microtubule inhibiting agent or DNA targeting agent such as CC1065, or an analog thereof. The immunoconjugate may bind CD138 with a targeting variation of less than 150%, 140%, 130%, 120%, 110%, 100%, 90%, 80%, 70%, 60% or 50%.

The immunoconjugate may, in certain embodiments of the methods disclosed herein, comprise:
a targeting agent targeting CD138 comprising
an isolated polypeptide comprising an amino acid sequence of an immunoglobulin heavy chain or part thereof, wherein said immunoglobulin heavy chain or part thereof has at least 70% sequence identity with SEQ ID NO:1. A constant region of said immunoglobulin heavy chain or said part thereof may be an IgG4 isotype constant region.

The targeting agent of the immunoconjugate may comprise a light chain sequence having at least about 70% sequence identity with SEQ ID NO:2. The targeting agent of the immunoconjugate may also comprise a heavy chain sequence having at least about 70% sequence identity with SEQ ID NO:1.

The present invention is also directed at a pharmaceutical composition comprising any of the immunoconjugates specified herein for the inhibition, delay and/or prevention of the growth of tumors and/or spread of tumor cells, and one or more pharmaceutically acceptable excipients.

The pharmaceutical composition may include cytotoxic agents as specified herein.

The present invention is also directed at a kit comprising, in separate containers, said pharmaceutical composition in one or more dosage forms and, in a separate container, instructions how to administer the one or more dosage forms to a subject, in particular a human subject in need thereof, e.g., as repeated single dose or other treatment regime discussed herein.

In particular, in certain embodiments, the present invention also provides the immunoconjugate described herein for use in treating a disease associated with target cells expressing CD138, wherein the immunoconjugate is to be administered in the schedules and/or at the dosages described herein. The immunoconjugate for use in this manner can be comprised in a pharmaceutical composition. The immunoconjugate or pharmaceutical composition may also be comprised in a kit, where the kit further comprises the cytotoxic agent and/or the unconjugated antibody targeting CD138, also described herein, in separate containers. The immunoconjugate/pharmaceutical composition and the cytotoxic agent and/or the unconjugated antibody are to be simultaneously, separately or sequentially administered as described herein. Similarly, the immunoconjugate/pharmaceutical composition, the cytotoxic agent and/or the unconjugated antibody targeting CD138 can be in the form of a combined preparation for simultaneous, separate or sequential use in the manner described herein.

In one aspect of the invention the administration of any of the immunoconjugates disclosed herein is to a subject or cells of such a subject, in particular a human subject, benefiting from such administration. The immunoconjugate can also be used for the manufacture of a medicament for the treatment of such a disorder.

Use of an immunoconjugate for the manufacture of a medicament for the treatment of a disease in a subject associated with target cells expressing CD138, wherein the immunoconjugate comprises:
(i) at least one targeting agent targeting CD138 expressing cells, and
(ii) at least one effector molecule, optionally in combination with one or more cytotoxic agents
wherein the targeting agent is functionally attached to the effector molecule to form the immunoconjugate, wherein the subject does not respond (refractory disease), or responds poorly or is relapsed from, to treatment with one or more cytotoxic agents including immunomodulators and/or proteasome inhibitors, and wherein the immunoconjugate is to be administered to the subject, preferably intravenously.

A combined preparation of an immunoconjugate and an agent for treating adverse side effects, for simultaneous, separate or sequential use in treating a disease in a subject associated with target cells expressing CD138, wherein the immunoconjugate comprises:

(i) at least one targeting agent targeting CD138 expressing cells, and (ii) at least one effector molecule, wherein the targeting agent is functionally attached to the effector molecule to form the immunoconjugate, wherein the subject does not respond to, responds poorly to or is relapsed from, treatment with one or more cytotoxic agents including immunomodulators and/or proteasome inhibitors, and wherein the immunoconjugate is to be administered to the subject, preferably intravenously, in a pharmacokinetic equivalent of 5 mg/m$^2$ to 140 mg/m$^2$ of the immunoconjugate when administered alone.

Use of an immunoconjugate and an agent for treating adverse side effects for the manufacture of a combined preparation for simultaneous, separate or sequential use in treating a disease in a subject associated with target cells expressing CD138, wherein the immunoconjugate comprises:

(i) at least one targeting agent targeting CD138 expressing cells, and (ii) at least one effector molecule, wherein the targeting agent is functionally attached to the effector molecule to form the immunoconjugate, wherein the subject does not respond to, or responds poorly to or is relapsed from, treatment with one or more cytotoxic agents including immunomodulators and/or proteasome inhibitors, and wherein the immunoconjugate is to be administered to the subject, preferably intravenously, in a pharmacokinetic equivalent of 5mg/m$^2$ to 840mg/m$^2$ of the immunoconjugate when administered alone.

The invention is also directed at an anticancer combination comprising at least one cytotoxic agent and at least one immunoconjugate comprising a targeting agent targeting CD138 expressing cells, and at least one effector molecule, wherein said targeting agent is functionally attached to said effector molecule to form said immunoconjugate, wherein (a) the combination has a synergy ratio of more than 1, more than 1.1, more than 1.2, more than 1.3, more than 1.4, or (b) the combination has a synergy ratio of about 1 and the effector molecule and the cytotoxic agent have overlapping modes of action, and wherein said anticancer combination is a pharmaceutical composition or a kit comprising the at least one cytotoxic agent and the at least one immunoconjugate in separate containers.

The cytotoxic agent may be a proteasome inhibitor, an immunomodulatory or an anti-angiogenic agent, a DNA alkylating agent, a histone deacetylase, or a mixture of two or more thereof.

The cytotoxic agent may be bortezomib or carfilzomib, thalidomide, lenalidomide or pomalidomide, melphalan or a mixture of two or more thereof.

The effector molecule and the cytotoxic agent of the anticancer combination may have overlapping modes of action and wherein these modes of action involve preferably inhibition of microtubule or induction of cell cycle arrest (melphalan, bortezomib and lenalidomide or thalidomide are cytotoxic agents that induce cell cycle arrest). Alternatively, they may have non-overlapping modes of action.

If the anticancer combination is part of a pharmaceutical composition, the pharmaceutical composition may comprise at least one pharmaceutically acceptable excipient.

The anticancer combination may also be part of a kit in which the at least one cytotoxic agent and the at least one immunoconjugate are stored in separate containers.

The invention is also directed at a method for treating a disease associated with target cells expressing CD138, comprising:

administering to a patient in need thereof an effective amount of the anticancer combination mentioned herein or an anticancer combination comprising at least one cytotoxic agent and at least one immunoconjugate comprising a targeting agent targeting CD138 expressing cells and at least one effector molecule, wherein said targeting agent is functionally attached to said effector molecule to form said immunoconjugate, and wherein the immunoconjugate overcomes a refractory phenotype of a patient against said cytotoxic agent.

The invention is also directed at a method for treating a disease associated with target cells expressing CD138, comprising:

administering to a patient in need thereof an effective amount of an anticancer combination discussed herein and wherein the immunoconjugate overcomes a refractory phenotype.

The invention is also directed at a method for treating a non-plasmaproliferative disease associated with target cells expressing CD138, comprising:

administering to a subject in need thereof or to cells affected by said non-plasmaproliferative disease an effective amount of an immunoconjugate comprising at least one targeting agent targeting CD138 expressing cells, and at least one effector molecule, wherein said targeting agent is functionally attached to said effector molecule to form said immunoconjugate, wherein said CD138 is, in said subject, expressed on said target cells and on non-target cells at comparable levels or wherein said CD138 is, in said subject, expressed on said target cells at levels below that of said non-target cells expressing CD138.

Said non-target cells expressing CD138 may be epithelium cells.

The invention is also directed at a method for treating a non-plasmaproliferative disease associated with target cells expressing CD138, comprising:

administering to a subject in need thereof or to cells affected by said non-plasmaproliferative disease an effective amount of an immunoconjugate comprising at least one targeting agent targeting CD138 expressing cells, and at least one effector molecule, wherein said targeting agent is functionally attached to said effector molecule to form said immunoconjugate, wherein the target cells of said disease shed CD138 over a period of 24 hours, 2, 3, 4, 5, 6 days or permanently.

Said disease may be mammary carcinoma.

A combined preparation of at least one cytotoxic agent and at least one immunoconjugate, for simultaneous, separate or sequential use in treating in a subject a disease associated with target cells expressing CD138, wherein the immunoconjugate comprises:
(i) a targeting agent targeting CD138 expressing cells, and
(ii) at least one effector molecule,
wherein the targeting agent is functionally attached to the at least one effector molecule to form the immunoconjugate, and wherein the subject has a refractory phenotype, relapsed after treatment or has not undergone treatment before.

Use of at least one cytotoxic agent and at least one immunoconjugate for the manufacture of a combined preparation for simultaneous, separate or sequential use in treating in a subject a disease associated with target cells expressing CD138, wherein the immunoconjugate comprises:
(i) a targeting agent targeting CD138 expressing cells and
(ii) at least one effector molecule
wherein the targeting agent is functionally attached to the at least one effector molecule to form the immunoconjugate, and wherein the subject has a refractory phenotype, relapsed after treatment or has not undergone treatment before.

In a preferred embodiment the combination of the at least one cytotoxic agent and at least one immunoconjugate has a synergy ratio of more than 1, more than 1.1, more than 1.2, more than 1.3 or more than 1.4. Alternatively, the combination of the at least one cytotoxic agent and the at least one immunoconjugate has a synergy ratio of about 1 and the effector molecule and the cytotoxic agent have overlapping modes of action.

In a preferred embodiment the combination of at least one cytotoxic agent and at least one immunoconjugate has a higher efficacy compared to each of the agents alone. A higher efficacy is defined by changes in efficacy blood parameters, for example M-Protein levels, Free kappa light chain, and other relevant parameters, which positively change relative to each single agent. In particular, the higher efficacy can be defined by e.g. % decline in M-Protein level, the extent of the decline in the M-Protein level, or of the duration of the decrease in M-Protein.

An immunoconjugate for treating a non-plasmaproliferative disease in a subject associated with target cells expressing CD138, wherein the immunoconjugate comprises:
(i) at least one targeting agent targeting CD138 expressing cells, and
(ii) at least one effector molecule,
wherein the targeting agent is functionally attached to the effector molecule to form the immunoconjugate,
and wherein in the subject CD138 is expressed on the target cells at levels comparable (equivalent) to or below the levels at which CD138 is expressed on non-target cells.

Use of an immunoconjugate for the manufacture of a medicament for treating in a subject a non-plasmaproliferative disease associated with target cells expressing CD138, wherein the immunoconjugate comprises:
(i) at least one targeting agent targeting CD138 expressing cells, and
(ii) at least one effector molecule,
wherein the targeting agent is functionally attached to the effector molecule to form the immunoconjugate, and wherein in the subject CD138 is expressed on the target cells at levels comparable (equivalent) to or below the levels at which CD138 is expressed on non-target cells.

The invention is also directed at a method for treating a non-plasmaproliferative disease associated with target cells expressing CD138, comprising:
administering to a subject in need thereof or to cells of said non-plasmaproliferative disease an effective amount of an immunoconjugate comprising
at least one targeting agent targeting CD138 expressing cells, and
at least one effector molecule, wherein said targeting agent is functionally attached to said effector molecule to form said immunoconjugate, wherein immunoconjugate induces at least tumor stasis, preferably remission of a solid tumor.

This remission may be a remission followed by a time interval which is free of re-growth of said tumor (complete remission). This time interval may be more than 1, 2, 3, 4, 5, 6, 7, 8, 9, 10 weeks, half a year or 1 year or more.

The solid tumor may be a pancreatic carcinoma or a mammary carcinoma.

The disease may renal cell carcinoma, endometrial cancer, cervical cancer, prostate adenocarcinoma, pancreatic carcinoma, gastric cancer, bladder cancer, mammary carcinoma, hepato-carcinoma, colorectal carcinoma, colon carcinoma, squamous cell carcinoma, lung cancer in particular squamous cell lung carcinoma, non Hodgkin lymphoma, thymus, uterus, urinary or ovarian carcinoma, both in form of primary tumors as well as metastatic tumors derived from primary tumors.

The solid tumor may be a mammary carcinoma, which are estrogen receptor negative and/or progesterone receptor negative and/or Her2/neu negative. A solid tumor according to the present invention may also be a mammary carcinoma, which does not or poorly respond to taxane therapy or is hormone refractory.

The receptor occupancy at target cells, such as bone marrow cells, may be more than 70%, more than 80%, more than 90% or more than 75%, 1, 2, 3, 4, 5, 6, 7, 8, 9, 10, 11 or 12 hours after completion of an administration of the immunoconjugate.

BRIEF DESCRIPTION OF THE FIGURES

FIG. 1 provides a schematic representation of nBT062 having effector molecules attached.

FIG. 2 is a chemical representation of BT062.

Figure 3:
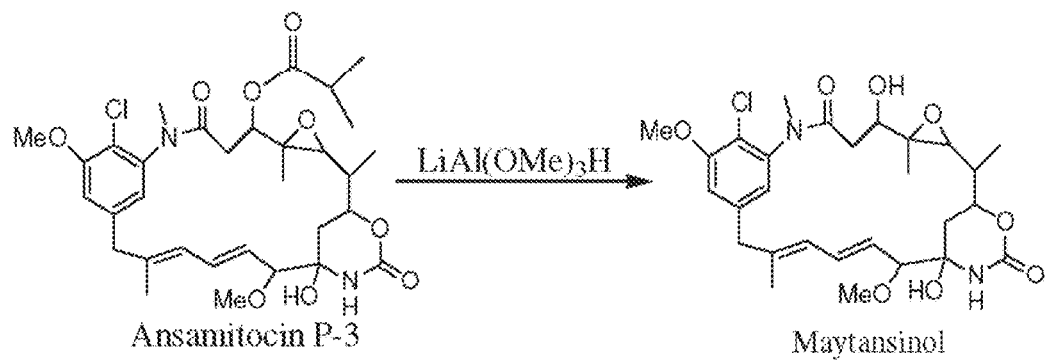
FIG. 3 shows the conversion of ansamitocin P-3 to maytansinol (stereochemistry is omitted for simplicity).

Docetaxel was as effective as the highest concentration of BT062 and allowed for maintenance of the low tumor volume over time.

DETAILED DESCRIPTION OF VARIOUS AND PREFERRED EMBODIMENTS OF THE INVENTION

The present invention relates to the administration to subjects, in particular human subjects (patients), in need thereof, of immunoconjugates comprising CD138 targeting agents described herein and the delivery of the effector molecule(s) of the immunoconjugates to target sites and the release of effector(s) molecule in or at the target site, in particular target cells, tissues and/or organs. More particularly, the present invention relates to immunoconjugates comprising such CD138 targeting agents and potent effector molecules that are attached to the targeting agents. The effector molecules may be activated by cleavage and/or dissociation from the targeting agent portion of the immunoconjugate in or at a target site. The immunoconjugates may be administered alone or as part of an anticancer combination that includes a cytotoxic agent such as, but not limited to, a proteasome inhibitor (e.g., bortezomib, carfilzomib), immunomodulatory agent/anti-angiogenic agent (e.g., thalidomide, lenalidomide or pomalidomide), DNA alkylating agent (e.g., melphalan) or corticosteroid (e.g., dexamethasone), wherein the anticancer combination has synergistic effects or unexpected additive effects in the treatment of cancer over the immunoconjugate used alone in monotherapy, the cytotoxic agent used alone in monotherapy or both.

The immunoconjugates according to the present invention may be administered to a subject in need of treatment or to cells isolated from such a subject in need of treatment. The effector molecule or molecules may be released from the immunoconjugate by cleavage/dissociation in or at a target cell, tissue and/or organ.

In one example, the immunoconjugate BT062, which targets CD138 expressing cells via the nBT062 antibody and comprises DM4 as an effector molecule, was administered to a patient with relapsed/refractory multiple myeloma 14 times in an amount of 40 mg/m$^2$ as in a repeated multiple dose regime, wherein the length of each active treatment cycle was 21 days with three doses/per cycle being administered on days, 1, 8, and 15 of the cycle and an resting period of one week was inserted before the next active treatment cycle was started. Expressed differently, the treatment cycle was 28 days with three doses/per cycle being administered on days, 1, 8, and 15 of the cycle and none administered on day 22, resulting, in this example, in a treatment free period of about two weeks. In this example, the immunoconjugate was administered intravenously to the patient so that it could better concentrate in and/or at tumor cells. Measurements of the plasma concentration of BT062 showed that in an initial measurement phase (up to 2 hours after the end of administration) Cmax values for BT062 were significantly below the theoretically calculated value while no DLTs (dose limiting toxicities) were observed, suggesting that BT062 concentrates at the tumor target rather than randomly attaching to target and non-target CD138. A "buffer effect" resulting from sCD138 (soluble CD138) could be excluded (compare FIG. 17). As will be discussed below in the context of administrations at 80 mg/m$^2$, a rapid concentration at the target cells could be confirmed.

An active treatment cycle is a treatment cycle that is defined by a regular administration of the active agent, here generally the immunoconjugate, and excludes any resting periods. An active treatment cycle includes typically three weeks of active treatment and is considered to end not with the last dose administered, but at the time when a further administration would be due. Thus an active treatment cycle including a dose of 120 mg/m$^2$ on day 1, 65 mg/m$^2$ on both days 8 and 15, would be considered to end on day 21 and to be 21 days long. While an active treatment cycle generally lasts 21 days, it may range from at least two weeks (14 days) to four weeks (28 days). In the latter case an active treatment cycle and a "full" or "complete" treatment cycle are the same. Within the period of an active treatment cycle, the active agent, is regularly administered. This includes, e.g., in alternating 2 and 3 day intervals, in 4 day intervals, in progressive increasing intervals such as on day 1, 3, 6, 10, 15. A treatment cycle may in addition to the active treatment further comprise a resting period. E.g. in the example above, the above administration scheme in a treatment cycle of 28 days would be considered to comprise no administration of day 22. Such a treatment cycle, including a resting period, is also referred to herein as "full" or "complete" treatment cycle. A treatment free period describes the time during which no treatment is given. Thus, in the above example, the treatment free period would start at day 16. At the beginning of the resting period, no immunoconjugate is administered to the patient. In a preferred embodiment no treatment of any sort is administered during this period. The resting period may lasts, e.g., 5, 6, 7, 8, 9, 10, 11, 12, 13, 14 days or more typical is one week. A treatment free period may last 14, 15, 16, 17, 18, 19, 20, 21 days or more.

Figure 20:
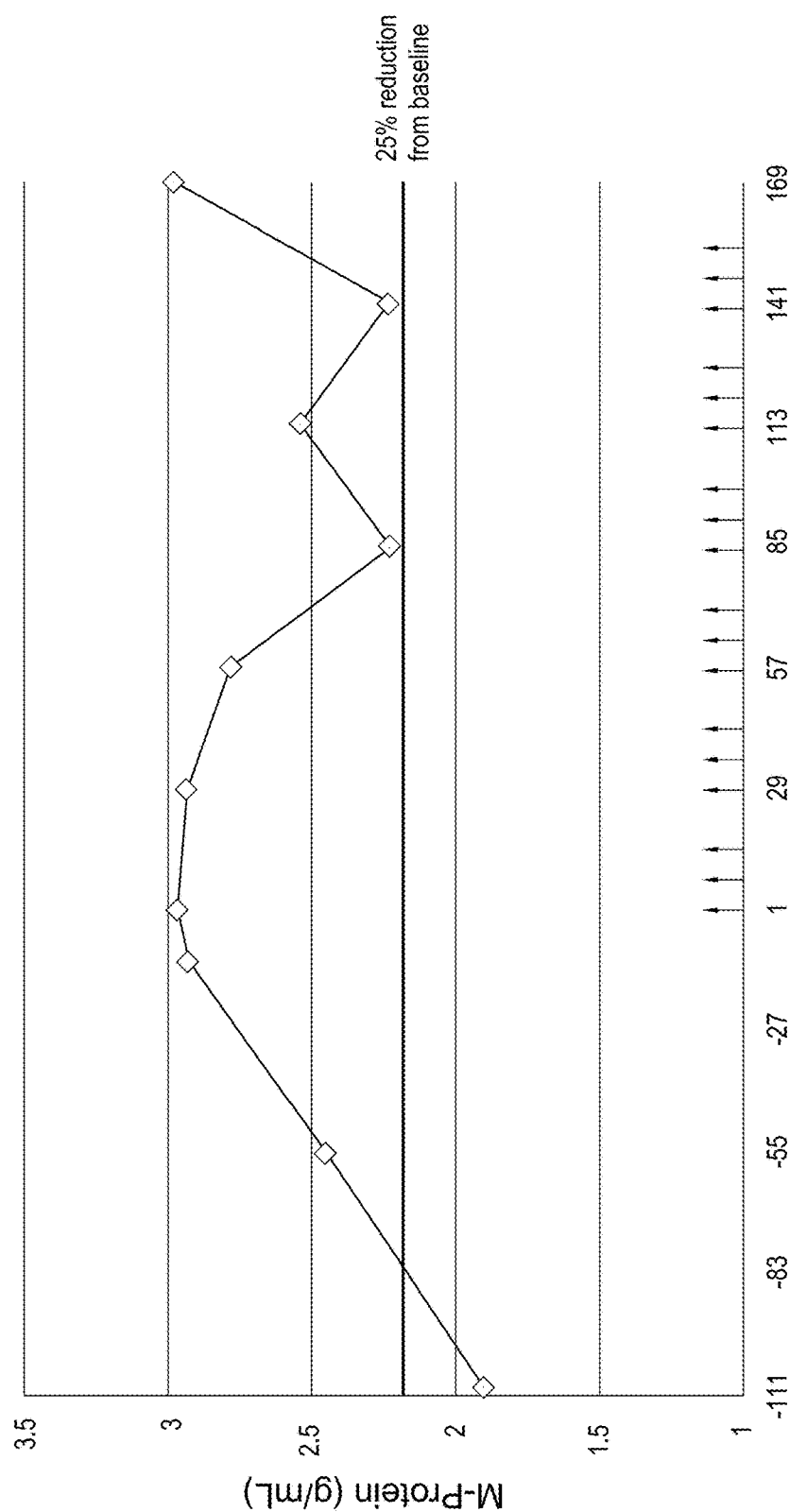
FIG. 20 shows the level of serum M-protein measured for a patient receiving 50 mg/m$^2$ weekly for three weeks, followed by a 7 day resting period. Days −111 to 169 are shown. Arrows indicate treatment with BT062.

In another example, the immunoconjugate BT062 was administered to a patient with relapsed/refractory multiple myeloma 18 times in an amount of 50 mg/m$^2$ each as repeated multiple doses, wherein the length of each treatment cycle was 21 days with three doses/per cycle being administered on days, 1, 8, and 15 of the cycle and an resting period of one week was inserted before the next treatment cycle was started. Expressed differently, the treatment cycle was 28 days with three doses/per cycle being administered on days, 1, 8, and 15 of the cycle and none administered on day 22. In this example, the immunoconjugate was administered intravenously to the patient so that it could better concentrate in and/or at tumor cells. No additional means were provided to release the effector molecule from the immunoconjugate. Six treatment cycles were well tolerated and at least stable disease could be achieved over six cycles, with a decrease of serum M-protein by nearly 25% during after the $3^{rd}$ and 5th treatment cycle (FIG. 20).

Figure 21:
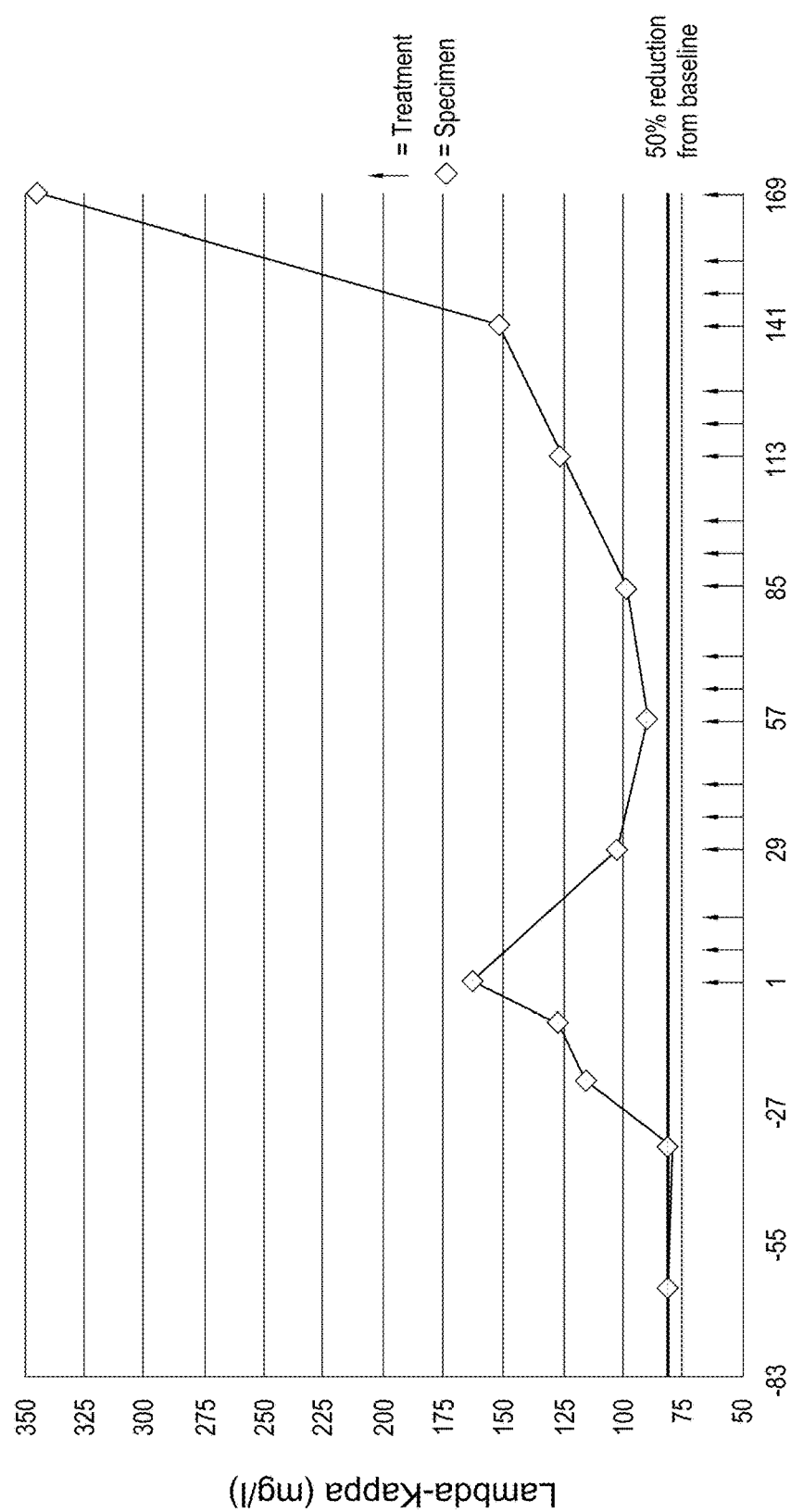
FIG. 21 shows the level of lambda-kappa FLC (strong increase before first treatment, strong decrease from day 1 to 57) measured for a patient (oligo-secretory multiple myeloma) receiving 65 mg/m$^2$ weekly for three weeks, followed by a 7 day resting period. Days −83 to 163 are shown.

In yet another example, the immunoconjugate BT062 was administered to a patient with relapsed/refractory multiple myeloma 19 times in an amount of 65 mg/m$^2$ as repeated multiple doses, wherein the length of each treatment cycle was 28 days with three doses/per cycle being administered on days, 1, 8, and 15 of the cycle and none administered on day 22. The treatment free period was thus 14 days before the next treatment cycle started. At this concentration plasma levels were still below the theoretical Cmax (mean percentage from theoretical Cmax=60%; Table 11a), but not to the degree observed with lower doses, e.g., 40 mg/m$^2$ or 50 mg/m$^2$ (mean percentage from theoretical Cmax=33% Table 11a). However, a strong decrease of the serum FLC level could be observed after just a single treatment cycle and could be maintained for two months (FIG. 21). Besides the higher percentage from theoretical Cmax reached at does level of 65 mg/m$^2$, the total plasma concentration missing to the theoretical Cmax (here mean total 17.7 mg/m$^2$, Table 11b) was similar to the one ones observed at lower concentrations of 40 mg/m$^2$ or 50 mg/m$^2$ (mean total 18.6 mg/m$^2$ and 23.0 mg/m$^2$, Table 11b). Thus, the total plasma concentrations missing to the theoretical Cmax may stay at different concentrations, despite an increase of the mean percentage from the theoretical Cmax by more than 10% more than 20% or more than 25%, preferably between 15 and 25%, stayed within the range of 15-25 mg/m$^2$, namely around 20 mg/m$^2$. For 14 patients (out of 32 on the study) progression free survival of at least 3 months has been reported (FIG. 18), for four of these patients progression free survival of at least 168 days has been reported. One of these four patients showed clear reduction of serum M protein after 9 treatments (Patient No. 6, please see also FIG. 20) and for another patient a strong decrease in FLC could be observed within the first 2 months (Patient No. 19, see also FIG. 24). The first DLT was observed in the 140 mg/m$^2$ cohort (Patient No. 23), but no DLT was reported for the six other patients at this dose level. For two out of the four patients (Patient Nos. 30 and 32) that were treated with weekly doses of 160 mg/m$^2$ DLT was observed and prompted a reduction of the dose to of 140 mg/m$^2$ in subsequent cycles.

In yet another example, the immunoconjugate BT062 was administered to a patient with non-secretory relapsed/refractory multiple myeloma (Patient No. 12 in FIG. 18) for 15 cycles in an amount of 80 mg/m$^2$ as repeated multiple doses, wherein the length of each treatment cycle was 28 days with three doses/per cycle being administered on day 1, 8, and 15 of the cycle and none administered on day 22. In this example, the immunoconjugate was administered intravenously to the patient so that it could better concentrate in and/or at tumor cells. At this concentration plasma levels were still below the theoretical Cmax, but not to the degree observed with lower doses, e.g. 40 mg/m$^2$ (mean percentage from theoretical Cmax-33%; Table 11a). After three administrations at 80 mg/m$^2$, totaling an administration of 240 mg/m$^2$ (aggregate dose) within three weeks, the immunoconjugate remained well tolerated. A rapid concentration at the tumor target could be confirmed at this dosage. Table 12 shows the results of receptor occupancy (RO) measurements. Here the binding of BT062 to the receptor (CD138) was measured on multiple myeloma cells in the bone marrow, ergo the site of the tumor, in the Multiple Myeloma patient. Receptor (CD138) bound BT062 was stained with anti-May antibodies (Sample 1). Total CD138 was measured with anti-May antibodies after receptor saturation with BT062 (Sample 2). Incubation with an IgG1 isotype determined unspecific binding to the sample (Sample 3). The first row in Table 12 shows the results of a measurement within four hours after completition of the administration. As can be seen, the receptor occupancy within 4 hours after end of administration is, in this case, 99%. The patient showed a partial response. The duration of an administration (administration time) obviously differs with the mode of administration.

Administration times in intravenous (IV) administrations are generally defined by mg/min (1 mg/min for first 15 min and if tolerated 3 mg/min for the rest) and therefore increase with the dose levels assigned to the patient. The times for flushing the administration line after administration vary as well. In the present study, for doses between 10 mg/m$^2$ and 200 mg/m$^2$, the shortest infusion time was 18 minutes and maximum infusion time was 3 hours and 2 minutes with a mean of 1 hour and 36 min. If 200 mg/m$^2$ are administered completely at 1 mg/min this could result in an administration up to 8 hours. In an alternative embodiment, the immunoconjugate may be administered as IV bolus within a minute.

Thus, an administration according to the present invention is "completed" any time between 0 and 8 hours after start of an administration, generally within 0 and 4, often within 2 hours from the start of an administration.

Figure 22:
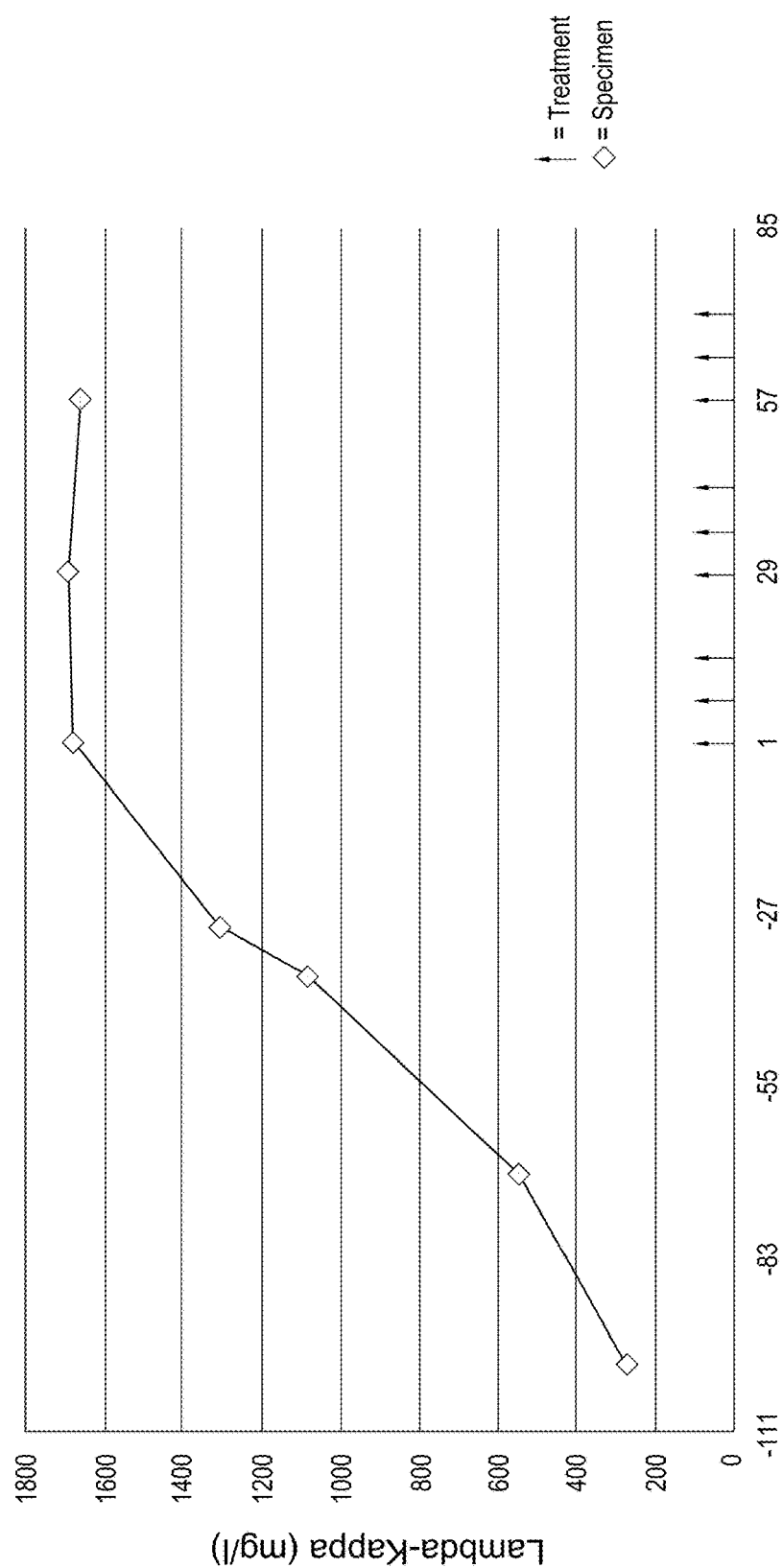
FIG. 22 shows the level of lambda-kappa FLC (strong increase before first treatment, stabilization for two cycles) measured for a patient (oligo-secretory multiple myeloma) receiving 80 mg/m$^2$ weekly for three weeks, followed by a 7 day resting period. Days −111 to 85 are shown.

FIG. 22 shows a patient (13 in FIG. 18) subjected to the same administration scheme (80 mg/m$^2$ as repeated multiple doses, wherein the length of each treatment cycle was 28 days with three doses/per cycle being administered on day 1, 8, and 15 of the cycle and none administered on day 22) which was administered to a relapsed/refractory patient. The strong increase of lambda-kappa before the first treatment day could be stabilized for 2 cycles.

Figure 18:
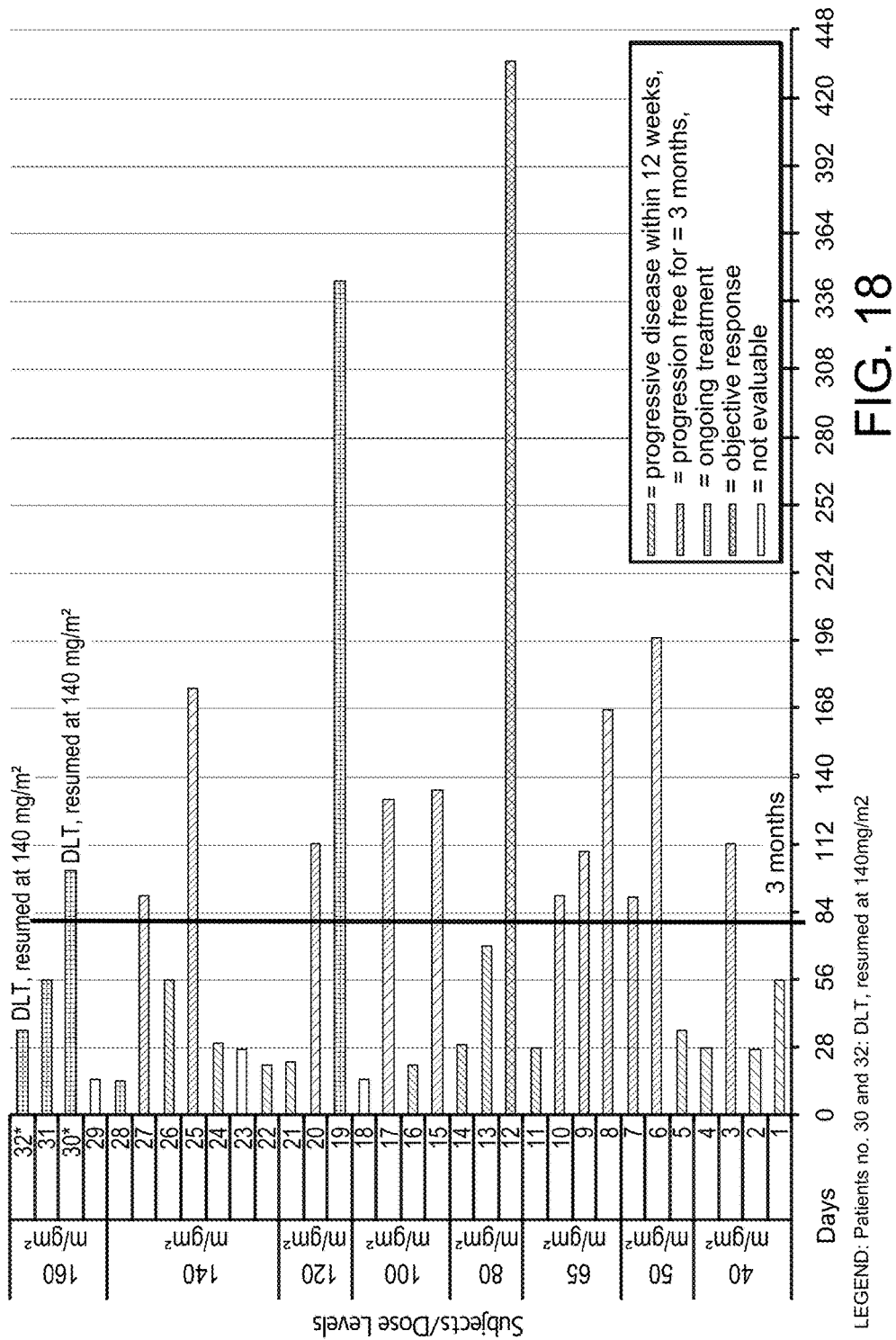
FIG. 18 depicts the progression free survival for human subjects treated with different dosages of BT062 administered in the course of the indicated treatment cycles, wherein each active treatment cycle lasted 21 days and the respective dosage was administered on days 1, 8 and 15 of each cycle. Each cycle of 21 days was followed by a 7 day resting period (28 indicate the 21+7 days, per "cycle")
As can be seen 14 patients were on study treatment for more than 3 months. For two of these patients progression free survival of at least 300 days (about 10 months) has been reported.

Patient 12 in FIG. 18 (80 mg/m$^2$ as repeated multiple doses as above), showed a partial response for about 8 months.

In a further example, the immunoconjugate BT062 was administered to a patient with relapsed/refractory multiple myeloma six times in an amount of 100 mg/m$^2$ as repeated multiple doses, wherein the length of each active treatment cycle was 21 days with three doses/per cycle being administered on day 1, 8, and 15 and a resting period of 1 week (no administration at day 22 leading effectively to a two weeks break of administration). In this example, the immunoconjugate was administered intravenously to the patient so that it could better concentrate in and/or at tumor cells.

Figure 23:
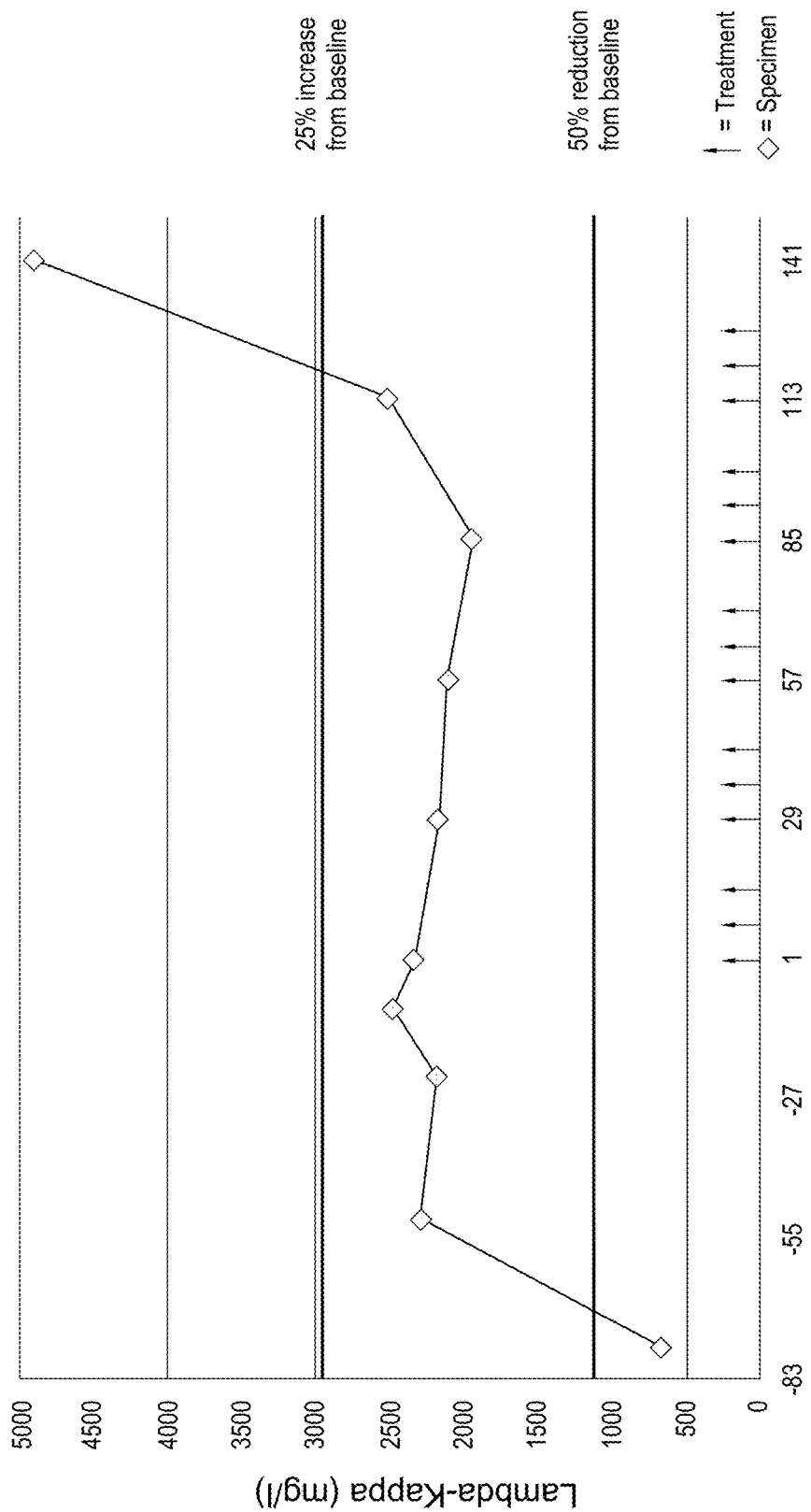
FIG. 23 shows the level of lambda-kappa FLC (decrease for three months) measured for a patient (oligo-secretory multiple myeloma) receiving 100 mg/m$^2$ weekly for three weeks, followed by a 7 day resting period. Days −83 to 141 are shown.

FIG. 23 shows the result of this dosage scheme with patient 15 (FIG. 18, relapsed refractory with oligo-secretory MM), who showed progression free survival for more than 3 months.

At this concentration plasma level was only below the theoretical Cmax during the first two administrations (Table 11a) pointing towards an accumulation of the immunoconjugate after weekly dosing at this dose. However, in the equivalent experiments with 120 mg/m$^2$ as repeated multiple dose, these values went down, indicating that the 100 mg/m$^2$ outcomes might be a deviation in a single patient and also indicating that at even higher dosages no significant accumulation might take place. After three administrations at 100 mg/m$^2$, at 120 mg/m$^2$ and, for the most part, at 140 mg/m$^2$ and totaling an administration of 300 mg/m$^2$, 360 mg/m$^2$ and 420 mg/m$^2$, respectively within three weeks, the immunoconjugate remained well tolerated. No DLTs were observed after three 21 day cycles of 3×100 mg/m$^2$ (300 mg/m$^2$) or 3×120 mg/m$^2$ (360 mg/m$^2$) in each cycle (3×300 mg/m$^2$=900 mg/m$^2$ in 12 weeks and 3×360 mg/m$^2$=1080 mg/m$^2$ in 12 weeks) compared to 640 mg/m$^2$ (four 21 day cycles of 160 mg/m$^2$ each).

In a further example, the immunoconjugate BT062 was administered to a patient with relapsed/refractory multiple myeloma six times in an amount of 120 mg/m$^2$ as repeated multiple doses, wherein the length of each active treatment cycle was 21 days with three doses/per cycle being administered on day 1, 8, and 15 and a resting period of 1 week. In this example, the immunoconjugate was administered intravenously to the patient so that it could better concentrate in and/or at tumor cells.

Figure 24:
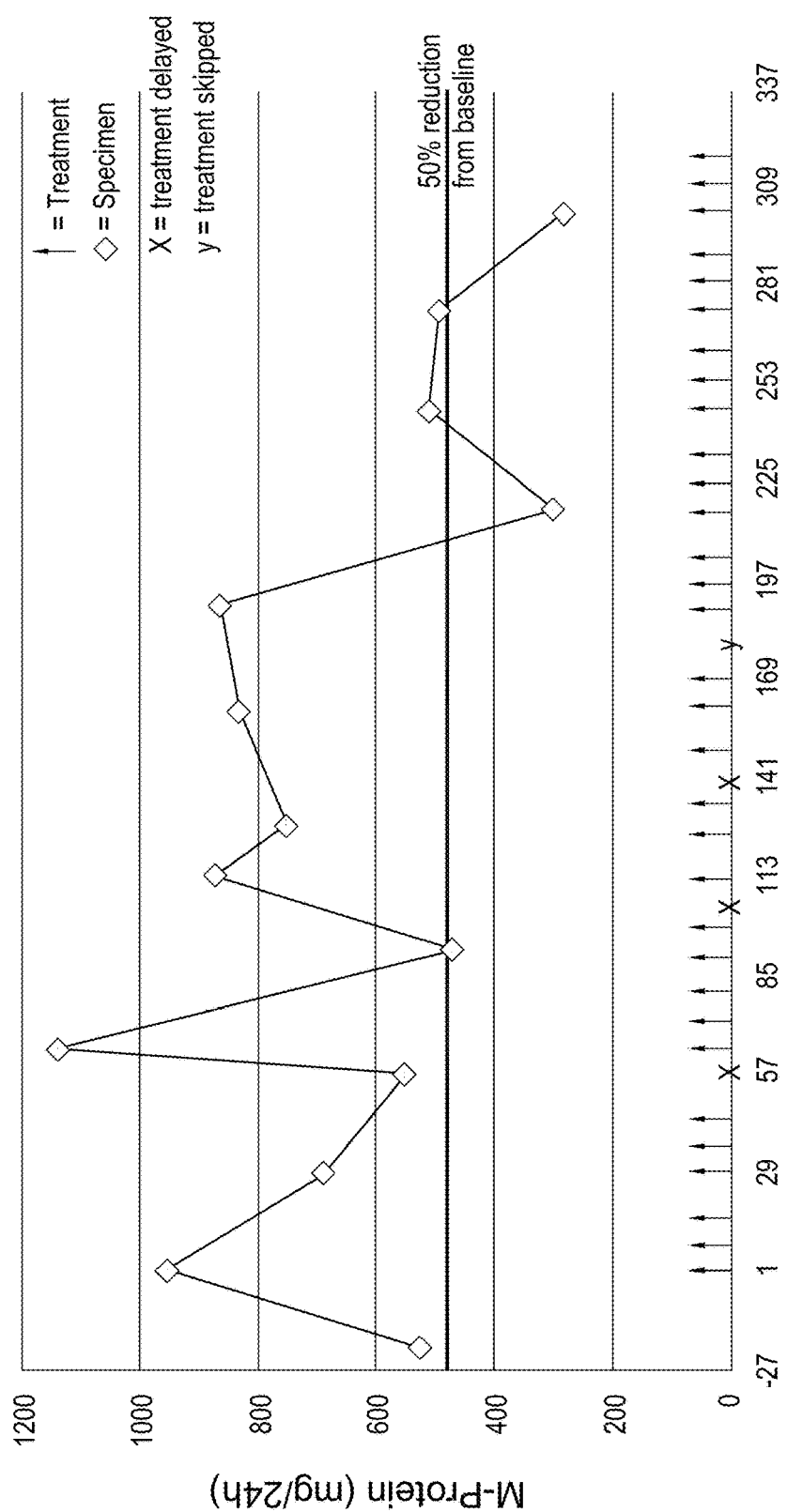
FIG. 24 shows the level of urine M-protein measured for a patient receiving 3×120 mg/m$^2$ weekly for three weeks, followed by a 7 day resting period. Days −27 to 337 are shown.

FIG. 24 shows the result of this dosage scheme with patient 19 (FIG. 18, relapsed refractory with oligo-secretory MM), who showed an unconfirmed minor response, despite a number of a number of treatment delays (x).

At this concentration the plasma level was still below the theoretical Cmax (Table 11a) indicating no relevant accumulation of the immunoconjugate after weekly dosing at this dose. After three administrations at 120 mg/m$^2$, totaling an administration of 360 mg/m$^2$ within three weeks, the immunoconjugate remained well tolerated. No DLTs were observed after three 21 day cycles of 3×120 mg/m$^2$ (360 mg/m$^2$) in each cycle.

Figure 25:
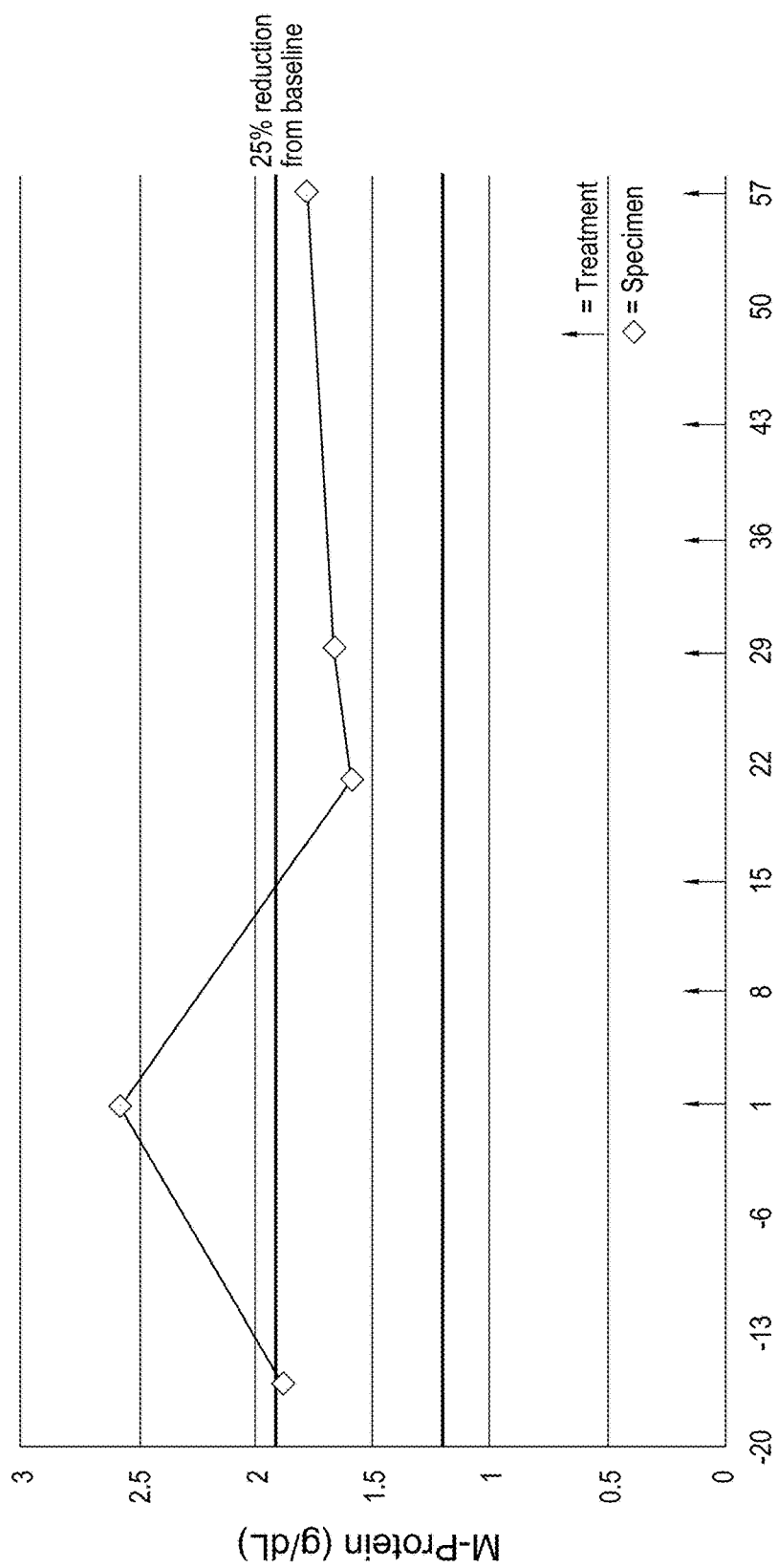
FIG. 25 shows the level of serum M-protein measured for a patient receiving 3×160 mg/m$^2$ weekly for three weeks, followed by a 7 day resting period. Days −20 to 57 are shown, which indicate a minor response.

In a further example, the immunoconjugate BT062 was administered to a patient with relapsed/refractory multiple myeloma seven times in an amount of 160 mg/m$^2$ as repeated multiple doses, wherein the length of each active treatment cycle was 21 days with three doses/per cycle being administered on day 1, 8, and 15 and a resting period of 1 week. In this example, the immunoconjugate was administered intravenously to the patient so that it could better concentrate in and/or at tumor cells. FIG. 25 shows the results (M-protein decreased by more than 25% qualifying for minor response) for patient 31, which as can be seen from FIG. 18 did not display DLT at this concentration.

As indicated in FIG. 18, 2 out of 4 patients displayed DLTs at 160 mg/m$^2$ (elevated liver enzymes, neutropenia) but could resume treatment at 160 mg/m$^2$. In this administration scheme, MAD was 160 mg/m$^2$, while 140 mg/m$^2$ was determined to be the MTD (1 out of 6 patients displayed DLT at this concentration)

TABLE 1

Total amount of BT062 delivered within 3 weeks results in different tolerability of the drug. A single dose of 200 mg/m$^2$ in a 3 week period resulted in DLTs (target related toxicities). Similar total doses (3 × 80 mg/m$^2$, 3 × 100 mg/m$^2$, 3 × 120 mg/m$^2$, 3 × 140 mg/m$^2$) administered in 3 intervals during a 3 week period did not result in any serious drug related toxicities in patients.

| Single dose every three weeks | Single dose every three weeks | Repeated single dose |
|---|---|---|
| 160 Drug-related adverse events such as eye toxicity | 200 DLTs | 240, 300, 360, 420 No serious drug-related toxicities (up to now), one DLT (palmar-plantar erythrodysaethesia syndrome) at 420 out of six |

Figure 34:
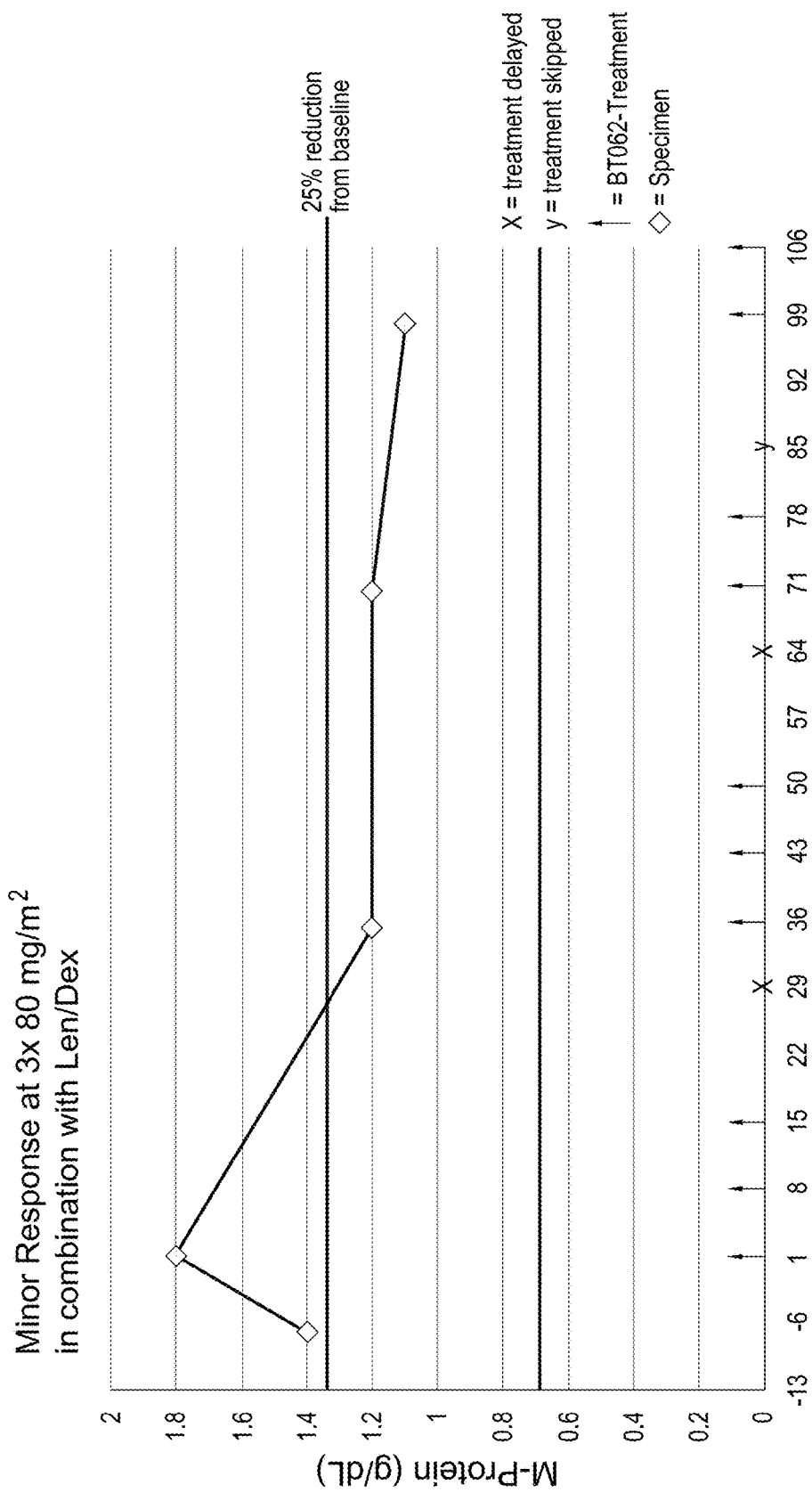
FIG. 34 shows the level of serum M-protein measured for a patient scheduled to receive 80 mg/m$^2$ of BT062 weekly for three weeks, followed by a 7 day resting period. BT062 was administered in combination with Lenalidomide and Dexamethasone. Days −13 to 106 are shown, which indicate a minor response.

In yet another example, the immunoconjugate BT062 was co-administered to a patient with relapsed multiple myeloma for four cycles in an amount of 80 mg/m$^2$ as repeated multiple doses, wherein the length of each treatment cycle is 28 days with three doses/per cycle being administered on days, 1, 8, and 15 of the cycle and none administered on day 22. At the same time a 25 mg daily oral dose of lenalidomide is administered at 1 to 21 and 40 mg of dexamethasone is administered weekly (days 1, 8, 15, 22). In this example, the immunoconjugate is administered intravenously to the patient so that it can better concentrate in and/or at tumor cells. Despite delayed start of treatment cycle 2 and 3 and skipping the dose of BT062 at day 15 of Cycle 3 and lenalidomide on day 15 to 21 in cycle 3, a minor response achieved after the first cycle was maintained (FIG. 34).

In another example, the immunoconjugate BT062 is co-administered to a patient suffering from a pancreatic tumor as repeated multiple dose of 220 mg/m$^2$, as solid tumors trap immunoconjugate more quickly than malignancies not associated with solid masses wherein the length of each treatment cycle is 28 days with three doses/per cycle being administered on days 1, 8, and 15 of the cycle and none administered on day 22. At the same time a 10 mg daily oral dose of the Immunomodulatory agent lenalidomide is administered. In this example, the immunoconjugate is administered intravenously to the patient so that it could better concentrate in and/or at tumor cells. The administration is followed by a maintenance treatment consisting of a repeated single dose of 160 mg/m$^2$ of the immunoconjugate at day 1 of a 21 day cycle for 4 months.

CD138 or syndecan-1 (also described as SYND1; SYNDECAN; SDC; SCD1; CD138 ANTIGEN, SwissProt accession number: P18827 human) is a membrane glycoprotein that was originally described to be present on cells of epithelial origin, and subsequently found on hematopoietic cells (Sanderson, 1989). CD138 has a long extracellular domain that binds to soluble molecules (e.g., the growth factors EGF, FGF, HGF) and to insoluble molecules (e.g., to the extracellular matrix components collagen and fibronectin) through heparan sulfate chains (Langford, 1998; Yang, 2007) and acts as a receptor for the extracellular matrix. CD138 also mediates cell to cell adhesion through heparin-binding molecules expressed by adherent cells. It has been shown that CD138 has a role as a co-receptor for growth factors of myeloma cells (Bisping, 2006). Studies of plasma cell differentiation showed that CD138 must also be considered as a differentiation antigen (Bataille, 2006).

In malignant hematopoiesis, CD138 is highly expressed on the majority of MM cells, ovarian carcinoma, kidney carcinoma, gall bladder carcinoma, breast carcinoma, prostate cancer, lung cancer, colon carcinoma cells and cells of Hodgkin's and non-Hodgkin's lymphomas, chronic lymphocytic leukemia (CLL) (Horvathova, 1995), acute lymphoblastic leukemia (ALL), acute myeloblastic leukemia (AML) (Seftalioglu, 2003 (a); Seftalioglu, 2003 (b)), solid tissue sarcomas, colon carcinomas as well as other hematologic malignancies and solid tumors that express CD138 (Carbone et al., 1999; Sebestyen et al., 1999; Han et al., 2004; Charnaux et al., 2004; O'Connell et al., 2004; Orosz and Kopper, 2001). Expression of CD138 is also associated with different types of gastrointestinal malignancies (Conejo et al., 2000). As shown in Table 2, a number of tumorgenic cell lines exist which are associated with CD138 expression/overexpression.

TABLE 2

CD138 expression on different cell lines. In the context of MM it was shown that the sensitivity towards BT062 correlates with a higher expression of CD138 (RFI = relative fluorescence index).

| cell line | Origin | Sensitivity $IC_{50}$ (nM) | CD138 Expression RFI* | receptors/cell |
|---|---|---|---|---|
| NCI-H929 | MM | 0.38 | 502 | 788,752 |
| PC-3 | prostate cancer | 0.79 | 541 | 195,671 |
| U266 | MM | 1.59 | 617 | 782,987 |
| MOLP-2 | MM | 1.78 | 425 | 161,064 |
| SK-BR-3 | breast carcinoma | 2.72 | 485 | 444,350 |
| LNCaP | postate cancer | 7.39 | 179 | 23,388 |
| CAPAN-2 | pancreas carcinoma | 15.51 | 328 | n.d. |
| PANC-1 | pancreas carcinoma | 36.38 | 34 | 18,085 |
| T47D | breast carcinoma | 89.28 | 217 | 42,264 |
| Jurkat | T cell lymphoma | 39.00 | n.d. | 0 |

The observed sensitivity of, e.g., the breast carcinoma cell lines and pancreas carcinoma cell lines was substantially lower than that of that of the MM cell lines. Nonetheless, as described in the experimental section in xenograft mouse models using cells from patients with breast cancer and pancreatic cancer, not only comparable, but significantly better results than in comparable xenograft models for MM were obtained. In both instances complete remission could eventually be obtained, while comparable MM models showed marked delay in tumor growth, but not complete remission.

While in pancreatic cancer there appears to be no difference in syndecan-1 mRNA expression between early and advanced tumors, in mammary carcinoma, it was reported that CD138 can be lost over time as reflected by weak or lacking IHC staining. CD138 loss of expression had been reported and was often correlated with a shift of expression, i.e., de novo expression on surrounding stroma (Loussouarn, 2008). As a result, fewer targets for CD138 targeting agents can be expected over time.

Other cancers that have been shown to be positive for CD138 expression are many ovarian adenocarcinomas, transitional cell bladder carcinomas, kidney clear cell carcinomas, squamous cell lung carcinomas; and uterine cancers (see, for example, Davies et al., 2004; Barbareschi et al., 2003; Mennerich et al., 2004; Anttonen et al., 2001; Wijdenes, 2002).

The treatment of active (symptomatic) multiple myeloma and related plasmaproliferative disorders shall serve as an example of diseases that can be treated via immunoconjugates of the present invention.

Plasmaproliferative disorder as used herein means plasma cell and/or hematologic disorders such as MGUS, SMM, active (symptomatic) MM, Waldenström's Macroglobulinemia, solitary plasmacytoma, systemic AL amyloidosis and POEMS syndrome.

Multiple myeloma (MM) refers to a malignant proliferation of plasma cells that typically originates in bone marrow, involves chiefly the skeleton of a patient, and presents clinical features attributable to the particular sites of involvement and abnormalities in formation of plasma proteins. The condition is usually characterized by numerous diffuse foci or nodular accumulations of abnormal or malignant plasma cells in the marrow of various bones (especially the skull), causing palpable swellings of the bones, and occasionally in extraskeletal sites. Upon radiological exam, the bone lesions may have a characteristic "punched out" appearance. The cells involved in the myeloma typically produce abnormal proteins and/or abnormal protein levels in the serum and urine. The disease typically develops from monoclonal gammopathy of undetermined significance (MGUS) to smoldering multiple myeloma (SMM) to active multiple myeloma (MM). Symptoms of these conditions vary, but may include hypercalcemia, renal insufficiency, fatigue, anemia, bone pain, spontaneous fractures, increased frequency or duration of infection, or abnormal urine color or odor. When the present invention refers to Multiple Myeloma it refers to (MGUS), smoldering multiple myeloma (SMM) and active multiple myeloma (MM) as well as other malignant proliferation of plasma cells that may eventually develop into active MM.

MGUS, a clinically benign precursor condition of MM is more common than MM, occurring in 1% of the population over age 50 and 3% of those over age 70 (Greipp and Lust, 1995). It is important to distinguish patients with MGUS from those with MM, as MGUS patients may be safely observed without resort to therapy. However, during long-term follow-up, of 241 patients with MGUS, 59 patients (24.5%) went on to develop MM or a related disorder (See Kyle et al., 1993).

The term gammopathy refers to a primary disturbance in immunoglobulin synthesis of a patient.

Monoclonal gammopathy refers to any of a group of disorders that are typically associated with the proliferation of a single clone of lymphoid or plasma cells (normally visible on serum protein electrophoresis (SPEP) as a single peak) and characterized by the presence of monoclonal immunoglobulin in the serum or urine of a patient.

Smoldering MM (SMM) has been reported to precede the onset of symptomatic multiple myeloma in the elderly. Smoldering multiple myeloma is often considered as an advanced phase of MGUS; even at the time of progression, smoldering multiple myeloma usually lacks osteolytic lesions or other cardinal features of symptomatic multiple myeloma.

Clinical symptoms of MM include anemia, hypercalcemia, renal insufficiency, and lytic bone lesions. Distinctions in the course and the severity of the disease as it develops from monoclonal gammopathy of undetermined significance (MGUS) to smoldering multiple myeloma (SMM) to multiple myeloma (MM) are provided in Table 3 below. The table also summarizes methods of detection, diagnosis, and monitoring of these conditions. Such symptoms and techniques are familiar to those of skill in the art.

TABLE 3

Comparison of Clinical Features of MM, SMM, or MGUS

| Characteristic | MM | SMM | MGUS |
| --- | --- | --- | --- |
| Marrow plasma Cells | >=10% | >=10% | <10% |
| Serum M-protein | >=3 g/dL | >=3 g/dL | <3 g/dL |
| Bence-Jones protein in urine | >=1 g/24 h<br>Yes | <1 g/24 h<br>Yes | <1 g/24 h<br>Yes |
| Anemia | usually present | Maybe | Absent |
| Hypercalcemia, renal insufficiency | may be present | absent | Absent |
| Lytic bone lesions | usually present | absent | Absent |

MM = multiple myeloma
SMM = smoldering multiple myeloma
MGUS = monoclonal gammopathy of undetermined significance
Classifying stages by severity and clinical features of multiple myeloma
Stages of disease progression
Stage I (active MM)
Relatively few cancer cells have spread throughout the body. The number of red blood cells and the amount of calcium in the blood are normal. No tumors (plasmacytomas) are found in the bone. The amount of M-protein in the blood or urine is very low. There may be no symptoms of disease.
Stage II (active MM)
A moderate number of cancer cells have spread throughout the body
Stage III (active MM)
A relatively large number of cancer cells have spread throughout the body. There may be one or more of the following:
A decrease in the number of red blood cells, causing anemia.
The amount of calcium in the blood is very high, because the bones are being damaged.
More than three bone tumors (plasmacytomas) are found.
High levels of M-protein are found in the blood or urine.
Clinical features of MM
Hypercalcemia
Renal insufficiency
Anemia
Monoclonal protein:
SPEP (serum protein electrophoresis)
SPIEP (serum protein immunoelectrophoresis)
Urine protein immunoelectrophoresis (Bence-Jones protein)
Diagnosis of MM
>10% plasma cells in marrow or aggregates on biopsy or a plasmacytoma
Monoclonal protein:
Serum M-protein >3 g/dl or
M-protein in urine Active multiple myeloma (MM) is typically recognized clinically by the proliferation of malignant plasma cells in the bone marrow of a patient. These neoplastic plasma cells produce immunoglobulins and evolve from B-lymphocytes. The immunoglobulins that are produced by the plasma cells may be detected in the blood serum and/or urine of a patient by electrophoresis testing.

As indicated in Table 3, the measurement of serum M-protein is an important tool for assessing MM at different stages.

"M-protein" refers to a monoclonal protein that is typically visualized as a narrow band on electrophoretic gel, or an abnormal arc in immunoelectrophoresis. It represents a proliferation of homogenous immunoglobulin produced by clone cells originating from a single common cell, e.g., a monoclonal immunoglobulin characterized by a heavy chain of a single class and subclass, and light chain of a single type (also referred to as a M-spike and more broadly as a paraprotein).

"Serum protein electrophoresis" (SPE or SPEP) and "immunofixation electrophoresis" (IFE) can detect monoclonal immunoglobulin, which is produced in several plasma cell proliferative disorders including multiple myeloma (MM). Population-wide, up to 61% of these findings are not associated with clinical symptoms, allowing for a diagnosis of monogammopathy of undetermined significance (MGUS). SPE and IFE do not, however, detect all monoclonal immunoglobulins, particularly when only light chains are secreted.

Those "free light chain molecules" (FLCs) include $\lambda$ and $\kappa$ light chains. Plasma cells produce one of the five heavy chain types together with either $\kappa$ or $\lambda$ molecules. There is normally approximately 40% excess free light chain production over heavy chain synthesis. Plasma cells secrete free light chains (FLC, kappa or lambda) in addition to intact immunoglobulin molecules, and serum light chain levels are determined by the relative rates of synthesis ($\kappa > \lambda$) and renal excretion ($\kappa > \lambda$). In the presence of a monoclonal immunoglobulin, $\kappa:\lambda$ ratios may be either higher or lower than the normal range, depending on the class of the involved FLC. The serum half-life of FLCs is 2-6 hours, compared with 5 days for IgA, 6 days for IgM and 21 days for IgG. Thus, measurement of serum FLC levels allows a far more rapid evaluation of tumor response to therapy than measurement of intact immunoglobulin. Likewise, serum FLC measurements allow earlier detection of relapse.

Non-plasmaproliferative diseases also are associated with CD138 expression.

Pancreatic Carcinoma The majority of cases comprise exocrine type. The majority of these exocrine cancers represent ductal adenocarcinoma (further more rare subtypes comprise cystic tumors, tumors of acinar cells and sarcoma). Endocrine cancer of the pancreas represents a hormone producing tumor.

Carcinoma in situ refers to the early stage of cancer, when it is confined to the layer of cells where it began. In breast cancer, in situ means that the cancer cells remain confined to ducts (ductal carcinoma in situ) or lobules (lobular carcinoma in situ). They have not grown into deeper tissues in the breast or spread to other organs in the body, and are sometimes referred to as non-invasive or pre-invasive breast cancers. Invasive (infiltrating) carcinoma.

The exocrine cells and endocrine cells of the pancreas form completely different types of tumors.

Exocrine Tumors

These are by far the most common type of pancreas cancer and most pancreatic exocrine tumors are malignant. About 95% of cancers of the exocrine pancreas are adenocarcinomas (an adenocarcinoma is a cancer that starts in gland cells). These cancers usually begin in the ducts of the pancreas, but they sometimes develop from the cells that make the pancreatic enzymes (acinar cell carcinomas).

Less common types of ductal cancers of the exocrine pancreas include adenosquamous carcinomas, squamous cell carcinomas, and giant cell carcinomas.

Endocrine Tumors

Tumors of the endocrine pancreas are uncommon. As a group, they are known as pancreatic neuroendocrine tumors (NETs), or sometimes as islet cell tumors. There are several subtypes of islet cell tumors. Each is named according to the type of hormone-making cell it starts in:

The main system used to describe the stages of cancers of the exocrine pancreas is the American Joint Committee on Cancer (AJCC) TNM system as provided by the American Cancer Society (ACS). The TNM system for staging contains 3 key pieces of information:

T describes the size of the primary tumor(s), measured in centimeters (cm), and whether the cancer has spread within the pancreas or to nearby organs. Distinctions are made between TX, T0, T1, T2, T3 and T4, wherein a higher number indicates advancement of the disease.

N describes the spread to nearby (regional) lymph nodes. N categories include, NX, N0 and N1.

M indicates whether the cancer has metastasized (spread) to other organs of the body. (The most common sites of pancreatic cancer spread are the liver, lungs, and the peritoneum—the space around the digestive organs.) M categories include: MX, M0 and M1.

After the T, N, and M categories have been determined, this information is combined to assign a stage, a process called stage grouping.

Stage 0 (Tis, N0, M0): The tumor is confined to the top layers of pancreatic duct cells and has not invaded deeper tissues. It has not spread outside of the pancreas. These tumors are sometimes referred to as pancreatic carcinoma in situ or pancreatic intraepithelial neoplasia III (PanIn III).

Stage IA (T1, N0, M0): The tumor is confined to the pancreas and is less than 2 cm in size. It has not spread to nearby lymph nodes or distant sites.

Stage IB (T2, N0, M0): The tumor is confined to the pancreas and is larger than 2 cm in size. It has not spread to nearby lymph nodes or distant sites.

Stage IIA (T3, N0, M0): The tumor is growing outside the pancreas but not into large blood vessels. It has not spread to nearby lymph nodes or distant sites.

Stage IIB (T1-3, N1, M0): The tumor is either confined to the pancreas or growing outside the pancreas but not into nearby large blood vessels or major nerves. It has spread to nearby lymph nodes but not distant sites.

Stage III (T4, Any N, M0): The tumor is growing outside the pancreas into nearby large blood vessels or major nerves. It may or may not have spread to nearby lymph nodes. It has not spread to distant sites.

Stage IV (Any T, Any N, M1): The cancer has spread to distant sites.

Although not formally part of the TNM system, other factors are also important in determining prognosis (outlook). The grade of the cancer (how abnormal the cells look under the microscope) is sometimes listed on a scale from G1 to G4, with G1 cancers looking the most like normal cells and having the best outlook.

For patients who have surgery, another important factor is the extent of the resection—whether or not the entire tumor is removed. This is sometimes listed on a scale from R0 (where all visible and microscopic tumor was removed) to R2 (where some visible tumor could not be removed).

From a practical standpoint, how far the cancer has spread often can't be determined accurately without surgery. That's why doctors often use a simpler staging system, which divides cancers into groups based on whether or not it is likely they can be removed surgically. These groups are called resectable, locally advanced (unresectable), and metastatic. These terms can be used to describe both exocrine and endocrine pancreatic cancers.

Resectable: If the cancer is only in the pancreas (or has spread just beyond it) and the surgeon can remove the entire tumor, it is called resectable.

Locally advanced (unresectable): If the cancer has not yet spread to distant organs but it still can't be completely removed with surgery, it is called locally advanced. Often the reason the cancer can't be removed is because too much of it is present in nearby blood vessels.

Metastatic: when the cancer has spread to distant organs, it is called metastatic. Surgery may still be done, but the goal would be to relieve symptoms, not to cure the cancer.

Pancreatic neuroendocrine cancers are not staged like cancers of the exocrine pancreas. Instead the statistics are broken down into different stages: localized (only in the pancreas), regional (spread to nearby lymph nodes or tissues), and distant (spread to distant sites, such as the liver).

Bladder tumors are grouped by the way the cancer cells look under a microscope.

Transitional cell carcinoma (also called urothelial carcinoma) is by far the most common type of bladder cancer. Within this group are also subtypes. They are named depending on the shape of the cells and whether they tend to spread and invade other organs. (If they are likely to grow deeper into the bladder wall they are called invasive, if not likely they are non-invasive.) These tumors are divided into grades based on how the cells look under the microscope. If the cells look more like normal cells, the cancer is called a low-grade cancer. When the cells look very abnormal, the cancer is high-grade. Lower-grade cancers tend to grow more slowly and have a better outcome than higher-grade cancers.

Also included in the definition, are squamous cell carcinoma (uncommon; usually invasive); adenocarcinoma (uncommon; almost all are invasive); small cell (rare). Other rare bladder cancers are also included in this definition.

Bladder cancer is also staged:

Stage 0a (Ta, N0, M0):

The cancer is a noninvasive papillary carcinoma. It has grown toward the hollow center of the bladder but has not grown into the muscle or connective tissue of the bladder wall. It has not spread to lymph nodes or distant sites.

Stage 0is (Tis, N0, M0):

The cancer is a flat, noninvasive carcinoma, also known as flat carcinoma in situ (CIS). The cancer is growing in the lining layer of the bladder only. It has neither grown inward toward the hollow part of the bladder nor has it invaded the muscle or connective tissue of the bladder wall. It has not spread to lymph nodes or distant sites.

Stage I (T1, N0, M0):

The cancer has grown into the layer of connective tissue under the lining layer of the bladder without growing into the thick layer of muscle in the bladder wall. The cancer has not spread to lymph nodes or to distant sites.

Stage II (T2, N0, M0):

The cancer has grown into the thick muscle layer of the bladder wall but, it has not passed completely through the muscle to reach the layer of fatty tissue that surrounds the bladder. The cancer has not spread to lymph nodes or to distant sites.

Stage III (T3 or T4a, N0, M0):

The cancer has grown completely through the bladder into the layer of fatty tissue that surrounds the bladder (T3). It may have spread into the prostate, uterus, or vagina (T4a). It is not growing into the pelvic or abdominal wall. The cancer has not spread to lymph nodes or to distant sites.

Stage IV (T4b, N0, M0) or (any T, N 1 to 3, M0) or (any T, any N, M1):

The cancer has spread through the bladder wall to the pelvic or abdominal wall (T4b) and/or has spread to lymph nodes (N1-3) and/or to distant sites such as bones, liver, or lungs (M1).

Types of Gall Bladder Carcinoma

More than 9 out of 10 gallbladder cancers are adenocarcinomas. An adenocarcinoma is a cancer that starts in the cells with gland-like properties that line many internal and external surfaces of the body (including the inside the digestive system).

A type of gallbladder adenocarcinoma that deserves special mention is called papillary adenocarcinoma or just papillary cancer. These are gallbladder cancers whose cells are arranged in finger-like projections when viewed under a microscope. In general, papillary cancers are not as likely to grow into the liver or nearby lymph nodes. They tend to have a better prognosis (outlook) than most other kinds of gallbladder adenocarcinomas. About 6% of all gallbladder cancers are papillary adenocarcinomas. There are other types of cancer that can develop in the gallbladder, such as adenosquamous carcinomas, squamous cell carcinomas, and small cell carcinomas, but these are uncommon.

Following stages of gall bladder carcinomas are distinguished based on the TNM system of the AJCC:

Stage 0: Tis, N0, M0: There is a small cancer only in the epithelial layer of the gallbladder. It has not spread outside of the gallbladder.

Stage IA: T1(a or b), N0, M0: The tumor grows into the lamina propria (T1a) or the muscle layer (T1b). It has not spread outside of the gallbladder.

Stage IB: T2, N0, M0: The tumor grows into the perimuscular fibrous tissue. It has not spread outside of the gallbladder.

Stage IIA: T3, N0, M0: The tumor extends through the serosa layer and/or directly grows into the liver and/or one other nearby structure. It has not spread to lymph nodes or to tissues or organs far away from the gallbladder.

Stage IIB: T1 to T3, N1, M0: In addition to any growth in the gallbladder, the tumor has spread to nearby lymph nodes (N1). It has not spread to tissues or organs far away from the gallbladder.

Stage III: T4, any N, M0: Tumor invades the main blood vessels leading into the liver or has reached more than one nearby organ other than the liver. It may or may not have spread to lymph nodes. It has not spread to tissues or organs far away from the gallbladder.

Stage IV: Any T, any N, M1: The tumor has spread to tissues or organs far away from the gallbladder.

Mammary Carcinoma An adenocarcinoma refers generally to a type of carcinoma that starts in glandular tissue (tissue that makes and secretes a substance). In the context of breast cancer, the ducts and lobules of the breast are glandular tissue, so cancers starting in these areas are often called adenocarcinomas. There are several types of breast cancer, although some of them are quite rare. In some cases a single breast tumor can have a combination of these types or have a mixture of invasive and in situ cancer.

Ductal carcinoma in situ (DCIS; also known as intraductal carcinoma) is the most common type of non-invasive breast cancer.

Invasive (or infiltrating) ductal carcinoma (IDC) is the most common type of breast cancer. Invasive (or infiltrating) ductal carcinoma (IDC) starts in a milk passage (duct) of the breast, breaks through the wall of the duct, and grows into the fatty tissue of the breast. At this point, it may be able to spread (metastasize) to other parts of the body through the lymphatic system and bloodstream. About 8 of 10 invasive breast cancers are infiltrating ductal carcinomas. IDC patients revealed expression of CD138 (Loussouarn et al., 2008).

Triple-negative breast cancer describe breast cancers (usually invasive ductal carcinomas) whose cells lack estrogen receptors and progesterone receptors, and do not have an excess of the HER2 protein on their surfaces. Triple-negative breast cancers tend to grow and spread more quickly than most other types of breast cancer. Because the tumor cells lack these certain receptors, neither hormone therapy nor drugs that target HER2 are effective against these cancers (although chemotherapy can still be useful if needed).

Some other breast cancers that fall under the term "mammary carcinoma" are Inflammatory breast cancer, medullary carcinoma, metaplastic carcinoma, mucinous carcinoma, tubular carcinoma, papillary carcinoma, adenoid cystic carcinoma (adenocystic carcinoma), phyllodes tumor.

Surgery, radiation or chemotherapy constitutes standard cancer therapies. Hormone therapy is sometimes employed. Hormone therapy is a form of systemic therapy. It is most often used as an adjuvant therapy to help reduce the risk of cancer recurrence after surgery, although it can be used as neoadjuvant treatment, as well. It is also used to treat cancer that has come back after treatment or has spread. Estrogen promotes the growth of about 2 out of 3 of breast cancers—those containing estrogen receptors (ER-positive cancers) and/or progesterone receptors (PR-positive cancers). Because of this, several approaches to blocking the effect of estrogen or lowering estrogen levels are used to treat ER-positive and PR-positive breast cancers. However, hormone therapy is ineffective for patients lacking ERs or PRs.

Mammary carcinoma also follows such a staging system:

Stage 0: Atypical cells have not spread outside of the ducts or lobules, the milk producing organs, into the surrounding breast tissue. Referred to as carcinoma in situ, it is classified in two types: "Ductal Carcinoma In Situ" (DCIS), which is very early cancer that is highly treatable and survivable and "Lobular Carcinoma In Situ" (LCIS), which is not a cancer but an indicator that identifies a woman as having an increased risk of developing breast cancer.

Stage I: The cancer is no larger than two centimeters (approximately an inch) and has not spread to surrounding lymph nodes or outside the breast.

Stage II: This stage is divided into two categories according to the size of the tumor and whether or not it has spread to the lymph nodes:

Stage II A Breast Cancer—the tumor is less than two centimeters and has spread up to three auxiliary underarm lymph nodes. Or, the tumor has grown bigger than two centimeters, but no larger than five centimeters and has not spread to surrounding lymph nodes.

Stage II B Breast Cancer—the tumor has grown to between two and five centimeters and has spread to up to three auxiliary underarm lymph nodes. Or, the tumor is larger than five centimeters, but has not spread to the surrounding lymph nodes.

Stage III: This stage is also divided into two categories:

Stage III: A Breast Cancer—the tumor is larger than two centimeters but smaller than five centimeters and has spread to up to nine auxiliary underarm lymph nodes.

Stage III B Breast Cancer—the cancer has spread to tissues near the breast including the skin, chest wall, ribs, muscles, or lymph nodes in the chest wall or above the collarbone.

Stage IV: Here, the cancer has spread to other organs or tissues, such as the liver, lungs, brain, skeletal system, or lymph nodes near the collarbone.

Lung Cancer

There are 4 types of neuroendocrine lung tumors, namely, large cell neuroendocrine carcinoma, atypical carcinoid tumor, typical carcinoid tumor and small cell lung cancer. Carcinoid tumors are tumors that start from cells of the diffuse neuroendocrine system. Typical and atypical carcinoid tumors look different under the microscope. Typical carcinoids grow slowly and only rarely spread beyond the lungs and about 9 out of 10 lung carcinoids are typical carcinoids.

For treatment purposes two main types of lung cancer, which are very differently treated, are distinguished, namely, small cell lung cancer (SCLC) and non-small cell lung cancer (NSCLC). If the cancer has features of both types, it is called mixed small cell/large cell cancer.

About 10% to 15% of all lung cancers are the small cell type. Other names for SCLC are oat cell carcinoma and small cell undifferentiated carcinoma.

This cancer often starts in the bronchi near the center of the chest. Although the cancer cells are small, they can divide quickly, form large tumors, and spread to lymph nodes and other organs throughout the body. Surgery is rarely an option and never the only treatment given. Treatment includes cytotoxic agents, such as drugs to kill the widespread disease.

There are 3 sub-types of NSCLC, namely squamous cell carcinoma; adenocarcinoma; large-cell (undifferentiated) carcinoma.

Staging of Non-Small Cell Lung Cancer

The system used to stage non-small cell lung cancer is the AJCC (American Joint Committee on Cancer) system. Stages are described using Roman numerals from 0 to IV (0 to 4). Some stages are further divided into A and B. As a rule, the lower the number, the less the cancer has spread. A higher number, such as stage IV (4), means a more advanced cancer.

A respective staging system, including Stages I to IV, was also developed for squamous cell carcinoma (head and neck cancer). Stage I cancers are small, localized and usually curable, stage II and III cancers typically are locally advanced and/or have spread to local lymph nodes and Stage IV cancers usually are metastatic (have spread to distant parts of the body) and generally are considered inoperable.

Treatment in the context of the present invention includes preventing or slowing the progression, stabilizing the disease state, remitting the disease or ameliorating one or more symptoms of a disorder associated with cells expressing CD138. Treatment thus includes preventing or slowing down the increase of severity or the remission of the disorder. In the case of MM generally only patients with stage II or III active MM receive primary therapy (stage I patients or patients with SMM are initially only observed in 3 to 6 month intervals), a treatment according to the present invention does not only include the treatment of, e.g., any active stage of MM, but also includes the treatment of forms of disease states that precede the traditionally treated disease state. Treatment in particular also includes preventing the progression from one disease state to the next: in the case of MM, this would, e.g., be the progression from MGUS to SMM or from SMM to active MM stage I or another stage of MM. In case of cancers of the exocrine pancreas, e.g., a progression from Stage I to Stage II, including any worsening as reflected by the categories established by the AJCC within the stages, e.g. from IA to IB. However, the term also includes maintaining the status quo, such as to maintain stable disease and, as discussed below, eliciting certain responses in the patient treated. A patient is also successfully "treated" if the patient shows observable and/or measurable reduction in or absence of, inter alia, one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. In general, an effect of a certain treatment on the disease status of a patient can be monitored, in the case of MM, by measuring the M-protein levels in the patient's serum and/or urine and/or the FLC levels in the patient's serum and/or urine. In the case of other disorders associated with cells expressing CD138, other parameters are measured to assess the effect of a treatment according to the present invention. CRP(C-reactive protein) is an unspecific inflammation parameter for clinical cancer monitoring. To name just a few, for pancreatic cancer, relevant parameters that may be measured are CA 19-9 (carbohydrate antigen 19.9, a tumor marker often elevated in pancreatic cancer), bilirubin, or CRP. In addition imaging such as sonography, CT, MRT are used. In head and neck cancer, biomarkers which depend on the tumor type are used (e.g., NSE (neuron-specific enolase) for Merkel cell or CEA (carcinoembryonic antigen); in breast carcinoma, CA 15-3Her$_2$ expression and Cadherin expression may be used as markers, while the treatment is monitored by serum markers such as NSE.

The bladder tumor antigen (BTA) and the NMP22 tests can be used along with cystoscopy (using a thin, lighted tube to look in the bladder) in diagnosing the condition in symptomatic subjects. These tests are also being used to follow some patients after treatment, though cystoscopy and urine cytology (using a microscope to look for cancer cells in the urine) are still recommended as the standard tests for diagnosis and follow-up. BTA and NMP22 tests are often used between cystoscopies. Normal values may allow cystoscopy to be done less often. However, these test tests cannot replace urine cytology and cystoscopy.

For advanced bladder cancer, some of the markers used for other cancers such as CEA, CA 125, CA 19-9, and TPA (tissue polypeptide antigen) may be elevated and can be used to follow patients during and after treatment. For lung cancer, no established marker exists, but CEA pr NSE might be elevated.

Tumor cells such as myeloma cells or mammary carcinoma cells are known to shed CD138. The loss of surface CD138 is correlated with poor prognosis in myeloma. High levels of soluble CD138 have been also detected in other oncologic indications such as head and neck or lung cancer (Anttonen et al. 1999). The loss of surface Syndecan-1 is correlated with EMT (epithelial mesenchymal transition) this process describes the transformation of a malignant cell into a less or poorly differentiated cell associated with invasiveness and metastatic stage. This is e.g. reported for metastatic breast cancer (Loussouarn et al., 2008).

An effective amount of an agent, in particular, an immunoconjugate or a pharmaceutical composition comprising an immunoconjugate according to the present invention refers to an amount required to "treat" a disease or disorder in a subject, in particular a human subject (patient). In the case of cancer such as MM, the effective amount of the agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent, one or more of the symptoms associated with the cancer. See the definition herein of "treatment".

"A pharmacokinetic equivalent" of, e.g., 200 mg/m$^2$ refers to the amount of immunoconjugate that results in equal pharmacokinetics observed at dosages of 200 mg/m$^2$ when the immunoconjugate is administered in combination, including co-administered with an agent for treating actual including potential adverse side effects primarily on non-target cells that also express CD138. Those equivalents might be somewhat less than 200 or somewhat more than 200, depending on the other agent. Included are, e.g., effective amounts of less than 160, less than 170, less than 180, less than 190 and less than 210, less than 220, less than 230 and less than 240 mg/m². For example, the person skilled in the art would expect that co-administration with corticosteroids or with antibiotics would allow slightly higher doses of the immunoconjugate even in cases of side effects on skin, which, can, however, be readily ascertained by the person skilled in the art.

To evaluate the success of the administration of a drug, here an immunoconjugate (i.e., its ability to produce a functional response, i.e., its efficacy), different "responses" to an administration are distinguished.

Responses are often evaluated by measuring efficacy blood parameters. Typical efficacy blood parameters are M-protein level, FLC level or other markers that correlate to the disease in question to the efficacy of the immunoconjugate (disease specific marker), in particular the cancer in question. The efficacy indicates the capacity for beneficial change of a given treatment.

In the context of MM and other plasmaproliferative diseases, responses are distinguished as follows:

the term complete response (CR) refers to the negative immunofixation of serum and urine and disappearance of any soft tissue plasmacytomas and <5% plasma cells in bone marrow;

the term stringent complete response (sCR) refers to CR as defined above, plus normal FLC ratio and absence of clonal cells in bone marrow by immunohistochemistry or immunofluorescence;

the term very good partial response (VGPR) refers to serum and urine M-component detectable by immunofixation, but not on electrophoresis or ≤90% or greater reduction in serum M-component plus urine M-component <100 mg per 24 h;

the term partial response (PR) refers to ≤50% reduction of serum M protein and reduction in 24-h urinary M protein by ≥90% or to <200 mg per 24 h, if the serum and urine M protein are immeasurable, a ≥50% decrease in the difference between involved and uninvolved FLC levels is required in place of the M protein criteria, if serum and urine M protein are immeasurable, and serum free light assay is also immeasurable, ≥50% reduction in bone marrow plasma cells is required in place of M protein, provided baseline percentage was ≥30%, in addition to the above criteria, if present at baseline, ≥50% reduction in the size of soft tissue plasmacytomas is also required (Durie et al., 2006).

The term minor response (MR) in relation to patients with relapsed/refractory myeloma refers in the context of the present invention to ≥25% but <49% reduction of serum M protein and reduction in 24 h urine M protein by 50-89%, which still exceeds 200 mg per 24 h, in addition to the above criteria, if present at baseline, 25-49% reduction in the size of soft tissue plasmacytomas is also required, no increase in size or number of lytic bone lesions (development of compression fracture does not exclude response).

However, a response, though not formally classified, also includes an at least 30%, preferably at least 40% or 50% reduction in serum FLC levels. This is in particular of significance in cases where M-protein cannot be measured.

The term stable disease (SD) refers, in the context of the plasmaproliferative diseases of the present invention, to the not meeting of the criteria for CR, VGPR, PR or progressive disease, while the term progressive disease (PD) refers to the increase of 25% from lowest response value in any one or more of the following:

Serum M-component (absolute increase must be ≥0.5 g/100 ml) and/or

Urine M-component (absolute increase must be ≥200 mg per 24 h) and/or

Only in patients without measurable serum and urine M-protein levels: the difference between involved and uninvolved FLC levels (absolute increase must be >100 mg/l)

Bone marrow plasma cell percentage (absolute % must be ≥10%)

Definite development of new bone lesions or soft tissue plasmacytomas or definite increase in the size of existing bone lesions or soft tissue plasmacytomas Development of hypercalcemia (corrected serum calcium >11.5 mg/100 ml) that can be attributed solely to the plasma cell proliferative disorder.

The term relapsed myeloma refers herein to a form of active MM in a subject, wherein said subject underwent at least one prior treatment regime, and which does not meet the criteria for relapsed/refractory myeloma.

The term refractory myeloma generally refers to a state of the disease when the number of plasma cells continues to increase even though treatment is give, that is the disease has, at the time of assessment, been proven irrespective to the treatment regime administered.

The term relapsed/refractory myeloma refers herein to the relapse of disease while on salvage therapy, or progression within 60 days of most recent therapy.

The term refractory phenotype includes any type of refractory myeloma, that is, refractory and relapsed/refractory myeloma.

The term relapsed or refractory myeloma covers relapsed, refractory and relapsed/refractory myeloma.

A tumor or a CD138 target cell is said to be refractory to, e.g., a therapy/treatment if the CD 138 target cell continues dividing and/or the tumor continues growing at the same rate during such a therapy/therapy as without such therapy/treatment.

Tumor growth delay refers to a tumor growth that is delayed relative to regular tumor growth without treatment.

Tumor stasis refers to a state at which there is no further growth in tumor size.

Remission refers to a decrease in tumor size (partial remission), including the complete eradication of the tumor and absence of regrowth (complete remission).

Hormone therapy includes a therapy with a hormone. Cancer hormone therapy is employed to fight target cells. A hormone therapy is used, e.g., in the context of mammary carcinoma or prostate cancer and include the administration of estrogen and progesterone or derivatives thereof.

Chemotherapy is the treatment of cancerous cells with an antineoplastic drug such as taxane or with a combination of such drugs in a standardized treatment regime.

Maintenance therapy is a therapy that follows a prior treatment, and aims at maintaining the status obtained when completing said primary treatment. For example, if the prior treatment resulted in a partial response, the maintenance therapy is designed to maintain partial response.

In the clinical study discussed in more detail below, the subjects had been treated with at least one immunomodulator and a proteosome inhibitor therapy, which have failed, prior to entering the study. Disease was considered treatment refractory if the subject experienced progressive disease (PD) on his or her previous regimen.

The term "progression to", e.g., "active MM" in relation to patients with SMM refers in the context of the present invention to evidence of progression based on the IMWG (International Myeloma Working Group) criteria for progressive disease in MM and any one or more of the following felt related to the underlying clonal plasma cell proliferative disorder, development of new soft tissue plasmacytomas or bone lesions, hypercalcemia (>11 mg/100 ml), decrease in hemoglobin of ≥2 g/100 ml, and serum creatinine level ≥2 mg/100 ml. (Kyle & Rajkumar, 2009).

Progression free survival is the duration from start of a treatment to disease progression or death (regardless of cause of death), whichever comes first. When a reference is made to "progression free survival" without a reference to time period, lack of progression of more than 3 months is implied.

The pathogenesis of multiple myeloma involves binding of myeloma cells, via cell-surface adhesion molecules, to bone marrow stroma cells (BMSCs) as well as the extracellular matrix (ECM). This binding triggers, and thus can be made ultimately responsible, for multiple myeloma cell growth, drug resistance, and migration of MM cells in the bone marrow milieu (Munshi et al. 2008). In particular, the adhesion of multiple myeloma cells to ECM via syndecan-1 (CD138) to type I collagen induces the expression of matrix metalloproteinase 1, thus promoting bone resorption and tumor invasion (Hideshima et al. 2007). Interactions between multiple myeloma cells and the bone marrow microenvironment results in activation of a pleiotropic proliferative and anti-apoptotic cascade.

For multiple myeloma patients, but also for patients suffering from other diseases that are associated with bone pains, a number of supportive treatments exist to treat this and other symptoms. Appropriate medications include bisphosphonates (e.g. pamidronate, zoledronic acid) which can slow the bone damage. It has been demonstrated that these agents are able to reduce osteolytic bone lesions and prevent fractures (Ludwig et al., 2007). They are mostly given through a vein to decrease the risk of bone complications like fractures and to lower abnormally high blood calcium levels (Hypercalcemia). Data suggests that bisphosphonates reduce bone pain associated with MM. Patients may also have surgery if their bones are weak or break.

In one embodiment, the immunoconjugates reduce; in particular reduce to an acceptable level, bone pains and/or bone complications, such as osteonecrosis. A reduction to an acceptable level involves in particular the ability to discontinue the administration of a medication that alleviates these pains or is aimed at reducing said bone complications. Bisphosphonates, such as pamidronate, zoledronic acid and clodronate, are commonly administered to alleviate bone complications, such as osteonecrosis in MM patients and thereby to alleviate bone pains associated with said complications. Common bisphosphonates include, for oral administration, FOSOMAX, BONIVA, ACTONEL, DIDRONEL and SKELID, for intravenous administration, BONEFOS, AREDIA and ZOMETA.

Following the homing of multiple myeloma cells to the bone marrow stromal compartment, adhesion between multiple myeloma cells and BMSCs upregulates many cytokines like interleukin-6 (IL-6) and insulin like growth factor 1 (IGF-1) which have angiogenic and tumor growth promoting activities (Hideshima et al. 2007). The signalling cascades initiated by these cytokines eventually result in MM cell resistance to conventional therapeutics (Anderson et al. 2000; Hideshima et al. 2006).

In the normal human hematopoietic compartment, CD138 expression is restricted to plasma cells (Wijdenes, 1996; Chilosi, 1999) and CD138 is not expressed on peripheral blood lymphocytes, monocytes, granulocytes, and red blood cells. In particular, CD34$^+$ stem and progenitor cells do not express CD138, and anti-CD138 mAbs do not affect the number of colony forming units in hematopoietic stem cell cultures (Wijdenes, 1996). In non-hematopoietic compartments, CD138 is mainly expressed on simple and stratified epithelia within the lung, liver, skin, kidney and gut. Only a weak staining was seen on endothelial cells (Bernfield, 1992; Vooijs, 1996). It has been reported that CD138 exists in polymorphic forms in human lymphoma cells (Gattei, 1999). CD138 epithelial tissue of the gastrointestinal tract, skin, and eye are the non-target tissues that are most prone to be targeted by immunoconjugates of the present invention resulting in toxicities.

Monoclonal antibodies B-B4, BC/B-B4, B-B2, DL-101, 1 D4, MI15, 1.BB.210, 2Q1484, 5F7, 104-9, 281-2 in particular B-B4 have been reported to be specific to CD138. Of those B-B4, 1 D4 and MI15 recognized both the intact molecule and the core protein of CD138 and were shown to recognize either the same or closely related epitopes (Gattei, 1999). Previous studies reported that B-B4 did not recognize soluble CD138, but only CD138 in membrane bound form (Wijdenes, 2002).

The initial anti-CD138 antibody was developed by Diaclone SAS (Besançon, France) as the murine parental Mab B-B4 generated by immunization with the human multiple myeloma cell line U266, using standard hybridoma technology (Clement, 1995; Wijdenes, 1996). B-B4 binds to a linear epitope between residues 90-93 of the core protein on human syndecan-1 (CD138) (Wijdenes, 1996; Dore, 1998). Consistent with the expression pattern of CD138, B-B4 was shown to strongly react with plasma cell line RPMI8226, but not to react with endothelial cells. Also consistent with the expression pattern of CD138, B-B4 also reacted with epithelial cells lines A431 (keratinocyte derived) and HepG2 (hepatocyte derived). An immunotoxin B-B4-saporin was also highly toxic towards the plasma cell line RPMI8226, in fact considerably more toxic than free saporin. However, from the two epithelial cell lines tested, B-B4-saporin showed only toxicity towards cell line A431, although in a clonogenic assay B-B4-saporin showed no inhibitory effect on the outgrowth of A431 cells (Vooijs, 1996).

Other researchers reported lack of specificity of MM-associated antigens against tumors (Couturier, 1999).

B-B4 covalently linked to the maytansinoid DM1 showed selective cytotoxicity on multiple myeloma cell lines and cells, as well as anticancer activity in human multiple myeloma xenograft models in SCID mice (Tassone, 2004).

The present invention uses the term tumor cell to include cancer cells as well as pre-cancerous cells which may or may not form part of a solid tumor. Preferred tumor cells to be treated are cells of hematopoietic malignancies.

A solid tumor according to the present invention is an abnormal mass of tissue that usually does not contain cysts or liquid areas. A solid tumor according to the present invention comprises target tumor cells expressing CD138 and thus is a malignant solid tumor. Different types of solid tumors are named for the type of cells that form them. Examples of solid tumors are sarcomas, carcinomas, and lymphomas. Hematopoietic malignancies generally do not form solid tumors. Mammary carcinoma and prostate carcinoma are two examples of malignant solid tumors.

A targeting agent according to the present invention is able to associate with a molecule expressed by a target cell and includes peptides and non-peptides. In particular, targeting agents according to the present invention include targeting antibodies and non-immunoglobulin targeting molecules, which may be based on non-immunoglobulin proteins, including, but not limited to, AFFILIN® molecules, ANTICALINS® and AFFIBODIES®. Non-immunoglobulin targeting molecules also include non-peptidic targeting molecules such as targeting DNA and RNA oligonucleotides (aptamers), but also physiological ligands, in particular ligands of the antigen in question, such as CD138.

A targeting antibody according to the present invention is or is based on a natural antibody or is produced synthetically or by genetic engineering and binds to an antigen on a cell or cells (target cell(s)) of interest. A targeting antibody according to the present invention includes a monoclonal antibody, a polyclonal antibody, a multispecific antibody (for example, a bispecific antibody), or an antibody fragment. The targeting antibody may be engineered to, for example, improve its affinity to the target cells (Ross, 2003) or diminish its immunogenicity. The targeting antibody may be attached to a liposomal formulation including effector molecules (Carter, 2001). An antibody fragment comprises a portion of an intact antibody, preferably the antigen binding or variable region of the intact antibody. Examples of antibody fragments according to the present invention include Fab, Fab', F(ab')$_2$, and Fv fragments, but also diabodies; domain antibodies (dAb) (Ward, 1989; U.S. Pat. No. 6,005,079); linear antibodies; single-chain antibody molecules; and multispecific antibodies formed from antibody fragments. In a single chain variable fragment antibody (scFv) the heavy and light chains (VH and VL) can be linked by a short amino acid linker having, for example, the sequence (glycine$_4$serine)$_n$, which has sufficient flexibility to allow the two domains to assemble a functional antigen binding pocket. Addition of various signal sequences may allow for more precise targeting of the targeting antibody. Addition of the light chain constant region (CL) may allow dimerization via disulphide bonds, giving increased stability and avidity. Variable regions for constructing the scFv can, if a mAb against a target of interest is available, be obtained by RT-PCR which clones out the variable regions from mRNA extracted from the parent hybridoma. Alternatively, the scFv can be generated de novo by phage display technology (Smith, 2001). As used herein, the term "functional fragment", when used in reference to a targeting antibody, is intended to refer to a portion of the targeting antibody which is capable of specifically binding an antigen that is specifically bound by the antibody reference is made to. A bispecific antibody according to the present invention may, for example, have at least one arm that is reactive against a target tissue and one arm that is reactive against a linker moiety (United States Patent Publication 20020006379). A bispecific antibody according to the present invention may also bind to more than one antigen on a target cell (Carter, 2001). An antibody according to the present invention may be modified by, for example, introducing cystein residues to introduce thiol groups (Olafsen, 2004).

In accordance with the present invention, the targeting antibody may be derived from any source and may be, but is not limited to, a camel antibody, a murine antibody, a chimeric human/mouse antibody or a chimeric human/monkey antibody, in particular, a chimeric human/mouse antibody such as nBT062.

Humanized antibodies are antibodies that contain sequences derived from a human-antibody and from a non-human antibody and are also within the scope of the present invention. Suitable methods for humanizing antibodies include CDR-grafting (complementarity determining region grafting) (EP 0 239 400; WO 91/09967; U.S. Pat. Nos. 5,530,101; and 5,585,089), veneering or resurfacing (EP 0 592 106; EP 0 519 596; Padlan, 1991; Studnicka et al., 1994; Roguska et al., 1994), chain shuffling (U.S. Pat. No. 5,565,332) and DeImmunosation™ (Biovation, LTD). In CDR-grafting, the mouse complementarity-determining regions (CDRs) from, for example, mAb B-B4 are grafted into human variable frameworks, which are then joined to human constant regions, to create a human B-B4 antibody (hB-B4). Several antibodies humanized by CDR-grafting are now in clinical use, including MYLOTARG (Sievers et al., 2001) and HECEPTIN (Pegram et al, 1998).

The resurfacing technology uses a combination of molecular modeling, statistical analysis and mutagenesis to alter the non-CDR surfaces of antibody variable regions to resemble the surfaces of known antibodies of the target host. Strategies and methods for the resurfacing of antibodies, and other methods for reducing immunogenicity of antibodies within a different host, are disclosed, for example, in U.S. Pat. No. 5,639,641. Human antibodies can be made by a variety of methods known in the art including phage display methods. See also U.S. Pat. Nos. 4,444,887, 4,716,111, 5,545,806, and 5,814,318; and international patent application publications WO 98/46645, WO 98/50433, WO 98/24893, WO 98/16654, WO 96/34096, WO 96/33735, and WO 91/10741.

Targeting antibodies that have undergone any non-natural modification such as chimeric human/mouse antibodies or a chimeric human/monkey antibodies, humanized antibodies or antibodies that were engineered to, for example, improve their affinity to the target cells or diminish their immunogenicity but also antibody fragments, in particular functional fragments of such targeting antibodies that have undergone any non-natural modification, diabodies; domain antibodies; linear antibodies; single-chain antibody molecules; and multispecific antibodies are referred to herein as engineered targeting antibodies.

Chimerized antibodies, maintain the antibody binding region (ABR or Fab region) of the non-human antibody, e.g., the murine antibody they are based on, while any constant regions may be provided for by, e.g., a human antibody. Generally, chimerization and/or the exchange of constant regions of an antibody will not affect the affinity of an antibody because the regions of the antibody which contribute to antigen binding are not affected by this exchange. In a preferred embodiment of the present invention, the engineered, in particular chimerized, antibody of the present invention, may have a higher binding affinity (as expressed by $K_D$ values) than the respective non-human antibody it is based on. In particular, the nBT062 antibody and antibodies based thereon may have higher antibody affinity than the murine B-B4.

In another preferred embodiment of the present invention, immunoconjugates comprising those engineered/chimerized antibodies also display this higher antibody affinity. These immunoconjugates may also display in certain embodiments other advantageous properties, such as a higher reduction of tumor load than their B-B4 containing counterparts. In a preferred embodiment, the engineered, in particular chimerized targeting antibodies display binding affinities that are characterized by dissociation constants $K_D$ (nM) of less than 1.6, less than 1.5 or about or less than 1.4, while their murine counterparts are characterized by dissociation constants $K_D$ (nM) of about or more than 1.6. Immunoconjugates comprising targeting agents such as targeting antibodies may be characterized by dissociation constants of $K_D$ (nM) of less than 2.6, less than 2.5, less than 2.4, less than 2.3, less than 2.2, less than 2.1, less than 2.0, less than or about 1.9 are preferred, while immunoconjugates comprising the murine counterpart antibodies may be characterized by dissociation constants $K_D$ (nM) of about or more than 2.6 (compare Table 12 Materials and Methods).

The basic antibody molecule is a bifunctional structure wherein the variable regions bind antigen while the remaining constant regions may elicit antigen independent responses. The major classes of antibodies, IgA, IgD, IgE, IgG and IgM, are determined by the constant regions. These classes may be further divided into subclasses (isotypes). For example, the IgG class has four isotypes, namely, IgG1, IgG2, IgG3, and IgG4 which are determined by the constant regions. Of the various human antibody classes, only human IgG1, IgG2, IgG3 and IgM are known to effectively activate the complement system. While the constant regions do not form the antigen binding sites, the arrangement of the constant regions and hinge region may confer segmental flexibility on the molecule which allows it to bind with the antigen.

Different IgG isotypes can bind to Fc receptors on cells such as monocytes, B cells and NK cells, thereby activating the cells to release cytokines. Different isotypes may also activate complement, resulting in local or systemic inflammation. In particular, the different IgG isotypes may bind FcγR to different degrees. FcγRs are a group of surface glycoproteins belonging to the Ig superfamily and expressed mostly on leucocytes. The FcγR glycoproteins are divided into three classes designated FcγRI (CD64), FcγRII (CD32) and FcγRIII (CD16). While IgG1, IgG2 and IgG3 bind strongly to a variety of these classes of FcγR glycoproteins, IgG4 displays much weaker binding. In particular, IgG4 is an intermediate binder of FcγRI, which results in relatively low or even no ADCC (antibody dependent cellular cytotoxicity), and does not bind to FcγRIIIA or FcγRIIA. IgG4 is also a weak binder of FcγRIIB, which is an inhibitory receptor. Furthermore, IgG4 mediates only weak or no complement fixation and weak or no complement dependent cytotoxicity (CDC). In the context of the present invention, IgG4 may be specifically employed to prevent Fc-mediated targeting of hepatic FcR as it displays no interaction with FcRγII on LSECs (liver sinusoidal endothelial cells), no or weak interaction with FcRγI-III on Kupffer cells (macrophages) and no interaction with FcRγIII on hepatic NK cells. Certain mutations that further reduce any CDC are also part of the present invention. For example IgG4 residues at positions 327, 330 and 331 were shown to reduce ADCC (antibody dependent cellular cytotoxicity) and CDC (Amour, 1999; Shields, 2001). One of more mutations that stabilize the antibody is also part of the present invention (also referred to herein as "stabilizing mutations"). Those mutations include in particular, leucine-to-glutamic acid mutations in the CH2 region of IgG4 and serine-to-proline exchanges in the IgG4 hinge core. These mutations decrease, in certain embodiments of the invention, the amount of half-molecules to less than 10%, less than 5% and preferably less than 2% or 1%. Moreover, the in vivo half life of so stabilized antibodies might be increased several days, including 1, 2, 3, 4 or more than 5 days (Schuurman, 1999).

When the present invention refers to an immunoconjugate comprising an engineered targeting antibody conferring IgG4 isotype properties, this means that the engineered targeting antibody shows significantly reduced affinity to Fc receptor expressing cells as compared to the affinity of antibodies of IgG1 isotype. These properties are preferably conferred by a further antibody region, which is distinct from the ABR, wherein said further antibody region is in whole or part of a human antibody. The result is a significantly reduced (more than 90% relative to its IgG1 isotype counterpart) or the total lack of a potential to induce CDC or ADCC as compared to the potential to induce CDC or ADCC usually observed with IgG1 isotype antibodies. This property can be measured in cell based assays by using the engineered targeting antibody in its unconjugated form. CDC and ADCC can be measured via different methods such as the one disclosed in Cancer Immunol. Immunother., 36, 373 (1993) or the GUAVA Cell Toxicity Assay. The overall benefit of immunoconjugates comprising at least part of an engineered targeting antibody conferring IgG4 isotype properties is an improvement of binding specificity and a reduced toxicity. Also the resulting reduced affinity to Fc receptors improves antigen-specific targeting of tumor cells leading to reduced toxicity against CD138 negative cells.

Targeting agents, including targeting antibodies disclosed herein may also be described or specified in terms of their binding affinity to an antigen, in particular to CD138. Preferred binding affinities of targeting agents such as targeting antibodies are characterized by dissociation constants $K_D$ (nM) of less than 1.6, less than 1.5 or about or less than 1.4. For immunoconjugates comprising said targeting agents such as targeting antibodies dissociation constants $K_D$ (nM) of less than 1.6, less than 1.5 or less than 2.5, less than 2.4, less than 2.3, less than 2.2, less than 2.1, less than 2.0, less than or about 1.9 are preferred.

An antigen binding region (ABR) according to the present invention will vary based on the type of targeting antibody or engineered targeting antibody employed. In a naturally occurring antibody and in most chimeric and humanized antibodies, the antigen binding region is made up of a light chain and the first two domains of a heavy chain. However, in a heavy chain antibody devoid of light chains, the antigen binding region will be made up of, e.g., the first two domains of the heavy chain only, while in single chain antibodies (ScFv), which combine in a single polypeptide chain the light and heavy chain variable domains of an antibody molecule, the ABR is provided by only one polypeptide molecule. FAB fragments are usually obtained by papain digestion and have one light chain and part of a heavy chain and thus comprise an ABR with only one antigen combining site. On the other hand, diabodies are small antibody fragments with two antigen-binding regions. In the context of the present invention, however, an antigen binding region of a targeting antibody or on engineered targeting antibody is any region that primarily determines the binding specificity of the targeting antibody or the engineered targeting antibody.

If an ABR or another targeting antibody region is said to be "of a certain antibody", e.g., a human or non-human antibody, this means in the context of the present invention that the ABR is either identical to a corresponding naturally occurring ABR or is based thereon. An ABR is based on a naturally occurring ABR if it has the binding specificity of the naturally occurring ABR. However, such an ABR may comprise, e.g., point mutations, additions, deletions or post-translational modification such as glycosylation. Such an ABR may in particular have more than 70%, more than 80%, more than 90%, preferably more than 95%, more than 98% or more than 99% sequence identity with the sequence of the naturally occurring ABR.

nBT062 (see also FIG. 1) is a murine human chimeric IgG4 mAb, namely a chimerized version of B-B4. This chimerized version of B-B4 was created to reduce the HAMA (Human Anti-Mouse Antibody) response, while maintaining the functionality of the antibody binding region of the B-B4 for CD138. Surprisingly, the results obtained using an immunoconjugate comprising this engineered targeting antibody were much more homogenous (the variance in the results was reduced). The protocol for producing nBT062 is specified below. Chinese hamster ovary cells expressing nBT062 have been deposited with the DSMZ-Deutsche Sammlung von Mikroorganismen und Zellkulturen GmbH, Mascheroder Weg 1, D-38124 Braunschweig on Dec. 11, 2007. The identification number is DSM ACC2875. A CD138 specific chimeric antibody based on B-B4 is generically referred to herein as c-B-B4.

The amino acid sequence for both the heavy and the light chains has been predicted from the translation of the nucleotide sequence for nBT062. The amino acid sequences predicted for the heavy chain and light chain are presented in Table 4. Predicted variable regions are bolded, predicted CDRs are underlined.

TABLE 4

Predicted Amino Acid Sequence for nBT062 nBT062 heavy chain predicted sequence (SEQ ID NO: 1):

```
  1  QVQLQQSGSE LMMPGASVKI SCKATGYTFS NYWIEWVKQR PGHGLEWIGE

51  ILPGTGRTIY NEKFKGKATF TADISSNTVQ MQLSSLTSED SAVYYCARRD

101  YYGNFYYAMD YWGQGTSVTV SSASTKGPSV FPLAPCSRST SESTAALGCL

151  VKDYFPEPVT VSWNSGALTS GVHTFPAVLQ SSGLYSLSSV VTVPSSSLGT

201  KTYTCNVDHK PSNTKVDKRV ESKYGPPCPS CPAPEFLGGP SVFLFPPKPK

251  DTLMISRTPE VTCVVVDVSQ EDPEVQFNWY VDGVEVHNAK TKPREEQFNS

301  TYRVVSVLTV LHQDWLNGKE YKCKVSNKGL PSSIEKTISK AKGQPREPQV

351  YTLPPSQEEM TKNQVSLTCL VKGFYPSDIA VEWESNGQPE NNYKTTPPVL

401  DSDGSFFLYS RLTVDKSRWQ EGNVFSCSVM HEALHNHYTQKSLSLSLG(K)
```

The C-terminal lysine is prone to clipping and might be present due to incomplete clipping to a certain extent. The (K) in parenthesis is not part of SEQ ID NO: 1.

nBT062 light chain predicted sequence (SEQ ID NO: 2):

```
  1  DIQMTQSTSS LSASLGDRVT ISCSASQGIN NYLNWYQQKP DGTVELLIYY

51  TSTLQSGVPS RFSGSGSGTD YSLTISNLEP EDIGTYYCQQ YSKLPRTFGG

101  GTKLEIKRTV AAPSVFIFPP SDEQLKSGTA SVVCLLNNFY PREAKVQWKV

151  DNALQSGNSQ ESVTEQDSKD STYSLSSTLT LSKADYEKHK VYACEVTHQG

201  LSSPVTKSFN RGEC
```

Table 5. shows a comparision of the general CDR definitions of Krabat and Chothia and the predicted CDRs for nBT062

| nBT062 | | |
|---|---|---|
| Kabat CDR definition | | |
| Light chain | CDR1: residues 24-34 | CDR1: residues 24-34 |
| | CDR2: residues 50-56 | CDR2: residues 50-56 |
| | CDR3: residues 89-97 | CDR3: residues 89-97 |
| Heavy chain | CDR1: residues 31-35 | CDR1: residues 31-35 |
| | CDR2: residues 50-56 | CDR2: residues 51-68 |
| | CDR3: residues 95-102 | CDR3: residues 99-111 |
| Chothia CDR definition | | |
| Light chain | CDR1: residues 26-32 | CDR1: residues 24-34 |
| | CDR2: residues 50-52 | CDR2: residues 50-56 |
| | CDR3: residues 91-96 | CDR3: residues 89-97 |

| nBT062 | |
|---|---|
| Heavy chain | CDR1: residues 26-32    CDR1: residues 31-35 |
| | CDR2: residues 52-56    CDR2: residues 51-68 |
| | CDR3: residues 96-101   CDR3: residues 99-111 |

Fully human antibodies may also be used. Those antibodies can be selected by the phage display approach, where CD138 or an antigenic determinant thereof is used to selectively bind phage expressing, for example, B-B4 variable regions (see, Krebs, 2001). This approach is advantageously coupled with an affinity maturation technique to improve the affinity of the antibody. All antibodies referred to herein are isolated antibodies (See US Patent Publication 20090175863).

In one embodiment, the targeting antibody is, in its unconjugated form, moderately or poorly internalized. Moderate internalization constitutes about 30% to about 75% internalization of total antibody, poor internalization constitutes about 0.01% to up to about 30% internalization after 3 hours incubation at 37° C. In another preferred embodiment the targeting antibody binds to CD138, for example, antibodies B-B4, BC/B-B4, B-B2, DL-101, 1 D4, MI15, 1.BB.210, 2Q1484, 5F7, 104-9, 281-2 in particular B-B4. Hybridoma cells, which were generated by hybridizing SP02/0 myeloma cells with spleen cells of Balb/c mice have been deposited with the DSMZ-Deutsche Sammlung von Mikroorganismen und Zellkulturen GmbH, Mascheroder Weg 1, D-38124 Braunschweig on Dec. 11, 2007. The identification number of these B-B4 expressing hybridoma cells is DSM ACC2874. In another embodiment, the targeting antibody does not substantially bind non-cell-surface expressed CD138. When, in the context of the present invention, the name of a specific antibody is combined with the term "targeting antibody" such as "nBT062 targeting antibody," this means that this targeting antibody has the binding specificity of the antibody nBT062. If a targeting antibody is said to be "based on" a specified antibody, this means that this targeting antibody has the binding specificity of this antibody, but might take any form consistent with the above description of a targeting antibody. When, in the context of the present invention, the name of a specific antigen is combined with the term "targeting antibody" such as "CD138 targeting antibody," this means that this targeting antibody has binding specificity for CD138. If, in the context of the present invention, for example, a targeting antibody is said to do something "selectively" such as "selectively targeting cell-surface expressed CD138" or, to be "selective" for something, this means that there is a significant selectivity (i.e. a higher affinity towards CD138-positive cells compared with CD138-negative cells) for, in the case of the example provided, cell-surface expressed CD138, compared to any other cell-surface expressed antigen. Adverse side effects in a given environment may be substantially reduced or even avoided due to this selectivity.

"Non-immunoglobulin targeting molecules" according to the present invention include targeting molecules derived from non-immunoglobulin proteins as well as non-peptidic targeting molecules. Small non-immunoglobulin proteins which are included in this definition are designed to have specific affinities towards; in particular, surface expressed CD138. These small non-immunoglobulin proteins include scaffold based engineered molecules such as AFFILIN molecules that have a relatively low molecular weight such as between 10 kDa and 20 kDa. Appropriate scaffolds include, for example, gamma crystalline. Those molecules have, in their natural state, no specific binding activity towards the target molecules. By engineering the protein surfaces through locally defined randomization of solvent exposed amino acids, completely new binding sites are created. Former non-binding proteins are thereby transformed into specific binding proteins. Such molecules can be specifically designed to bind a target, such as CD138, and allow for specific delivery of one or more effector molecules (see, scil Proteins GmbH at www.scilproteins.com, 2004). Another kind of non-immunoglobulin targeting molecules are derived from lipocalins, and include, for example ANTICALINS, which resemble in structure somewhat immunoglobulins. However, lipocalins are composed of a single polypeptide chain with 160 to 180 amino acid residues. The binding pocket of lipocalins can be reshaped to recognize a molecule of interest with high affinity and specificity (see, for example, Beste et al., 1999). Artificial bacterial receptors such as those marketed under the trademark Affibody® (Affibody AB) are also within the scope of the present invention. These artificial bacterial receptor molecules are small, simple proteins and may be composed of a three-helix bundle based on the scaffold of one of the IgG-binding domains of Protein A (*Staphylococcus aureus*). These molecules have binding properties similar to many immunoglobulins, but are substantially smaller, having a molecular weight often not exceeding 10 kDa and are also comparatively stable. Suitable artificial bacterial receptor molecules are, for example, described in U.S. Pat. Nos. 5,831,012; 6,534,628 and 6,740,734.

Other "non-immunoglobulin targeting molecules" are physiological ligands of the antigen in question. Physiological ligands of CD138 include for example, but not limited to, ADAMTS4 (aggrecanase-1), antithrombin-3, bFGF, cathepsin G, CCL5 (RANTES), CCL7, CCL11, CCL17, CD44, collagens (collagen type 1, collagen type 2, collagen type 3, collagen type 4, collagen type 5, collagen type 6), CXCL1, elastase, gp120, HGF [hepatocyte growth factor], laminin-1, laminin-2, laminin-5, midkine, MMP-7, neutrophil elastase, and pleiotrophin (HBNF, HBGF-8). Non-peptidic targeting molecules include, but are not limited to, to DNA and RNA oligonucleotides that bind to CD138 (aptamers).

An "effector molecule" according to the present invention is a molecule or a derivative, or an analogue thereof which is attached to a targeting agent, in particular a targeting antibody and/or an engineered targeting antibody, and that exerts a desired effect, e.g., apoptosis, or another type of cell death, or a continuous cell cycle arrest on the target cell or cells. Effector molecules according to the present invention include molecules that can exert desired effects in a target cell and include, but are not limited to, cytotoxic drugs, including low molecular weight cytotoxic drugs (Molecular mass of less than 1500 Da, preferably less than 1400, less than 1200, less than 1000, less than 800, less than 700, less than 600, less than 500, less than 300 but generally more than 120 Da). These cytotoxic drugs are, according to the present invention, generally non-proteinaceous biological cytotoxic drugs and contain or induce, upon administration, the production of another cytotoxic drug of at least 5 C atoms, 10 C atoms, preferably more than 12 C atoms, often more than 20 C atoms and sometimes more than 30, 40 or 50 C atoms and generally at least one ring structure, such as a benzene ring, which is often substituted. However, often interconnecting ring structures are part of these molecules. These non-proteinaceous biological cytotoxic drugs may intercalate into DNA (DNA intercalators) or alkylate DNA, inhibit microtubule formation, are inhibitors of mitosis, inhibitors of enzymes involved in the structural integrity of DNA, such as histone deacetylate or inhibitors of enzymes that are otherwise vital to a cell and cause disruption of cell metabolism. Effectors can also be categorized as radionuclides, biological response modifiers, pore-forming agents, ribonucleases, proteins of apoptotic signaling cascades with apoptosis-inducing activities, antisense oligonucleotides, anti-metastatic agents, anti-oxidative substances, antibodies or cytokines as well as functional derivatives or analogues/fragments thereof.

In a preferred embodiment, the effector molecule increases internal effector delivery of the immunoconjugate, in particular when the natural form of the antibody on which the targeting antibody of the immunoconjugate is based is poorly internalizable. In another preferred embodiment the effector is, in its native form, non-selective. In certain embodiments the effector has high non-selective toxicity, including systemic toxicity, when in its native form. The "native form" of an effector molecule of the present invention is an effector molecule before being attached to the targeting agent to form an immunoconjugate. In another preferred embodiment, the non-selective toxicity of the effector molecule is substantially eliminated upon conjugation to the targeting agent. In another preferred embodiment, the effector molecule causes, upon reaching the target cell, death or cell cycle arrest, including continuous cell cycle arrest, in the target cell.

An effector molecule according to the present invention includes, but is not limited to, antineoplastic agents, in particular intracellular chemotherapeutic agents, which are defined below.

| Effector | Molecular mass (g/mol [Da] |
|---|---|
| Doxorubicin | 564 |
| Daunurubicin | 528 |
| Vinblastin | 811 |
| Docetaxel | 808 |
| Paclitaxel | 854 |
| Epothilone B | 508 |
| Vorinostat | 264 |
| Neocarzinostatin | 660 |
| Calicheamicin γ1 | 1368 |
| Esperamicin | 1342 |
| Methotrexate | 454 |
| Sylimarin components | 482 |
| Masoprocol | 302 |
| Aminolevulinic acid | 132 |
| Miltefosine | 407 |
| Epigallocatechin gallate (EGCG) | 459 |
| Psoralene | 186 |
| Melphalan | 304 |

Table 6 provides examples of low molecular weight cytotoxic drugs that may serve as effector molecules.

Low molecular weight cytotoxic drugs (see above for molecular weights) may preferably be antimitotics, more particular, tubulin affecting agents, which include inhibitors of tubulin polymerization such as maytansinoids, dolastatins (and derivatives such as auristatin) and crytophycin and potent taxoid (taxane) drugs (Payne, 2003). Further included in the definition of small highly cytotoxic drug are other tubulin interfering agents such as epothilones (e.g. ixabepilone) and colchicine derivatives (tubulin interfering agents are further discussed below).

An effector molecule that is a maytansinoid includes maytansinoids of any origin, including, but not limited to synthetic maytansinol and maytansinol analogue and derivative.

Maytansine is a natural product originally derived from the Ethiopian shrub *Maytenus serrata* (Remillard, 1975; U.S. Pat. No. 3,896,111). This drug inhibits tubulin polymerization, resulting in mitotic block and cell death (Remillard, 1975; Bhattacharyya, 1977; Kupchan, 1978). The cytotoxicity of maytansine is 200-1000-fold higher than that of anti-cancer drugs in clinical use that affect tubulin polymerization, such as Vinca alkaloids or taxol. However, clinical trials of maytansine indicated that it lacked a therapeutic window due to its high systemic toxicity. Maytansine and maytansinoids are highly cytotoxic but their clinical use in cancer therapy has been greatly limited by their severe systemic side-effects primarily attributed to their poor selectivity for tumors. Clinical trials with maytansine showed serious adverse effects on the central nervous system and gastrointestinal system.

Maytansinoids have also been isolated from other plants including seed tissue of *Trewia nudiflora* (U.S. Pat. No. 4,418,064)

Certain microbes also produce maytansinoids, such as maytansinol and C-3 maytansinol esters (U.S. Pat. No. 4,151,042).

The present invention is directed to maytansinoids of any origin, including synthetic maytansinol and maytansinol analogues which are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,371,533; 4,424,219 and 4,151,042.

In a preferred embodiment, the maytansinoid is a thiol-containing maytansinoid and is more preferably produced according to the processes disclosed in U.S. Pat. No. 6,333,410 to Chari et al or in Chari et al. (Chari, 1992).

DM-1 ($N^2$-deacetyl-$N^2$-(3-mercapto-1-oxopropyl)-maytansine) is a preferred effector molecule in the context of the present invention. DM1 is 3- to 10-fold more cytotoxic than maytansine, and has been converted into a pro-drug by linking it via disulfide bond(s) to a monoclonal antibody directed towards a tumor-associated antigen. Certain of these conjugates (sometimes called "tumor activated prodrugs" (TAPs)) are not cytotoxic in the blood compartment, since they are activated upon associating with a target cells and internalized, thereby releasing the drug (Blather, 2001). Several antibody-DM1 conjugates have been developed (Payne, 2003), and been evaluated in clinical trials. For example, huC242-DM1 treatment in colorectal cancer patients was well tolerated, did not induce any detectable immune response, and had a long circulation time (Tolcher, 2003).

Figure 4:
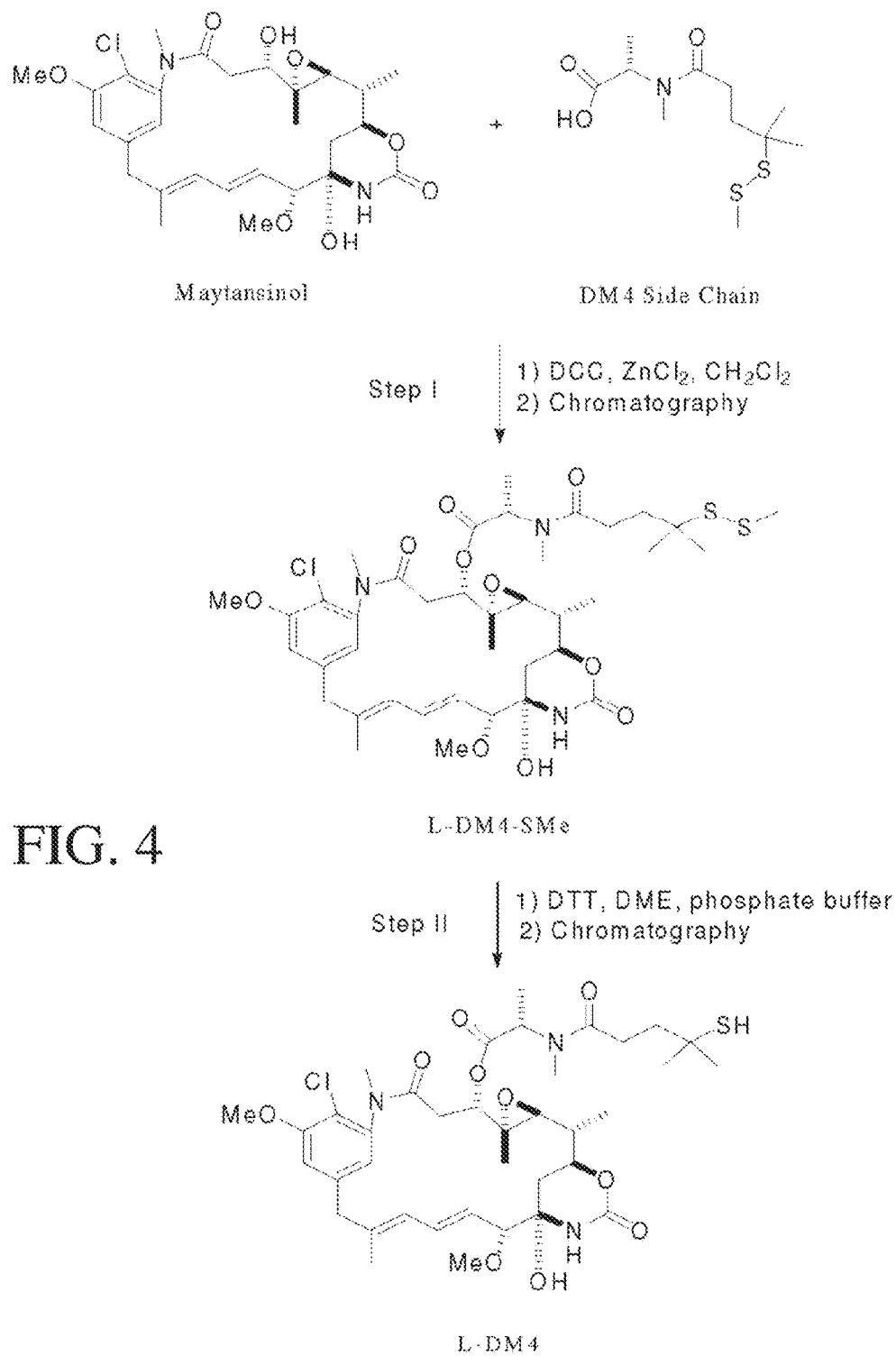
FIG. 4 shows a representative synthesis scheme of DM4.
Figure 5:
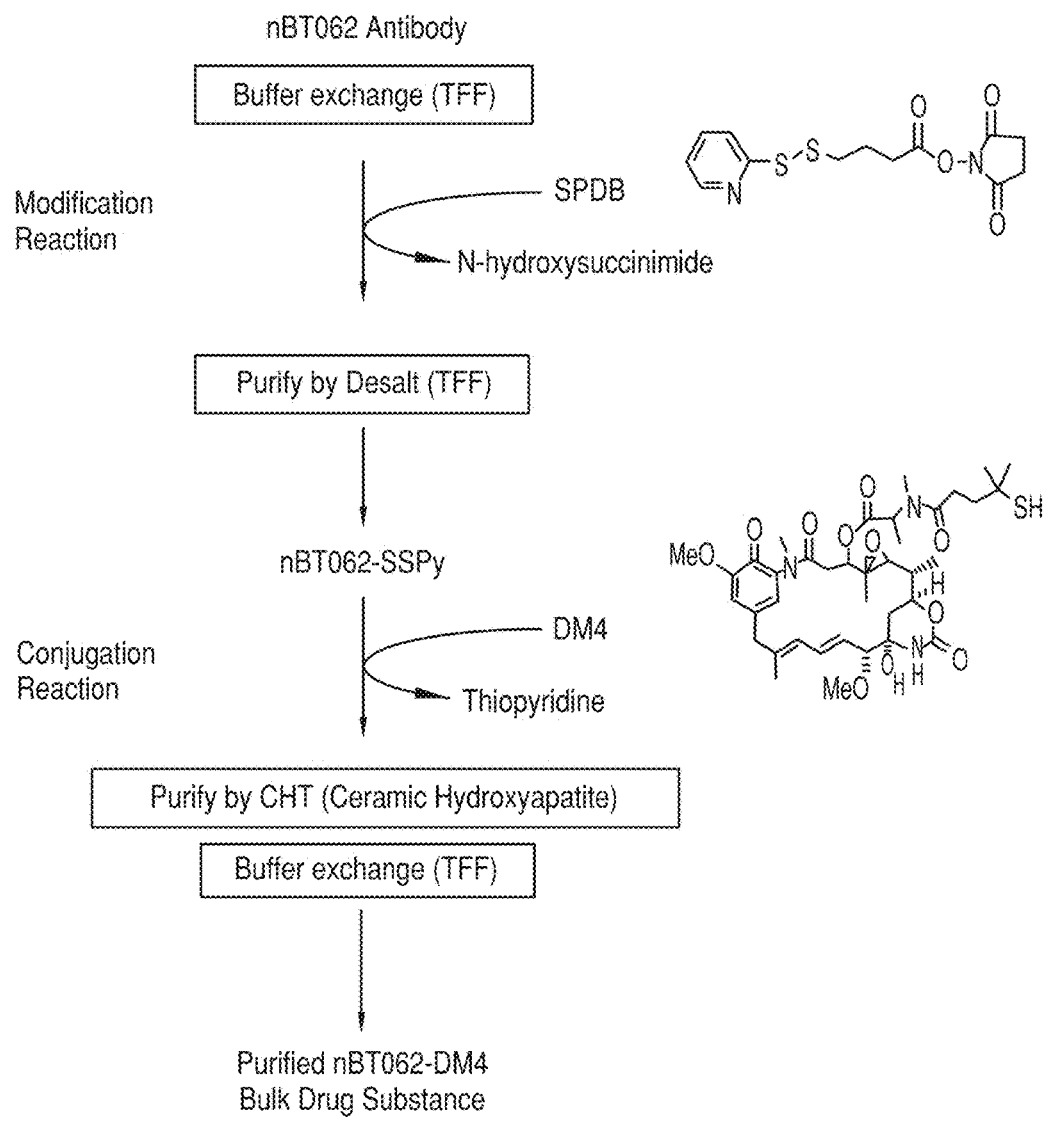
FIG. 5 is a schematic representation of an antibody conjugation (nBT062 to DM4).

Other particularly preferred maytansinoids comprise a side chain that contains a sterically hindered thiol bond such as, but not limited to, maytansinoids $N^{2'}$-deacetyl-$N^{2'}$-(4-mercapto-1-oxopentyl)-maytansine, also referred to as "DM3," and $N^{2'}$-deacetyl-$N^{2'}$-(4-methyl-4-mercapto-1-oxopentyl)-maytansine, also referred to as "DM4." The synthesis of DM4 is shown in FIGS. 3 and 4 and is described elsewhere herein. DM4 differs from DM1 and DM3 in that it bears methyl groups at its αC. This results in a sterical hindrance when DM4 is attached via a linker in particular, but not limited to, a linker comprising a disulfide bond, to a targeting agent such as nBT062. A wide variety of maytansinoids bearing a sterically hindered thiol group (possessing one or two substituents, in particular alkyls substituents, such as the methyl substituents of DM4) are disclosed U.S. Patent Publication 2004/0235840, published Nov. 25, 2004, which is incorporated herein in its entirety by reference. The steric hindrance conferred by alkyl groups such as the methyl groups on the carbon adjacent to the sulfur atom of DM3 and DM4 may affect the rate of intracellular cleavage of the immunoconjugate. The variable alkyl unit may therefore affect potency, efficacy, and safety/toxicity in vitro and in vivo.

As reported by Goldmakher et al. in U.S. Patent Publication 2006/0233814, such a hindrance induces alkylation (e.g., methylation) of the free drug once the drug is released at its target. The alkylation may increase the stability of the drug allowing for the so-called bystander effect. However, as the person skilled in the art will appreciate, other effector molecules comprising substituents such as alkyl groups at positions that result in a sterical hindrance when the effector is attached to a targeting agent via a linker are part of the present invention (U.S. Patent Publication 2004/0235840). Preferably this hindrance induces a chemical modification such as alkylation of the free drug to increase its overall stability, which allows the drug to not only induce cell death or continuous cell cycle arrest in CD138 expressing tumor cells but, optionally, also to affect auxiliary cells that, e.g., support or protect the tumor from drugs, in particular cells of the tumor stroma and the tumor vasculature and which generally do not express CD138 to diminish or lose their supporting or protecting function.

Maytansine was evaluated in Phase I and Phase II clinical trials sponsored by the National Cancer Institute (NCI) under IND #11,857 (submitted to FDA on Sep. 19, 1975). Both complete and partial responses were seen in patients with hematological malignancies and partial responses in patients with a broad spectrum of solid tumors (Blum and Kahlert., 1978, Issell and Crooke, 1978, Chabner et al., 1978, Eagan et al., 1978, Cabanillas et al., 1978). However, significant toxicities, including nausea, vomiting, diarrhea, elevations of liver function tests, lethargy, and peripheral neuropathy were noted (see Maytansine IND #11,857, Annual Report, February, 1984; Blum and Kahlert., 1978, Issell and Crooke, 1978, Chabner et al., 1978). Toxic effects precluded further development.

In another embodiment effector molecules might represent Taxanes. Taxanes are a class of tubulin interfering agents (Payne 2003). Taxanes are mitotic spindle poisons that inhibit the depolymerization of tubulin, resulting in an increase in the rate of microtubule assembly and cell death. Taxanes that are within the scope of the present invention are, for example, disclosed in U.S. Pat. Nos. 6,436,931; 6,340,701; 6,706,708 and United States Patent Publications 20040087649; 20040024049 and 20030004210. Other taxanes are disclosed, for example, in U.S. Pat. No. 6,002,023, U.S. Pat. No. 5,998,656, U.S. Pat. No. 5,892,063, U.S. Pat. No. 5,763,477, U.S. Pat. No. 5,705,508, U.S. Pat. No. 5,703,247 and U.S. Pat. No. 5,367,086. A preferred embodiment of the present invention might be highly potent Taxanes that contain thiol or disulfide groups. As the person skilled in the art will appreciate, PEGylated taxanes such as the ones described in U.S. Pat. No. 6,596,757 are also within the scope of the present invention.

The present invention includes further DNA affecting effector molecules, in more particular, intercalating agents such as anthracyclines and derivatives (daunorubicin, valrubicin, doxorubicin, aclarubicin, epirubicin, idarubicin, amrubicin, pirarubicin, zorubicin) and anthracenediones, such as *Streptomyces* derived substances (actinomycin, mitomycin, bleomycin, aactinomycin) or amsacrine.

An effector molecule might represent more particular DNA alkylating agents like, and more particular, Nitrogen mustard and analogues (e.g. Cyclophosphamide, Melphalan, Estramustin), Alkylsulfonates, Nitrosoureas, Aziridines, Hydrazines, Ethylene Imines, and other substances such as Trenimon and Mitobronitol (a mannitol analogue). In particular, preferred DNA alkylating agents are CC-1065 analogues or derivatives (U.S. Pat. Nos. 5,475,092; 5,585,499; 6,716,821) and duocarmycin.

CC-1065 represents a potent antitumor-antibiotic isolated from cultures of *Streptomyces zelensis* and has been shown to be exceptionally cytotoxic in vitro (U.S. Pat. No. 4,169,888). Within the scope of the present invention are, for example, the CC-1065 analogues or derivatives described in U.S. Pat. Nos. 5,475,092, 5,585,499 and 5,739,350. As the person skilled in the art will readily appreciate, modified CC-1065 analogues or derivatives as described in U.S. Pat. No. 5,846,545 and prodrugs of CC-1065 analogues or derivatives as described, for example, in U.S. Pat. No. 6,756,397 are also within the scope of the present invention. In certain embodiments of the invention, CC-1065 analogues or derivatives may, for example, be synthesized as described in U.S. Pat. No. 6,534,660.

Other DNA alkylating effector molecules such as platinum based substances are further included (e.g. e.g. carboplatin, nedaplatin, oxaliplatin, triplatin, satraplatin).

Among the DNA affecting effector molecules, also Topoisomerase I and II inhibitors are included, such as Camptotheca derived substances (belotecan, topotecan) and Podophyllotoxin and derivatives (etoposide, teniposide).

Further subclass of DNA affecting effector molecules include antimetabolites such as folic acid analogues (methotrexate, known as a dihydrofolate reductase inhibitors) or Aminopterin. Also included are metabolites interfering with purine or pyrimidine metabolism, in particular adenosine deaminase inhibitor (pentostatin), or halogenated/ribonucleotide reductase inhibitors (cladribine, clofarabine), thiopurine and tiazofurine. Further antimetabolites include DNA polymerase inhibitor (cytarabine), ribonucleotide reductase inhibitor (gemcitabine), and hypomethylating agents (azacitidine, decitabine) and ribonucleotide reductase inhibitors. More general included are also DNA crosslinking substances such as cisplatin.

Effector molecules according to the present invention may be antitumor antibiotics, defined as DNA modifying or damaging effector molecules including enediyne antibiotics such as calicheamicin which include, e.g., gamma 11, N-acetyl calicheamicin and other derivatives of calicheamicin. Calicheamicin binds in a sequence-specific manner to the minor groove of DNA, undergoes rearrangement and exposes free radicals, leading to breakage of double-stranded DNA, resulting in cell apoptosis and death. One example of a calicheamicin effector molecule that can be used in the context of the present invention is described in U.S. Pat. No. 5,053,394. This compound is used in immunoconjugates with the monoclonal antibodies published as gemtuzumab ozogamicin and inotuzumab ozogamicin.

A subgroup of enediyne comprises the chromoproteins esperamycin and neocarzinostatin. In particular, trabectedin, which is also categorized as a DNA damaging agent (antitumor antibiotics)? Trabectedin causes DNA backbone cleavage and can be isolated from a sea squirt (also known as ecteinascidin 743 or ET-743) is sold by ZELITA and JOHNSON & JOHNSON under the brand name YONDELIS.

Another group of preferred effector molecules are substances such as, but not limited to, toxins affecting cell metabolism. In particular enzyme inhibitors such as but not only, olaprib, or more preferred proteasome (e.g. bortezomib) and protein kinase inhibitors, or lipoxygenase inhibitors such as masoprocol are part of the present invention. Also included are receptor antagonists such as, but not limited to, endothelin A receptor antagonist (e.g. atrasentan), or sex steroids such as testolactone, interfering with estrone metabolism. Further included are estrogen receptor interacting substances such as plant derived polyphenols, for example but not only isoflavonoids, stilbenes, silymarin, phenylpropanoid glycosides.

Also suitable as effector molecules are substances affecting cell metabolism, such as substances used for photodynamic or radiation therapy, including, but not limited to, porphyrin derivatives e.g. δ-aminolevulinic acid. Efaproxiral represents a radiosensitizer, which increases oxygen levels by decreasing hemoglobin-oxygen affinity. Further included are retinoids (first, second and third generation), in particular tretinoine, all trans retinoic acid (ATRA), which is used to treat acute promyelocytic leukemia (APML) sold for this indication by ROCHE under the brand name VESANOID. Retinoids are a class of chemical compounds that are related chemically to vitamin A, exerting diverse functions as for example activation of tumor suppressor genes. At present they are used to treat skin cancer and inflammatory skin disorders.

In another preferred embodiment, effector molecules might affect signaling pathways, such as but not limited to, calcium signaling. Examples are arsenic trioxide or trimethyltin chloride, the latter of which is a highly toxic organotin compound.

The present invention also includes effector molecules that are affecting drug resistance mechanisms which might include, for example, anti-multidrug resistance activity (via P-glycoprotein inhibition). Bicyclic heteroaromatic compounds and derivatives might severe as non-limiting examples.

Another effector molecule class might include substances, or more particular proteins interfering with apoptotic signaling pathways, including, but not limited to, antisense oligonucleotides, more particular, oligodeoxynucleotides such as oblimersen (INN, trade name genasense; also known as augmerosen and bcl-2 antisense oligodeoxynucleotide G3139) which is an antisense oligodeoxyribonucleotide actually studied as a possible treatment for several types of cancer, including chronic lymphocytic leukemia, B-cell lymphoma, and breast cancer. It has been proposed that this compound may kill cancer cells by blocking the production of Bcl-2 and by rendering them more sensitive to chemotherapy. Further apoptosis inducing classes of substances that may serve as effector molecules comprise plant polyphenols such as, but not limited to, silymarins, which are able to interfere with cell cycle regulators and proteins involved in apoptosis Effector molecules might also be proteins, such as those of apoptotic signaling cascades with apoptosis-inducing activities, including, but are not limited to, Granzyme B, Granzyme A, Caspase-3, Caspase-7, Caspase-8, Caspase-9, truncated Bid (tBid), Bax and Bak.

Other effector molecules might include enzymes such as but not limited to, asparaginase or other enzymes with antineoplastic activities.

A drug-effector molecule according to the present invention may also be an antiprotozoal drug such as miltefosine.

In another embodiment effector molecules might represent plant polyphenoles, such as, but not limited to, psoralens and their hydroxy metabolites.

Plant polyphenoles such as flavonoids, tannins (proanthocyanidins), stilbenoids, curcuminoids and ligands having one of the above mentioned antitumor activities (e.g. apoptosis inducing, cell cycle arrest) or additional activity such as free radical scavenging, metal chelating activity, estrogen receptor interfering activity, antioxidant, interfering with drug metabolizing enzymes are also possible effector molecules. More specifically, psoralens and their hydroxy metabolites which are able to intercalate into DNA acting as metal chelators having antioxidant and cytoprotective properties are preferred effector molecules. Particularly preferred are reservatol and polyhydroxylated derivatives and flavonoids, such as catechins and epicatechins, more specifically epigallocatechin 3-O gallate, which may act as antioxidants.

Another embodiment of effector molecules might represent Toxins. Toxins may include bacterial toxins, such as, but not limited to, Diphtheria toxin or Exotoxin A, plant toxins, such as but not limited to, Ricin other alkaloids and polyphenols, mycotoxins, such as alpha amanitin or more specially Amatoxins and phallotoxins. Toxins might not only be of bacterial origin, but also fungal, plant, vertebrate and invertebrate origin, all of which can be genetically or chemically modified. Moreover toxins might also be environmental toxins such as, but not limited to, methylmercury. Toxins may also be dolastatins 10 and 15 are small peptides isolated from the marine sea hare *Dolabella auricularia* that have been shown to interact with tubulin A broad classification of effector molecules according to their mechanism is also possible:
Antineoplastic agents and immunomodulating agents (According to ATC code L01) in particular "Intracellular chemotherapeutic agents"
ATC: Anatomical Therapeutical Chemical classification system (WHO)
1) Antimitotics, or molecules affecting microtubules (tubulin binding agents) such as vinca alkaloids and analogues (Vinca alkaloids (Vinblastine, Vincristine, Vinflunine, Vindesine, Vinorelbine) and taxanes (Paclitaxel, Larotaxel, Docetaxel) dolastatins (and derivatives e.g. auristatin) and crytophycin, maytansine and colchicine derivatives, epothilones (e.g., ixabepilone)
2) affecting DNA replication
   a) Intercalating agents such as anthracyclines (Daunorubicin, Valrubicin, Doxorubicin, Aclarubicin, Epirubicin, Idarubicin, Amrubicin, pirarubicin, Zorubicin) and Anthracenediones, such as *Streptomyces* derived substances (Actinomycin, Mitomycin, Bleomycin, Dactinomycin) or Amsacrine
   b) Alkylating agents such as Nitrogen mustards, Nitrosoureas, Alkylsulfonates, Aziridines, Hydrazines (Procarbazine), Triazenes, Epoxides, Ethylene Imines, Altretamine, Mitobronitol, duocarmycin and analogues/stereoisomers, Trenimon, Estramustine, CC-1065
   c) Alkylating-like agents such as Platinum (e.g. Carboplatin Nedaplatin, Oxaliplatin, Triplatin Tetranitrate, Satraplatin)
   d) Topoisomerase I specific inhibitors such as camptotheca (Belotecan, Topotecan)
   e) Topoisomerase II specific inhibitors such as Podophyllotoxin and derivatives (Etoposide, Teniposide)
   f) Antimetabolites affecting DNA/RNA synthesis by interfering with
      folic acid such as Dihydrofolate reductase inhibitors (e.g. Aminopterin, Methotrexate), thymidilate synthase inhibitor
      purine such as adenosine deaminase inhibitor (Pentostatin), halogenated/ribonucleotide reductase inhibitor (Cladribine, Clofarabine), Thiopurine, Tiazofurine
      Pyrimidine such as DNA Polymerase inhibitor (Cytarabine), ribonucleotide reductase inhibitor (Gemcitabine), hypomethylating agent (Azacitidine, Decitabine)
      deoxyribonucleotide such as ribonucleotide reductase inhibitor Hydroxycarbamid
   g) other DNA crosslinking agents such as platinum based compounds (e.g. Cisplatin)
3) Other DNA interfering substances e.g. "antitumor/cytotoxic antibiotics" such as elsamicin A, further antibiotics such as CC-1065, and subclasses of antibiotics such as bacteria derived enediyne chalicheamin or chromoprotein enediyne esperamicin (extremely toxic DNA splicing agent) or neocarzinostatin (other members of the neocarzinostatin group of antibiotics are macromomycin, actinoxanthin, kedarcidin and maduropeptin.) or Trabectedin (DNA backbone cleavage)
4) toxins affecting cell metabolism e.g. HSP90 inhibitors, Lonidamide (inhibits both respiration and glycolysis leading to a decrease in cellular ATP)

a) Enzyme inhibitors e.g. Olaprib (PARP inhibitor), CDK inhibitors (Alvocidib), Proteasome (Bortezomib), Protein kinase inhibitors, Masoprocol (Lipoxyenase inhibitor)
b) Receptor antagonists such as tutin (Glycin receptor antagonist (plant toxin), Atrasentan, retinoid X receptor (Bexarotene), sex steroids such as testolactone, estrogen receptor interfering substances
c) Photosensitizers or other compounds used for photodynamic therapy (Porfirmer Sodium), Porphyrin derivatives e.g. δ-Aminolevulinic acid)
d) Radiosensitizer such as Efaproxiral which increases oxygen levels by decreasing hemoglobin-oxygen affinity
e) Substances affecting signaling pathways e.g. $Ca^{2+}$ signaling such as arsenic trioxide and trimethyltin chloride
f) Other substances interfering with metabolism such as retinoids and derivatives Tretinoine (ATRA)
5) Affecting epigenetic processes such as HDAC inhibitors (e.g. Panobinostat, Vorinostat, Valporic acid, MGCD0103 (Mocetinostat), which are at present in clinical development for cutaneous T-cell lymphoma, acute myeloid leukemia, Hodgkin lymphoma or follicular lymphoma)
6) Affecting drug resistance mechanisms such as bicyclic heteroaromatic compounds, which inhibit P-glycoprotein
7) Substances inducing apoptotic signaling/mechanisms include proteins but also antisense oligodeoxynucleotides such as Oblimersen (trade name Genasense)
8) Enzymes such as Asparaginase
9) Antiprotozoal drugs such as Miltefosine
10) Plant polyphenoles such as Flavonoids, Tannins (Proanthocyanidins), Stilbenoids, curcuminoids and lignans having one of the above mentioned antitumor activities (e.g. apoptosis inducing, cell cycle arrest) or additional activity such as free radical scavenging, metal chelating activity, estrogen receptor interfering activity, antioxidant, interfering with drug metabolizing enzymes). More specifically psoralens and their hydroxy metabolites, reservatol and polyhydroxylated derivatives, Flavonoids, such as Catechins and Epicatechins, more specifically epigallocatechin 3-O gallate
11) Further natural substances and derivatives such as exotoxin A, diphtheria toxin, and derivatives thereof, wherein the derivatives can be chemically or genetically modified.

Effector molecules can also be categorized according to the substance class they belong to such as anorganic compounds, aromatic compounds, metal based compounds, proteins related to cell metabolism, enzymes, peptides, oligonucleotides, such as antisense nucleotides, bacterial toxins, plant derived toxins and polyphenols such as tannins, flavonoids and coumarins as well as terpenoids, alkaloids, anti-tumor antibiotics (e.g. enediyne antibiotics), mycotoxins, toxins from invertebrates as well as vertebrates, environmental toxins.

An immunoconjugate according to the present invention comprises at least one targeting agent, in particular targeting antibody and one effector molecule. The immunoconjugate might comprise further molecules for example for stabilization. For immunoconjugates, the term "conjugate" is generally used to define the operative association of the targeting agent with one or more effector molecules and is not intended to refer solely to any type of operative association, and is particularly not limited to chemical "conjugation". So long as the targeting agent is able to bind to the target site and the attached effector functions sufficiently as intended, particularly when delivered to the target site, any mode of attachment will be suitable. The conjugation methods according to the present invention include, but are not limited to, direct attachment of the effector molecule to the targeting antibody, with or without prior modification of the effector molecule and/or the targeting antibody or attachment via linkers. Linkers can be categorized functionally into, for example, acid labile, photolabile linkers, enzyme cleavable linkers, such as linkers that can be cleaved by peptidases. Cleavable linkers are preferred in many embodiments of the invention. Such cleavable linkers can be cleaved under conditions present in the cellular environment, in particular, an intracellular environment with no detrimental effect on the drug released upon cleavage. Low pHs such as pH of 4 to 5, as they exist in certain intracellular departments, will cleave acid labile linkers, while photolabile linkers can be cleaved by, e.g., infrared light. However, linkers that are cleaved by/under physiological conditions present in the majority of cells are preferred and are referred to herein as physiologically cleavable linkers. Accordingly, disulfide linkers are preferred in many embodiments of the invention. These linkers are cleavable through disulfide exchange, which can occur under physiological conditions. Preferred heterobifunctional disulfide linkers include, but are not limited to, N-succinimidyl 3-(2-pyridyldithio)propionate (SPDP) (see, e.g., Carlsson et al. (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), N-succinimidyl 4-(N-maleimidomethyl)cyclohexane-1-carboxylate (SMCC) (see, e.g., Yoshitake et al., (1979)), and N-succinimidyl 4-methyl-4-[2-(5-nitro-pyridyl)-dithio]pentanoate (SMNP) (see, e.g., U.S. Pat. No. 4,563,304). The most preferred linker molecules for use in the inventive composition are SPP, SMCC, and SPDB.

Other suitable linkers may include "non-cleavable" bonds, such as, but not limited to Sulfosuccinimidyl maleimidomethyl cyclohexane carboxylate (SMCC), which is a heterobifunctional linker capable of linking compounds with SH-containing compounds. Bifunctional and heterobifunctional linker molecules, such as carbohydrate-directed heterobifunctional linker molecules, such as S-(2-thiopyridyl)-L-cysteine hydrazide (TPCH), are also within the scope of the present invention (Vogel, 2004). The effector molecule, such as a maytansinoid, may be conjugated to the targeting antibody via a two reaction step process. This includes as a first step the modification of the targeting antibody with a cross-linking reagent such as N-succinimidyl pyridyldithiopropionate (SPDP) to introduce dithiopyridyl groups into the targeting antibody. In a second step, a reactive maytansinoid having a thiol group, such as DM1, may be added to the modified antibody, resulting in the displacement of the thiopyridyl groups in the modified antibody, and the production of disulfide-linked cytotoxic maytansinoid/antibody conjugate (U.S. Pat. No. 5,208,020). However, one-step conjugation processes such as the one disclosed in United States Patent Publication 20030055226 to Chari et al are also within the scope of the present invention. In one embodiment of the present invention multiple effector molecules of the same or different kind are attached to a targeting antibody. As discussed elsewhere herein, the nature of the linkers employed may influence bystander killing (Kovtun et al., 2006). See also U.S. Pat. Nos. 5,208,030; 5,416,064; 6,333,410; 6,441,163; 6,716,821; 6,913,748;

7,276,497 and US Application No. 2005/0169933 for method for preparing immunoconjugates.

CC-1065 analogues or derivatives may be conjugated to the targeting agent via, for example, PEG linking groups as described in U.S. Pat. No. 6,716,821.

Calicheamicins may be conjugated to the targeting antibodies via linkers (U.S. Pat. No. 5,877,296 and U.S. Pat. No. 5,773,001) or according to the conjugation methods disclosed in U.S. Pat. No. 5,712,374 and U.S. Pat. No. 5,714,586. Another preferred method for preparing calicheamicin conjugates is disclosed in Unites States Patent Publication 20040082764. The immunoconjugates of the present invention may take the form of recombinant fusion proteins.

Operational association in form of an attachment with or without a linker is referred to herein as "functional attachment."

One milligram (mg) of immunoconjugate BT062 comprises approx. 3.5 DM4 molecules (1 DM4 has an approximate molecular weight of 800 Da), thus 1 mg immunoconjugate comprises 2800 Da of DM4.

The molecular weight of BT062 is about 150000 Da. Thus, 1 mg immunoconjugate comprises about 1/53 mg DM4 molecules. Thus 4 mg/ml of antibody corresponds to about 4/53 DM4 molecules, which is 75 µg/ml. 160 mg/m² of immunoconjugate corresponds to about 2.5 to 3.5, in particular to about 3 mg/m² of DM4.

According to the present invention more than 2, 2.5, 3, 3.5 or even 4 mg/m² DM4 can be administered to a subject in either repeated single doses or multiple doses, including repeated multiple doses, without DLTs.

An immunoconjugate consisting essentially of certain components means in the context of the present invention that the antibody/immunoconjugate consists of the specified components and any additional materials or components that do not materially affect the basic characteristics of the antibody.

Some of the immunoconjugates of the present invention have an effector molecule that is sterically hindered and contains a cleavable linker (HICL—hindered immunoconjugate, cleavable linker). An unhindered counterpart (UI: unhindered immunoconjugate) of an immunoconjugate comprising an engineered targeting antibody against CD138 attached to an effector molecule via a cleavable linker (CL) and is described herein as UICL. The UICL is an immunoconjugate equivalent to the HICL comprising an engineered targeting antibody in which the effector molecule is, however, not sterically hindered. Examples of a pair of HICL/UICL are BT062 and nBT062-SPP-DM1. An unhindered counterpart of such an immunoconjugate comprising a non-cleavable linker (UINCL) refers to the equivalent immunoconjugate comprising an engineered targeting antibody in which the effector molecule is not sterically hindered and comprises a noncleavable linker. For BT062 (nBT062-SPDB-DM4), nBT062-SMCC-DM1 would constitute an example of such an unhindered counterpart comprising a non-cleavable linker (UNICL).

A growth of a tumor inhibiting activity (=tumor growth inhibiting activity) of an immunoconjugate is a relative measure. It describes the tumor growth inhibiting activity of a conjugate relative to the activity of the highest performing immunoconjugate whose activity is set as 100%. For example, if the activity of the highest performing immunoconjugate, say, BT062, which causes a tumor growth delay (TGD) of 32 days, is set as 100%, the activity of, e.g., nBT062-DM1, which displays a tumor growth delay (TGD) of 18 days is calculated as follows:

Tumor Growth Inhibiting Activity=100× $(TGD_{nBT062\text{-}DM1}/TGD_{BT062})$, more generically:

Tumor Growth Inhibiting Activity=100× $(TGD_{Sample}/TGD_{Reference})$.

TABLE 7

Tumor growth delay (TGD) and % Activity of nBT062-DMx against MOLP-8 tumor xenografts in SCID mice based on treatment groups receiving a 450 µg/kg dose.

|  | TGD* (days) | % Activity** |
|---|---|---|
| PBS | 0 | 0 |
| nBT062-SMCC-DM1 | 18 | 56 |
| BT062 | 32 | 100 |
| nBT062-SPP-DM1 | 13 | 40 |

*Tumor growth delay in days (TGD) as mean time in days for treatment group to reach a predetermined size (160 mm³) minus the mean time for the control group to reach this predetermined size.
**Tumor Growth Inhibiting Activity = 100 × $(TGD_{Sample}/TGD_{BT062})$. The activity of BT062 is defined to be 100%.

In the example provided in Table 7, BT062 provides a growth of a tumor inhibiting activity that exceeds that of its unhindered counterpart (nBT062-SPP-DM1) by 60%, and a growth of a tumor inhibiting activity that exceeds that of its unhindered counterpart immunoconjugate comprising a non-cleavable linker (nBT062-SMCC-DM1) by 44%.

As discussed above, certain drugs such as maytansinoids, while effective, are highly toxic, destroying in their native, i.e., unconjugated form, cells non-selectively. Linking the cytotoxic maytansinoid to an antibody can keep the drug inactive until it reaches the target cell (Lambert 2005). Several antibody-maytansinoid conjugates have undergone clinical development.

Phase I and II studies with IMGN901 (huN901-DM1, BB-10901) for treating CD56-positive solid tumors (small cell lung cancer and neuroendocrine cancers) were performed. In these studies IMGN901 was administered on 4 consecutive weeks every 6 weeks and was generally well tolerated (Fossella et al., 2005, Lorigan et al., 2006, McCann et al., 2007, Carter and Senter, 2008, Johnson et al. 2008). The antibody portion of the immunoconjugate, huN901, shows significant CDC or ADCC activity. The same immunoconjugate is investigated for treatment of CD56-positive multiple myeloma. In a phase I study administration of IMGN901 on 2 consecutive weeks every 3 weeks to patients with CD56-positive multiple myeloma who have failed established multiple myeloma treatments has shown preliminary evidence of safety as well as clinical activity. Eighteen patients were reported to have received IMGN901 (3 patients each at 40, 60, 75, 90, 112, and 140 mg/m²/week). Preliminary pharmacokinetic (PK) results were reported to indicate an approximately linear relationship between dosing and observed maximal serum concentration. Interesting clinical activity has been observed with a tolerable safety profile. A confirmed minor response (MR) was documented in 3 heavily pretreated patients (1 patient each at 60, 90, and 112 mg/m²/week) using the European Bone Marrow Transplant criteria. Durable stable disease was reported at doses of 60, 90, 112, and 140 mg/m²/week (Chanan-Khan et al., 2007, Chanan-Khan et al., 2008). IMGN901 at a dose of 75 mg/m²/week will be taken forward for further investigation in the expansion phase of the trial. At higher doses, peripheral neuropathy was reported with the treatment combination with lenalidomide and dexamethasone, the standard treatment regimen for multiple myeloma.

MLN2704 (huJ591-DM1) is investigated for treating castration-resistant prostate cancer (Milowsky et al., 2006, Brand and Tolcher 2006). A Phase I trial of MLN2704 in patients with progressive metastatic castration-resistant prostate cancer investigated the safety profile, pharmacokinetics, immunogenicity, and antitumor activity of MLN2704 when administered once every four weeks. Results demonstrated that therapeutic doses of MLN2704 can be administered safely on a repetitive basis (Galsky et al., 2008). Parallel trials were performed with another DM1-immunoconjugate, namely bivatuzumab mertansine which targets CD44v6, which is expressed on head and neck carcinomas and other solid tumors. In the clinical trial with the most condensed administration schedule (weekly administration) binding to CD44v6 on skin keratinocytes mediated serious skin toxicity with a fatal outcome in one patient, which led to the termination of the development program of bivatuzumab mertansine (Tijink et al., 2006, Sauter et al., 2007, Rupp et al., 2007, Riechelmann et al., 2008).

CD44v6 is not only expressed on various cancer cells, but also in normal skin tissue and resembles in this respect CD138 which is also expressed not only on cancer cells but in normal skin tissue. Surprisingly, it was found that BT062 shows clinical efficacy without intolerable side effects like skin toxicity as found in bivatuzumab mertansine. See FIG. 28, which shows that repeated single doses BT062 of up to 160 mg/m$^2$ led to at least stable disease with manageable side effects over extended periods of time. The figure in particular shows a minor response defined by serum M-protein (M-protein levels were reduced by ≥25%). Only after a hold period (days 400 to 421) did the M-protein levels increase, but could be stabilized after the next dose was received. In sum, there was progression free survival for about 22 months, with a duration of a minor response for 19 months. It was also previously shown that 10 repeated single doses of 20 mg/m$^2$ (treatment over more than 6 months), 5 repeated single doses of 40 mg/m$^2$, 5 repeated single doses of 80 mg/m$^2$, 6 repeated single doses of 160 mg/m$^2$, and 1 single doses of 200 mg/m$^2$ followed by 6 repeated single doses of 160 mg/m$^2$ (ergo, a total dose of 1160 mg/m$^2$) were well tolerated (See also US Patent Publication 20110123554).

CD138 is also expressed on normal blood cells and other cells whose destruction would lead to intolerable side effects, ergo severe adverse events (SAES) discussed later herein. Irrespective of this, no dose limiting toxicity towards non-cancer/non-tumor cells expressing CD138 of any sort were found in the repeated single dose treatment regimens up to 120 mg/m$^2$. An aggregate dose of 360 mg/m$^2$ resulted in 3 weeks (21 days) when 120 mg/m$^2$ was administered ion day 1, 8, and 15 and a resting period of 1 week. Thus, while the aggregate maximum tolerable dose (AMTD) in the context of this once a week treatment regime is higher than the maximum tolerable dose (MTD) which, in the case of BT062, has previously been determined to be 160 mg/m$^2$ when the immunoconjugate was only administered as a single dose, here on day one in a 21 day cycle. In fact, the AMTD is higher, including more than 50%, 60%, 70%, 80%, 90%, 100% higher than the previously determined dose limiting toxicity (DLT), in the case of BT062, 200 mg/m$^2$ for administration of the immunoconjugate as a single dose, e.g., once, e.g. on day 1, in a three week (21 days) active treatment cycle. This constitutes a significant difference to other immunoconjugates, where no difference in the DLT or MTD could be found between an administration of the immunoconjugate as a single dose (including repeated single dose), e.g., a one time administration within three weeks and in multiple dose regimen, e.g., a three time administration once a week for three weeks (21 days).

The effects aggregate maximum tolerable dose (AMTD) are identical to the effects of an MTD defined elsewhere herein. However, the term "aggregate" conveys that the administration is not performed as a single dose or repeated single dose within a certain time period, e.g. an active treatment cycle of, e.g., three weeks (e.g., 21 days), but that, within said certain time period, the immunoconjugate is administered in intervals, e.g., weekly intervals such as on day 1, 8 and 15 of a 21 day period.

Preferably, equal doses are administered, e.g., in 7 day intervals (e.g., day 1, 8 and 15), 3 day intervals (e.g., day 1, 4, 7, 10, 13 and 16), 4 day intervals, 5 day intervals or 6 day intervals. However, slight variation in the administrations such as an initial booster administration described elsewhere herein are also within the scope of the present invention. The administration intervals may be increased or decreased after each cycle (see also maintenance therapy discussed elsewhere herein). For example, the first and optional second cycle might involve administration every 3$^{rd}$ day, while in the following cycles the intervals may be, e.g., progressively, increased to 4, 5, 6 or 7 days. A fraction of a of the AMTD includes e.g. about 95% of the AMTD, about 90% of the AMTD, about 85%, about 80%, about 75% about 70%, about 65%, about 60%, about 55%, about 50%, about 45% of the AMTD. Assuming, e.g., that the AMTD of a theoretical immunoconjugate is 100 mg/m$^2$, a 95% fraction would be, e.g., 95 mg/m$^2$.

Adverse events (AEs) can be evaluated according to the NCI-CTCAE version 4.0 (Cancer Therapy Evaluation Program, Common Terminology Criteria for Adverse Events, Version 3.0, DCTD, NCI, NIH, DHHS Mar. 31, 2003), National Cancer Institute, US National Institutes of Health, Publishing Date: Aug. 9, 2006). For AEs not listed in the CTCAE v4.03, severity will be assessed by the Investigator by the following criteria:

Only grade 1 and grade 2 AEs are acceptable, whereby Grade 1 (Mild) requires minimal or no treatment and does not interfere with the patient's daily activities and Grade 2 (Moderate) results in a low level of inconvenience or concern with the therapeutic measures. Moderate events may cause some interference with the subject's functioning.

AEs of Grade 3 (Severe) and Grade 4 (Life threatening) are considered not acceptable their occurrence defines the DLT (dose limiting toxicity), if not otherwise defined by study specific DLT criteria (see below).

AEs of Grade 3 and 4 are also referred to as severe adverse events (SAE) and include lymphopenia, leucopenia, thrombopenia, neutropenia, cardiac arrest, atrial fibrillation, pulmonary embolism and deep vein thrombosis. Other study specific criteria may be employed (see below).

Dose limiting toxicities (DLT) are determined using the grading according to NCI CTCAE v4.0 referenced to above. Generally, all toxicities of at least grade 3 are defined as DLT. Further study specific DLT criteria which can be employed are listed below:

Nonhematological:
Alopecia, of any grade, is not considered a DLT
Grade 3-4 nausea and vomiting lasting longer than 3 days despite optimal antiemetic medication.[a]
Grade 3-4 diarrhea lasting longer than 3 days despite optimal antidiarrheal medication.[a]

a. Optimal antidiarrheal and antiemetic treatment were determined by each investigator.

Hematologic:

Grade 4 neutropenia lasting longer than 5 days.

Grade 3 or higher neutropenia with temperature greater than or equal 101° F., for 2 consecutive determinations spaced 4 hours apart.

Grade 4 thrombocytopenia

Grade 3 or higher thrombocytopenia with bleeding and requiring the use of platelet transfusion.

Grade 3 neutropenia, grade 3 thrombocytopenia were NOT considered DLTs.

The maximum tolerated dose (MTD) is defined as the dose at which any subject to whom a single dose or a repeated single dose has been administered experiences dose limiting toxicities (DLTs). As is readily apparent, a MTD can be readily determined for a wide variety of immunoconjugates according to the present invention. These DLTs may occur in a first or a subsequent treatment cycle. In particular, 1 out of 6 subjects to whom a single dose or a repeated single dose has been administered experience DLTs. Preferably DLTs in the first cycle are considered.

During dose escalations, preferably only DLTs in the first cycle are considered.

Study Specific Adverse Event (AE)

Any unfavorable or unintended sign, symptom, or disease that appears or worsens in a patient or clinical investigation subject during the period of observation in a clinical study. The AE may be any of the following:

a new illness an exacerbation of a sign or symptom or the underlying condition under treatment or of a concomitant illness, unrelated to participation in the clinical study or an effect of the study medication or comparator drug, a combination of one or more of the above factors.

Generally, no causal relationship with the study medication is implied by the use of the term "adverse event".

Serious Adverse Event (SAE)

An SAE is any untoward medical occurrence or effect that at any dose:

results in death, death is an outcome of an AE and not an AE in itself. All deaths, regardless of cause or relationship must be reported for patients on study is life-threatening, life-threatening means that the patient was at immediate risk of death from the event as it occurred. This does not include an event that might have led to death if it had been more severe results in persistent or significant disability or incapacity, is a congenital anomaly or birth defect, or is another medically important condition An important medical event that is not immediately life-threatening or will result in death or hospitalization, but which may jeopardize the patient/subject or may require medical intervention to prevent one of the outcomes listed above, should be reported as "serious" as well Causality of Adverse Event Refers to the relationship of the AE to investigational product. Causality will be categorized according to the following criteria:

Not Related

AEs for which a reasonable explanation for an alternative cause is considered plausible, e.g., non investigational product taken, plausible clinical alternative like accidental injury, expected progression of underlying or concomitant disease, pharmacologically incompatible temporal relationship, intercurrent illness Related AEs for which a reasonably possible clinical and/or pharmacological relationship to investigational product cannot be excluded, e.g. lacking plausible alternatives.

Phase I studies with the immunoconjugated form of trastuzumab (T-DM1) for treatment of HER2 over-expressing metastatic breast cancer are performed to investigate safety and pharmacokinetics of T-DM1 administered weekly or once every 3 weeks. In both studies AEs of grade ≥2 related to T-DM1 have been infrequent and manageable. Objective tumor responses have been observed at doses at or below the MTD (Burris et. al., 2006, Krop et al., 2007, Beeram et al., 2008, Holden et al., 2008). A phase II study investigating T-DM1 in HER2-positive metastatic breast cancer when administered once every 3 weeks has been initiated (Beeram et al., 2008, Carter and Senter, 2008, Holden et al., 2008). A Phase III clinical trial evaluating T-DM1 for second-line HER2-positive metastatic breast cancer and Phase II clinical trials evaluating T-DM1 for first-, second- and third-line HER2-positive metastatic breast cancer are ongoing. A Phase 1b clinical trial in combination with pertuzumab for HER2-positive metastatic breast cancer patients who have been progressed on Herceptin-based treatment is planned. Three phase I clinical trials have been completed with cantuzumab mertansine, a DM1-conjugate of the huC242 antibody that targets an antigen found on colorectal cancers and other C242-expressing cancers. Treatment with huC242-DM1 administered on a weekly basis as well as once every 3 weeks was found to be safe and tolerated (Rowinsky et al., 2002, Tolcher et al., 2003, Helft et al., 2004). Four studies are investigating immunoconjugates using the thiol-containing DM4 maytansinoid, which is also a component of BT062:

An analog of cantuzumab mertansine, IMGN242 (huC242-DM4), was investigated in a phase I study in subjects with CanAg-expressing cancer (Tolcher et al., 2006). Subjects received a single IV infusion of IMGN242 once every 3 weeks with a dose ranging from 18 to 297 mg/m$^2$. Dose-limiting toxicity was experienced by 2 of 6 subjects treated at the 223 mg/m$^2$ dose level during their second cycle of treatment. The drug was well tolerated at the 168 mg/m$^2$ level and did not induce any detectable antibody response (Mita et al., 2007). Based on first safety results from the Phase I study, a Phase II study was initiated to evaluate IMGN242 for treating CanAg-expressing gastric cancer at the dose of 168 mg/m$^2$ (Sankhala et al., 2007). Forty-five patients have been treated with IMGN242 in two clinical trials. Based on the safety and thorough clinical pharmacokinetic (PK)/pharmacodynamic (PD) analyses, the Phase II study was amended to treat patients with low plasma CanAg levels at the dose of 126 mg/m$^2$ and patients with high plasma CanAg levels at 168 mg/m$^2$ (Qin et al. 2008). A phase I study with huMy9-6 antibody conjugated to DM4 (AVE9633) was also performed for the treatment of subjects with CD33-positive Acute Myeloid Leukemia (AML). The treatment regimen consisted of IV infusions once every 3 week using a dose range of 15 to 260 mg/m$^2$. Neither associated myelosuppression nor responses have been noted in a single-dose study (Giles et al., 2006). A second phase I study investigating AVE9633 with a treatment regimen consisting of IV infusions on day 1 and day 8 of a 28-day cycle also shows that AVE9633 was well tolerated; it also provides evidence of antileukemia activity including 1 subject with complete response (inadequate platelet response, transfusion dependent) lasting for at least 4 months (Legrand et al., 2007). Two further DM4-immunoconjugates (SAR3419 and BIIB015) have entered into clinical trials.

SAR3419 (huB4-DM4) is an antibody-drug conjugate composed of a humanized IgG1 monoclonal antibody, huB4, which specifically targets the CD19 antigen, conjugated through a disulfide link to the maytansinoid derivative DM4. Expression of the CD19 molecule is found on all B lymphocytes, including pro-B cells, but is lost during maturation to plasma cells. The CD19 antigen is also expressed on the membrane of follicular dendritic cells and on most stabilized B cell lines. After binding to the CD19 antigen, SAR3419 undergoes internalization and intracellular release of DM4. In a phase I/II study SAR3419 was administered by intravenous infusion, weekly with 8 to 12 doses, to patients with relapsed/refractory B-cell NHL expressing CD19. Forty-four patients were enrolled at 7 dose levels from 10 to 70 mg/m$^2$. Main histologies were follicular (18; 41%) and diffuse large B-cell (17; 39%). The median number of prior regimens was 3 (1-8) and 19 patients had received prior transplantation. Twenty-eight patients were enrolled in the dose escalation part. Of 6 patients at 70 mg/m$^2$, 1 patient had a protocol defined dose limiting toxicity (DLT) of neutropenia and 2 patients had grade 2 significant toxicities with late onset: blurred vision associated with corneal deposits and left bundle branch block. The maximum tolerated dose (MTD) was defined at 55 mg/m$^2$, while the MTD in a regimen involving a single administration every three weeks was 160 mg/m$^2$. Of 22 patients at the MTD of 55 mg/m$^2$, 4 patients had related reversible grade 3-4 toxicities after 6-8 doses: optic neuropathy, paraesthesia, neutropenia and thrombocytopenia. Of 38 patients at doses of 20 mg/m$^2$ or higher, 12 (32%) patients achieved an objective response including 6 CR/CRu (complete response/complete response unconfirmed), with no obvious dose effect. Of 22 patients at the MTD (55 mg/m$^2$), 8 (36%) had a response, including 3 CR/CRu. Of 9 patients evaluable for response duration (RD), 4 patients had a RD ranging from 6 to at least 12 months. In sum it can be said that the aggregate maximum tolerated dose (AMTD) in a three weeks (21 days) dosing regimen involving 3 doses did not exceed the MTD in a three weeks (21 days) dosing regimen involving a single dose (e.g., on day one).

TABLE 8

Comparison of Immunoconjugates administered in repeated multiple dose regimens (once weekly).

| | Once weekly regimens | Corresponds to total concentration of (assuming 70 kg and 1.9 m$^2$ body surface area) |
|---|---|---|
| BT062 | MTD 140 mg/m$^2$ | 266 mg |
| SGN-35 (Batlett et al., 2008) | Up to 1.2 mg/kg | 84 mg |
| SAR3419 (Coiffer et al., 2011) | MTD 55 mg/m$^2$ | 110 mg |
| T-DM1 (Holden et al., 2008) | MTD at 2.4 mg/kg | 168 mg |
| SGN-75 (anti-CD70; MMAF) (SEATTLE GENETICS) | Study 0.3 to 0.6 mg/kg (MTD has not been reached) | |

As can be seen from the table above, BT062 can be administered at higher doses once weekly (at least in total an amount of 266 mg). In contrast to the other immunoconjugates listed, BT062 displayed characteristic pharmacokinetics. In particular BT062 shows a characteristic discrepancy between observed and theoretical Cmax values BT062 described elsewhere herein.

Also, it is known from other immunoconjugates, such as Mylotarg which is targeting CD33, that the activity of the immunoconjugate may not be sufficient to treat patients at low doses. This problem has been alleviated by, e.g., administration of recombinant human granulocyte colony-stimulating factor (rhG-CSF) to sensitize CD33 expressing target cells (Fianchi et al., Annals of Oncology 2008 19(1):128-134).

The above studies demonstrate that the responses to different immunoconjugates, in particular maytansinoid (such as DM1 or DM4) containing immunoconjugates, vary widely. The BT062 trials in human subjects showed not only tolerable toxicity against non-cancer cells expressing CD138 at different stable disease doses, especially at doses up to 160 mg/m$^2$, but also fast plasma clearance at dosages up to about 50 mg/m$^2$ in a weekly administration scheme.

The immunoconjugate described herein can be administered in combination with cytotoxic agents. These combinations are also referred to herein as anticancer combinations.

Selection of Drug Combination Partners

A set of guidelines for designing combination chemotherapy regimens has been developed (Takimoto, 2006). Abiding to these guidelines will generally increase the chances that a particular combination realizes at least one of the three most important theoretical advantages of combination chemotherapy over single-agent therapy:

1.) Maximize cell kill while minimizing host toxicities by using agents with noninterfering dose-limiting toxicities;
2.) Increasing the range of drug activity against tumor cells with endogenous resistance to specific types of therapy; and
3.) Preventing or slowing the development of newly resistant tumor cells.

Recommended principles to consider for selecting agents for use in combination chemotherapy regimens comprise:
a) selecting drugs known to induce complete remission as single agents,
b) selecting drugs with different mode of actions and with additive or synergistic cytotoxic effects,
c) selecting drugs with different dose limiting toxicities,
d) selecting drugs with different patterns of resistance to minimize cross resistance.

Also, drugs should be administered at their optimal dose and schedule (e), and the administration should be performed at consistent intervals, whereas the treatment free period should be as short as possible to allow for recovery of the normal tissue (f) (Takimoto et al, 2009).

Synergistic effects or just additive effects can be counteracted by a variety of factors: For example, the components of an anticancer combination might inactivate each other, e.g., by binding each other. In addition, one component of an anticancer combination might interfere with the mode of action of another component. For example: Lenalidomide downregulates cell adhesion receptors such as CD138, which is the target of the immunoconjugate of present invention (Quach et al., 2010, Udi et al, 2010). The proteasome inhibitor bortezomib causes G2/M cell cycle arrest (Wang et al., 2009) which is also affected by anti-mitotic agents. Thus, if the effector molecule of the immunoconjugate is a maytansinoid, it will share a target for action with bortezomib, which is considered disadvantageous.

Dosages, routes of administration and recommended usage of the cytotoxic agents according to the present invention which have been widely used in cancer therapy are known in the art and have been described in such literature as the Physician's Desk Reference (PDR). The PDR discloses dosages of the agents that have been used in treatment of various cancers. The dosing regimen and dosages of these cytotoxic agents that are effective will depend on the particular cancer being treated, the extent of the disease and other factors familiar to the physician of skill in the art and can be determined by the physician. The 2006 edition of the Physician's Desk Reference (PDR) discloses the mechanism of action and preferred doses of treatment and dosing schedules for thalidomide (p 979-983), VELCADE (p 2102-2106) and melphalan (p 976-979). One of skill in the art can review the PDR, using one or more of the following parameters, to determine dosing regimen and dosages of the chemotherapeutic agents and conjugates that can be used in accordance with the teachings of this invention. These parameters include:

1. Comprehensive index according to a) Manufacturer b) Products (by company's or trademarked drug name) c) Category index (for example, "proteasome inhibitors", "DNA alkylating agents," "melphalan" etc.) d) Generic/chemical index (non-trademark common drug names).

2. Color images of medications

3. Product information, consistent with FDA labeling including a) Chemical information b) Function/action c) Indications & Contraindications d) Trial research, side effects, warnings.

In the present context, one goal of employing combinations are a reduction in the effective doses of the immunoconjugate of the present invention, lowering their side effects and opening new therapeutic windows with acceptable side effects. Another goal is to reduce the effective dose of previously employed cytotoxic agents such as VELCADE or lenalidomide and preferably reducing the side effects of these agents. Similarly, the dosages Positive consequences include, but are not limited to, prolongation of treatment, higher dosages, other application schedules, better and more sustained response to treatment.

Patients displaying a refractory phenotype towards drugs such as lenalidomide, melphalan (study ongoing) might be rendered sensitive again by the use of immunoconjugates according to the present invention.

The term "cytotoxic agents" comprises "cytotoxic/cancer drugs" including chemotherapeutic agents, in particular chemotherapeutic agents that are generally used in rapidly dividing cells, namely:

Alkylating agents such as nitrogen mustards (e.g. melphalan, cyclophosphamide, mechlorethamine, uramustine, chlorambucil, ifosfamide) or nitrosureas (e.g. carmustine, lomustine, streptozocin) or alkylsulfonates;

Alkylating like agents such as cisplatin, carboplatin, nedaplatin, oxaliplatin; or non classical alkylating agents such as tetrazines, dacarbizine, procarbazine, altretamine Anthracyclines such as doxorubicin and liposomal doxorubicin (DOXIL)

Alkaloids such as vincristine

The term "cytotoxic agents" also comprises immunomodulatory drugs (ImiDs) such as thalidomide (or analogs), lenalidomide (CC-5013), pomalidomide, actimid, which are used for myeloma therapy in view of their pleitropic immunomodulatory properties. They commonly display anti-inflammatory activity by inhibition of TNF alpha production, but display also anti-angiogenic activity and immunomodulatory properties such as T-cell co stimulation and influence on regulatory T-cells (Quach et al., 2010).

The term "cytotoxic agent" also comprises steroids, such as, but not limited to, dexamethasone and prednisone as well as proteasomal inhibitors such as bortezomib (VELCADE) or carfilzomib which induces the activation of programmed cell death in neoplastic cells dependent upon suppression of pro-apoptotic pathways. Further potent cytotoxic agents, include etoposide, which inhibits the enzyme topoisomerse II, cytarabine, which, upon conversion damages DNA when a cell cycle holds in the S phase (synthesis of DNA) and thus in particular affects rapidly dividing cells such as cancer cells. In addition, microtubule inhibitory agents such as vinca alkaloids, taxanes (as described above in the context of effector molecules) can also serve as cytotoxic agents according to the present invention.

Also included in the definition are kinase inhibitors such as sorafenib or HDAC (histone deacetylase), inhibitors such as romidepsin as well as growth inhibitory agents, anti-hormonal agents, anti-angiogenic agents, cardioprotectants, immunostimulatory agents, immunosuppressive agents, angiogenesis inhibitors and protein tyrosine kinase (PTK) inhibitors.

Further included in this definition are antibody based cytotoxic agents including immunoconjugates and antibodies that have an art recognized cytotoxic effect. Anti-CD40 is a preferred antibody. Other antibodies include, but are not limited to, e.g., AVASTIN (bevacizumab) or MYELO-MACIDE (milatuzumab).

Thalomide (α-(N-phthalimido) glutarimide; thalidomide), is an immunomodulatory agent. The empirical formula for thalidomide is $C_{13}H_{10}N_2O_4$ and the gram molecular weight is 258.2. The CAS number of thalidomide is 50-35-1. It appears to have multiple actions, including the ability to inhibit the growth and survival of myeloma cells in various ways and to inhibit the growth of new blood vessels.

Lenalidomide (REVLIMID) is a derivative of thalidomide representing the second generation of immunomodulatory compounds (ImiDs) which were initially developed as inhibitors of TNF alpha. Effects of lenalidomide include growth arrest or apoptosis, abrogation of myeloma cell adhesion to bone marrow stromal cells and modulation of cytokines promoting cell growth, survival and drug resistance of myeloma cells (Morgan et al., 2006). Lenalidomide is effective in patients refractory to thalidomide. In addition to effects on immune cells, ImiDs such as lenalidomide were suggested to cause cell cycle arrest in G0/G1 phase. In addition, it is assumed that ImiDs downregulate cell adhesion receptors (VLA-4, VLA-5, CD138) (Quach et al., 2010; Udi et al, 2010). A downregulation of CD138 would be expected to cause a reduced binding of any CD138 targeting agent, such as BT062, to target cells.

Proteasomal inhibitors can be divided into further subgroups:

a) naturally occurring peptide derivatives which have a C-terminal epoxy ketone structure, beta-lactone derivatives, aclacinomycin A, lactacystin, clastolactacystin; and b) synthetic inhibitors (comprising modified peptide aldehyds, alpha, beta epoxyketon structures, vinyl sulfones, boric acid residues, pinacolesters. A preferred proteasomal inhibitor of the present invention is bortezomib (PS 341; VELCADE, see discussion below). One of the proposed mechanisms suggests that proteasomal inhibition may prevent degradation of pro-apoptotic factors, permitting activation of programmed cell death in neoplastic cells dependent upon suppression of pro-apoptotic pathways. In addition, bortezomib causes G2/M cell cycle arrest (Wang et al., 2009). Thus, bortezomib might interfere with anti-mitotic agents which are part of the immunoconjugate of the present invention, e.g., with the effect of maytansinoid DM4, which acts also at this cell cycle phase. Furthermore, PARP (Poly(ADP-ribose) Polymerase) cleavage, which takes part in apoptosis, is also affected by both DM4 and bortezomib. Accordingly, the combination of an immunoconjugate comprising an anti-mitotic agent and a proteasomal inhibitor displaying the features of bortezomib do not conform to the general guidelines set forth previously to obtain synergistic effects (Takimoto et al, 2009).

VELCADE (bortezomib) is a proteasome inhibitor used to treat multiple myeloma. It is believed that VELCADE acts on myeloma cells to cause cell death, and/or acts indirectly to inhibit myeloma cell growth and survival by acting on the bone microenvironment. Without being limited to a specific theory or mode of action, VELCADE thus disrupts normal cellular processes, resulting in proteasome inhibition that promotes apoptosis.

Dexamethasone is a synthetic glucocorticoid steroid hormone that acts as an anti-inflammatory and immunosuppressant. When administered to cancer patients, dexamethasone can counteract side effects of cancer therapy. Dexamethasone can also be given alone or together with other anticancer agents, including thalidomide, lenalidomide, bortezomib, adriamycin or vincristine.

Substances for treatment, which may be used in combination with BT062 also include immunomodulatory agents (e.g. thalidomide, and lenalidomide, and pomalidomide), proteasome inhibitors (e.g. bortezomib and carfilzomib), steroids (e.g. dexamethasone), alkylating agents and high-dose chemotherapy, combinations (e.g. Melphalan and Prednisone (MP), Vincristine, doxorubicin (Adriamycin), and dexamethasone (VAD)), and bisphosphonates.

Currently, many combinations of in particular anti-myeloma drugs are investigated in clinical trials. The purpose of the use of a combination is generally either to enhance effectiveness, to overcome a refractory phenotype, e.g., of myeloma cells, to reduce side effects due to the use of lower concentrations of one of the combination partners or a combination thereof. Using a low dose, for example, of lenalidomide plus a low dose of dexamethasone was shown to reduce toxicity (Rajkumar et al., 2010).

Especially in patients with relapsed or refractory multiple myeloma several drug combination are and have been investigated.

A standard example for combined chemotherapeutics represents the triple combination of vincristine, dexamethasone, doxorubicin (VAD Regimen).

Proteasomal inhibitors such as bortezomib (VELCADE) have been combined with myeloma drugs such as melphalan and prednisone (VMP). This combination resulted in a complete response rate of 16% and an overall response rate of 89% (Mateos et al., 2006).

Bortezomib has been also approved for use in combination with liposomal doxorubicin for relapsed or refractory patients (Ning et al., 2007).

Bortezomib is investigated in several clinical studies for use in combination with dexamethasone, melphalan, prednisone and/or thalidomide.

Bortezomib is also under investigation combined with liposomal doxorubicin, cyclophosphamide and dexamethasone in multiple myeloma patients. Combinations with vorinostat are currently under investigation aiming at resensitizing patients to bortezomib which are refractory to this drug.

Thalidomide, which is administered orally, has been combined with melphalan/prednisone (MPT) (Facon et al., 2006) or dexamethasone or bendamustine (Pönisch et al., 2008).

Moreover, lenalidomide (REVLIMID), an immunomodulatory drug, used in combination with dexamethasone, resulted in a prolonged time to tumor progression and increased survival compared to dexamethasone alone (Weber et al., 2006). Lenalidomide combined with dexamethasone has been also studied in newly diagnosed patients (Rajkumar et al., 2005) as well as the combination with melphalan/prednisone (RMP) (Palumbo et al., 2006).

US Patent Publication 2010/0028346 to Lutz et al., describes synergistic effects of certain immunoconjugates with chemotherapeutic agents.

The term "in combination with" is not limited to the administration at exactly the same time. Instead, the term encompassed administration of the immunoconjugate of the present invention and the other regime (e.g. radiotherapy) or agent, in particular the cytotoxic agents referred to above in a sequence and within a time interval such that they may act together to provide a benefit (e.g., increased activity, decreased side effects) that is increased compared to treatment with only either the immunoconjugate of the present invention or, e.g., the other agent or agents. It is preferred that the immunoconjugate and the other agent or agents act additively, and especially preferred that they act synergistically. Such molecules are suitably provided in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration. As used in the context of the present invention "co-administration" refers to administration at the same time as the immunoconjugate, often in a combined dosage form.

Synergistic effects that are effects of two components such as an immunoconjugate and a cytotoxic agent that exceeds a strictly additive effect. These synergistic effects might be counteracted by a number of factors further discussed below.

Synergism has been calculated as follows (Yu et al., 2001; Gunaratnam et al., 2009):

$$RATIO(r) = \text{expected } FTV(\text{combination})/\text{observed } FTV(\text{combination})$$

FTV: Fractional tumor volume=mean tumor volume (test)/mean tumor volume (control)

A ratio>1 is regarded as synergistic, whereas r<1 is less than additive.

The ratio (r) is, when above 1, also referred to herein as "SYNERGY RATIO."

The ACTIVITY RATING is another measurement for the effects of a combination. This rating is based on the $Log_{10}$) cell kill $$Log_{10} \text{ cell kill} = (T-C)/T_d \times 3.32$$

where (T—C) or tumor growth delay, is the median time in days required for the treatment group (T) and the control group (C) tumours, to reach a predetermined size (600 mm$^3$). $T_d$ is the tumor doubling time, based on the median tumor volume in the control mice, and 3.32 is the number of cell doublings per log of cell growth (Bissery et al., 1991).

A $Log_{10}$, cell kill of higher than 2.8 indicates that the combination is highly active, a $log_{10}$ cell kill of 2.0-2.8 indicates that the combination is very active, a $log_{10}$ cell kill of 1.3-1.9 indicates that the combination is active, a $log_{10}$ cell kill of 0.7-1.2 indicates that the combination is moderately active and a $log_{10}$ cell kill of less than 0.7 indicates that the combination is inactive.

As the person skilled in the art will appreciate, the amino acid sequence of the preferred engineered targeting antibody portion of an immunoconjugate, nBT062, can be varied without loss of the functionality of the antibody portion in targeting CD138. This is in particular true when the heavy chain variable region CDR3 comprising amino acid residues 99 to 111 of SEQ ID NO: 1, and light chain variable region CDR3 comprising amino acid residues 89 to 97 of SEQ ID NO: 2, respectively of the antigen binding region (ABR). Advantageously, the heavy chain variable region CDR1 and CDR2 comprising amino acid residues 31 to 35 and 51 to 68 of SEQ ID NO: 1, and/or (b) light chain variable region CDR1 and CDR 2 comprising amino acid residues 24 to 34 and 50 to 56 of SEQ ID NO: 2, respectively of the antigen binding region (ABR) are also maintained.

The term "sequence identity" refers to a measure of the identity of nucleotide sequences or amino acid sequences. In general, the sequences are aligned so that the highest order match is obtained. "Identity", per se, has recognized meaning in the art and can be calculated using published techniques. (See, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., SIAM J Applied Math 48:1073 (1988)).

Whether any particular nucleic acid molecule is at least 50%, 60%, 70%, 75%, 80%, 85%, 90%, 95%, 96%, 97%, 98% or 99% identical to, for instance, the nBT062 nucleic acid sequence, or a part thereof, can be determined conventionally using known computer programs such as DNAsis software (Hitachi Software, San Bruno, Calif.) for initial sequence alignment followed by ESEE version 3.0 DNA/protein sequence software (cabot@trog.mbb.sfu.ca) for multiple sequence alignments.

Whether the amino acid sequence is at least 50%, 60%, 70%, 75%, 80%, 85%, 90%, 95%, 96%, 97%, 98% or 99% identical to, for instance SEQ ID NO:1 or SEQ ID NO:2, or a part thereof, can be determined conventionally using known computer programs such the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences.

When using DNAsis, ESEE, BESTFIT or any other sequence alignment program to determine whether a particular sequence is, for instance, 95% identical to a reference sequence according to the present invention, the parameters are set such that the percentage of identity is calculated over the full length of the reference nucleic acid or amino acid sequence and that gaps in homology of up to 5% of the total number of nucleotides in the reference sequence are allowed.

If, in the context of the present invention, reference is made to a certain sequence identity with a combination of residues of a particular sequence, this sequence identity relates to the sum of all the residues specified.

As discussed above, BT062 is an immunoconjugate comprising the CD138 targeting chimeric antibody nBT062 that is attached via a linker, here SPDB, to the cytostatic maytansinoid derivative DM4. A chemical representation of BT062 is provided in FIGS. 1 and 2. Immunoconjugates comprising nBT062 and a maytansinoid effector molecule are often characterized in terms of their linker and maytansinoid effector, e.g., nBT062-SMCC-DM1, is an immunoconjugate comprising nBT062, SMCC (a "noncleavable" linker containing a thioester bond) and DM1 as an effector. More generically, an immunoconjugate containing nBT062 and an effector molecule may also be described as nBT062-linker-effector or just as nBT062-effector (nBT062N, wherein N is any effector described herein (see also US Patent Publication 20090232810).

In one example, BT062 binds to CD138-positive multiple myeloma cells. Once the target cell internalizes and/or releases the immunoconjugate, DM4 is released from the targeting molecule, thereby restoring its original cytotoxic potency of DM4. Thus, BT062 provides a targeted antibody payload (TAP), wherein the functional attachment of DM4 to nBT062 keeps the cytotoxic drug inactive until it reaches/is internalized into the CD138 expressing target cell.

Data from nonclinical studies investigating cytotoxicity of BT062 in multiple myeloma cells and animal models discussed herein demonstrate that BT062 has highly significant antimyeloma activity at doses that are well tolerated in a murine model.

A phase I open-label, dose escalation, repeated single dose study in patients with relapsed or relapsed/refractory multiple myeloma has been conducted (US patent publication: 20110123554; International publication: WO 2010 128087).

The immunoconjugates disclosed herein can be administered by any route, including intravenously, parenterally, orally, intramuscularly, intrathecally or as an aerosol. The mode of delivery will depend on the desired effect. A skilled artisan will readily know the best route of administration for a particular treatment in accordance with the present invention. The appropriate dosage will depend on the route of administration and the treatment indicated, and can readily be determined by a skilled artisan in view of current treatment protocols.

Pharmaceutical compositions containing the immunoconjugate of the present invention and/or any further cytotoxic agent as active ingredients can be prepared according to conventional pharmaceutical compounding techniques. See, for example, Remington's Pharmaceutical Sciences, 17th Ed. (1985, Mack Publishing Co., Easton, Pa.). Typically, effective amounts of active ingredients will be admixed with a pharmaceutically acceptable carrier. The carrier may take a wide variety of forms depending on the form of preparation desired for administration, for example, intravenous, oral, parenteral, intrathecal, transdermal, or by aerosol.

The anticancer combinations of the present invention can preferably be either in the form of pharmaceutical compositions or in the form of kits comprising the components of the anticancer combination in different containers. The components of the kit are usually administered in combination with each other, often they are co-administered either in a combined dosage form or in separate dosage forms. Such kits can also include, for example, other components, a device for administering the components or combination, a device for combining the components and/or instructions how to use and administer the components.

For oral administration, the immunoconjugate and/or cytotoxic agent can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent must be stable to passage through the gastrointestinal tract. If necessary, suitable agents for stable passage can be used, and may include phospholipids or lecithin derivatives described in the literature, as well as liposomes, microparticles (including microspheres and macrospheres).

For parenteral administration, the immunoconjugate and/or cytotoxic agent may be dissolved in a pharmaceutical carrier and administered as either a solution or a suspension. Illustrative of suitable carriers are water, saline, phosphate buffer solution (PBS), dextrose solutions, fructose solutions, ethanol, or oils of animal, vegetative or synthetic origin. The carrier may also contain other ingredients, for example, preservatives, suspending agents, solubilizing agents, buffers and the like. When the unconjugated targeting agent and/or immunoconjugate and/or cytotoxic agent are being administered intracerebroventricularly or intrathecally, they may also be dissolved in cerebrospinal fluid.

Dosages administered to a subject may be specified as amount, per surface area of the subject (which includes humans as well as non-human animals). The dose may be, in a (multiple) single dose regimen, generally lasting 21 days, administered to such a subject in amounts, preferably, but not exclusively from about 5 mg/m$^2$ to about 300 mg/m$^2$, including about 10 mg/m$^2$, about 20 mg/m$^2$, about 40 mg/m$^2$, about 50 mg/m$^2$, about 60 mg/m$^2$, about 80 mg/m$^2$, about 100 mg/m$^2$, about 120 mg/m$^2$, about 140 mg/m$^2$, about 150 mg/m$^2$, about 160 mg/m$^2$ and about 200 mg/m$^2$. In a (repeated) multiple dose regimen, the aggregate dose may administered within one cycle, generally lasting 21 days, to such a subject may preferably, but not exclusively be from about 120 mg/m$^2$ to about 840 mg/m$^2$, including about 120 mg/m$^2$, about 130 mg/m$^2$, about 140 mg/m$^2$, about 150 mg/m$^2$, about 180 mg/m$^2$, about 195 mg/m$^2$, about 240 mg/m$^2$, about 300 mg/m$^2$, about 360 mg/m$^2$, about 420 mg/m$^2$, about 450 mg/m$^2$, about 480 mg/m$^2$, 600 mg/m$^2$, 720 mg/m$^2$ about 840 mg/m$^2$. The aggregate dose is administered preferably in at least three individual doses, wherein the dose administration can be isochronously, e.g., once every week, preferably on days 1, 8, 15 or anisochronously within, e.g., the period of 21 days. Individual dosages administered may be about 3×40 mg/m$^2$, about 3×50 mg/m$^2$, about 3×60 mg/m$^2$, about 3×65 mg/m$^2$, about 3×80 mg/m$^2$, about 3×100 mg/m$^2$, about 3×120 mg/m$^2$, about 3×140 mg/m$^2$, about 3×150 mg/m$^2$, about 3×160 mg/m$^2$, 3×200 mg/m$^2$, 3×240 mg/m$^2$ about 3×280 mg/m$^2$.

The immunoconjugates are suitably administered at one time or over a series of treatments. In a multiple dose regime these amounts may be administered once a day, once a week or once every two weeks. Loading doses with a single high dose or, alternatively, lower doses that are administered shortly after one another followed by dosages timed at longer intervals constitute a preferred embodiment of the present invention. E.g., in a multiple dose regimen, a loading dose of anywhere between 100 to 160 mg/$^2$ could be combined with one or two subsequent doses of 40 to 100 mg/m$^2$. In a preferred embodiment, the timing of the dosages are adjusted for a subject so that enough time has passed prior to a second and/or any subsequent treatment so that the previous dose has been metabolized substantially, but the amount of immunoconjugate present in the subject's system still inhibits, delays and/or prevents the growth of a tumor. An exemplary "repeated multiple dose" regime comprises administering doses of immunoconjugate of about 10, 20, 40, 50, 60, 65, 80, 100, 120, 140, 160, 180, 200, 220 or 240 mg/m$^2$ once every week. Alternatively, a high initial dose of, e.g., 160 mg/m$^2$ may be followed by a one, two, or tri-weekly maintenance dose of, e.g., about 20 mg/m$^2$. Other combinations can be readily ascertained by the person skilled in the art. However, other dosage regimens may be useful. The progress of this therapy is easily monitored by known techniques and assays. Dosage may vary, amongst others, depending on whether they are administered for preventive or therapeutic purposes, the course of any previous therapy, the patient's clinical history, the patient's disease status, the patient's tumor load, the patient's genetic predisposition, the patient's concomitant diseases, the disease stage upon first treatment and response to the targeting agent/immunoconjugate, the side effects experienced by the patient and the discretion of the attending physician.

When a dose X of an immunoconjugate is said to significantly exceed another dose Y, it means that total (e.g., aggregate) dose X exceeds total (e.g., single) dose Y by at least 10% (e.g., if dose X is 100 mg/m$^2$, a dose Y that significantly exceeds dose X is at least 110 mg/m$^2$), preferably about 20% more preferably about 30%, 40%, 50%, 60% or even more.

The term individual dose is in particular when used in the context of a multiple dose regime used to describe a defined dose administered in a single administration and can be contrasted to the aggregate dose administered, e.g., in an active treatment cycle, which is the sum of the individual doses administered in said treatment cycle. E.g., three individual doses in an active treatment cycle lasting, e.g., 21 days of 100 mg/m$^2$ result in an aggregate dose of 300 mg/m$^2$.

The level of an immunoconjugate in a patient's body fluid such a, e.g., in the patient's plasma, serum or plasma is measured by methods well known in the art. Plasma levels can be assessed via different pharmacokinetic (PK) assay like the one described under Materials and Methods. The levels of the immunoconjugate in the serum or plasma or other blood derived body fluid is generally determined 2 to 4 hours after the start of the respective administration, respectively, wherein said administrations are preferably in form of an infusion. This generally corresponds to 0-2 hours after completion of an administration, in particular an infusion.

Figure 28:
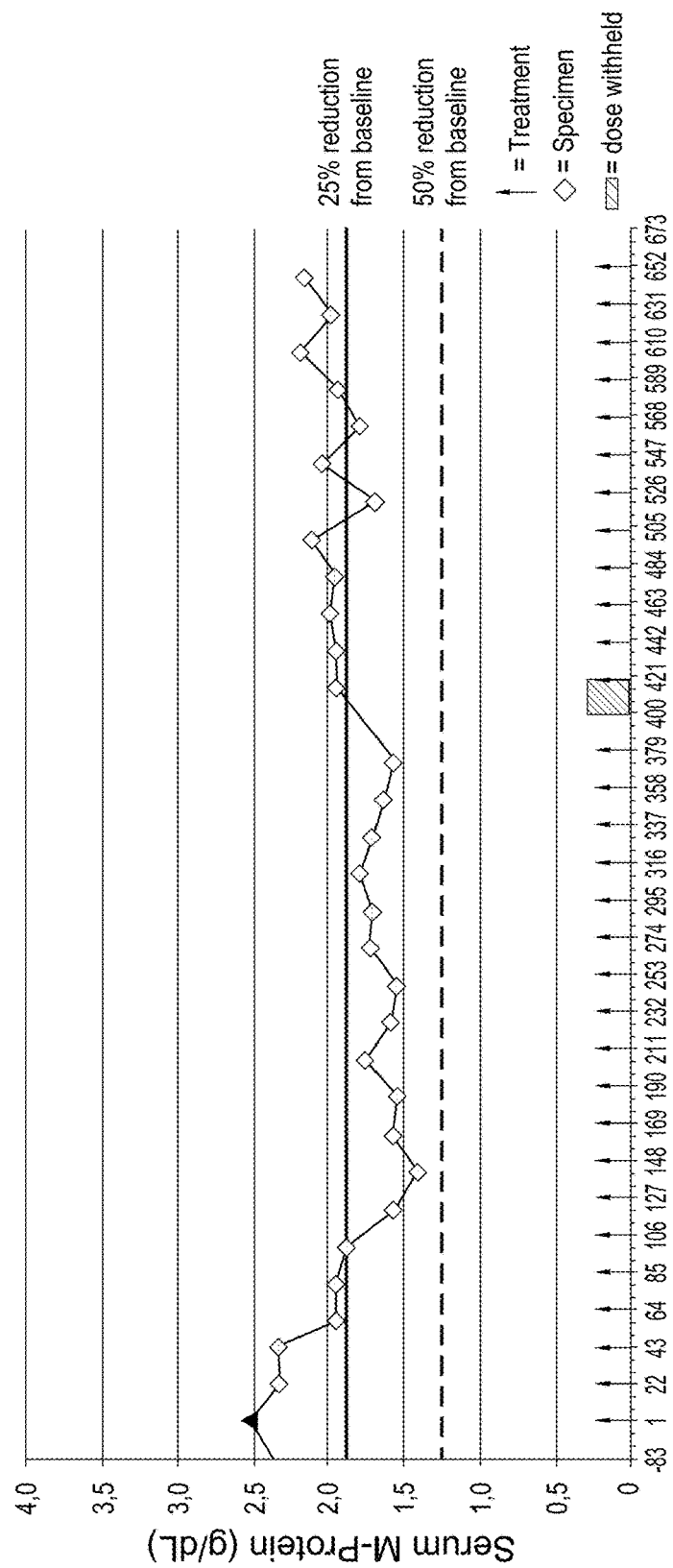
FIG. 28 shows serum M-protein levels during an extended administration of BT062 as repeated single doses BT062 of 160 mg/m$^2$, which lead to minor response with manageable side effects.

The present invention is, in one embodiment, directed to a maintenance therapy. As can be seen in FIG. 28 long-term therapy with up to 160 mg/m$^2$ once every 21 days is successfully achieving stable disease or even minor response, but at least progression free survival. The Figure also shows that plasma concentrations of BT062 increased over time indicating a decrease of tumor burden under treatment. This type of therapy is well suited to follow a repeated multiple dose regimen of, e.g., weekly administration. A typical maintenance therapy with dosing up to 160 mg/m² once every three weeks may follow a repeated multiple dose regimen (e.g. once every week for three weeks). Depending on the tumor burden, lowering the doses may be employed, whereby, e.g., plasma levels of the immunoconjugate or other relevant parameters may serve to determine the appropriate dosing for maintenance therapy. Maintenance can be achieved by threshold levels of the immunoconjugate, which are permanently present/maintained in the subject, so that there is a constant amount of immunoconjugate available. In a preferred embodiment, a tumor in a subject/the target cells are permanently exposed to immunoconjugate, so that no new tumor cells can grow, or that they are quickly destroyed due to a constant presence of the immunoconjugate in the subject, which is reflected by a certain measurable level of immunoconjugate in the subject's, e.g., plasma.

The maintenance therapy preferably reduces administration frequency. However, other maintenance therapies resulting in particular in, e.g., reduced aggregate doses of immunoconjugate administered are also preferred. The particular design of a maintenance therapy will depend, among others, on tumor burden. The level immunoconjugate and/or other efficacy blood parameters such as M-protein, FLC or a tumor/cancer specific marker can be determined in a body fluid, such as the plasma, serum or urine of the subject (patient) and the maintenance dose and frequency of the dose can be made dependent on the level or a change in the level of the efficacy blood parameter. A kit that may be employed in this as well as other contexts of the present invention may include markers, in particular antibodies, preferably labeled antibodies, against the immunoconjugate, e.g., against the toxin portion of the immunoconjugate, which can be used to quantify the immunoconjugate in a body fluid of a subject. A signal obtained from the binding of the, e.g. labeled antibody, can be correlated to the amount of immunoconjugate present in the body fluid of a subject. Suitable individual dose levels, both for repeated multiple doses as well as repeated single doses, for maintenance therapy are, e.g., 60-160 mg/m².

Extended treatment free periods may be beneficial for the patient. Surprisingly, it was found that after even an extended resting period (see days 400 to 421) stable disease could still be maintained (see FIG. 28).

The present invention is, in one embodiment, directed to an administration regimen, preferably with rapid plasma clearance. The regimen provides generally less than about 280 mg/m², less than 120 mg/m², less than 100 mg/m², less than 80 mg/m², including no more than about 40 mg/m², more preferably no more than about 20 mg/m², even more preferably no more than about 10 mg/m² in a given week for at least three consecutive weeks which define an interval (cycle). The 10 mg/m² to 280 mg/m² range translates to an average daily dose of about 1.43 mg/m² to 40 mg/m² Thus, average daily doses of about 0.4 mg/m² to about 17.14 mg/m², including about 5.7 mg/m², about 7.1 mg/m², 8.58 mg/m², 9.28 mg/m², 11.4 mg/m², 14.28 mg/m², 17.1 mg/m², 22.85 mg/m², 25.7 mg/m² (180 mg/m²), 28.58 mg/m² 34.2 mg/m², 40 mg/m² are part of the present invention. Low dose administration schemes up to 100 mg/m² are associated with rapid plasma clearance at the in early elimination phase, that is, any time during administration up to two hours after administration is completed. What distinguishes the low dose administration regime from other low dose regimens is the rapid plasma clearance, which is defined by a measured Cmax during that period that is preferably less than 55%, less than 50%, less than 40%, or less than 35% of the theoretical Cmax (Tables 11).

Administration regimens are, at higher levels, accompanied by less rapid plasma clearance, that is by plasma clearances that exceed 55%, often 60%, 70% 80% or 90% of the theoretical Cmax value, which are referred to herein as moderate (equal or >55%, but <80% of the theoretical Cmax value) or slow plasma clearance (equal or >80% of the theoretical Cmax value). At these clearances it was surprisingly found that, despite the relative high concentration of immunoconjugate in the plasma, these administration regimens still did not result in DLTs. This is despite the fact that expression levels of CD138 on non target cells that express CD138, e.g., cells of vital organs, such as the epithelium which are not target of any treatment, are also relative high in CD138 (immunohistochemistry analyses with the CD138 antibody BB4 showed that the reactivity to this antibody to the epithelium matched that of MM patient plasma cells (US Patent Publication 20070183971)). Expression levels of CD138 on target and non target cells that produce equal scores (e.g. plus three ((+++) as in the above example) in immunohistochemistry analyses are referred to herein as comparable expression levels and are part of the present invention. In an alternative embodiment, the expression levels on target cells were actually consistently below that of the epithelium (e.g., plus one (+) or plus two (++) vs. plus three (+++) for the epithelium). Some tumor target cells show mixed expression levels, such as, that some cells have an expression level of plus two and some an expression level of plus three. The mean of a representative number of cells (such as 100 randomly sampled cells) will determine whether these tumor target cells in question fall under the definition of having expression levels comparable or below that of the epithelium. These treatment regimens are generally above 40 mg/m², but below 180 or even 280 mg/m² given weekly at least for three consecutive weeks which define an active treatment cycle, which translates to a daily doses of about 5.71 mg/m² to about 25.71 mg/m² (180), 40 mg/m² (280).

With respect to Patient 8 (see FIG. 18 for numbering) it was noticeable, that this patient had, during the entire treatment of 168 days, while there was an increase in FLC until day 141, no disease progression (see also FIG. 21), reflecting the efficacy of BT062 administration, while Patient 6 showed no disease progression for 6 cycles (FIG. 20).

Figure 19A:
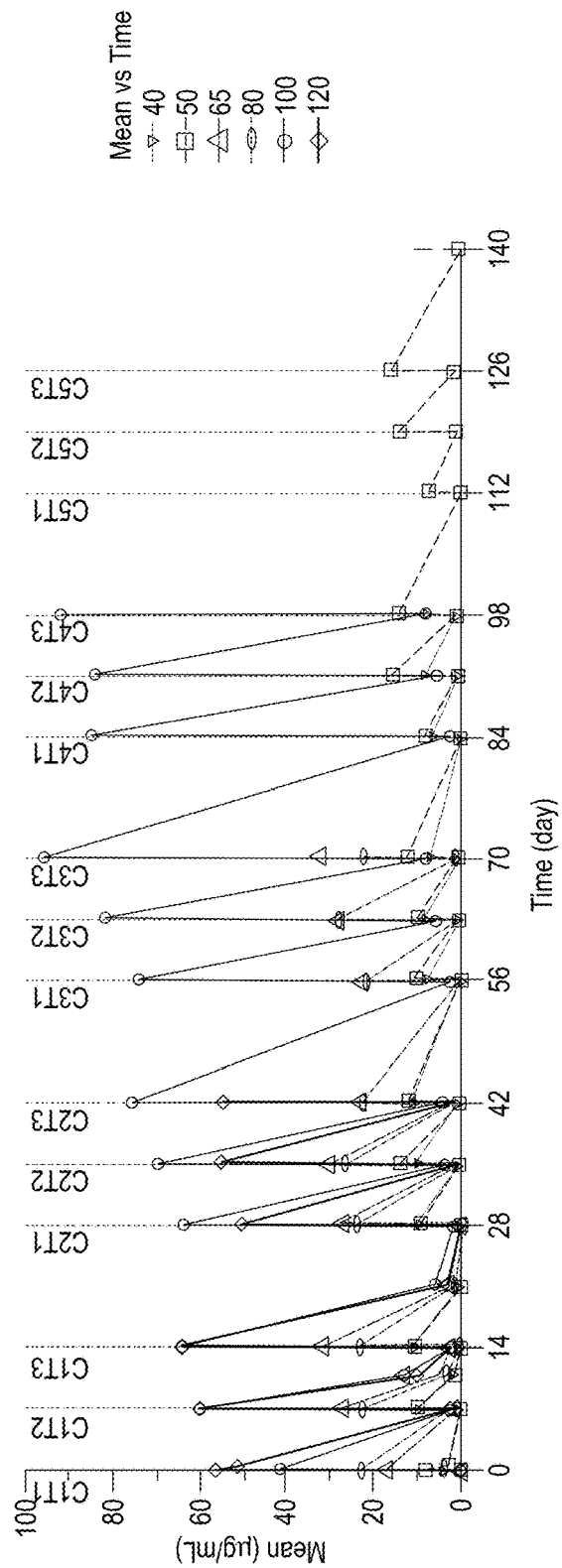
FIG. 19 shows in (A) the course of Cmax values with different dosages administered weekly for three weeks followed by a week long resting period and in (B) the Cmax values, 0-2 hours after completion of the administration, for different doses. The theoretical Cmax values are also shown.
Figure 19B:
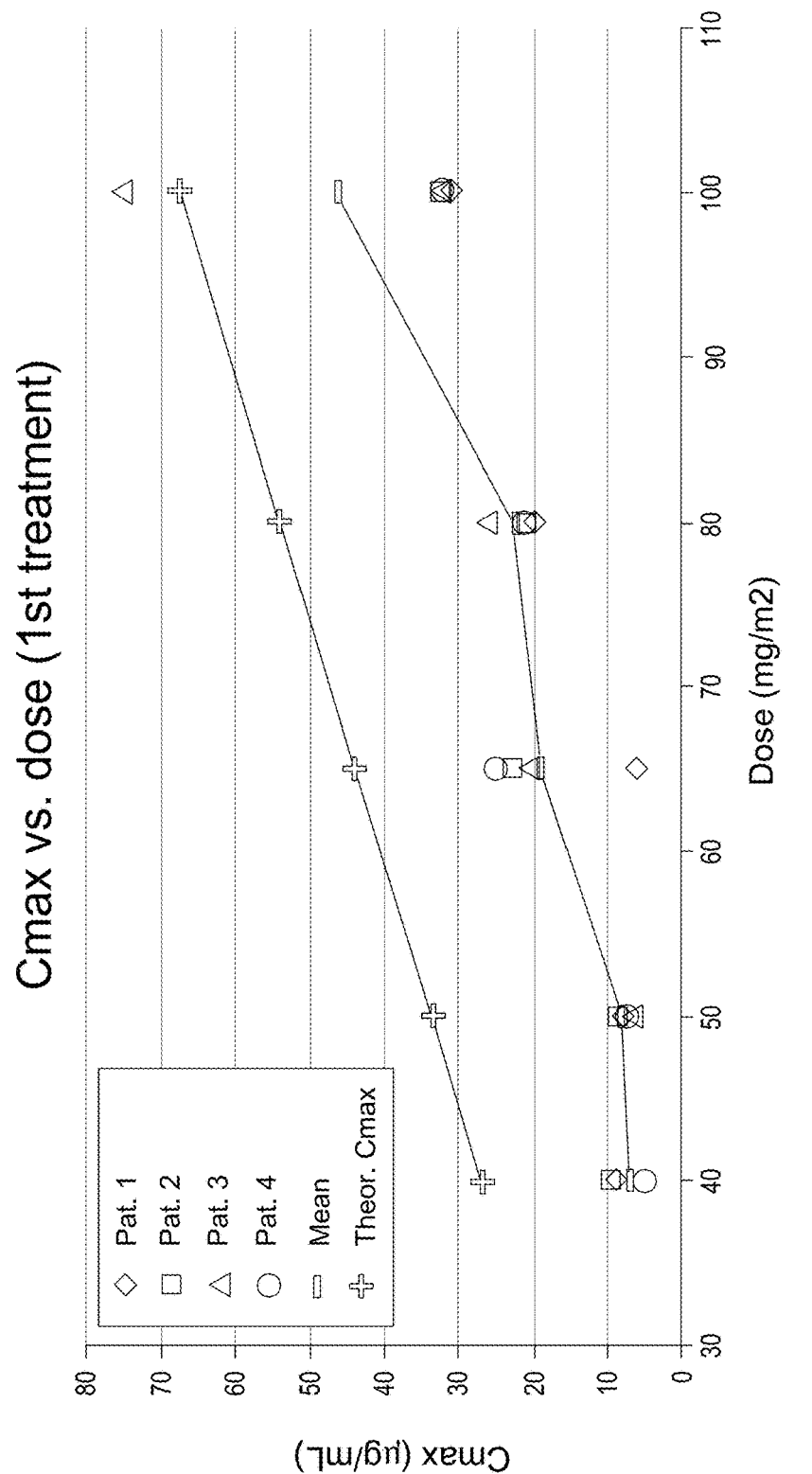

FIG. 19B clearly demonstrates that a constant amount of approx. 20 µg/ml is lost, presumable during infusion. This has been calculated from the difference between the plasma levels (defined here as Cmax) determined in the samples and the theoretically achievable Cmax value. In Table 11c the absolute values for the plasma level determined between 0 and 2 hours after the end of infusion are displayed and compared to the theoretically achievable Cmax plasma values ("Theoretical Cmax" as calculated by the formula below)

Theoretical Cmax was Calculated According to the Following Assumed Parameters:

| | |
|---|---|
| Patient's Body Surface Area | 1.9 m² |
| Patient's Weight | 70 Kg |
| Patient's Plasma Volume | 40 ml/kg |

$$\frac{(\text{Administered dose} \times \text{surface area})/\text{body weight}}{\text{Plasma Volume}}$$

In certain embodiments, the invention is also directed to a treatment regimen, wherein the dose can be adapted according to the measured level of an efficacy blood parameter found in a body fluid such as plasma. This allows for a patient tailored treatment. For example, the dose of BT062 may be adapted according to plasma levels determined between 0 and 4 hours after completion of an administration, such as an infusion.

Figure 29:
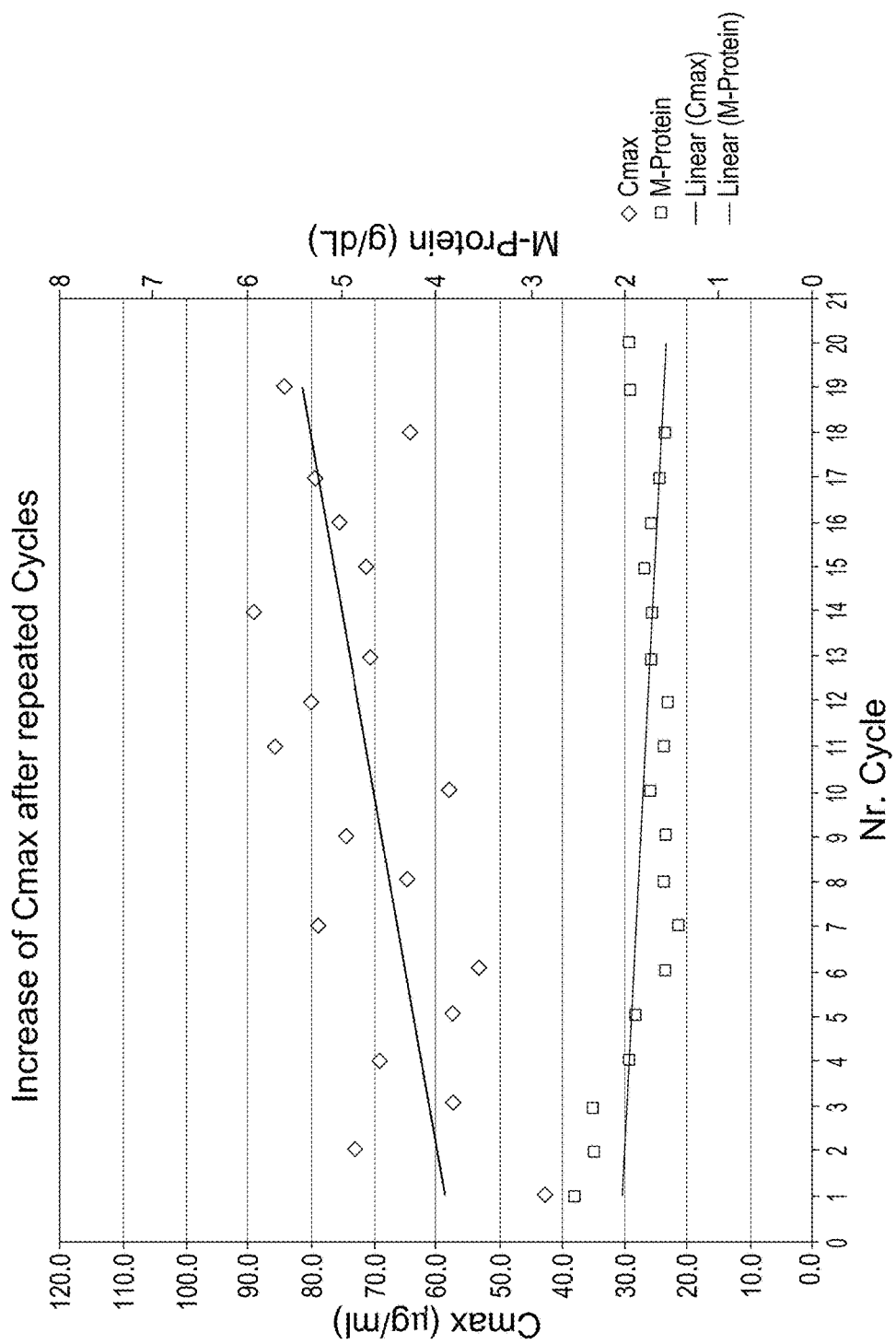
FIG. 29 shows serum M protein levels and Cmax values over time in a repeated single dose administration for a patient treated with a repeated single dose of BT062 of 160 mg/m$^2$ (see also FIG. 28).

As can be seen in FIG. 29, the parameter M-protein (decrease in its level) indicated in this patient disease improvement. At the same time plasma levels (Cmax values) of BT062 increased. With increasing treatment cycles, the tumor load was reduced and concomitantly, plasma levels ("Cmax values") determined in the plasma after 0-4 hours after completition of the infusion with BT062 increased, so that a negative correlation between the M-protein level and the Cmax were observed. The increase in Cmax values can be explained by a decrease in tumor volume, which means that fewer tumor cells are present, which is reflected in the decrease in M-Protein level. Less CD138 as a target source would lead to less binding sites for BT062. As a consequence, more BT062 can be detected in the plasma. Thus, the Cmax values can be used to evaluate the response to treatment (increase in Cmax correlates with efficacy). If, in a given instance, the Cmax values increases, when compared to Cmax of a prior injection (or any injection, where no efficacy was seen) e.g. by 10%, 20% or more, this indicates that fewer binding sites on the tumor are present and that thus tumor size decrease. In this example, the dose can be adjusted to a lower dose in the next treatment cycle. As a result, a lower amount of drug needed and toxicities can be prevented.

A repeated single dose refers to a sequence of administrations, wherein the administration following an administration is regarded to be independent of this preceding administration. Thus, in the present context, the level of immunoconjugate in a subject's blood can be regarded as equal after each administration. Each time the immunoconjugate is administered, it is expected that equal levels of immunoconjugate are initially present in the blood.

Administration intervals between the "single doses" of the repeated single doses are defined according to the theoretically calculated half life of an isotype of an immunoconjugate, in the case of BT062, IgG4.

In general, the half life of therapeutic antibodies depends mainly on the antibody characteristics/its structural features (e.g. binding to Fc receptors) and the target. For example, the binding affinity of the Fc part to the neonatal receptor FcRn is affecting the half life. By binding to FcRn in endosomes, the antibody is salvaged from lysosomal degradation and recycled to the circulation, which prolongs the half life. For an IgG4 a half life of 15.6 (+/−4.5) days (Alyanakian et al., 2003; Salfeld et al., 2007) has been reported. In the study referenced herein, a "repeated single dose" has been chosen that has administration intervals of three weeks. However, about three weeks, about four weeks, but also about five or about six weeks are alternative intervals for repeated single doses. A reference to "about" refers in the context of three weeks to +/−96 hours and in the context of four to six weeks to +/−120 hours.

A multiple dose regimen or a multiple dose refers to a sequence of administrations, wherein the administration following an administration is regarded to be dependent of the preceding administration. Thus, in the present context, the level of immunoconjugate in a subject's blood is expected in a second and subsequent administration to be above the base level that existed prior to the initial administration. At each administration following the initial administration of the immunoconjugate, a certain level of immunoconjugate is expected to be present in the blood. Administration intervals between the individual "doses" of the multiple doses are defined, as in the context of the repeated single doses, according to the theoretically calculated half life of an isotype of an immunoconjugate, in the case of BT062, IgG4. For an IgG4 a half life of 15.6 (+/−4.5) days (Alyanakian et al., 2003; Salfeld et al., 2007) has been reported. In the study referenced herein, a "multiple dose" has been chosen that has administration intervals of one week. However, even shorter administration intervals may be chosen such as 4 days or even 3 days. Alternatively, a longer interval can be chosen. However, at a minimum a multiple dose implies at least 2 administrations in a 21 day period. A reference to "about" refers in the context of one week to +/−32 hours, in the context of 4 days, +/−18 hours and in the context of 3 days +/−12 hours. A repeated multiple dose refers to multiple doses administered in subsequent treatment cycles, which may include intermittent resting period(s) or treatment free period(s), including extended resting period(s) or treatment free period(s), that do not obliterate in whole the effects of the previously administered multiple dose(s).

The actual level of immunoconjugate after the first and each subsequent administration, however, depends on the de facto "clearance" of the immunoconjugate from the, e.g., the plasma ("plasma clearance") immediately during/after completion of the administration, in particular, 0-2 hours after completion of administration. At 40 mg/m² median infusion time was 40 min within a range of 32 min to 1 hour 30 min. At the dose level of 120 mg/m² median infusion time was 2 hours 2 min within a range of 1 hour 40 min to 2 hour 30 min. Accordingly, in an IV administration, about 1 mg/m² may, in certain embodiments, be administered on average per minute, but administration times, of about 1 mg/m² per 30 seconds to about 1 mg/m² per 120 seconds are well within range. Surprisingly, it was found that BT062 cleared from the plasma considerably faster than either the theoretical expected values or the values encountered with similar immunoconjugates. This observation allowed for the design of new administration regimens for the immunoconjugate both alone in a monotherapy as well as in combination with other relevant agents, in particular cytotoxic agents to provide effective anticancer combinations.

Aggregate effective amount is the effective amount of immunoconjugate administered within a period of a dosing regimen, preferably in equal doses, e.g., once a week, for e.g. three weeks such as on days 1, 8, and 15 of a 21 day dosing regimen or on days 1, 8, 15 of a 28 day dosing regimen wherein no dose is administered on day 22.

The progress of the therapy is easily monitored by known techniques and assays. Dosage may vary, amongst others, depending on whether they are administered for preventative or therapeutic purposes, the course of any previous therapy, the patient's clinical history, the patient's disease status, the patient's tumor load, the patient's genetic predisposition, the patient's concomitant diseases, the disease stage upon first treatment and response to the targeting agent/immunoconjugate, the side effects experienced by the patient and the discretion of the attending physician.

The advantages of a low dose regime are wide-ranging. However, the probably most significant advantage is minimizing the risk of adverse side effects. While immunoconjugates generally permit sensitive discrimination between target and normal cells, resulting in fewer toxic side effects than most conventional chemotherapeutic drugs, many immunoconjugates are still not completely free of side effects. Despite superior targeting, the antigen of interest is generally also expressed on non-cancer cells whose destruction during therapy can lead to adverse side effects. In the case of CD138, the antigen is in particular expressed on epithelial cells. Also, the immunoconjugate might undergo processing within the body that is unrelated to the procession in or at a target cell and a certain percentage of effector molecules might be released at locations remote from the target cells leading to toxic side effects.

It was shown that the immunoconjugate of the present invention was effective at low doses, while displaying clinically acceptable toxicities (dosages up to 160 mg/m$^2$ provided once every three weeks). At doses up to at least 120 mg/m$^2$ but in any event at doses of less than 160 mg/m$^2$ provided once every three weeks (e.g., on day 1), the tested immunoconjugate also showed rapid plasma clearance in human subjects. Tables 9 and 10 show the clearance observed in repeated single dose regimens.

TABLE 9

Plasma concentrations after end of infusion and effective Cmax mean values of BT062 from plasma obtained in patients having received a single dose/repeated single dose BT062 (first and fourth cycle). Repeated dose administration in cycles of 21 days. Cmax values were obtained between 0 and 2 hours post infusion. Administration cycles: cycle 1: day 1, cycle 2: day 22; cycle 3: day 43; cycle 4: day 64 etc.

| | | plasma level of BT062 (µg/ml) human | |
|---|---|---|---|
| dosage BT062 (mg/m$^2$) | theoretical Cmax | effective Cmax (cycle 1) mean (lowest; highest) | effective Cmax (cycle 4) mean (lowest; highest) |
| 10 | 7 | 1.11 | n.a. |
| 20 | 14 | 2.9 (1.66; 4.44) | 7.06 (6.79; 7.34) |
| 40 | 27 | 4.31 (0.97; 9.86) | 2.51 (1.02; 3.68) |
| 80 | 54 | 18.8 (13.4; 23.6) | 14.2 (7.4; 21) |
| 120 | 81 | 21.4 (15.1; 28.7) | n.a. |
| 160 | 109 | 81.2 (73.7; 85.5) | 77.4 |
| 200 | 136 | 82.0 (68.0; 102.4) | n.a. | n.a. data not available

TABLE 10

Effective Cmax mean values of BT062 from plasma obtained in patients having received a single dose/repeated single dose BT062 (first and fourth cycle). Repeated dose administration in cycles of 21 days. Maximum values were obtained within the first 2 hours post injection. Cmax values were obtained between 0 and 2 hours post infusion. Effective Cmax is indicated in percentage of theoretically calculated Cmax. Administration cycles: cycle 1: day 1, cycle 2: day 22; cycle 3: day 43; cycle 4: day 64 etc.

| | | plasma level of BT062 (µg/ml) human | | |
|---|---|---|---|---|
| Dosage BT062 (mg/m$^2$) | theoretical Cmax | effective Cmax (cycle 1) | percentage of theoretical Cmax (n) | effective Cmax (cycle 4) | percentage of theoretical Cmax (n) |
| 10 | 7 | 1.1 | 15% (3) | n.a. | n.a. |
| 20 | 14 | 2.9 | 20% (4) | 7.06 | 49% (2) |
| 40 | 27 | 4.31 | 16% (3) | 2.51 | 9% (3) |
| 80 | 54 | 18.8 | 34% (3) | 14.2 | 26% (2) |
| 120 | 81 | 21.4 | 26.5% (3) | n.a. | n.a. |
| 160 | 109 | 81.2 | 74.5% (4) | 77.4 | 71% (1) |
| 200 | 136 | 82.0 | 60% (3) | n.a. | n.a | n.a. data not available
n: number of patients

The theoretical Cmax was calculates as described above.

Although the half life of BT062 in plasma of human subjects treated proved to be significantly lower than the plasma half life observed in cynomolgus monkeys (days) and in human plasma ex vivo (14 days), the immunoconjugate still showed efficacy in human subjects, even at administrations as low as 20 mg/m$^2$ suggesting an accelerated tumor targeting and tumor cell binding which results in an increased efficacy.

The accelerated tumor targeting could be confirmed by measurements of the receptor (CD138) occupancy on multiple myeloma cells in the bone marrow of a multiple myeloma patients. As can be seen in Table 11e at different repeated multiple doses regimen, the receptor occupancy at the tumor site in the bone marrow came close to 100% within four hours after the end of the administration of the immunoconjugate, supporting an antibody mediated accelerated tumor targeting. Accordingly, the present invention is directed at immunoconjugates having an early, that is 0-12, 0-10, 0-8, 0-6 or 0-4 hours after completion of administration, target tissue receptor (CD138) occupancy of between 70-100%, preferably 80-100%, more preferably 90-100%, even more preferably more than 94, 95, 96, 97 or 98% "receptor occupancy" (RO). The "receptor" is hereby CD138 and the RO is measured according to the following formula:

$$RO=(MFI\ Sample\ 1-MFI\ Sample\ 3)/(MFI\ Sample\ 2-MFI\ Sample\ 3)$$

MFI=Mean Fluorescence Intensity measured via flow cytometry

Samples of myeloma cells in bone marrow aspirates.

Sample 1: Bound immunoconjugate, here, BT062 was stained with anti-May (May=matansinoid) antibodies.

Sample 2: Total CD138 was measured with anti-May antibodies after receptor saturation with the immunoconjugate.

Sample 3: unspecific binding measure by incubation with an IgG1 isotype antibody.

As noted above, unusual rapid clearance from plasma of treated MM patients was observed in the early elimination phase (observed already during infusion and about 0 to 2 hours post infusion, ergo completition of infusion) followed by generally normal terminal elimination phase at dose levels up to 120 mg/m², whereas a more typical clearance profile was observed for all 4 patients at the 160 mg/m² and 200 mg/m² dose (3 patients), even though the clearance was still below the theoretical Cmax value. In addition, in the administration regimens that showed rapid plasma clearance at the early elimination phase, e.g. 20, 40, 80 and 120 mg/m²) not only rapid plasma clearance at the early elimination phase was observed, but a response (decrease of urine M-protein) was observed, including responses that manifested themselves in a decrease of urine M-protein by more than 50% after repeated single dosages (results not shown).

As discussed above, data supports that the rapid clearance from plasma of treated MM patients observed in the early elimination phase can be correlated to a high receptor occupancy at the target cells.

Surprisingly it was found that in a multiple dose regimen rapid plasma clearance occurred at aggregate dosages that were well above the 120 mg/m² and in fact close to the determined DLT of 160 mg/m² for a repeated single dose regime, which opened up the possibility for potent mono- or combination therapies due to low the toxicities of the immunoconjugate in the multiple dose regime.

Table 11a shows the % of theoretical Cmax values following differently dosed weekly administration schemes lasting for 3 weeks (21 days), ergo multiple dose regimens. The percent of theoretical Cmax in the 65 mg/m² cohort is higher than in the lower dosed cohorts shown:

TABLE 11a

|  | 40 mg/m² | 50 mg/m² | 65 mg/m² | 80 mg/m² | 100 mg/m² | 120 mg/m² |
|---|---|---|---|---|---|---|
| C1, D 1 | 29% | 24% | 43% | 42% | 61% | 69% |
| C1, D 8 | 39% | 29% | 63% | 42% | 81% | 74% |
| C1, D 15 | 43% | 31% | 72% | 44% | 89% | 79% |
| C2, D 1 | 33% | 26% | 52% | 45% | 94% | 62% |
| C2, D 8 | 37% | 40% | 61% | 50% | 102% | 67% |
| C2, D 15 | 41% | 35% | 52% | 43% | 111% | 67% |
| C3, D 1 | 28% | 30% | 52% | 39% | 109% | |
| C3, D 8 | 30% | 29% | 71% | 53% | 121% | |
| C3, D 15 | 26% | 35% | 73% | 41% | 142% | |
| C4, D 1 | 24% | 24% | | | 125% | |
| C4, D 8 | 30% | 45% | | | 123% | |
| C4, D 15 | 35% | 42% | | | 135% | |
| Mean (%) | 33% | 33% | 60% | 44% | 108% | 69% |
| Standard deviation | 6% | 7% | 11% | 4% | 24% | 6% |

% of theoretical Cmax: CX refers to the number of cycle: C1 is cycle 1, wherein each cycle is 21 days long followed by one treatment free week (or each cycle is considered 28 days long with no administration on day 22). DX is the day within the cycle at which the immunoconjugate is administered; D 8 is day 8 of the cycle. The % theoretical Cmax was calculated as set forth above. The high standard deviation for 100 mg/m² and the relative lower percentiles of Cmax at 120 mg/m² indicate that the high percentiles at 100 mg/m² are a deviation.

TABLE 11b

| | Conc. Missing to theor. Cmax [mg/m²] | | | | | |
|---|---|---|---|---|---|---|
| | 40 mg/m² | 50 mg/m² | 65 mg/m² | 80 mg/m² | 100 mg/m² | 120 mg/m² |
| C1, D 1 | 19.3 | 25.7 | 24.9 | 31.5 | 26.5 | 25.4 |
| C1, D 8 | 16.4 | 24.2 | 16.3 | 31.4 | 13.0 | 21.6 |
| C1, D 15 | 15.5 | 23.5 | 12.2 | 30.5 | 7.2 | 17.5 |
| C2, D 1 | 18.2 | 24.9 | 21.2 | 29.7 | 4.3 | 31.2 |
| C2, D 8 | 16.9 | 20.3 | 17.3 | 27.0 | −1.5 | 26.6 |
| C2, D 15 | 16.0 | 21.9 | 21.2 | 31.0 | −7.7 | 26.8 |
| C3, D 1 | 19.4 | 23.8 | 21.3 | 33.0 | −6.0 | |
| C3, D 8 | 19.1 | 24.2 | 12.8 | 25.8 | −14.4 | |
| C3, D 15 | 19.9 | 21.9 | 11.7 | 32.1 | −28.4 | |
| C4, D 1 | 20.6 | 25.8 | | | −17.1 | |
| C4, D 8 | 19.0 | 18.8 | | | −15.8 | |

TABLE 11b-continued

| | Conc. Missing to theor. Cmax [mg/m²] | | | | | |
|---|---|---|---|---|---|---|
| | 40 mg/m² | 50 mg/m² | 65 mg/m² | 80 mg/m² | 100 mg/m² | 120 mg/m² |
| C4, D 15 | 17.7 | 19.7 | | | −24.1 | |
| Mean | 18.6 | 23.0 | 17.7 | 29.9 | 6.8 | |
| SD | 1.5 | 2.4 | 4.7 | 1.0 | 13.2 | |

TABLE 11c

| | Mean conc. missing to theor. Cmax per Cycle | | | | | |
|---|---|---|---|---|---|---|
| | 40 mg/m² | 50 mg/m² | 65 mg/m² | 80 mg/m² | 100 mg/m² | 120 mg/m² |
| C1, D 1 | 17.1 | 24.5 | 17.8 | 31.1 | 15.6 | 21.5 |
| C1, D 8 | | | | | | |
| C1, D 15 | | | | | | |
| C2, D 1 | 17.0 | 22.4 | 19.9 | 29.2 | −1.7 | 28.2 |
| C2, D 8 | | | | | | |
| C2, D 15 | | | | | | |
| C3, D 1 | 19.5 | 23.3 | 15.3 | 30.3 | −16.3 | |
| C3, D 8 | | | | | | |
| C3, D 15 | | | | | | |
| C4, D 1 | 19.1 | 21.4 | | | −19.0 | |
| C4, D 8 | | | | | | |
| C4, D 15 | | | | | | |

Table 11b and 11c: CX refers to the number of cycle. C1 is cycle 1, wherein each cycle is 21 days long followed by one treatment free week (or each cycle is considered 28 days long with no administration on day 22). DX is the day within the cycle at which the immunoconjugate is administered; D8 is day 8 of the cycle. Shown in 11b are the concentrations (mg/m²) in absolute terms that, based on the actual Cmax, are missing at each dosage level to reach the theoretical Cmax. In 11c the actual numbers per administration are shown, on the right side the mean concentrations in each cycle are shown. It is also noticeable that the mean concentration (11c) within one cycle and over the three cycles shown is comparable and constant. Apart from a deviation at 100 mg/m², the missing concentration also remains relatively constant.

| Dose (mg/m²) | Time (days) | Patient | Plasma level/Mean (µg/ml) | SD (µg/ml) |
|---|---|---|---|---|
| 40 | Pre-dose | 4 | 0 | 0 |
| 40 | 0 (day of administration), 2 (hr after completion of administration) | 4 | 7.78 | 2.23 |
| 40 | before next dose | 4 | 0.69 | 0.33 |
| 40 | 7.2 | 4 | 10.67 | 4.93 |
| 40 | before next dose | 4 | 0.63 | 0.55 |
| 40 | 14.2 | 4 | 11.61 | 5.50 |
| 40 | before next dose | 4 | 0.70 | 0.62 |
| 50 | Predose | 3 | 0 | 0 |
| 50 | 0.2 | 3 | 8.20 | 0.90 |
| 50 | before next dose | 3 | 0.45 | 0.46 |
| 50 | 7.2 | 3 | 9.70 | 3.58 |
| 50 | before next dose | 3 | 0.49 | 0.45 |
| 50 | 14.2 | 3 | 10.43 | 3.47 |
| 50 | before next dose | 2 | 0.38 | 0.53 |
| 65 | Predose | 4 | 0 | 0 |
| 65 | 0.2 | 4 | 19.18 | 8.43 |
| 65 | before next dose | 4 | 1.41 | 0.66 |
| 65 | 7.2 | 4 | 27.83 | 8.95 |
| 65 | before next dose | 4 | 1.63 | 0.66 |
| 65 | 14.2 | 4 | 31.94 | 18.12 |

-continued

| Dose (mg/m²) | Time (days) | Patient | Plasma level/Mean (μg/ml) | SD (μg/ml) |
|---|---|---|---|---|
| 65 | before next dose | 4 | 1.77 | 0.93 |
| 80 | Predose | 3 | 0 | 0 |
| 80 | 0.2 | 3 | 22.81 | 3.20 |
| 80 | before next dose | 3 | 1.30 | 0.53 |
| 80 | 7.2 | 3 | 22.91 | 6.37 |
| 80 | before next dose | 3 | 1.27 | 0.68 |
| 80 | 14.2 | 3 | 23.81 | 6.46 |
| 80 | before next dose | 3 | 1.41 | 0.70 |
| 100 | Predose | 4 | 0 | 0 |
| 100 | 0.2 | 4 | 41.40 | 23.02 |
| 100 | before next dose | 3 | 3.77 | 0.78 |
| 100 | 7.2 | 3 | 54.85 | 24.34 |
| 100 | before next dose | 3 | 4.13 | 1.82 |
| 100 | 14.2 | 3 | 60.70 | 29.81 |
| 100 | before next dose | 3 | 6.04 | 2.63 |
| 120 | Predose | 2 | 0 | 0 |
| 120 | 0.2 | 2 | 56.00 | 32.46 |
| 120 | before next dose | 2 | 2.35 | 2.74 |
| 120 | 7.2 | 2 | 59.85 | 30.96 |
| 120 | before next dose | 2 | 2.50 | 6.68 |
| 120 | 14.2 | 2 | 63.90 | 28.82 |
| 120 | before next dose | 2 | 3.05 | 10.42 |

Table 11d represents the mean values of plasma level (μg/ml) of immunoconjugate at dose levels between 40 and 120 mg/m² before and after the weekly administration. The mean plasma level before the next administration ("before next dose") starts to increase slightly. At 65 and 80 mg/m², plasma levels before the next dose stay above 1 μg/ml. At 100 and 120 mg/m², the level before the next administration is between approx. 2 and 4 μg/ml, thus the plasma levels of subsequent treatments, are somewhat higher than those in the first cycle, indicating some accumulation prior to the next injection.

TABLE 12

Receptor Occupancy (RO) in Repeated Multiple Dose Regimen: Bone marrow receptor occupancy was measured via flow cytometry. Myeloma cells in bone marrow aspirates were characterized by CD138 and CD38 staining (not shown). Bound BT062 was stained with anti-May antibodies (Sample 1). Total CD138 was measured with anti-May antibodies after receptor saturation with BT062 (Sample 2). Incubation with an IgG1 isotype antibody determined unspecific binding to the sample (Sample 3). The occupancy of CD138 was calculated with the following equation.
RO = (MFI Sample 1 − MFI Sample 3)/(MFI Sample 2 − MFI Sample 3)

| Patient ID | Weekly Dose Level (mg/m²) | No. Cycles at Term. | Receptor occupancy (RO) |
|---|---|---|---|
| 12 | 80 | C8D15* | 99% |
| 12 | 80 | C13D15** | 37% |
| 12 | 80 | C14D15** | 51% |
| 22 | 140 | C1D1* | 86% |
| 23 | 140 | C1D1* | Background to high |
| 26 | 140 | C1D1* | 95% |
| 28 | 140 | C1D8** | 58% |
| 24 | 140 | C1D1* | 94% |
| 25 | 140 | C1D1* | 98% |
| 30 | 160 | C1D1* | 98% |
| 31 | 160 | C1D1* | 76% | wherein, MFI = Mean Fluorescence Intensity
Each cycle lasted 28 days with administration of the indicated dose on days 1, 8 and 15. C13D15, for example, indicates the dose administered on day 15 in the 13$^{th}$ cycle. In three of the above, measurements are based on samples that were taken just prior (within 12 hours) to the next administration and are marked with double asterisks (**) and thus more than 6 days after the last administration. The remainder of the measurements were taken directly after an administration of BT062, here within 4 or 12 or 24 hours after completion of administration (*). As can be seen, the RO was relatively low just prior to the next administration, while the RO was high right after administration.

Figure 13:
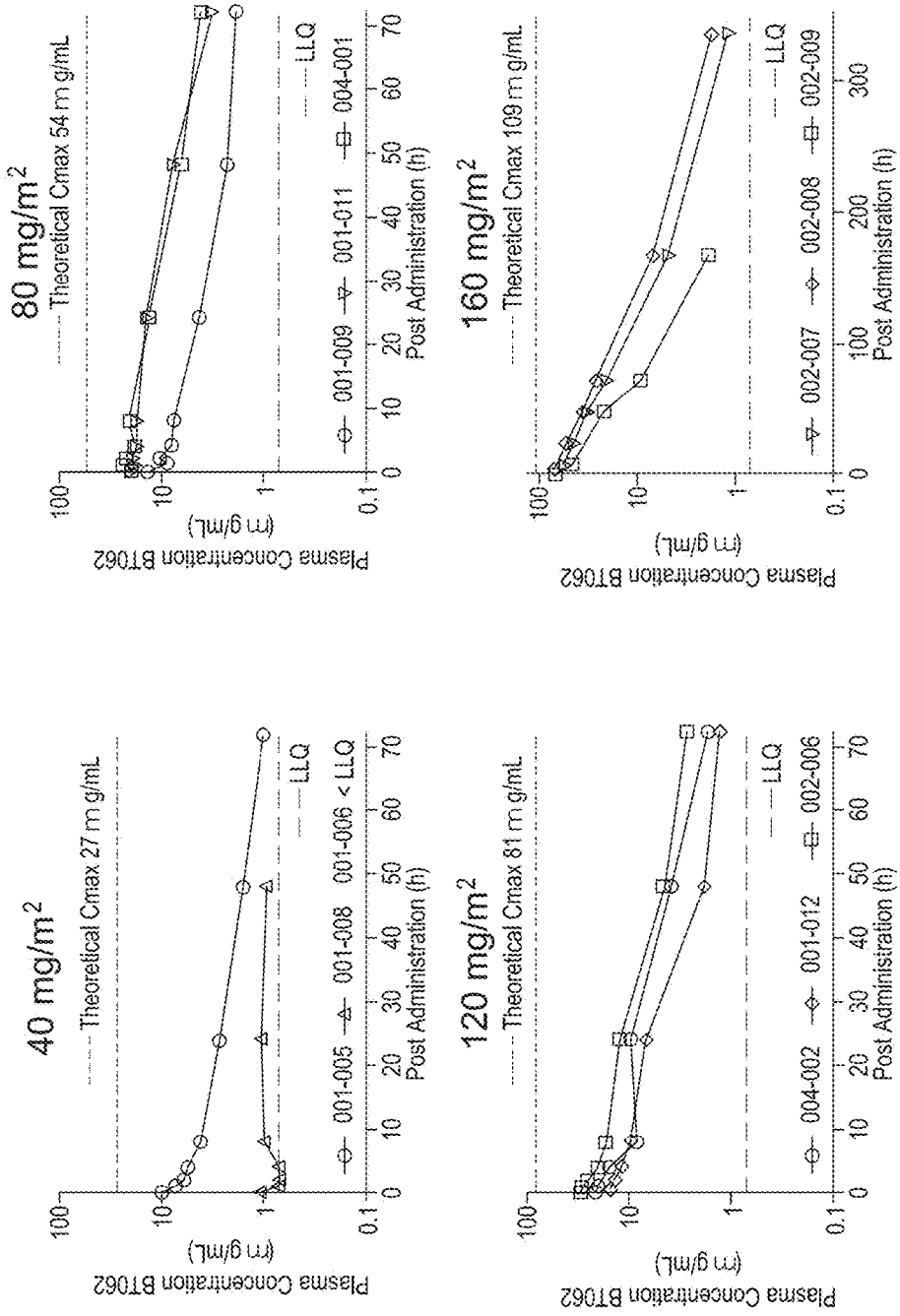
FIG. 13 illustrates the rapid plasma clearance for dosages ranging from 40 mg/m$^2$ to 120 mg/m$^2$, while higher doses as illustrated here by a dose of 160 mg/m$^2$, showed plasma clearance closer to the expected value.
Figure 14:
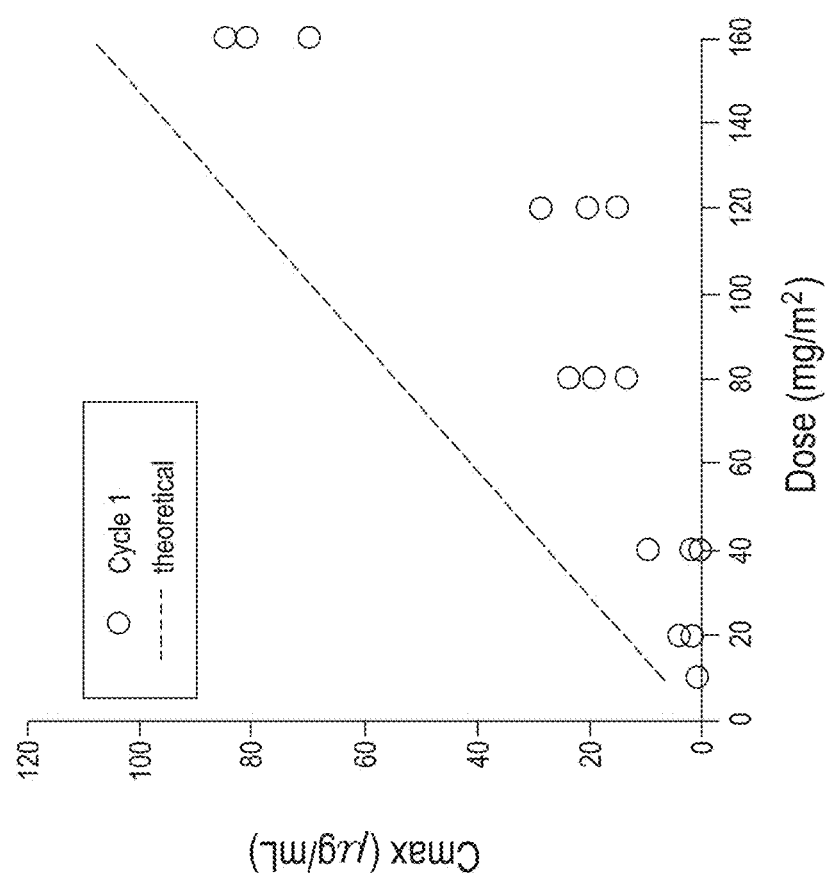
FIG. 14 shows the measured Cmax values of BT062 compared to the theoretical Cmax values.
Figure 15:
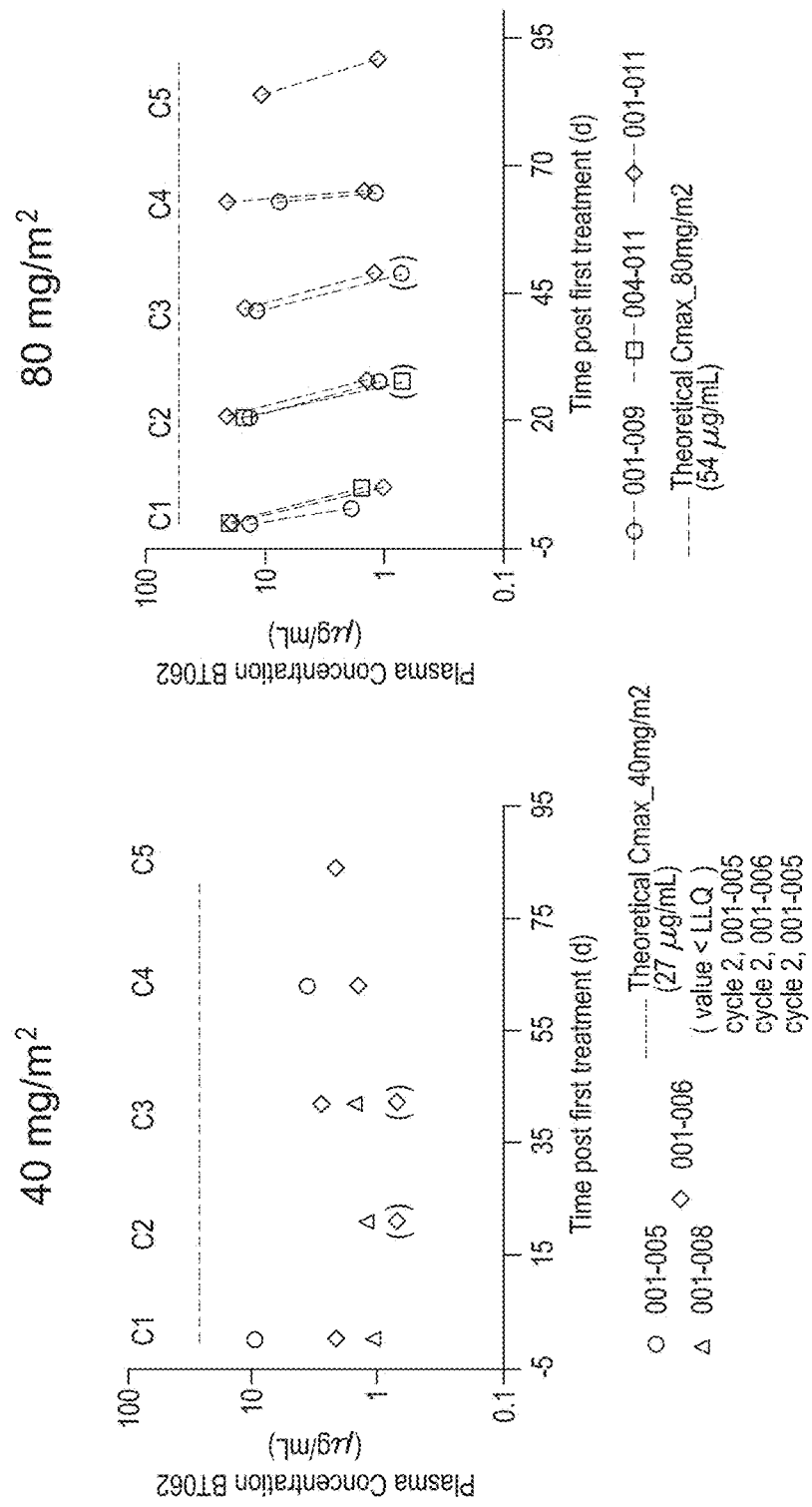
FIGS. 15 and 16 show that the Cmax values are generally similar over several treatment cycles in a repeated single dose regime as indicated.
Figure 16:
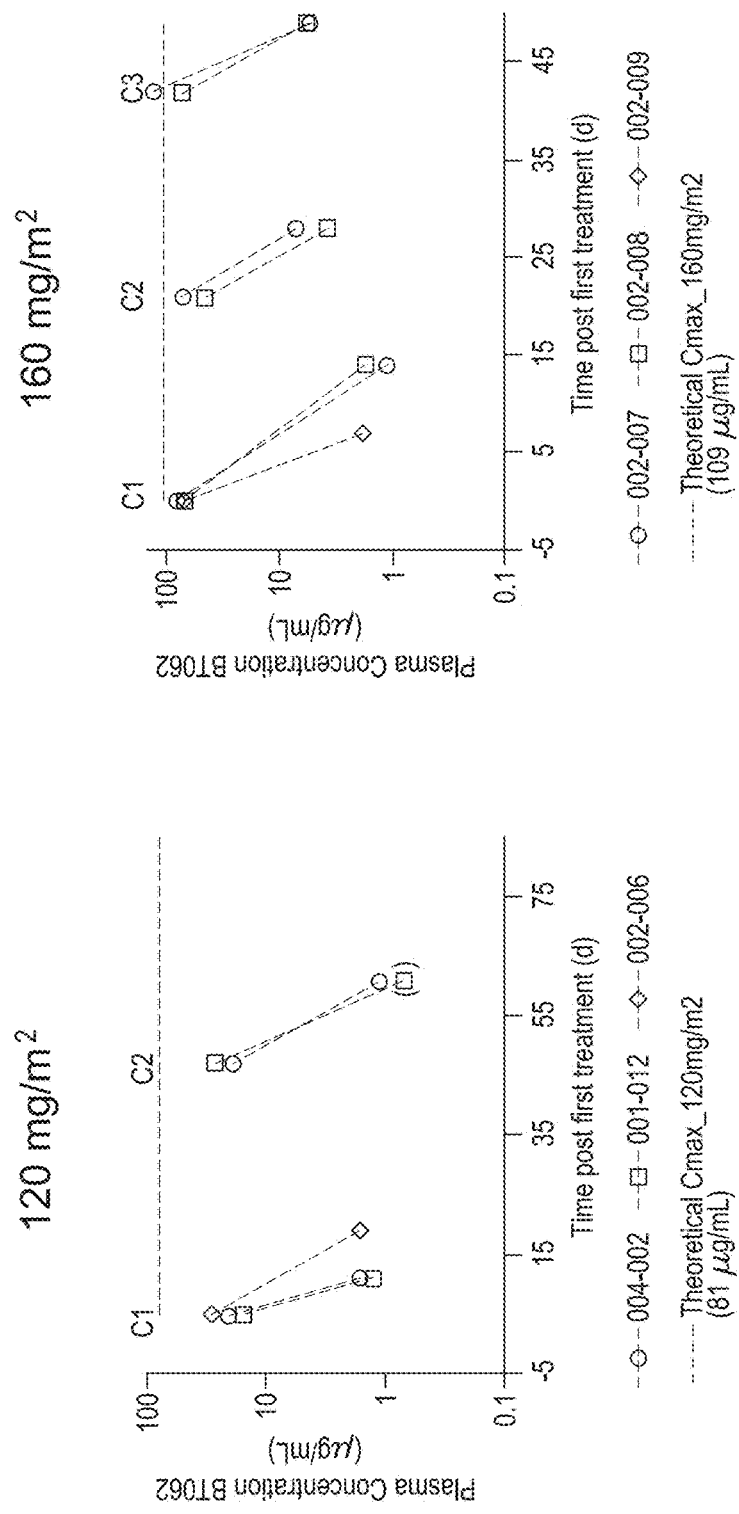
Figure 17:
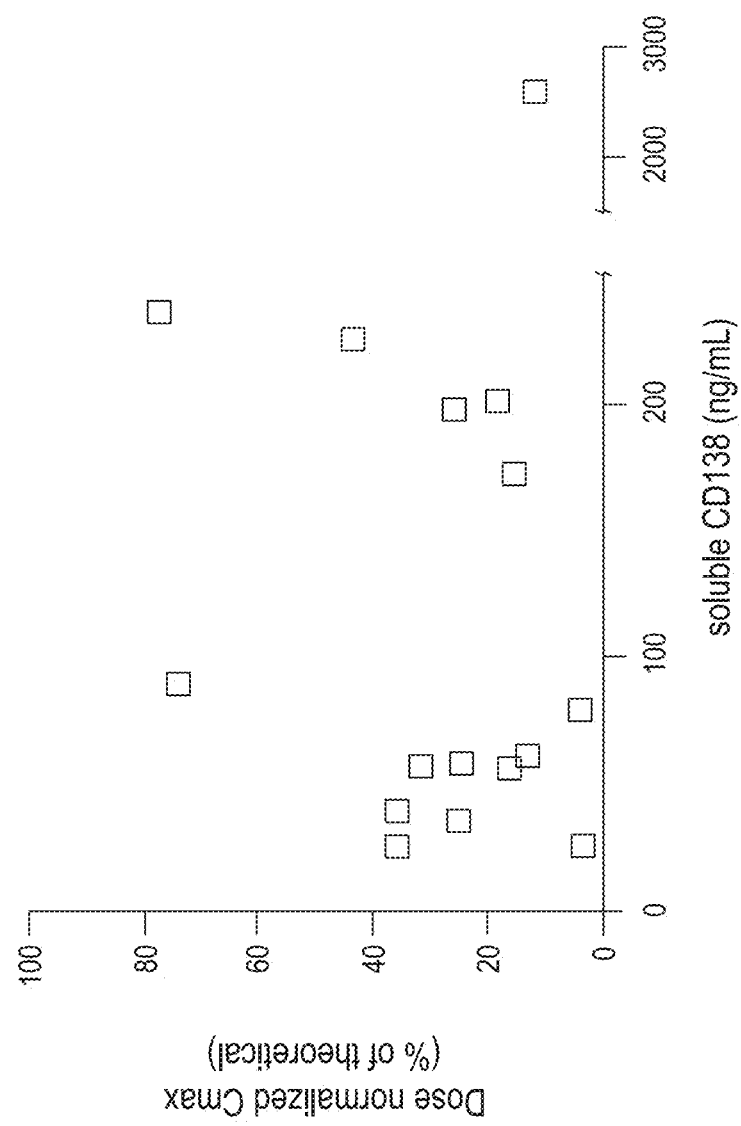
FIG. 17 clarifies that the rapid plasma clearance cannot be attributed to a buffering effect caused by soluble CD138.

FIG. 13 illustrates the rapid plasma clearance for single dose administrations ranging from 40 mg/m² to 120 mg/m², while higher doses as illustrated here by a dose of 160 mg/m², showed plasma clearance closer to the theoretical value. FIG. 17 clarifies that the rapid plasma clearance cannot be attributed to a buffering effect caused by soluble CD138. FIG. 14 shows how the measured Cmax values of BT062 compared to the theoretical Cmax values.

FIGS. 19A and 19A as well as Table 11a illustrate the rapid plasma clearance in an administration scheme involving multiple doses. As can be seen in a scheme that involves individual doses that are administered on days 1, 8, and 15 and that add up within a cycle (e.g., 21 days) to nearly a dosage that corresponds to DLTs of a repeated single dose (3×50 mg/m²=150 mg/m²$^t$, vs. 160 mg/m²) of the immunoconjugate, the actual Cmax values remain well beneath 50% of the theoretical Cmax value, while at the DLT levels in a repeated single dose, the actual Cmax values are well over 50% of the theoretical Cmax value.

Table 11b shows that at concentrations at which the actual Cmax is on average already well above 50% of the theoretical Cmax, the concentration missing to the theoretical Cmax, remains on average similar, in the examples provided, namely around 20 μg/ml (see also FIG. 19B). This may point towards a "sink", which "ab/adsorps" a certain portion of the immunoconjugate quickly, but becomes less noticeable as doses increase. In fact at 100 mg/m² this effect appears only to occur during the first individual dose. However, it rebounded at 120 mg/m² making it likely that that 100 mg/m² are a deviation. However, the sink of 20 μg/ml is observed here also at higher cycles.

Accordingly, the invention is also directed to a method of pretreatment with an targeting agent, preferably an unconjugated antibody, that is fed into this sink instead of the immunoconjugate, which contain effector molecules, which are not only toxic, but generally also costly. As the person skilled in the art will understand, the sink may include tumor target cells as well as CD138 expressing cells of other tissues. Thus, in one aspect of the invention, the constant amount of +/−20 μg/ml of immunoconjugate which is consistently missing to reach the theoretically Cmax value (FIG. 19B) promptly after or during infusion, ergo is considered quickly to be ad-/absorbed by/bind to said sink (also referred to herein as "antigen sink"). Such a sink is filled in such an embodiment not by the immunoconjugate, but by another agent, preferably an agent that binds to CD138. In this embodiment, rather than having the immunoconjugate being ad-/absorbed during/after administration, an alternative ad-/absorbent, e.g., unconjugated antibody, is administered. Assuming that the immunoconjugate is lost in the sink, and thus potentially does not contribute to the therapeutic effect, a pretreatment can be used to a) minimize the toxicities which might be related to that "sink" and b) lower the required amount of immunoconjugate to obtain equivalent results.

This pretreatment may consist of administration of 20 μg/ml (+/−) of an unconjugated anti-CD138 antibody or fragment thereof, preferably nBT062 and may fill this sink.

Figure 26:
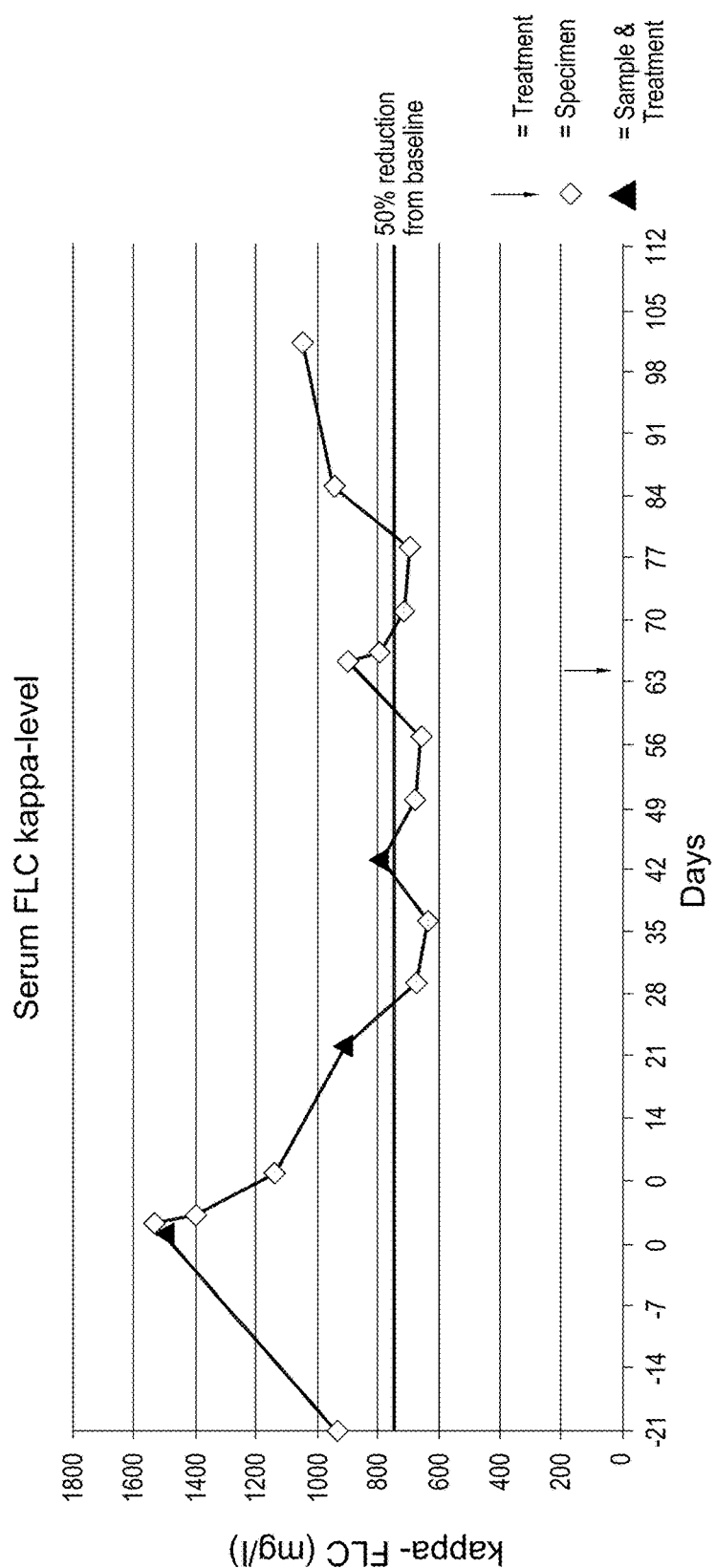
FIG. 26 shows the level of kappa FLC measured for a patient receiving 160 mg/m$^2$ at three weeks intervals. Days −21 to 101 are shown.
Figure 27:
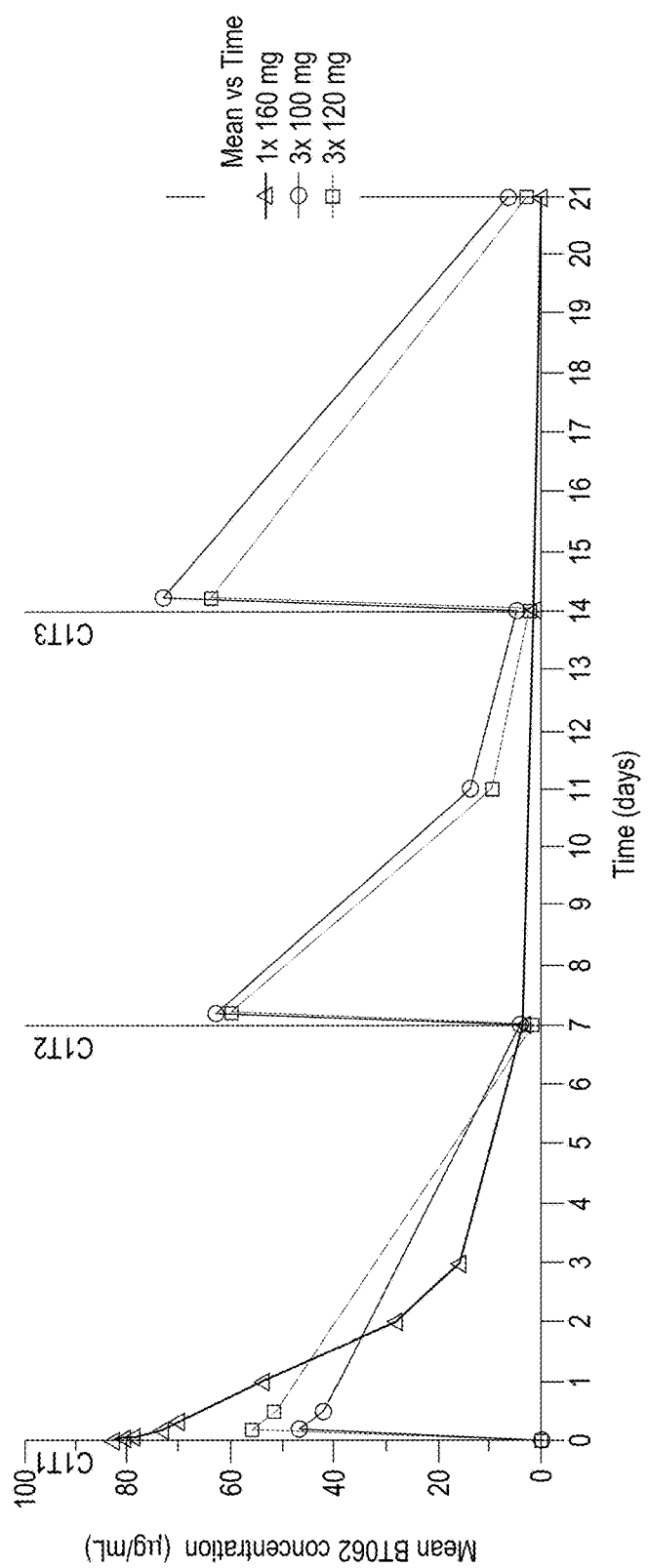
FIG. 27 shows a comparison of plasma levels of BT062 administered as a repeated single dose of 160 mg/m$^2$ in comparison to a multiple dose of 100 mg/m$^2$ and 120 mg/m$^2$ administered three times in an active treatment cycle of equal length (21 days).

At repeated single doses of 160 mg/m² which constitute a low dose compared to administration schemes of other immunoconjugates, terminal clearance profiles were closer to normal, that is, closer to the theoretical Cmax values. However, a rapid reduction of FLC in the serum could be observed after just a single administration, which manifested itself in a partial response after the 2$^{nd}$, 3$^{rd}$ and 4$^{th}$ administration (FIG. 26).

Analogues and Derivatives

One skilled in the art of therapeutic agents, such as cytotoxic agents, will readily understand that each of such agents described herein can be modified in such a manner that the resulting compound still retains the specificity and/or activity of the starting compound. The skilled artisan will also understand that many of these compounds can be used in place of the therapeutic agents described herein. Thus, the therapeutic agents of the present invention include analogues and derivatives of the compounds described herein.

For illustrative purposes of the uses of the immunoconjugates some non-limiting applications will now be given and are illustrated.

Materials and Methods

Chimeric Antibody Construction (cB-B4: nBT062)

B-B4

Murine antibody B-B4 as previously characterized (Wijdenes et al., Br J. Haematol., 94 (1996), 318) was used in these experiments.

Cloning and Expression of B-B4 and cB-B4/nBT062

Standard recombinant DNA techniques were performed as described in detail in text books, for example in J. Sambrook; Molecular Cloning, A Laboratory Manual; 2nd Ed. (1989), Cold Spring Harbor Laboratory Press, USA, or as recommended by the manufacturer's instruction in the cases when kits were used. PCR-cloning and modification of the mouse variable regions have been conducted using standard PCR methodology. Primers indicated in the respective results section have been used.

Expression of cB-B4/nBT062

Exponentially growing COS cells, cultured in DMEM supplemented with 10% FCS, 580 µg/mL-glutamine, 50 Units/ml penicillin and 50 µg/ml streptomycin were harvested by trypsinisation and centrifugation and washed in PBS. Cells were resuspended in PBS to a final concentration of $1 \times 10^7$ cells/ml. 700 µl of COS cell suspension was transferred to a Gene Pulser cuvette and mixed with heavy and kappa light chain expression vector DNA (10 µg each or 13 µg of Supervector). Cells were electroporated at 1900 V, 25 µF using a Bio-Rad Gene Pulser. Transformed cells were cultured in DMEM supplemented with 10% gamma-globulin free FBS, 580 µg/ml L-glutamine, 50 Units/ml penicillin and 50 µg/ml streptomycin for 72 h before antibody-containing cell culture supernatants were harvested.

Capture ELISA to Measure Expression Levels of cB-B4/nBT062

96 well plates were coated with 100 µl aliquots of 0.4 µg/ml goat anti-human IgG antibody diluted in PBS (4° C., overnight). Plates were washed three times with 200 µl/well washing buffer (PBS+0.1% Tween-20). Wells were blocked with 0.2% BSA, 0.02% Tween-20 in PBS, before addition of 200 µl cell culture supernatants containing the secreted antibody (incubation at 37° C. for one hour). The wells were washed six times with washing buffer, before detection of bound antibody with goat anti-human kappa light chain peroxidase conjugate.

Purification of cB-B4/nBT062 from Cell Culture Supernatants

The cB-B4 antibody was purified from supernatants of transformed COS 7 cells using the Protein A ImmunoPure Plus kit (Pierce, Rockford, Ill.), according to the manufacturer's recommendation.

cB-B4 Binding and Competition Assay

Analysis of binding activity of B-B4 and cB-B4 to CD138 was performed using the Diaclone (Besancon, France) sCD138 kit according to the manufacturer's recommendation, considering the changes described in the results section.

RNA Preparation and cDNA Synthesis

Hybridoma B-B4 cells were grown and processed using the QIAGEN Midi kit (Hilden, Germany) to isolate RNA following the manufacturer's protocol. About 5 µg of B-B4 RNA was subjected to reverse transcription to produce B-B4 cDNA using the Amersham Biosciences (Piscataway, N.J.) 1st strand synthesis kit following the manufacturer's protocol.

Cloning of B-B4 Immunoglobulin cDNA

Immunoglobulin heavy chain (IgH) cDNA was amplified by PCR using the IgH primer MHV7 (5'-ATGGGCAT-CAAGATGGAGTCACAGACCCAGG-3') [SEQ ID NO:3] and the IgG1 constant region primer MHCG1 (5'-CAGTG-GATAGACAGATGGGGG-3') [SEQ ID NO:4]. Similarly, immunoglobulin light chain (IgL) was amplified using the three different Igκ primers MKV2 (5'-ATGGAGACAGA-CACACTCCTGCTATGGGTG-3') [SEQ ID NO:5], MKV4 (5'-ATGAGGGCCCCTGCTCAGTTTTTTGGCTTCTTG-3') [SEQ ID NO:6] and MKV9 (5'-ATGGTATCCACAC-CTCAGTTCCTTG-3') [SEQ ID NO:7], each in combination with primer MKC (5'-ACTGGATGGTGGGAAGATGG-3') [SEQ ID NO:8]. All amplification products were directly ligated with the pCR2.1-TOPO vector using the TOPO-TA cloning kit (Invitrogen, Carlsbad, Calif.) according to the manufacturer's instruction.

*E. coli* TOP10 bacteria (Invitrogen) transformed with the ligated pCR2.1 vector constructs were selected on LB-ampicillin-Xgal agar plates. Small scale cultures were inoculated with single white colonies, grown overnight and plasmids were isolated using the QIAprep Spin Miniprep kit according to the manufacturer's instruction.

cDNA Sequence Determination

Plasmids were sequenced using the BigDye Termination v3.0 Cycle Sequencing Ready Reaction Kit (ABI, Foster City, Calif.). Each selected plasmid was sequenced in both directions using the 1210 and 1233 primers cycled on a GeneAmp9600 PCR machine. The electrophoretic sequence analysis was done on an ABI capillary sequencer.

The complete cycle of RT-PCR, cloning and DNA sequence analysis was repeated to obtain three completely independent sets of sequence information for each immunoglobulin chain.

B-B4 Vκ DNA Sequence

1st strand synthesis was performed in three independent reactions. The PCR products generated by using primers MKC and MKV2 (sequences given above) were ligated into pCR2.1-TOPO vectors according to the manufacturer's instruction. Clones from each independent set of RT-PCR reactions were sequenced in both directions. MKV2-primed product sequence was highly similar to sterile kappa transcripts originating from the myeloma fusion partner such as MOPC-21, SP2 and Ag8 (Carroll et al., Mol. Immunol., 25 (1988), 991; Cabilly et al., Gene, 40 (1985); 157) and was therefore disregarded.

The PCR products using MKC with MKV4 and MKV9 primers were similar to each other and differed only at the wobble positions within the leader sequence primer.

B-B4 VH DNA Sequence

1st strand synthesis was performed in three independent reactions and PCR products were cloned and sequenced from each 1st strand product. Five clones were sequenced from each 1st strand.

Construction of Chimeric cB-B4 Expression Vectors

The construction of the chimeric expression vectors entails adding a suitable leader sequence to VH and Vκ, preceded by a BamHI restriction site and a Kozak sequence. The Kozak consensus sequence is crucial for the efficient translation of a variable region sequence. It defines the correct AUG codon from which a ribosome can commence translation, and the single most critical base is the adenine (or less preferably, a guanine) at position −3, upstream of the AUG start. The leader sequence is selected as the most similar sequence in the Kabat database (Kabat et al., NIH National Technical Information Service, 1991). These additions are encoded within the forward (For) primers (both having the sequence 5'-AGAG<u>AAGCTT</u>GCCGC-CACCAT-GATTGCCTCTGCTCAGTTCCTTGGTCTCC-3' [SEQ ID NO:9]; restriction site is underlined; Kozak sequence is in bold type). Furthermore, the construction of the chimeric expression vectors entails introducing a 5' fragment of the human gamma1 constant region, up to a natural ApaI restriction site, contiguous with the 3' end of the J region of B-B4 and, for the light chain, adding a splice donor site and HindIII site. The splice donor sequence is important for the correct in-frame attachment of the variable region to its appropriate constant region, thus splicing out the V:C intron. The kappa intron+CK are encoded in the expression construct downstream of the B-B4 Vκ sequence. Similarly, the gamma-4 CH is encoded in the expression construct downstream of the B-B4 VH sequence.

The B-B4 VH and Vκ genes were first carefully analyzed to identify any unwanted splice donor sites, splice acceptor sites, Kozak sequences and for the presence of any extra sub-cloning restriction sites which would later interfere with the subcloning and/or expression of functional whole antibody. An unwanted HindIII site was found in the Vκ sequence which necessarily was removed by site-directed mutagenesis via PCR without changing the amino acid sequence. For this reactions, oligonucleotide primers BT03 (5'-CAACAGTATAGTAAGCTCCCTCGGACGTTCG-GTGG-3') [SEQ ID NO:10] and BT04 (5'-CCAC-CGAACGTCCGAGGGAGCTTACTATACTGTTG-3') [SEQ ID NO:11] were used and mutagenesis was performed according to the Stratagene (La Jolla, Calif.) Quickchange Mutagenesis Kit protocol.

Kappa Chain Chimerization Primers

The non-ambiguous B-B4 Vκ leader sequence, independent of the PCR primer sequence, was aligned with murine leader sequences in the Kabat database. The nearest match for the B-B4 VH leader was VK-10 ARS-A (Sanz et al., PNAS, 84 (1987), 1085). This leader sequence is predicted to be cut correctly by the SignalP algorithm (Nielsen et al., Protein Eng, 10 (1997); 1). Primers CBB4Kfor (see above) and g2258 (5'-CGC<u>GGATCC</u>ACTCACG-TTTGATTTCCAGCTTGGTGCCTCC-3' [SEQ ID NO:12]; Restriction site is underlined) were designed to generate a PCR product containing this complete leader, the B-B4 Vκ region, and HindIII and BamHI terminal restriction sites, for cloning into the pKN100 expression vector. The forward primer, CBB4K introduces a HindIII restriction site, a Kozak translation initiation site and the VK-10 ARS-A leader sequence. The reverse primer g2258 introduces a splice donor site and a BamHI restriction site. The resulting fragment was cloned into the HindIII/BamHI restriction sites of pKN100.

Heavy Chain Chimerization Primers

The non-ambiguous B-B4 VH leader sequence, independent of the PCR primer sequence, was aligned with murine leader sequences in the Kabat database. The nearest match for the B-B4 Vκ leader was VH17-1A (Sun et al., PNAS, 84 (1987), 214). This leader sequence is predicted to be cut correctly by the SignalP algorithm. Primers cBB4Hfor (see above) and g22949 (5'-CGAT<u>GGGCCC</u>TTGGTG-GAGGCTGAGGA-GACGGTGACTGAGGTTCC-3' [SEQ ID NO:13]; Restriction site is underlined) were designed to generate a PCR product containing VH17-1A leader, the B-B4 VH region, and terminal HindIII and ApaI restriction sites, for cloning into the pG4D200 expression vector. The forward primer cBBHFor introduces a HindIII restriction site, a Kozak translation initiation site and the VH17-1A leader sequence. The reverse primer g22949 introduces the 5' end of the gamma4 C region and a natural ApaI restriction site. The resulting fragment was cloned into the HindIII/ApaI restriction sites of pG4D200, resulting in vector pG4D200cBB4.

Production of cBB4 Antibody

One vial of COS 7 cells was thawed and grown in DMEM supplemented with 10% Fetal clone I serum with antibiotics. One week later, cells (0.7 ml at $10^7$ cells/ml) were electroporated with pG4D200cBB4 plus pKN100cBB4 (10 µg DNA each) or no DNA. The cells were plated in 8 ml growth medium for 4 days. Electroporation was repeated seven times.

Detection of Chimeric Antibody

A sandwich ELISA was used to measure antibody concentrations in COS 7 supernatants. Transiently transformed COS 7 cells secreted about 6956 ng/ml antibody (data not shown).

Binding Activity of cB-B4

To assay the binding activity of cB-B4 in COS 7 culture supernatants, the Diaclone sCD138 kit has been used, a solid phase sandwich ELISA. A monoclonal antibody specific for sCD138 has been coated onto the wells of the microtiter strips provided. During the first incubation, sCD138 and biotinylated B-B4 (bio-B-B4) antibody are simultaneously incubated together with a dilution series of unlabeled test antibody (B-B4 or cB-B4).

The concentrations of bio-B-B4 in this assay have been reduced in order to obtain competition with low concentrations of unlabeled antibody (concentration of cB-B4 in COS 7 cell culture supernatants were otherwise too low to obtain sufficient competition). Results from this assay reveal that both antibodies have the same specificity for CD138 (data not shown).

Purification of cB-B4

Chimeric B-B4 was purified from COS 7 cell supernatants using the Protein A ImmunoPure Plus kit (Pierce), according to the manufacturer's recommendation (data not shown).

$K_D$-Determination: Comparison nBT062/BB4

Purification of Soluble CD 138

Soluble CD138 antigen from U-266 cell culture supernatant was purified by FPLC using a 1 ml "HiTrap NHS-activated HP" column coupled with B-B4. Cell culture supernatant was loaded in PBS-Buffer pH 7.4 onto the column and later on CD138 antigen was eluted with 50 mM tri-ethylamine pH 11 in 2 ml fractions. Eluted CD138 was immediately neutralised with 375 µL 1 M Tris-HCl, pH 3 to prevent structural and/or functional damages.

Biotinylation of CD 138

Sulfo-NHS-LC (Pierce) was used to label CD138. NHS-activated biotins react efficiently with primary amino groups like lysine residues in pH 7-9 buffers to form stable amide bonds.

For biotinylation of CD138, 50 µl of CD138 were desalted using protein desalting spin columns (Pierce). The biotinylation reagent (EZ-Link Sulfo NHS-LC-Biotin, Pierce) was dissolved in ice-cooled deionised $H_2O$ to a final concentration of 0.5 mg/ml. Biotinylation reagent and capture reagent solution were mixed having a 12 times molar excess of biotinylation reagent compared to capture reagent (50 pmol CD138 to 600 pmol biotinylation reagent) and incubated 1 h at room temperature while shaking the vial gently. The unbound biotinylation reagent was removed using protein desalting columns.

Immobilization of bCD 138

The sensorchip (SENSOR CHIP SA, BIACORE AB) used in the BIACORE assay is designed to bind biotinylated molecules for interaction analysis in BIACORE systems. The surface consists of a carboxymethylated dextran matrix pre-immobilized with streptavidin and ready for high-affinity capture of biotinylated ligands. Immobilization of bCD138 was performed on SENSOR CHIP SA using a flow rate of 10 µl/min by manual injection. The chip surface was conditioned with three consecutive 1-minute injections of 1 M NaCl in 50 mM NaOH. Then biotinylated CD138 was injected for 1 minute.

$K_D$-Determination of Different Antibodies Using BIACORE

The software of BIACORE C uses pre-defined masks, so called "Wizards" for different experiments where only certain settings can be changed. As the BIACORE C was originally developed to measure concentrations, there is no wizard designed to carry out affinity measurements. However, with the adequate settings, the wizard for "non-specific binding" could be used to measure affinity rate constants and was therefore used for $K_D$-determination. With this wizard, two flow cells were measured and the dissociation phase was set to 90 s by performing the "Regeneration 1" with BIACORE running buffer. "Regeneration 2" which is equivalent to the real regeneration was performed with 10 mM Glycine-HCl pH 2.5. After this step, the ligand CD138 was in its binding competent state again. During the whole procedure HBS-EP was used as running and dilution buffer. To determine binding of the different antibodies (~150 kDa) to CD138, association and dissociation was analysed at different concentrations (100, 50, 25 12.5, 6.25 and 3.13 nM). The dissociation equilibrium constants were determined by calculating the rate constants ka and kd. Afterwards, the $K_D$-values of the analytes were calculated by the quotient of kd and ka with the BIAevaluation software. The results are shown in Table 13.

TABLE 13

Comparative analysis of $K_D$ values of nBT062 and B-B4. Standard deviations are given for mean $K_D$ values.

| Antibody | Affinity | |
| --- | --- | --- |
| | $K_D$ (nM) | mean $K_D$ (nM) |
| nBT062 | 1.4 | 1.4 +/− 0.06 |
| | 1.4 | |
| | 1.5 | |
| B-B4 | 1.7 | 1.6 +/− 0.06 |
| | 1.7 | |
| | 1.6 | |
| nBT062-SPDB-DM4 | 1.9 | 1.9 +/− 0.00 |
| | 1.9 | |
| | 1.9 | |
| B-B4-SPP-DM1 | 2.6 | 2.6 +/− 0.06 |
| | 2.7 | |
| | 2.6 | |

Discussion

Mean $K_D$ values for each antibody were calculated from three independent experiments. The results show that in all measurements nBT062 exhibits slightly decreased $K_D$ values compared to B-B4 (mean $K_D$ values were 1.4 and 1.6 nM, respectively).

Preparation of Immunoconjugates
nBT062-DM1 and huC242-DM1

The thiol-containing maytansinoid DM1 was synthesized from the microbial fermentation product ansamitocin P-3, as previously described by Chari (Chari et al., Cancer Res. 1 (1992), 127). Preparation of humanized C242 (huC242) (Roguska et al., PNAS, 91 (1994), 969) has been previously described. Antibody-drug conjugates were prepared as previously described (Liu et al., PNAS, 93 (1996), 8618). An average of 3.5 DM1 molecules was linked per antibody molecule.

nBT062-DM4

BT062 is an antibody-drug conjugate composed of the cytotoxic maytansinoid drug, DM4, linked via disulfide bonds through a linker to the nBT062 chimerized monoclonal antibody. Maytansinoids are anti-mitotics that inhibit tubulin polymerization and microtubule assembly (Remillard et al., Science 189 (1977), 1002). Chemical and schematic representations of BT062 (nBT062-DM4) are shown in FIGS. 1 and 2.

FACS Analysis and WST Cytotoxicity Assays

FACS Analysis

OPM-2 cells are plasma cell leukaemia cell lines showing highly expressing CD138. OPM-2 cells were incubated with nBT062, nBT062-SPDB-DM4, nBT062-SPP-DM1 or nBT062-SMCC-DM1 at different concentrations (indicated in FIG. 6). The cells were washed and CD138-bound antibody or conjugates were detected using a fluorescence-labelled secondary antibody in FACS analysis. The mean fluorescence measured in these experiments was plotted against the antibody concentration.

Cell Viability Assay

CD138$^+$ MOLP-8 cells were seeded in flat bottom plates at 3000 cells/well. CD138$^−$ BJAB control cells were seeded at 1000 cells/well. The cells were treated with nBT062-SPDB-DM4, nBT062-SPP-DM1 or nBT062-SMCC-DM1 at different concentrations (indicated in FIG. 7) for five days. WST reagent (water-soluble tetrazolium salt, ROCHE) was added in order to measure cell viability according to the manufacturer's instruction (ROCHE). The reagent was incubated for 7.5 h on MOLP-8 cells and for 2 h on BJAB cells. The fraction of surviving cells was calculated based on the optical densities measured in a microplate reader using standard procedures.

Discussion

Figure 6:
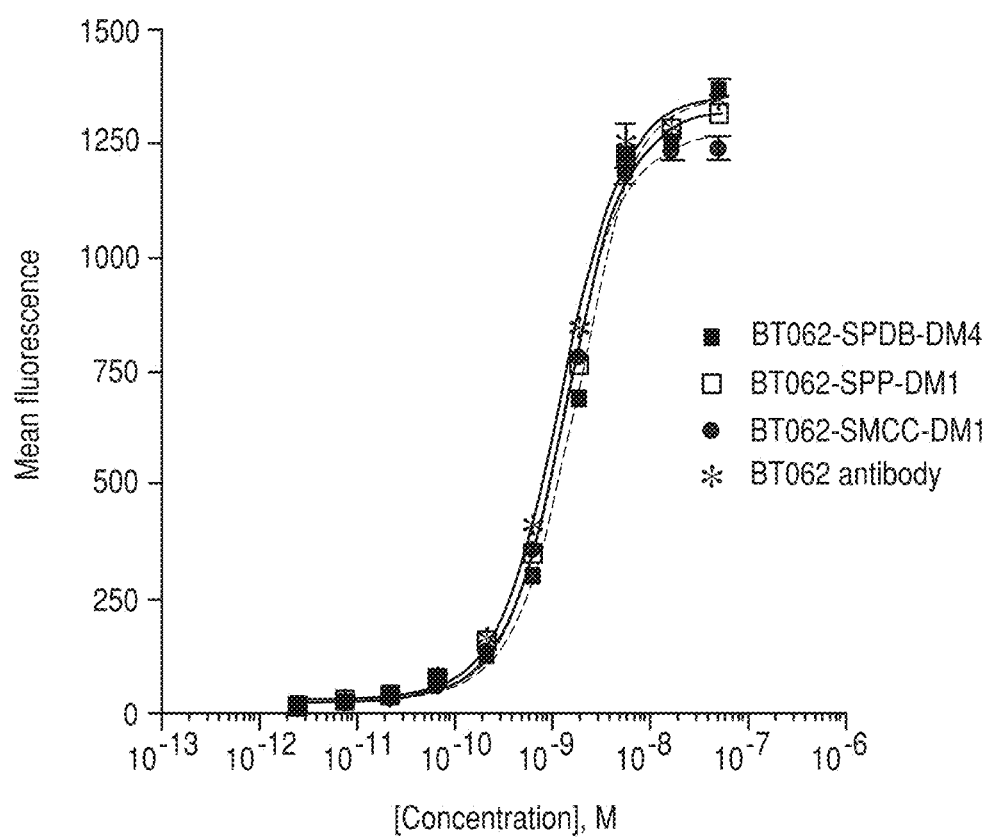
FIG. 6 shows an analysis of the binding of nBT062-SPDB-DM4, nBT062-SPP-DM1, nBT062-SMCC-DM1 and nBT062 antibody to OPM-2 cells. Different concentrations of nBT062 and conjugates were given to the cells and mean fluorescence was measured by FACS analysis.
Figure 7A:
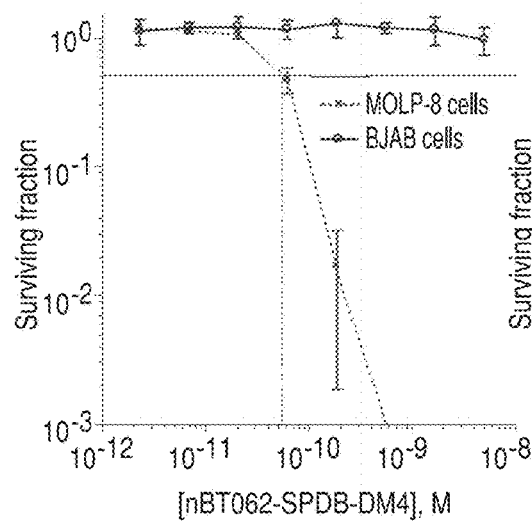
FIG. 7(A)-(D) depict in vitro cytotoxicity of nBT062-DMx conjugates towards MOLP-8 (CD138$^+$) and BJAB (CD138$^-$) cells. The cells were cultured in flat bottom plates and incubated with the indicated concentrations of immunoconjugates for 5 days. WST reagent was added for further 3 hours to assess cell viability. In (D) cytotoxic activity of nBT062-SPDB-DM4 was analyzed in the presence or absence of blocking antibody (1 μM nBT062).
Figure 7B:
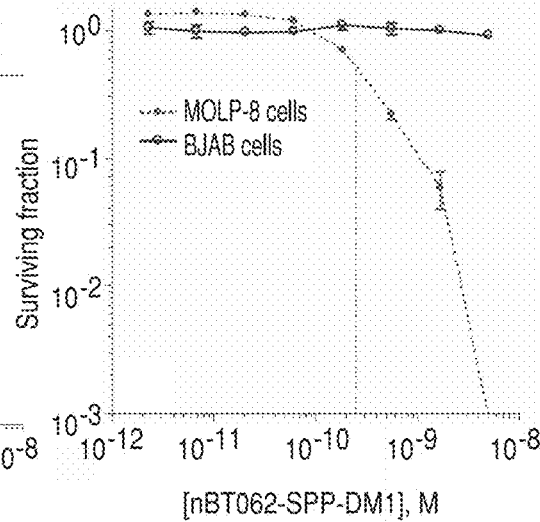
Figure 7C:
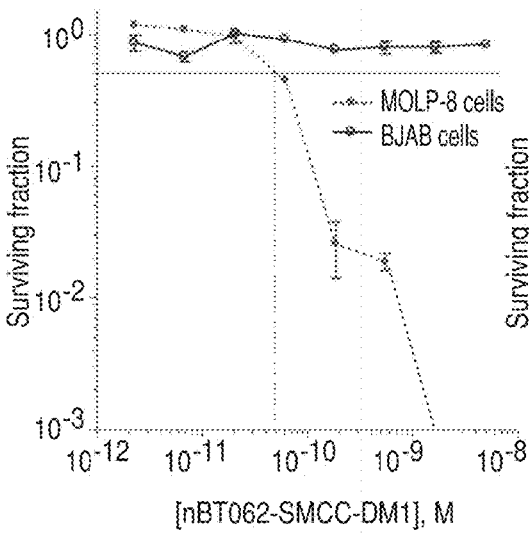
Figure 7D:
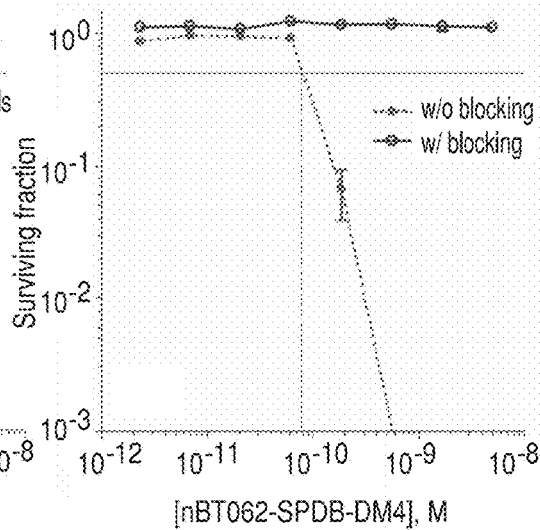

Binding of nBT062-SPDB-DM4, nBT062-SPP-DM1, nBT062-SMCC-DM1 or nBT062 was analyzed by FACS. CD138$^+$ OPM-2 as target cells were incubated with nBT062 or immunoconjugates and cell-bound molecules were detected using a fluorescence-labeled secondary antibody. In FIG. 6, the mean fluorescences as measure for the amount of cell bound antibody is plotted against different antibody or conjugate concentrations. The results show, that nBT062-SPDB-DM4, nBT062-SPP-DM1 and nBT062-SMCC-DM1 show very similar binding characteristics. In addition, the results strongly suggest that the binding characteristics of the unconjugated antibody is not affected by the conjugated toxins.

In cell viability assays, the cytotoxic activity of the antibody against CD138$^+$ MOLP-8 target cells and against CD138$^−$ BJAB B-lymphoblastoma control cells were analyzed. Both cell lines were seeded in flat-bottom plates and incubated with increasing concentrations of the immunoconjugates. Unconjugated antibody was used as a control. The cytotoxic activity was analyzed five days after addition of the immunoconjugates by using WST reagent in order to measure cell viability. In FIG. 7 (A)-(C), the fraction of surviving cells relative to control cells treated with vehicle control is plotted against increasing immunoconjugate concentrations. The results show that cytotoxic activity of nBT062-SPDB-DM4, nBT062-SPP-DM1 and nBT062-SMCC-DM1 against MOLP-8 cells is very similar. As expected, CD138⁻ BJAB control cells were not killed by the immunoconjugates, indicating that all immunoconjugates act via cell specific binding to CD138. In competition experiments, in which MOLP-8 cells were preincubated with a molar excess of unconjugated nBT062. Preincubation substantially blocked the cytotoxicity of nBT062-SPDB-DM4, providing further evidence that the immunoconjugates kill the cells via specific binding to CD138 onto the cell surface (FIG. 7 (D)).

Indicator: Pancreas/Mammary and Other Carcinoma—Xenograft Models General Experimental Set-up In accordance with the CD138 expression analysis (Immunohistochemistry analysis on tumor tissue microarrays) tumor candidates were selected from a primary tumor collection, that is, from patient derived tumors. These tumors display similar characteristics as the patient tumors, since they are passaged in mice at low numbers, to retain original characteristics. Following subcutaneous transplantation and establishment of tumors (induction time 30 days), the immunoconjugate BT062 was injected intravenously at 2 different concentrations of the maytansinoid DM4, 450 µg/kg and 250 µg/kg (each based on the molecular weight of the linked DM4 (1 mg of DM4 is conjugated to 52 mg of antibody, equalling a total mass of 53 mg; 450 µg/kg DM4=23.850 µg) The immunoconjugate was administered once weekly for 10 weeks (in case of treatment of pancreatic tumor implanted mice) and 5 weeks (in case of mammary, lung and bladder tumor implanted mice). A treatment free observation period followed to investigate a possible tumor regrowth.

EXAMPLE 1

Pancreas Carcinoma

Pancreatic tumor tissue (PAXF 736 (Kuesters et al., 2006) was implanted (bilateral) into NMRI mice. The implanted tumor originated from a patient's primary pancreatic carcinoma (poorly differentiated, infiltrating adenocarcinoma (an exocrine carcinoma)). No side effects were observed. The tumor of this patient was identified as a high CD138 expressing tissue by immunohistochemistry studies. However, CD138 is not expressed to a degree comparable to myelomatous plasma cells in multiple myeloma patients, as detected on tumorgenic cell lines by flow cytometric surface staining.

Treatment with BT062 was initiated after tumors have reached a size of approx. 6-8 mm diameter (minimum 5 mm). Tumor diameters have been measured two times a week. Tumor volumes were calculated according to the formula a×b×b/2 where "a" is the longest axis and "b" the perpendicular axis thereto. Inhibition of tumor volume in the test groups relative to the vehicle control group was calculated as the ratio of the median relative tumor volumes (T/C).

Tumor inhibition for a particular day (T/C in %) was calculated from the ratio of the median RTV (relative tumor volume) values of test versus control groups multiplied by 100%.

$$T/C(Day_x) = \frac{\text{Median relative tumor volume of the test group } Day_x}{\text{Median relative tumor volume of the control group } Day_x} \times 100\%$$

Figure 8:
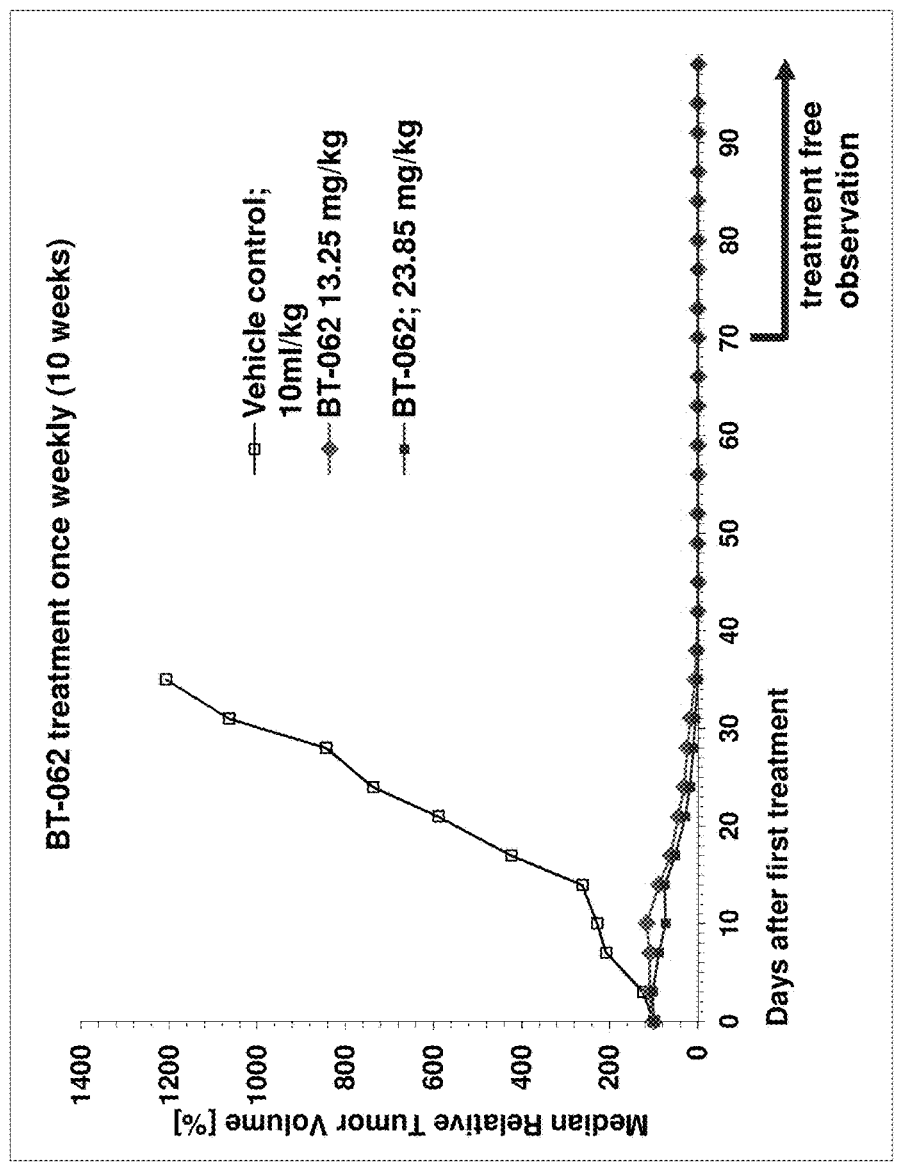
FIG. 8 shows the complete remission of a xenograft pancreas carcinoma in mice treated with BT062 vs. a control. Complete remission is maintained: in the treatment free observation period, no tumor re-growth was observed.

Tumor volume could be significantly reduced by this weekly administration of BT062. As can be seen in FIG. 8, dose dependent partial and complete remission was observed. The Figure shows that at a dose of 23.85 mg/kg, complete remission could be obtained 28 days after tumor implantation, while at a dose of 13.25 mg/kg, complete remission could be obtained 35 days after tumor implantation. Notably, after 52 days all mice in the 13.25 mg/kg administration regimens were still alive (8/8), while the eight mice of the control group had been reduced to 1. A T/C value below 10% indicates complete remission (CR) (Bissery et al., 1991). According to this criteria, CR was achieved in both treatment groups, reflecting the complete remission that was achieved by BT062. Remarkably in a treatment free observation phase, no tumor regrowth was detected, confirming the complete curance of in this model.

TABLE 14

Tumor volume is pancreatic cancer xenograft mouse model

| Relative Tumor Volume (%) | Day 52: Mean (±) | Range | T/C (%) |
|---|---|---|---|
| Control | 2055 | 2055 | |
| BT062-DM4; 13.25 mg/kg | 0 (±1.0) | 0-3.5 | 0.0 |
| BT062-DM4; 23.85 mg/kg | 0 (±0.01) | 0-0.1 | 0.0 |

EXAMPLE 2

Mammary Carcinoma

NMRI (nude) mice were implanted (bilateral) with primary mammary tumor of a patient (determined via IHC analysis as strongly CD138 positive). A breast carcinoma skin metastasis was taken at stage M1. It was a tumor which did not respond to Herceptin (low Her₂ with an intermediate expression). The tumor was estrogen receptor negative and progesterone receptor negative and thus not responsive towards hormone therapy. Tumors to be implanted were selected according to IHC staining results (strong, homogenous expression of CD138 detected by BT062 (triple negative expression of hormone receptors estrogen and progesterone); Her₂ expression scored 2 or less (regarded as Herceptin non responsive).

Treatment with BT062 was initiated after tumors had reached a size of approx. 100 mm³. Tumor volumes were calculated according to the formula a×b×b/2, with "a" being the longest axis and "b" the perpendicular axis thereto. Inhibition of tumor volume in the test groups relative to the vehicle control group was calculated as the ratio of the median relative tumor volumes (T/C). BT062 was administered once weekly at a loading dose of 13.25 mg/kg (which was given on day 1) followed by doses of 4 mg/kg once weekly. In the other dose group a high dose of 23.85 mg/kg was administered.

Figure 9:
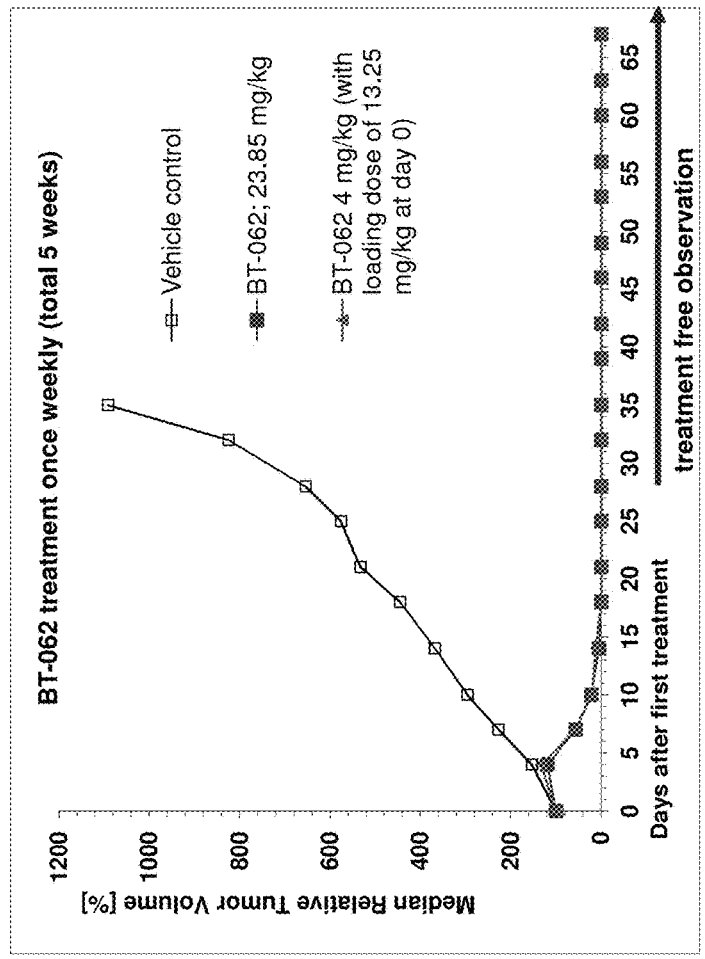
FIG. 9 shows the complete remission of a xenograft mammary carcinoma in mice treated with BT062 vs. a control. Complete remission is maintained, since in the treatment free observation period, no tumor re-growth was observed.
Figure 10:
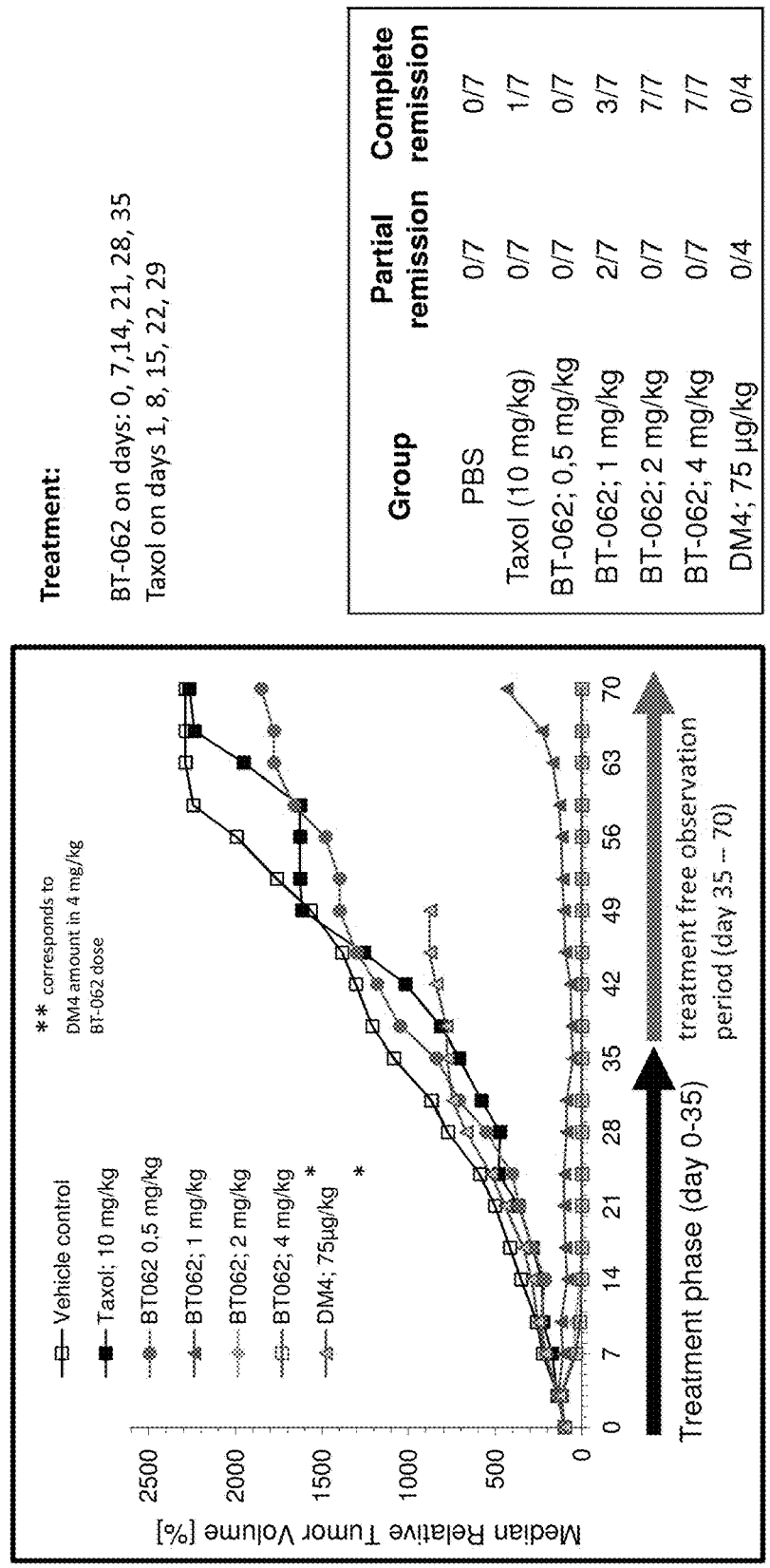
FIG. 10 shows the complete remission of a xenograft mammary carcinoma in mice treated with 2 mg/kg or 4 mg/kg BT062 (once weekly) vs. a control or Taxane. At 1 mg/kg BT-062 once weekly, tumor stasis is achieved. This is defined as the minimal effective dose.
Figure 11:
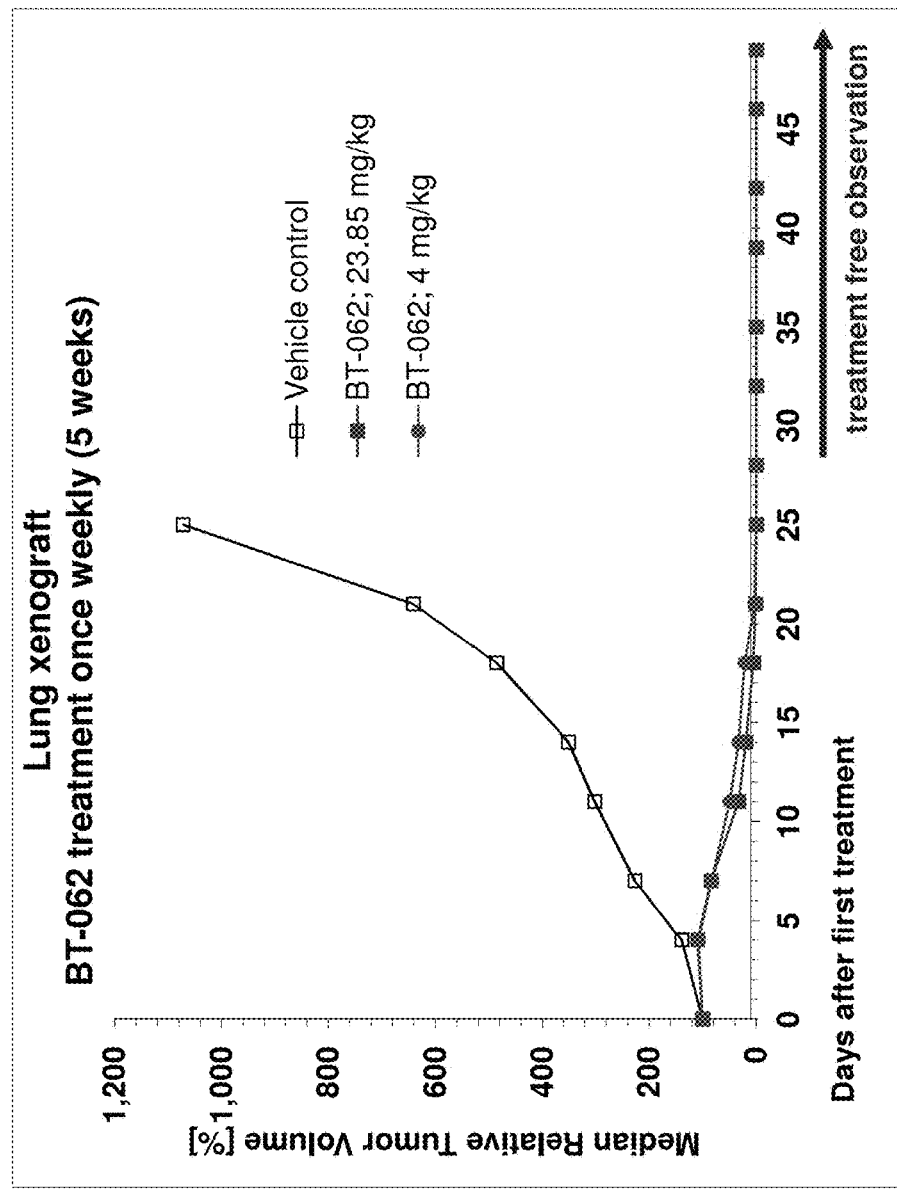
FIG. 11 shows the complete remission of a xenograft primary lung adenocarcinoma in mice treated with 4 mg/kg and 23.85 mg/kg BT062 (once weekly) vs. a vehicle control.
Figure 12:
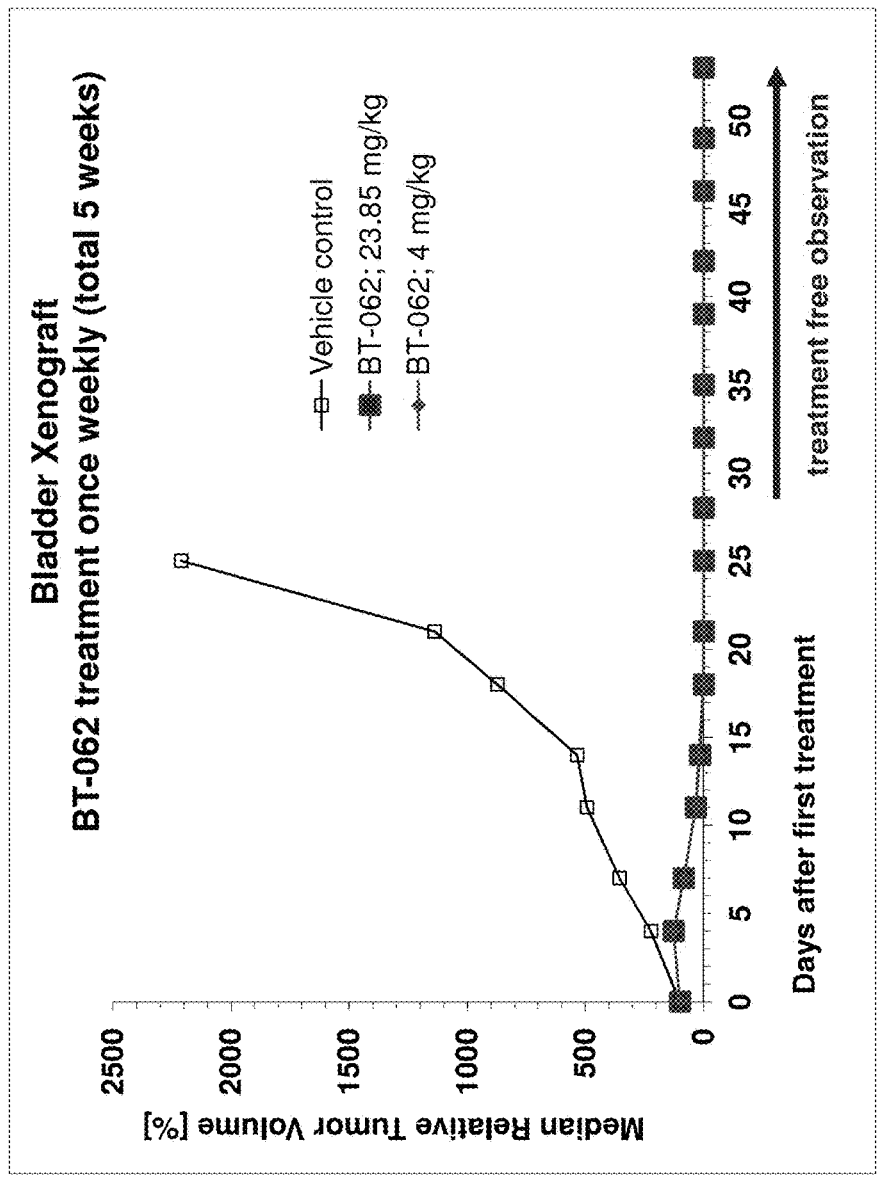
FIG. 12 shows the complete remission of a xenograft bladder (transitional cell) carcinoma (metastatic sample) in mice treated with 4 mg/kg and 23.85 mg/kg BT062 (once weekly) vs. a vehicle control.
Figure 35:
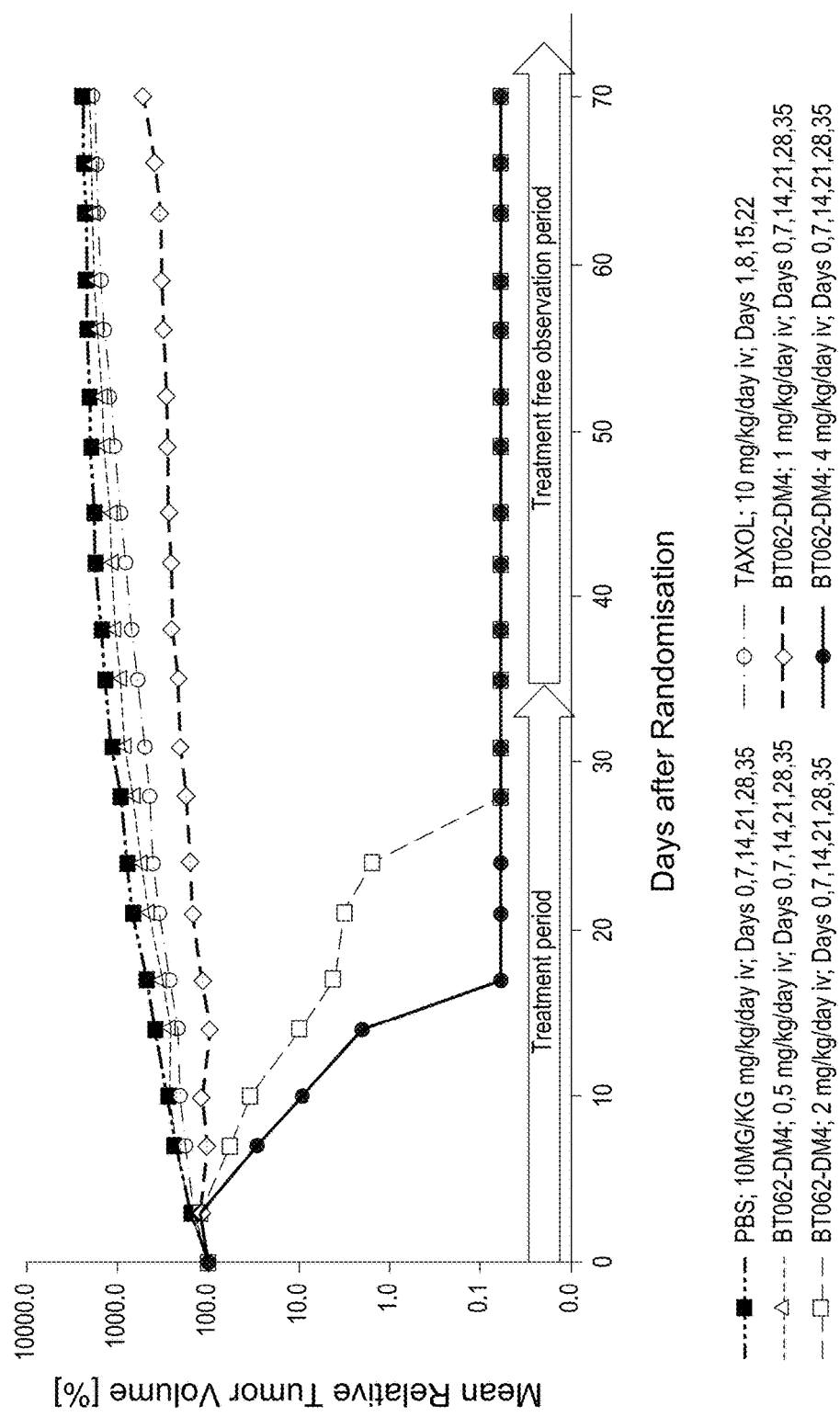
FIG. 35 shows the results of an in vivo (human derived breast cancer model in NMRI nude mice) study wherein BT062 (0.5 mg/kg, 1 mg/kg, 2 mg/kg, 4 mg/kg) was administered intravenously on days 0, 7, 14, 21, 28 and 35 and taxol (10 mg/kg) was administered intravenously on days 1, 8, 15 and 22. BT062 showed at higher concentrations superior results. The results are shown in terms of the effect on the mean relative tumor volume in the model relative to an intravenous administration of PBS. For the calculation of the median relative tumor volume on day, see FIG. 33.

Tumor volume could be significantly reduced by weekly administration of BT062. A dose dependent partial and complete remission was observed. The immunoconjugate was well tolerated, having no influence on body weight after each injection. A T/C value below 10% was obtained in both treatment groups, reflecting a complete remission achieved by the administration of BT062. As can be seen in FIG. 9, the anti-tumor effect (i.e., complete remission) was achieved after 21 days, which can be considered a rapid response to BT062. As can been seen from FIGS. 35 and 36, lower dose regimens were also effective. As can been seen from FIG. 37, a mouse model that did not respond to Docetaxel treatment, also did not respond to BT062 treatment, while a model that did not respond to taxol responded well to BT062 treatment (FIG. 35).

Compared to the pancreatic model, duration of treatment could be cut short by half (5 weeks instead of 10 weeks) and the low dose of 13.25 mg/kg was reduced to 4 mg/kg to achieve a similar effect, namely complete remission and no tumor regrowth. The shorter treatment period for mammary carcinoma was not expected, since on IHC analysis the level of CD138 expression was similar. Thus, no conclusions can be drawn from the level of CD138 expression to a general recommendation for the treatment duration. After 21 days all mice of both the treated groups as well as the control group were still alive. In a treatment free observation period (39 days after the last administration of the immunoconjugate) no tumor regrowth was detected, confirming the complete curance.

TABLE 15

Tumor volume is mammary carcinoma xenograft mouse model.

| Relative Tumor Volume (%) | Mean (Day 21) | Range | T/C |
|---|---|---|---|
| Control (PBS) | 533 (±149.5) | 339-878 | |
| BT062-DM4; 13.25 mg/kg/4 mg/kg | 0 (±0.02) | 0-0.1 | 0.0 |
| BT062-DM4; 23.85 mg/kg | 0 (±1.75) | 0-6.6 | 0.0 |

TABLE 16

Expression of CD138 on mammary carcinoma cells vs. epithelium cells

| FFPE tissue samples | Staining score (membrane) | |
|---|---|---|
| | 0.25 µg/ml | 0.05 µg/ml |
| Breast, tumor Mets, -061909-13 | 3 Homo | 2-3 Homo |
| Breast, tumor Unknown, -061909-12 | 2-3 Homo | 1-2 Hetero |
| Breast, tumor Mets, -061909-09 | 3 Hetero | 2 Focal |
| Breast, tumor Primary, -111904-4 | 3 Hetero | 1-3 Hetero |
| Breast, tumor Primary, -111904-1 | 3 Hetero | 1 Hetero |
| Normal Skin sample 1 | 3 Homo | 3 Homo |
| Normal Skin sample 1 | 3 Homo | 3 Homo |

EXAMPLE 3

Bladder Carcinoma

NMRI (nude) mice are implanted with a bladder tumor (determined via IHC analysis as CD138 strong positive), namely a transitional cell carcinoma.

Treatment with BT062 is initiated after tumors had reached a size of approx. 100 mm³. Tumor volumes are calculated according to the formula a×b×b/2, with "a" being the longest axis and "b" the perpendicular axis thereto. Inhibition of tumor volume in a test groups relative to the vehicle control group is calculated as the ratio of the median relative tumor volumes (T/C).

Tumor volume is sought to be significantly reduced by weekly administration of BT062. Any dose dependent partial and complete remission is tracked.

EXAMPLE 4

Lung Carcinoma

NMRI (nude) mice are implanted with a Lung carcinoma (determined via IHC analysis as CD138 strong positive).

Treatment with BT062 is initiated after tumors had reached a size of more than 5 mm. Tumor diameters are measured two times a week. Tumor volumes are calculated according to the formula a*b*b/2, with "a" being the longest axis and "b" the perpendicular axis thereto. Inhibition of tumor volume in a test groups relative to the vehicle control group is calculated as the ratio of the median relative tumor volumes (T/C).

Complete remission could be achieved in both dose groups (4 mg/kg and 23.85 mg/kg once per week). In a treatment free period, no re-growth was observed, confirming the complete eradication of the tumors.

EXAMPLE 5

To investigate metastatic tumors, NMRI (nude) mice were implanted with a metastatic patient tissues derived from a bladder tumor (determined via IHC analysis as CD138 strong positive).

Complete remission could be also achieved in this model, in both dose groups (4 mg/kg and 23.85 mg/kg once per week). In a treatment free period, no re-growth was observed, confirming the complete eradication of the tumors.

EXAMPLE 6

To investigate efficacy of BT062 at lower doses and in comparison with a clinically used drugs taxol (Paclitaxel), NMRI (nude) mice were implanted with the mammary tumor of example 2. Lower doses of BT062 (0.5 mg/kg, 1 mg/kg, 2 mg/kg and 4 mg/kg) were administered once weekly (FIG. 35). At 4 and 2 mg/kg once weekly, a complete remission was observed, without re-growth in a treatment free period. Taxol treated mice showed only a minor tumor growth delay at 10 mg/kg. DM4 was used in an amount corresponding to that in 4 mg BT062, but did not result in tumor response. At concentrations 1 mg/kg a "tumor stasis" could be achieved, i.e. the tumor neither grow but the volume did not decrease. This is also called the minimal effective dose, since in this group 2/7 mice had a partial remission and 3/7 mice had complete remission without tumor regrowth.

The minimal effective dose can also be somewhat lower than 1 mg/kg but higher than 0.5 mg/kg.

EXAMPLES 7 AND 8

Figure 36:
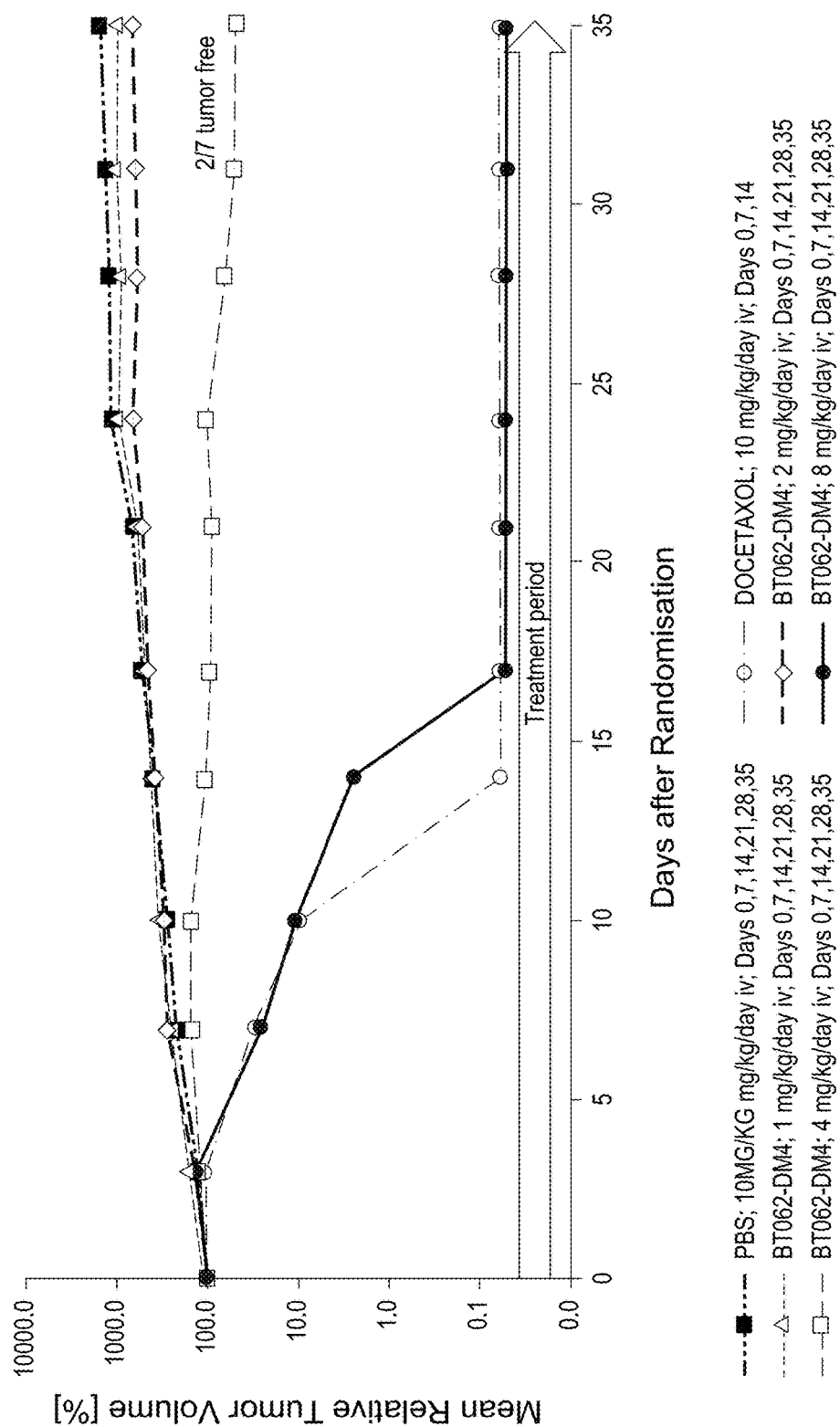
FIG. 36 shows the results of an in vivo (human derived breast cancer model with CD138 IHC score 2-3 in NMRI nude mice) study wherein BT062 (1 mg/kg, 2 mg/kg, 4 mg/kg, 8 mg/kg) was administered intravenously on days 0, 7, 14, 21, 28 and 35 and Docetaxel (10 mg/kg) was administered intravenously on days 0, 7 and 14. BT062 showed at higher concentrations superior results. Docetaxel was as effective as the highest concentration of BT062. The results are shown in terms of the effect on the mean relative tumor volume in the model relative to an intravenous administration of PBS. For the calculation of the median relative tumor volume on day, see FIG. 33.
Figure 37:
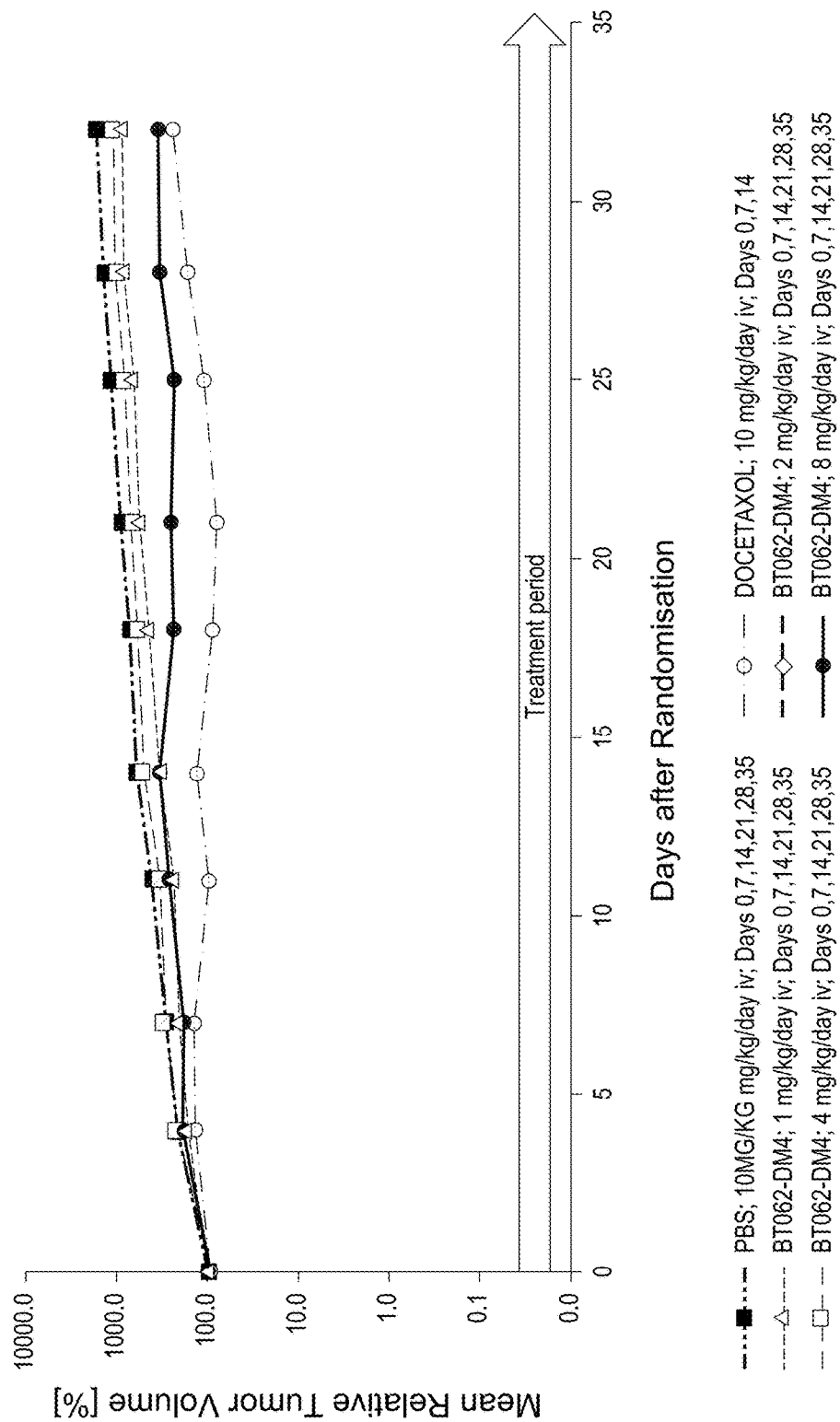
FIG. 37 shows the results of an in vivo (human derived breast cancer model with CD138 IHC score 1-2 in NMRI nude mice) study wherein BT062 (1 mg/kg, 2 mg/kg, 3 mg/kg, 4 mg/kg) was administered intravenously on days 0, 7, 14, 21, 28 and 35 and Docetaxel (10 mg/kg) was administered intravenously on days 0, 7 and 14. No difference in the treatment regimens was observed. The results are shown in terms of the effect on the mean relative tumor volume in the model relative to an intravenous administration of PBS. For the calculation of the median relative tumor volume on day, see FIG. 33.

Here BT062 was investigated at lower doses and compared with the clinically used drug docetaxel (10 mg/kg), as in Example 6. Lower doses of BT062 (1 mg/kg, 2 mg/kg, 4 mg/kg and 8 mg/kg) were administered once weekly. At 8 mg/kg once weekly, a complete remission was observed during treatment in mice that had tumors showing a 2-3 scored CD138 IHC staining and that also response to docetaxel, while mice that had tumors showing a 1-2 scored IHC staining and did not respond to docetaxel, also did not respond to BT062 (FIGS. 36 and 37).

EXAMPLE 9

Figure 38:
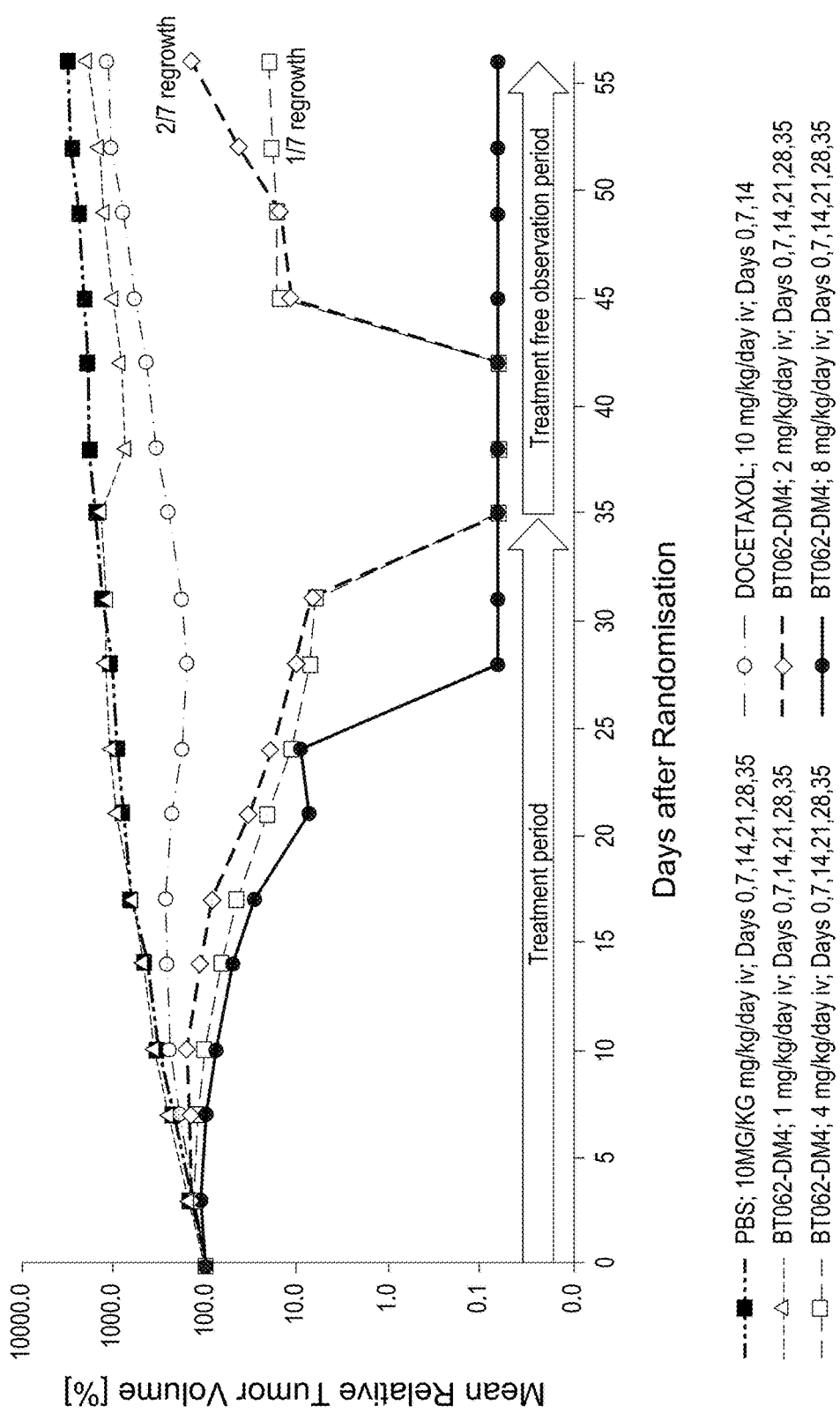
FIG. 38 shows the results of an in vivo (human derived prostate cancer model in NMRI nude mice) study wherein BT062 (1 mg/kg, 2 mg/kg, 4 mg/kg, 8 mg/kg) was administered intravenously on days 0, 7, 14, 21, 28 and 35 and Docetaxel (10 mg/kg) was administered intravenously on days 0, 7 and 14. BT062 showed at higher concentrations superior results. The results are shown in terms of the effect on the mean relative tumor volume.

To investigate efficacy of BT062 at lower doses and in comparison with a clinically used used drug docetaxel (10 mg/kg) NMRI (nude) mice were implanted with a primary pancreatic tumor. The patient derived tumor had a high but heterogeneous CD138 staining determined by IHC analysis and scored with 3. Lower doses of BT062 (1 mg/kg, 2 mg/kg, 4 mg/kg and 8 mg/kg) were administered once weekly (FIG. 38). At 4 and 8 mg/kg once weekly, a complete remission was observed, but re-growth in a treatment free period occurred which could be an effect of the heterogeneity of the tumor. Docetaxel treated mice showed complete remission during the treatment period as well as the treatment free period.

Human Trials with BT062

In the context of the present invention, human subjects responded well to a low dose regime. This was even the case in absence of any additional treatments that would compensate for potential variations in qualitative or quantitative expression of the CD138 on the target cells (compare MYLOTARG). While mouse models demonstrated that BT062 has highly significant antimyeloma activity at doses that are well tolerated in mice, effectiveness was considerably better at relatively high doses (results not shown), posing the question how higher doses would be tolerated by human subjects that express CD138 on a wide variety of non-tumor cells.

Phase I Research Study

This study was performed to test the effects (good and bad) and to determine the MTD (maximum tolerated dose) of BT062 in treating patients with relapsed or relapsed refractory multiple myeloma.

Up to now, 32 patients were recruited. At least 12 out of 32 patients experienced diminished disease progression as represented by receiving at least a forth treatment cycle. The trial is being performed at different sites, with groups of 3 and 4 patients being treated with different dose levels (10 mg/m$^2$, 20 mg/m$^2$, 40 mg/m$^2$, 80 mg/m$^2$, 120 mg/m$^2$, 160 mg/m$^2$, 200 mg/m$^2$) for anywhere between 1 to 31 treatment cycles (results not shown). As the person skilled in the art will appreciate a higher number of treatment cycles is possible and within the scope of the present inventions, such as 10 to 50, 10 to 100, 10 to 200 and more.

Disease progression diminished with relatively low dosage levels, namely 20 mg/m$^2$, 40 mg/m$^2$, 80 mg/m$^2$ and 120 mg/m$^2$, with one patient at the $2^{nd}$ dosage level of 20 mg/m$^2$ displaying no disease progression for 10 treatment cycles of 21 days. In some patients stable disease and responses, including minor and partial responses could be observed.

At these dose levels, as described above (see Tables 9 and 10), rapid clearance of BT062 from plasma was also observed. Some pharmacokinetic profiles of these low dose administration schemes are shown in FIG. 13. Doses of 160 mg/m$^2$ and 200 mg/m$^2$ were also administered. A dose of 160 mg/m$^2$ was identified as MTD and studies in this group were expanded. A dose of 200 mg/m$^2$ was identified as MAD.

Repeated single doses regimens of 10 mg/m$^2$, 20 mg/m$^2$, 40 mg/m$^2$, 80 mg/m$^2$, 120 mg/m$^2$, 160 mg/m$^2$, 200 mg/m$^2$ were performed every 21 day, meaning on day 1, day 22, day 43, day 64, day 85, day 106, and so forth. The disease has been and will be monitored by physician's assessment of hematology, clinical symptoms and clinical chemistry as well as by measuring M-Protein levels in the serum and urine of patients (in g/dL) and free light-chain (FLC) levels in the serum of patients over time (results not shown).

Immunoglobulin Assessment

The amount of 1 g antibodies including the determination of IgG subgroups was analyzed at screening.

M-Protein Quantification and Serum Free Light Chain Assay

Initially, the response to treatment was evaluated at day 1 of treatment cycles 1-3 by M-protein quantification using immunoelectrophoresis (IEP) and immunofixation electrophoresis (IFE) from serum and 24-hour urine collection. For treatment cycles 3 and beyond, M-protein quantification was performed at the Day 15 visit in order for the results to be available to assess response prior to initiating the next treatment cycle. A general quantitative immunoglobulin assessment was done together with M-protein quantification.

Serum samples were used to perform FLC assays to examine multiple myeloma subjects with no detectable M-protein (nonsecretory/oligosecretory myeloma) and to allow for detection of early response to treatment. Therefore serum FLC assays were performed on day 1, 2, 3, and 8 of treatment cycle 1, on day 2, 3, 8 and 15 of cycle 4, as well as on day 1, 8 and 15 of all other treatment cycles. M-protein and FLC were be analyzed at the screening and at the close-out visit. Evaluations at day 1 of cycle 1 served as baseline values.

| Dose mg/m$^2$ | Urine/Serum M-protein measurements and FLC measurements |
|---|---|
| 20 | During first seven cycles disease stabilization based on clinical symptoms and serum FLC, Urine M-Protein decreased after $8^{th}$ treatment M-Protein criteria for Minor Response reached after $8^{th}$ treatment Decrease in Urine M-Protein level from baseline by more than 50% Diseases progression after Cycle 10 Serum M-Protein between 0.06 and 0.1 g/dL (defined as not measurable) |
| 40 | Stable disease for 14 weeks Serum M-Protein decreased after $1^{st}$ treatment and stabilized for 14 weeks Diseases progression observed after treatment was held at the start of cycle 6 (day 105) Urine M-Protein increased from 0 at screening to a maximum of about 16 mg/24 h (defined as not measurable) |
| 160 | Serum FLC level increased during the screening period starting −21 days before day 1 of the treatment Serum FLC level decreased very soon after $1^{st}$ treatment and was already close to 25% decrease at day 8 In comparison to baseline, FLC levels are reduced by about 40% during $1^{st}$ cycle and by more than 50% after $2^{nd}$, $3^{rd}$ and $4^{th}$ treatment FLC criteria for Partial Response were reached very early Disease progression after the end of the $4^{th}$ treatment cycle Serum M-Protein not measurable = 0; Urine M-Protein decreased from 140 mg/24 h at baseline to 120 mg/24 h before $2^{nd}$ treatment (defined as not measurable) => non-secretory Myeloma |

Table 17 provides observations made regarding Urine/Serum M-protein and serum FLC measurements in selected patients in a repeated single dose regime. In a repeated single dose regimen of BT062, DLTs were observed in the mucosa of patients treated in the 200 mg/m$^2$ dose group. The target for BT062 (CD138) is expressed in the mucosa and toxicities in these tissues and organs con be considered as target related. Serious adverse events, not qualifying for DLT, were observed in eye patients. However, the eye toxicity is suggested to be rather related to the effector compound since this is a typical toxicity also found with other DM4 conjugates such as SAR3419, or IMGN388 that do not target CD138. This eye toxicity occurred in one patient in the repeated single dose study 3 days after the 3rd cycle and in the other patient 4 days after the $4^{th}$ cycle. In the maximal administered dose group (160 mg/kg) of the repeated single dose study, CD138 related toxicities occurred during the first days but also after repeated cycles, most of them were considered mild to moderate.

| Dose | FIG. | Urine/Serum M-protein measurements and FLC measurements |
|---|---|---|
| 3 × 50 mg/m2 | 20 | Serum M-Protein decrease for 6 cycles: At least stable disease could be achieved over 6 cycles, with a decrease of serum M protein by nearly 25% during/after 3rd and 5th treatment cycle |
| 3 × 65 mg/m2 | 21 | Free lambda-kappa light chain A strong decrease of the serum FLC level could be observed after just a single treatment cycle |
| 3 × 120 mg/m² | 24 | Urine M-Protein decrease A decease of urine M protein after first and repeated cycles, with a reduction of more than 50% achieved after 3rd, 7th and 10th cycle |

Table 18 provides observations made regarding Urine/Serum M-protein and serum FLC measurements in selected patients in a repeated multiple dose regimen.

Determination of BT062 and DM4 from Plasma

To assess single dose PK properties of BT062, after IV administration of BT062, extensive plasma sampling was performed during the first treatment cycle. The same evaluation was performed during treatment cycle 4. To a lesser extent plasma samples were also obtained at day 1 and 8 of all other treatment cycles, as well as on close-out and follow-up visit. The amount of BT062 in the plasma is determined via a PK ELISA method described as follows:

Experimental Description:

The wells of a microtiter plate are first coated with anti-maytansinoid (anti-DM4) antibody overnight at 2-8° C. and after blocking with assay buffer (0.5% BSA/TBS) incubated on the next day with plasma samples. These are diluted beforehand at least 1:100 in assay buffer. BT062 antibodies contained in the samples are bound by the anti-DM4 antibody immobilized in the plates. After incubation, unbound material is removed by washing. Then, a HRP-conjugated secondary antibody is added, which binds to the BT062 antibodies. Unbound secondary antibody is removed by another washing step. After this, TMB substrate solution is pipetted into all the wells. A color reaction develops proportional to the amount of BT062 bound during incubation of the sample. The color reaction is ended using a stop solution, which causes the color to change from blue to yellow. The final measurement is carried out with a photometer at a wavelength of 450 nm.

The relationship between concentration and optical density is evaluated using Magellan V6.6 software. If samples from clinical trials are measured (plasma samples from multiple myeloma patients), for each patient an individual standard curve should be prepared in 1:100 diluted "pre-dose" plasma (plasma before treatment with BT062). If in addition to the obligatory 1:100 dilution in assay buffer, a clinical test sample has to be diluted further (due to a high BT062 concentration), this dilution should be prepared in 1:100 diluted predose plasma (of the patient concerned). For stability tests (e.g. freezing/thawing stability, storage stability), the BT062 standard and also corresponding samples or in-process controls are prepared in 1:100 diluted heparin plasma pool.

Determination of Shed CD138 and NAPA

All pre-dose plasma samples were evaluated for levels of shed/soluble CD138 (sCD138) to investigate a potential correlation between levels of sCD138 and antitumor activity. These measurements also allowed to determine that the lower than expected Cmax values are not dependent on the amount of sCD138 present prior to administration of BT062 (see FIG. 17). Predose plasma samples from day 1 of each treatment cycle and from close out and follow-up visit were evaluated for the presence of humoral responses against BT062 (drug product) by assessment of human antiproduct antibodies (HAPA).

Shed CD138 Measurements Observed

In Myeloma patients high levels of sCD138 can be observed and might be an indicator of prognosis of myeloma patients (Maisnar et al., 2005).

Patients with MGUS and MM might display high levels of soluble CD138 concomitant with higher levels of β2-microglobulin and elevated plasma cell content in the bone marrow (Aref et al., 2003).

A kit was used for determining soluble CD138. Surprisingly, it was found that one patient (identified as 003-003) treated at 20 mg/m² of BT062 displayed a minor response with regard to urine M-protein levels, although this patient displayed high levels of sCD138 before treatment.

Soluble (s) CD138 values were determined in different subjects.

TABLE 19

Patient 003-003 (repeated single dose 20 mg/m²) displayed very high values of sCD138. Nonetheless, this patient achieved a minor response in M-Protein level.

| Subject | sCD138 (ng/ml) |
|---|---|
| 002-003 | 61.3 |
| 001-002 | 196 |
| 002-004 | 56.7 |
| 003-003 | 2583 |
| Mean | 724.1 |

Combination Studies

In a Phase I/IIa Multi-Dose Escalation Study, BT062 was Combined with Lenalidomide and Dexamethasone in Subjects with Relapsed or Relapsed/Refractory Multiple Myeloma.

One treatment cycle consisted of 28 days, or in other words, 21 days of active treatment followed by 7 days without treatment (resting period). BT062 was administered on days 1, 8 and 15 at a concentration of 80 mg/m², lenalidomide (Len) (25 mg) was administered once daily on days 1-21 and dexamethasone (Dex) (40 mg) was administered on days 1, 8, 15 and 22. Day 1 treatment of BT062 at all cycles should concured with day 1 of Len and dexamethasone. As can be seen from FIG. 34, a minor response was observed after the first treatment cycle and was maintained at the start of the $4^{th}$ cycle (day 99), even though start of cycle 2 and 3 was delayed by one week and treatment with BT062 was skipped on day 85 and treatment with Len was skipped on days 85 to 91 and the Dex dose was reduced to 20 mg/m² during cycle 3. As is clear to the person skilled in the art, either Lenalidomide, dexamethasone or BT062 concentrations may be lowered depending on toxicities and efficacy. Efficacy is assessed body fluids, preferably via efficacy blood parameters such as M-Protein or FLC (depending on the MM disease type), or other markers from body fluids or bone marrow reflecting disease status.

With this treatment regime disclosed here, combination with Len/Dex is possible with lower toxicities, or in combination with this immunoconjugate, administration of the combination partners can be adjusted e.g. lowered to minimize the toxicities associated with their administration. Since this regimen provides better tolerability it is applicable for combination with other drugs, having lower or at least not higher numbers of toxicities but the same or even better efficacy.

Possible anti-myeloma drug candidates have been evaluated as combination partners for BT062 in cell lines:

Cell Line Studies

Combination studies in xenograph mouse models were preceded by studies in cell lines. The synergy determination in different cell lines was performed according to Chou and Talley (1984), using the median effect analysis. Here, $IC_{50}$ values for the cytotoxic effects for each drug and each cell line are calculated, and then $IC_{50}$ ratios for each drug pair. The cells were then exposed to dilution series of either these drug mixtures, or the drugs alone. Experimental data were analyzed using the CompuSyn software (ComboSyn, Inc., Paramus, N.J.). Combination Indexes (CI) for each independent experiment were calculated and reported separately. In the analysis, CI less than 1, equal to 1 and more than 1 indicates synergy, additivity and antagonism, respectively. According to the classification of T.C. Chou (CompuSyn, User's guide, 2004), the author of the method, the scale of synergism and antagonism is as follows:

| Combination Index | Description |
| --- | --- |
| <0.1 | Very strong synergism |
| 0.1-0.3 | Strong synergism |
| 0.3-0.7 | Synergism |
| 0.7-0.85 | Moderate synergism |
| 0.85-0.9 | Slight synergism |
| 0.9-1.1 | Nearly additive |
| 1.1-1.2 | Slight antagonism |
| 1.2-1.45 | Moderate antagonism |
| 1.45-3.3 | Antagonism |
| 3.3-10 | Strong antagonism |
| >10 | Very strong antagonism |

TABLE 20

Estimates of synergistic results obtained in cell lines according to the method of Chou and Talalay (1984).

| | Cells | | |
| --- | --- | --- | --- |
| Drug | RPMI 8226 | MOLP8 | U266 |
| Bortezomib | Additive | Slightly antagonistic | Antagonistic |
| Thalidomide | Additive to synergistic | Additive to slightly antagonistic | Antagonistic |
| Lenalidomide | Synergistic | Additive to synergistic | Slightly to moderately antagonistic |
| Melphalan | Additive to synergistic | Slightly to moderately antagonistic | Additive to slightly synergistic |
| Dexamethasone | Not determined | additive | additive |

In this example MOLP 8 cell lines were used for combination of BT062 with bortezomib, thalidomide, lenalidomide, melphalan and dexamethasone.

Combination with thalidomide or bortezomib, did neither result in a synergistic nor an additive effect, but rather an antagonistic effect. In contrast to these cell culture studies combination with bortezomib was synergistic in the xenograft model described below.

Possible anti-myeloma drug candidates have been evaluated as combination partners for BT062 in Xenograft studies using MOLP8 human multiple myeloma cells.

EXAMPLE 1

Anti-Myeloma Effect of Combination Therapy with BT062 and Lenalidomide

Female SCID mice were subcutaneously inoculated with MOLP 8 human myeloma cells. Treatment with BT062 alone or in combination with Lenalidomide was initiated day 11 post tumor inoculation. BT062 was used in concentrations of 100 μg, 200 μg and 400 μg alone and in combination with Lenalidomide which was dosed intraperitoneally at 100 mg/kg on days 1 to 5 and days 8 to 12. A control group of animals received phosphate buffered saline (PBS) using the same schedule and route of administration. Tumor growth was monitored by measuring tumor size and calculated with the formula length×width×height×½, determined on days 10, 14, 18 and 21.

Synergism was calculated as follows (Yu et al., 2001; Gunaratnam et al., 2009):

RATIO($r$)=expected $FTV$(combination)/observed $FTV$(combination)

FTV: Fractional tumor volume=mean tumor volume (test)/mean tumor volume (control)

A ratio>1 is regarded as synergistic, whereas r<1 is less than additive.

The ratio (r) is, when above 1, referred to herein as "SYNERGY RATIO."

As can be seen from Table 21 synergism was observed after 28 days in concentrations of BT062 of 200 μg and 400 μg:

TABLE 21

Fractional tumor volume in MOLP 8 xenografts.

| Days | BT062 100 | Lenalidomide | BT062 100 + Len (observed) | BT062 100 + Len expected | ratio (exp/obs) |
| --- | --- | --- | --- | --- | --- |
| 10 | 0.93 | 1.00 | 0.97 | 0.93 | 0.96 |
| 14 | 0.75 | 0.82 | 0.59 | 0.61 | 1.04 |
| 17 | 0.52 | 0.45 | 0.23 | 0.23 | 1.02 |
| 21 | 0.53 | 0.42 | 0.19 | 0.22 | 1.19 |
| 24 | 0.44 | 0.55 | 0.18 | 0.24 | 1.30 |
| 28 | 0.33 | 0.46 | 0.17 | 0.15 | 0.90 |

| Days | BT062 200 | Lenalidomide | BT062 200 + Len (observed) | BT062 100 + Len expected | ratio (exp/obs) |
| --- | --- | --- | --- | --- | --- |
| 10 | 1.02 | 1.00 | 1.00 | 1.02 | 1.02 |
| 14 | 0.45 | 0.82 | 0.51 | 0.37 | 0.73 |
| 17 | 0.13 | 0.45 | 0.14 | 0.06 | 0.41 |
| 21 | 0.08 | 0.42 | 0.07 | 0.03 | 0.45 |
| 24 | 0.11 | 0.55 | 0.06 | 0.06 | 1.08 |
| 28 | 0.13 | 0.46 | 0.03 | 0.06 | 1.86 |

| Days | BT062 400 | Lenalidomide | BT062 400 + Len (observed) | BT062 100 + Len expected | ratio (exp/obs) |
| --- | --- | --- | --- | --- | --- |
| 10 | 0.94 | 1.00 | 0.91 | 0.95 | 1.04 |
| 14 | 0.44 | 0.82 | 0.24 | 0.36 | 1.49 |
| 17 | 0.09 | 0.45 | 0.06 | 0.04 | 0.63 |
| 21 | 0.04 | 0.42 | 0.04 | 0.02 | 0.44 |

TABLE 21-continued

Fractional tumor volume in MOLP 8 xenografts.

| 24 | 0.04 | 0.55 | 0.03 | 0.02 | 0.80 |
|----|------|------|------|------|------|
| 28 | 0.04 | 0.46 | 0.01 | 0.02 | 1.43 |

Different concentrations of BT062 either alone or in combination with Lenalidomide have been administered into tumor bearing xenograft.
FTV represents the relative tumor volume.
Synergistic effects are determined using Ratio values expected FTV versus observed FTV.
A ratio >1 indicates synergy.

TABLE 22

Lenalidomide BT062 combination: effects at different dosages.

| Agent | Dosage per injection | Total dose | T/C (%) (DAY 17) | Regressions Partial | Regressions Complete | Tumor free survivors day 77 | Result |
|---|---|---|---|---|---|---|---|
| PBS | (0.2 ml) | — | — | 0/6 | 0/6 | 0/6 | |
| BT062 | 100 ug/kg | 100 ug/kg | 35 | 0/6 | 0/6 | 0/6 | Active |
| BT062 | 200 ug/kg | 200 ug/kg | 14 | 0/6 | 0/6 | 0/6 | Active |
| BT062 | 400 ug/kg | 400 ug/kg | 9 | 4/6 | 1/6 | 0/6 | highly active |
| lenalidomide | 100 mg/kg | 1 g/kg | 31 | 0/6 | 0/6 | 0/6 | Active |
| BT062 lenalidomide | 100 ug/kg 100 mg/kg | 100 ug/kg 1 g/kg | 19 | 0/6 | 0/6 | 0/6 | Active |
| BT062 lenalidomide | 200 ug/kg 100 mg/kg | 200 ug/kg 1 g/kg | 12 | 2/6 | 0/6 | 0/6 | Active |
| BT062 Lenalidomide | 400 ug/kg 100 mg/kg | 400 ug/kg 1 g/kg | 6 | 5/6 | 4/6 | 0/6 | highly active |

Figure 30:
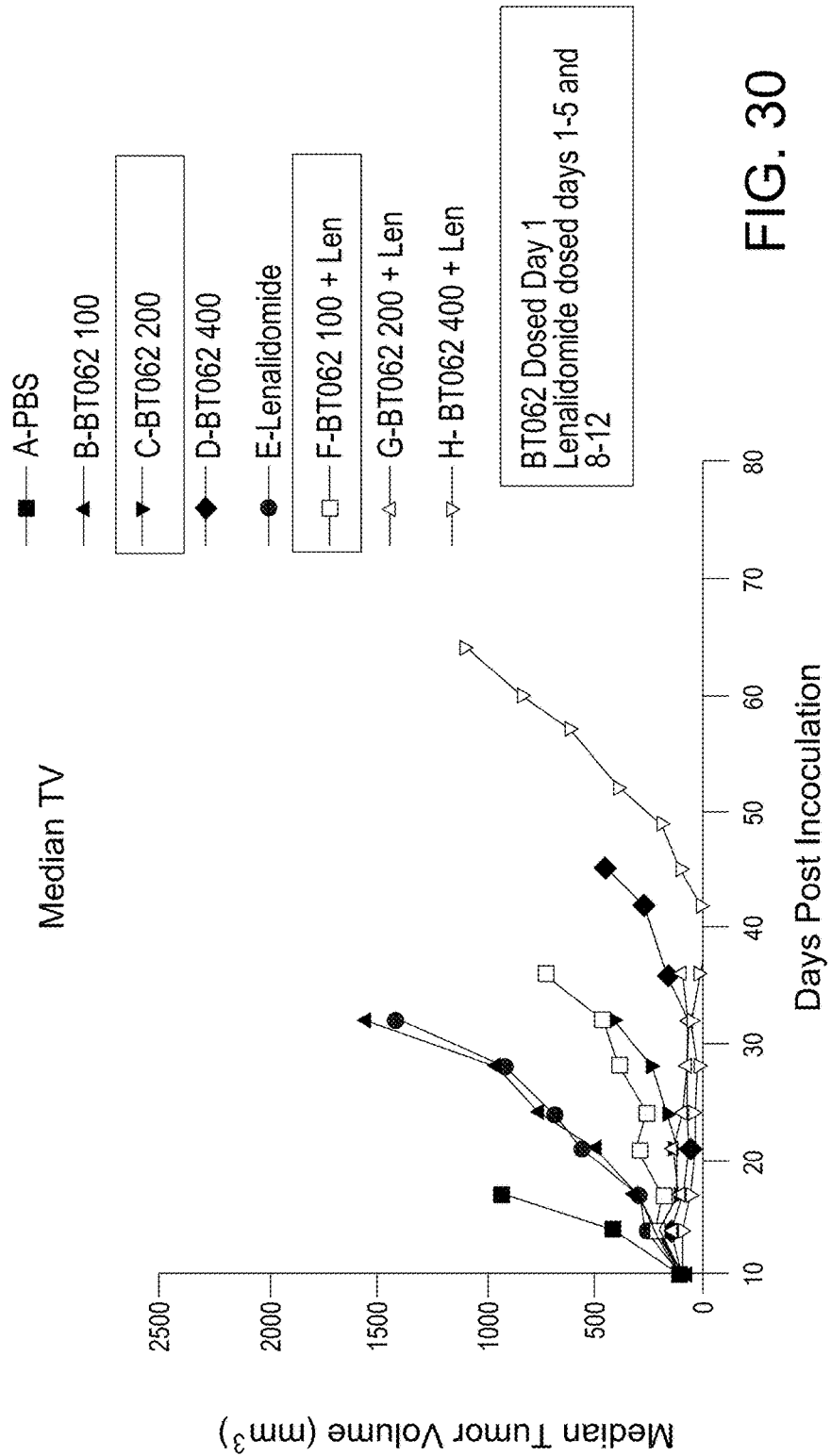
FIG. 30 shows the effect of the combination therapy on median tumor volume (TV) in a xenograft mouse model (MOLP-8 MM xenograph model). The results show the effects of the combination of BT062 and lenalidomide.
Figure 31:
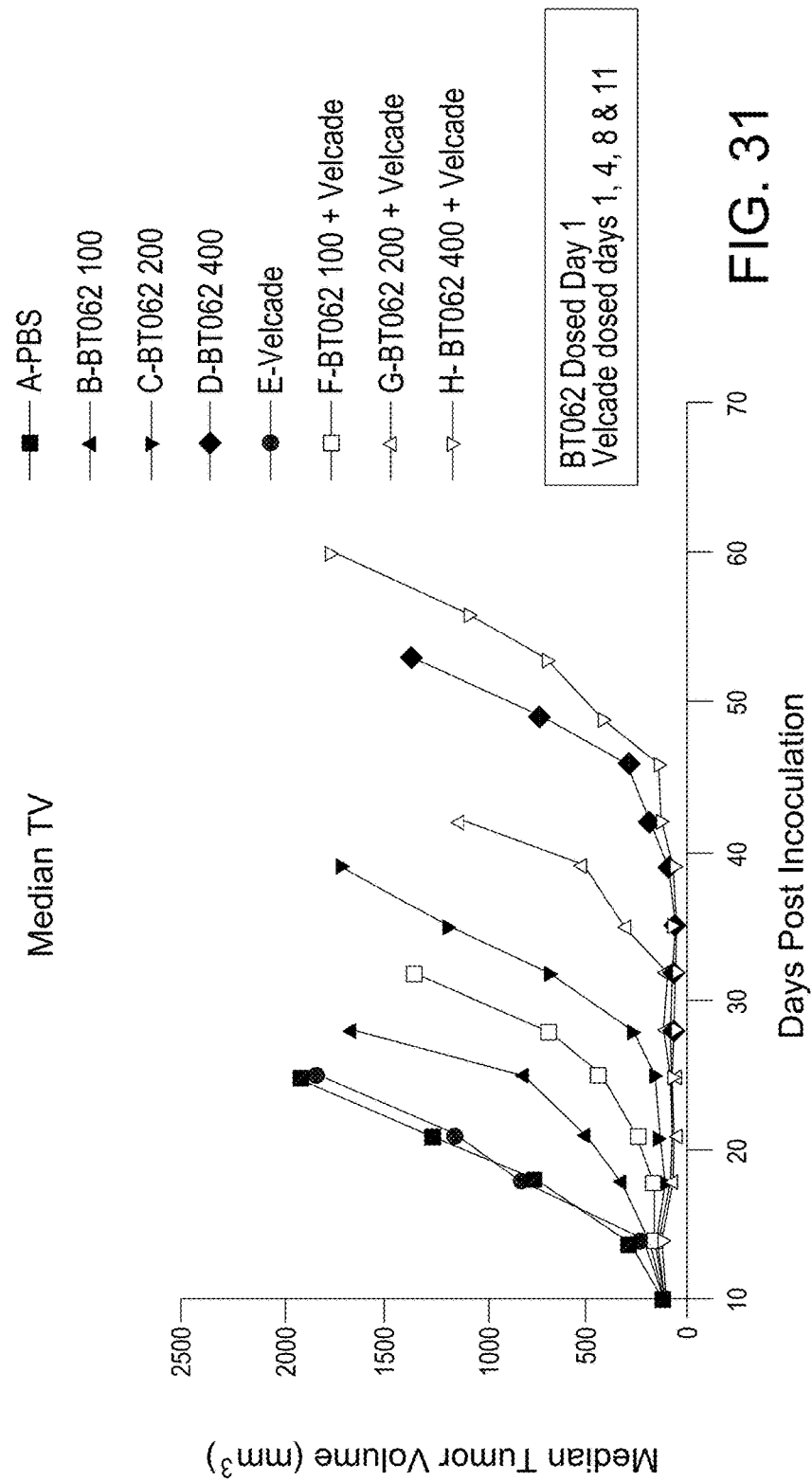
FIG. 31 shows the effect of the combination therapy on median tumor volume (TV) in a xenograft mouse model. The result shows the effects of the combination of BT062 and VELCADE.
Figure 32A:
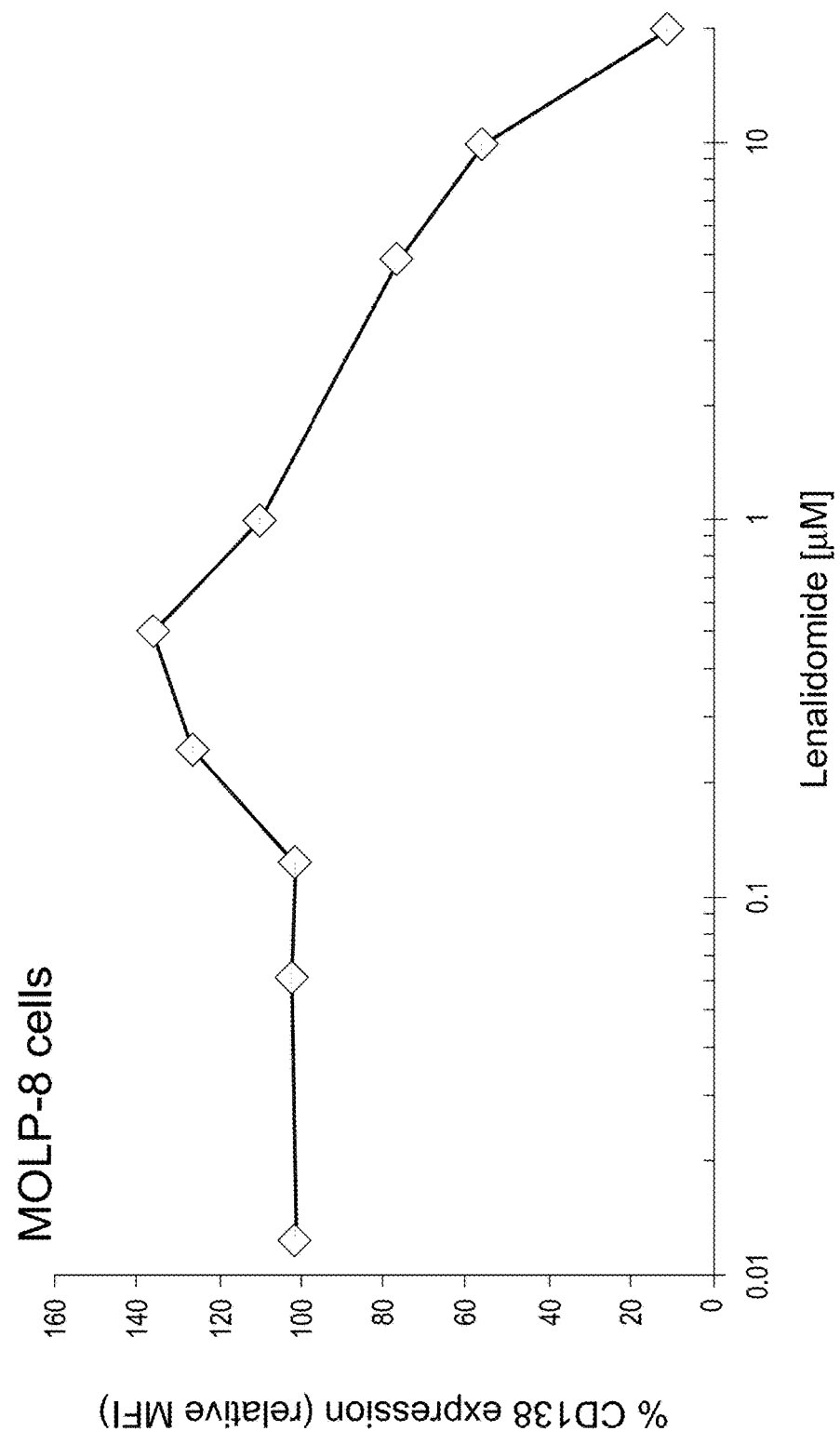
FIG. 32 shows the effect of lenalidomide on different CD138 expressing cells in vitro, in particular MOLP-A cells (A), RPMI8226 cells (B), NCI-H929 cells (C) and U266 cells (D). Notably CD138 expression was not affected in vivo (L363 MM xenograft model) by the treatment of the combination of lenalidomide and dexamethasone (data not shown).
Figure 32B:
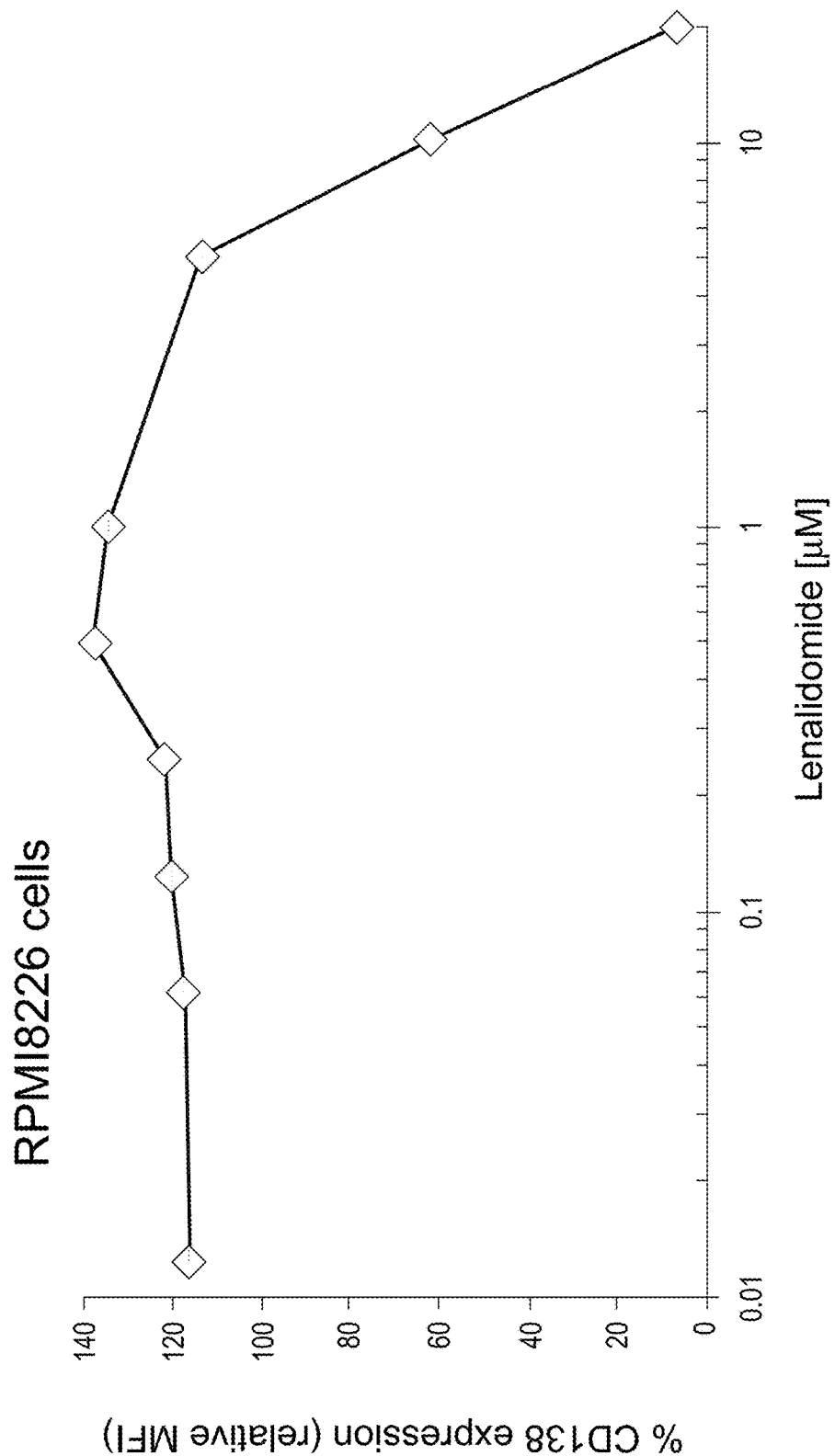
Figure 32C:
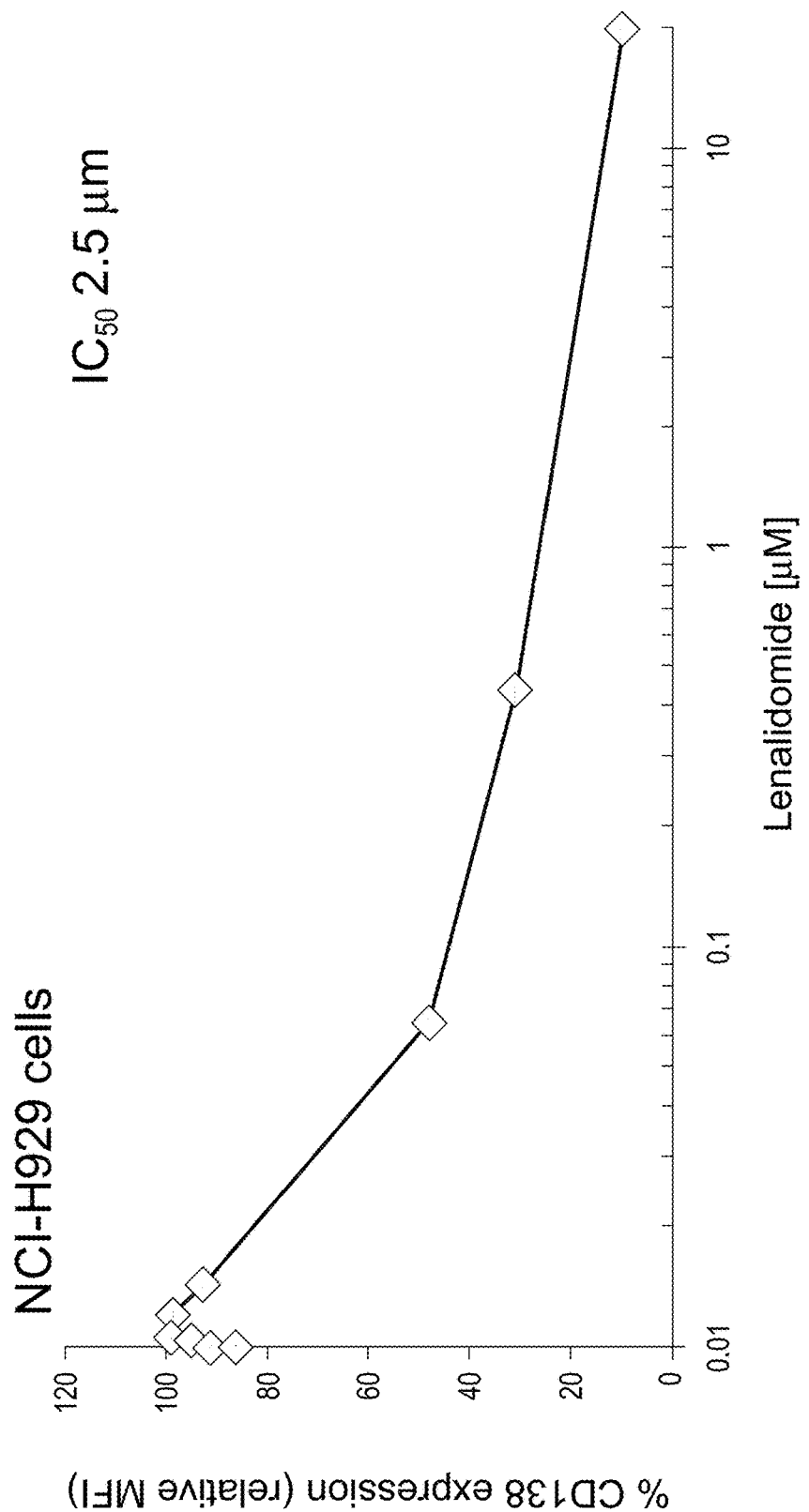
Figure 32D:
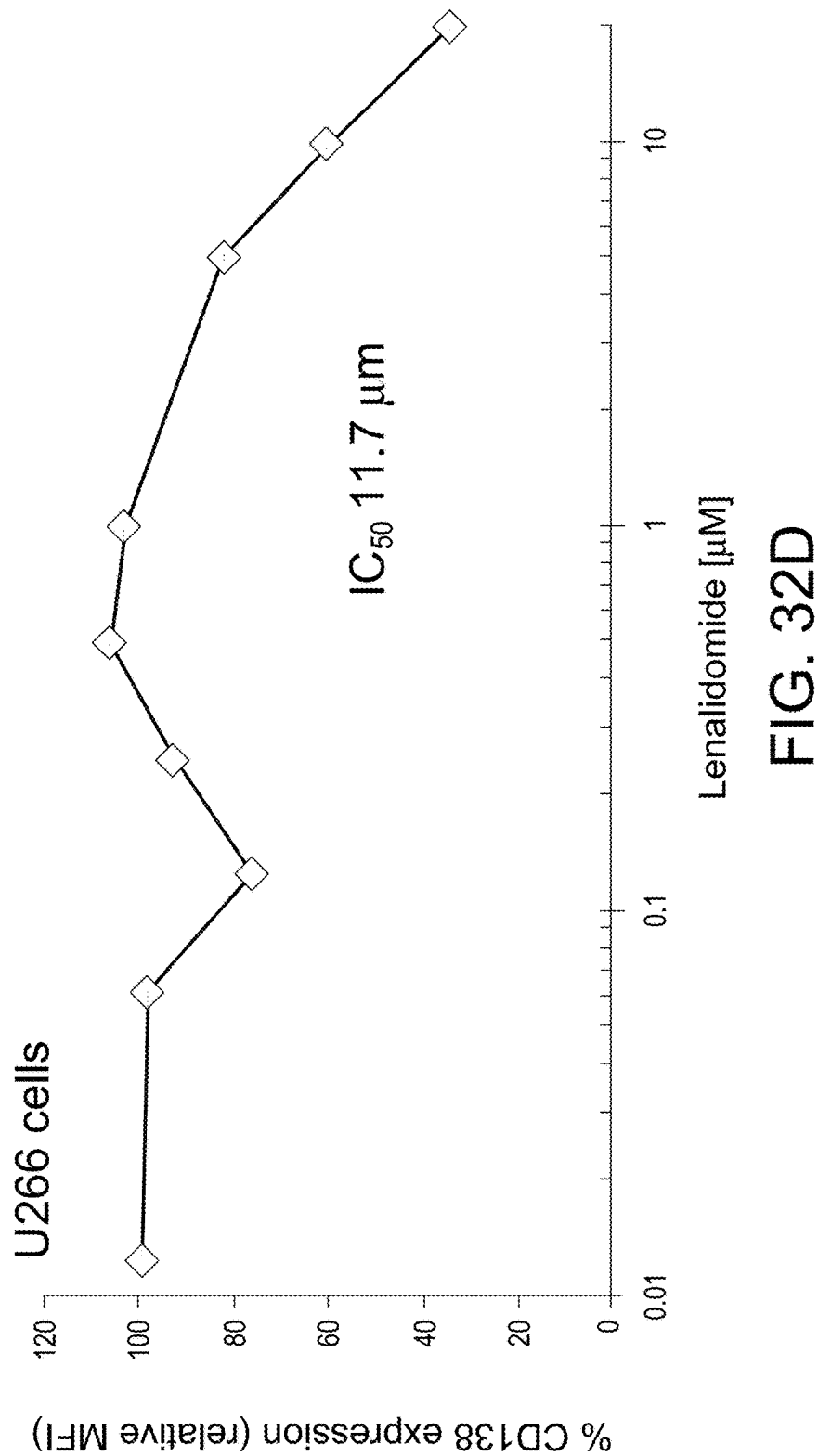

FIGS. 30 and 31 show the effect of the combination therapy on median tumor volume (TV) in a xenograft mouse model. The result in FIG. 30 show additive effects of the combination. Notably the combination resulted in a dose of 100 μg/kg of the immunoconjugate, when combined with a dose of 100 mg/kg lenalidomide. For synergy ratios, please refer to the table above.

EXAMPLE 2

Anti-Myeloma Effect of Combination Therapy with BT062 and VELCADE

VELCADE has been evaluated as potential multiple myeloma drug combination partner for BT062 in Xenograft studies using MOLP8 multiple myeloma cells (IMGN Inc.). Treatment with BT062 alone or in combination with VELCADE was initiated 11 days past tumor implantation. BT062 was used in concentrations of 100 μg, 200 μg and 400 μg alone and in combination with VELCADE which was dosed at 100 mg/kg on days 1, 4, 8 and 11. A control group of animals received phosphate buffered saline (PBS) using the same schedule and route of administration. Tumor growth was monitored by measuring tumor size and calculated with the formula length×width×height×½, determined on days 10, 14, 17, 21, 24 and 28, respectively.

Synergism was calculated as in Example 1 of the combination studies.

As can be seen from Table 23, synergy is observed in the combination BT062 with VELCADE at day 25 in all BT062 dose regimens. R values reported in the literature are even higher (Yu et al., 2001).

TABLE 23

Combination treatment with VELCADE.

| Day | BT062 100 | Velcade | BT062 100 + Velcade (observed) | expected | ratio (exp/obs) |
|---|---|---|---|---|---|
| 10 | 1.06 | 1.05 | 1.04 | 1.12 | 1.07 |
| 14 | 0.74 | 0.84 | 0.56 | 0.62 | 1.11 |
| 18 | 0.44 | 0.96 | 0.28 | 0.42 | 1.54 |

TABLE 23-continued

Combination treatment with VELCADE.

| 21 | 0.39 | 0.80 | 0.23 | 0.31 | 1.38 |
|----|------|------|------|------|------|
| 25 | 0.48 | 0.95 | 0.26 | 0.46 | 1.75 |

| Days | BT062 200 | Velcade | BT062 200 + Vel (observed) | expected | ratio (exp/obs) |
|---|---|---|---|---|---|
| 10 | 1.02 | 1.05 | 1.07 | 1.12 | 1.07 |
| 14 | 0.52 | 0.84 | 0.45 | 0.44 | 0.98 |
| 18 | 0.13 | 0.96 | 0.10 | 0.12 | 1.19 |
| 21 | 0.10 | 0.80 | 0.05 | 0.08 | 1.47 |
| 25 | 0.10 | 0.95 | 0.04 | 0.09 | 2.09 |

| Days | BT062 400 | Velcade | BT062 400 + Vel (observed) | expected | synergy ratio (exp/obs) |
|---|---|---|---|---|---|
| 10 | 1.09 | 1.05 | 1.04 | 1.15 | 1.10 |
| 14 | 0.45 | 0.84 | 0.43 | 0.38 | 0.88 |
| 18 | 0.08 | 0.96 | 0.09 | 0.08 | 0.89 |
| 21 | 0.05 | 0.80 | 0.04 | 0.04 | 0.98 |
| 25 | 0.04 | 0.95 | 0.02 | 0.03 | 1.36 |

Fractional tumor volume (FTV) represents the mean tumor volume (test)/mean relative tumour volume (control).
Ratio of expected FTV (combination) vs. observed FTV (observed).
Ratio value >1 indicate synergy, values less than 1 indicate an additive effect.

TABLE 24

VELCADE BT062 combination: effects at different dosages.

| Agent | Dosage per injection | Treatment days (TX start date = day 10 post inoc.) | T/C (%) | (T-C) in days | log cell kill | Regressions Partial | Regressions Complete | Tumor free survivors day 67 | Result |
|---|---|---|---|---|---|---|---|---|---|
| PBS | (0.2 ml) | Day 1 | — | — | — | 0/6 | 0/6 | 0/6 | |
| BT062 | 100 ug/kg | Day 1 | 43 | 5.5 | 0.5 | 0/6 | 0/6 | 0/6 | Inactive |
| BT062 | 200 ug/kg | Day 1 | 11 | 14.5 | 1.3 | 1/6 | 0/6 | 0/6 | Active |
| BT062 | 400 ug/kg | Day 1 | 7 | 31.5 | 2.8 | 4/6 | 2/6 | 0/6 | highly active |
| Velcade | 1 mg/kg | days 1, 4, 8, 11 | 100 | 0.5 | 0.0 | 0/6 | 0/6 | 0/6 | Inactive |
| BT062 Velcade | 100 ug/kg 100 mg/kg | Day 1 days 1, 4, 8, 11 | 20 | 10.5 | 0.9 | 1/6 | 0/6 | 0/6 | Active |
| BT062 Velcade | 200 ug/kg 100 mg/kg | Day 1 days 1, 4, 8, 11 | 7 | 23.5 | 2.1 | 4/6 | 1/6 | 0/6 | highly active |
| BT062 | 400 ug/kg | Day 1 | 7 | 36.5 | 3.2 | 6/6 | 0/6 | 0/6 | highly active |

FIG. 31 shows the effect of the combination therapy on median tumor volume (TV) in a xenograft mouse model. The result show that in the model used, VELCADE treatment alone had no effect on the tumor volume. The combination with BT062 provided synergistic effects. Notably the synergism resulted in a dose of 100 µg/kg of the immunoconjugate, when combined with a dose of 100 mg/kg VELCADE. For synergy ratios, please refer to the table above.

EXAMPLE 3

BT062/Melphalan

RPMI cells have been implanted subcutaneously into nude mice. Mice were randomized when tumor reached a total volume of approx 100 mm³. BT062 was injected intravenously at 2 different concentrations: 400 µg/kg and 100 µg/kg; each based on the molecular weight of the linked DM4. PBS served as negative control. Per group, 8 mice with one tumor each (unilateral implantation) were used. BT062 was dosed weekly followed by melphalan once weekly (3 mg/kg) one day after BT062 injection intraperitoneally (results not shown).

EXAMPLE 4

In Vivo Drug Combination Studies BT062/Lenalidomide/Dexamethasone

While in vitro different cell lines showed a concentration dependent CD138 decrease after 24 h lenalidomide incubation (FIG. 32(A) to (D)), in vivo drug combination studies showed that a combination of 4 mg/kg, 20 mg/kg lenalidomide and 1.25 mg/kg dexamethasone was highly effective in a L363 MM xenograft model.

Figure 33:
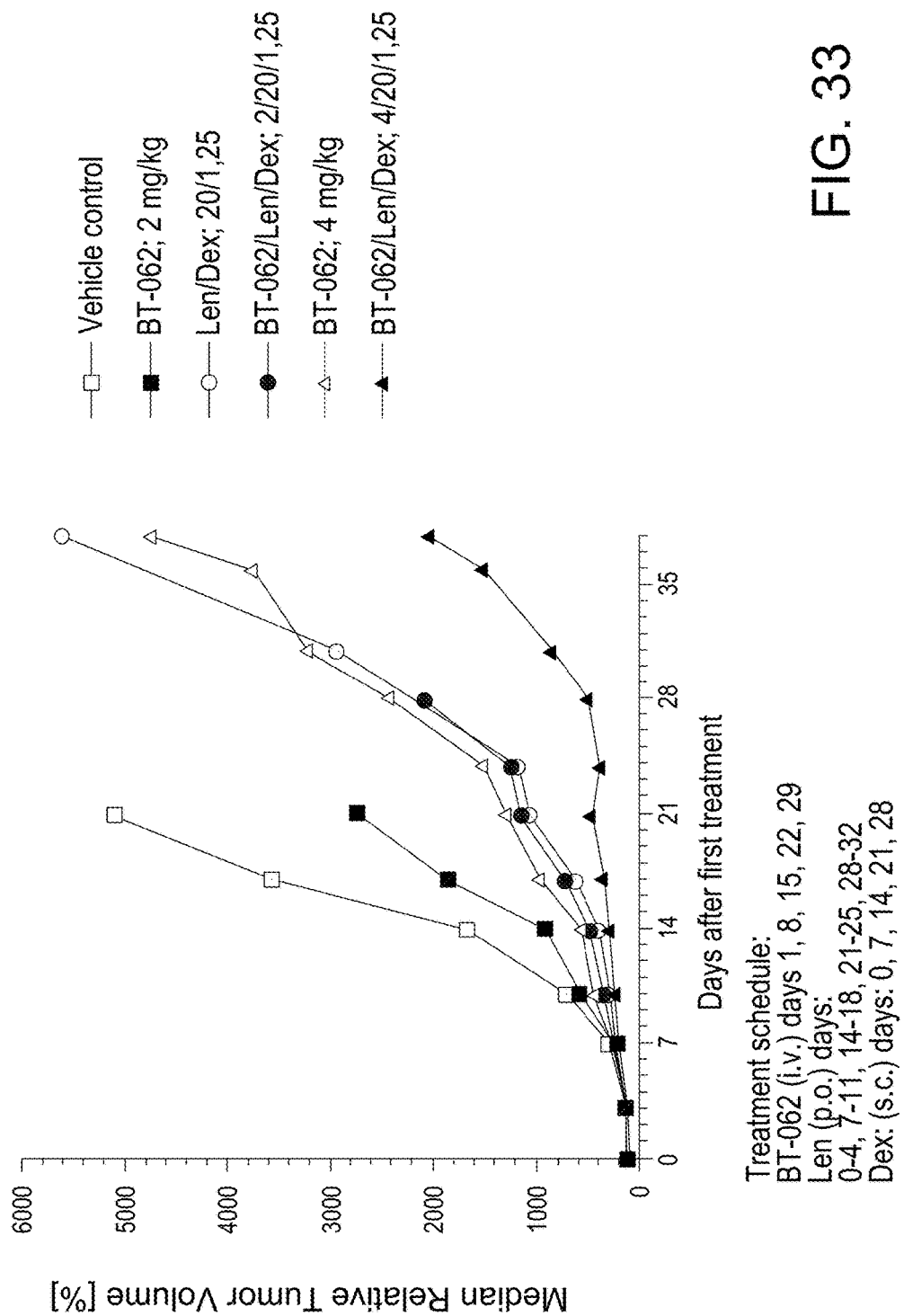
FIG. 33 shows the results of an in vivo (L363 MM xenograft model) drug combination study wherein BT062 (2 mg/kg, 4 mg/kg) was administered intravenously on days 1, 8, 15, 22 and 29; lenalidomide was administered orally on days 0-4, 7-11, 14-18, 21-25, 28-32 and dexamethasone was administered subcutaneously on days 0, 7, 14, 21 and 28. A considerable reduction in tumor volume relative to the simple combination of lenalidomide and dexamethasone can in particular be seen in the context of the 4 mg/kg BT062 dosage scheme. The results are shown in terms of the effect on the median relative tumor volume in the model relative to an intravenous administration of a vehicle control. The median relative tumor volume on day X was, here and in the subsequent figures calculated as follows: The relative volumes of individual tumors (Individual RTVs) for Day X were calculated by dividing the individual tumor volume on Day X (Tx) by the individual volume of the same tumor on Day 0 (T0) multiplied by 100%. Group tumor volumes were expressed as the median or mean (geometric) RTV of all tumors in a group (group median/mean RTV).

In this model, a highly aggressive CD138 expressing plasma cell myeloma cell line L363 was subcutaneously implanted into NOD/SCID mice. Treatment started when tumors reached a size of approx. 100 mm³. BT062 was injected intravenously once weekly on days 1, 8, 15, 22, 29 at concentrations of 2 mg/kg or 4 mg/kg either alone or in combination with lenalidomide, which was given orally on days 0-4, 7-11, 14-18, 21-25 and 28-32 and Dexamethasone, which was given intraperitoneally on days 0, 7, 14, 21 and 28. Tumor size was measured once weekly. 4 mg/kg BT062 alone was active in reducing the tumor growth. Combination of 4 mg/kg BT062 with Len/Dex showed higher activity with regard to tumor growth inhibition leading than the single agents (Len/Dex alone; BT062 alone) (FIG. 33).

Once given the above disclosure, many other features, modifications, and improvements will become apparent to the skilled artisan. Such other features, modifications, and improvements are therefore considered to be part of this invention, the scope of which is to be determined by summary of the invention and the following claims.

BIBLIOGRAPHY

Abdelkefi et al.; "Single autologous stem-cell transplantation followed by maintenance therapy with thalidomide is superior to double autologous transplantaion in multiple myeloma: results of a multicenter randomized clinical trial;" Blood; 111; 2008; pp.: 1805-1810.

Akkina et al.; "Modeling human lymphoid precursor cell gene therapy in the SCID-hu mouse;" Blood; 84; 1994; pp.: 1393-1398.

Armour et al.; "Recombinant human IgG molecules lacking Fcgamma receptor I binding and monocyte triggering activities;" Eur J Immunol; 29(8); 1999; pp.: 2613-24.

Anderson et al.; "Multiple Myeloma: New Insights and Therapeutic Approaches;" Hematology; 2000; pp.: 147-165.

Anderson et al.; "Multiple Myeloma; Hematology Am Soc Hematol Educ Program;" 2002; pp.: 214-40.

Anttonen et al.: "Syndecan-1 expression has prognostic significance in head and neck carcinoma;" Br J of Cancer 79 (3/4), 1999, pp.: 558-564.

Anttonen et al.; "High syndecan-1 expression is associated with favourable outcome in squamous cell lung carcinoma treated with radical surgery;" Lung Cancer; 32(3); June 2001; pp.: 297-305.

Aref et al.: "Syndecan-1 in multiple myeloma: relationship to conventional prognostic factors;" Hematology; 8; 2003; pp.:221-228.

Barbareschi et al.; "High syndecan-1 expression in breast carcinoma is related to an aggressive phenotype and to poorer prognosis;" Cancer; 98(3); Aug. 1, 2003; pp.: 474-83.

Bartlett et al., "A phase 1 multidose study of SGN-30 immunotherapy in patients with refractory or recurrent CD30+ hematologic malignancies," Blood, vol. 111, 2008, pp.: 1848-1854.

Bataille et al.; "The phenotype of normal, reactive and malignant plasma cells. Identification of "many and multiple myelomas" and of new targets for myeloma therapy;" Haematologica; 91(9); September 2006; pp.: 1234-40.

Bayer-Garner et al.; "Syndecan-1 (CD138) immunoreactivity in bone marrow biopsies of multiple myeloma: shed syndecan-1 accumulates in fibrotic regions;" Mod Pathol.; 14(10); October 2001; pp.: 1052-8.

Beeram et al.; "A phase I study of trastuzumab-DM1 (T-DM1), a first-in-class HER2 antibody-drug conjugate (ADC), in patients (pts) with advanced HER2+ breast cancer (BC);" ASCO Meeting; Abstracts; May 20, 2008; pp.: 1028.

Berenson et al.; "New drugs in multiple myeloma;" Curr Opin Support Palliat Care; 2(3); September 2008; pp.: 204-10.

Bernfield et al.; "Biology of the syndecans: a family of transmembrane heparan sulfate proteoglycans;" Annu Rev Cell Biol; 8; 1992; pp.: 365-393.

Beste et al.; "Small antibody-like proteins with prescribed ligand specificities derived from the lipocalin fold;" Proc. Natl. Acad. Sci. USA; 96; 1999; pp.: 1898-1903.

Bhattacharyya et al.; "Maytansine binding to the vinblastine sites of tubulin;" FEBS Lett.; 75; 1977; pp.: 159-162.

Bisping et al., "Targeting receptor kinases by a novel indolinone derivative in multiple myeloma: abrogation of stroma-derived interleukin-6 secretion and induction of apoptosis in cytogenetically defined subgroups;" Blood; 107(5); Mar. 1, 2006; pp.: 2079-89.

Bissery et al., "Experimental Antitumor Activity of Taxotere (RP 56976, NSC 628503), a Taxol Analogue", Cancer Research 51, 1991, PP.: 4845-4852.

Bladé et al.; "Advances in therapy of multiple myeloma;" Curr Opin Oncol; 20(6); November 2008; pp.: 697-704.

Blum et al.; "Maytansine: A Phase I study of an ansa macrolide with antitumor activity;" Cancer Treat Rep; 62; 1978; pp.: 435-438.

Brand et al.; "Management of high risk metastatic prostate cancer: the case for novel therapies;" J Urol December; 176 (6Pt 2); 2006; pp.: S76-80.

Blather et al.; "Drugs to Enhance the Therapeutic Potency of Anticancer Antibodies: Antibody-Drug Conjugates as Tumor-Activated Prodrugs;" Ojima, I., Vite, G.D. and Altmann, K.-H., Editors; Anticancer Agents-Frontiers in Cancer Chemotherapy, American Chemical Society, Washington, D.C., 2001; 2001; pp.: 317-338.

Bross et al.; "Approval summary: gemtuzumab ozogamicin in relapsed acute myeloid leukemia;" Clin Cancer Res; 7; 2001; pp.: 1490-1496.

Burris et al.; "A Phase I study of a first-in-class HER2 antibody-drug conjugate in subjects with HER2-overexpressing metastatic breast cancer;" 29th Annual San Antonio Breast Cancer Symposium (SABCS); Poster Abstract #2070; 2006.

Cabanillas et al., "Phase I study of maytansine using a 3 day schedule;" Cancer Treat Rep; 62; 1978; pp.: 425-428.

Carbone et al.; "AIDS-related plasma-blastic lymphomas of the oral cavity and jaws: a diagnostic dilemma.Ann;" 0 to 1. Rhinol. Laryngol; 108; 1999; pp.: 95-99.

Carlsson et al., "Protein thiolation and reversible protein-protein conjugation. N-succinimidyl-3-(2-pyridyldithio) propionate, a new heterobifunctional reagent;" Biochem J; 173; 1978; pp.: 723-737.

Carter P; "Improving the efficacy of antibody-based cancer therapies;" Nat Rev Cancer; 1; 2001; pp.:118-129.

Carter and Senter, "Antibody-Drug Conjugates", The Cancer Journal, Vol. 14(3), 2008, pp.: 154-169

Chabner et al.; "Initial clinical trials of maytansine, an antitumor plant alkaloid;" Cancer Treat Rep; 62; 1978; pp.: 429-433.

Chanan-Khan et al.; "Phase I Study of huN901-DM1 (BB-10901) in Patients with Relapsed and Relapsed/Refractory CD56-Positive Multiple Myeloma;" Blood; 108(11); Abstract #1174 (ASH Meeting); Nov. 16, 2007.

Chanan-Khan et al.; "Phase I Study of IMGN901 in Patients with Relapsed and Relapsed/Refractory CD56-Positive Multiple Myeloma;" Blood (ASH Annual Meeting Abstracts); 112; November 2008; pp.: 3689.

Chari et al.; "Immunoconjugates containing novel maytansinoids: promising anticancer drugs;" Cancer Res; 52; 1992; pp.: 127-131.

Chari et al.; "Enhancement of the selectivity and antitumor efficacy of a CC-1065 analogue through immunoconjugate formation;" Cancer Res.; 55; 1995; pp.: 4079-4084.

Charnaux et al.; "RANTES (CCL5) induces a CCR5-dependent accelerated shedding of syndecan-1 (CD138) and syndecan-4 from HeLa cells and forms complexes with the shed ectodomains of these proteoglycans as well as with those of CD44;" Glycobiology; 15(2); 2005; pp.: 119-130.

Chen et al.; "Engraftment of human hematopoietic precursor cells with secondary transfer potential in SCID-hu mice;" Blood; 84; 1994; pp.: 2497-2505.

Chilosi et al.; "CD138/syndecan-1: a useful immunohistochemical marker of normal and neoplastic plasma cells on routine trephine bone marrow biopsies;" Mod Pathol.; 12; 1999; pp.: 1101-1106.

Choi et al.; "Syndecan-1, a key regulator of cell viability in endometrial cancer;" Int J Cancer 121(4); 2007; pp.: 741-50.

Chou and Talalay; "Quantitative analysis of dose-effect relationships: the combined effects of multiple drugs on enzyme inhibitors;" Adv. Enzyme Regul. 22; 1984, pp.: 27-55.

Clément et al.; "B-B2 and B-B4, two new mAb against secreting plasma cells;" Leucocyte Typing V; Oxford Press.; 1; 1995; pp.: 714-715.

Coiffier et al., "Phase I/II study of the anti-CD19 maytansinoid immunoconjugate SAR3419 administered weekly to patients with relapsed/refractory B-cell non-Hodgkin's lymphoma (NHL)," 2011 ASCO Annual Meeting, Chicago, Ill., June 2011, Unpublished conference proceedings, 2011.

Conejo et al.; "Syndecan-1 expression is up-regulated in pancreatic but not in other gastrointestinal cancers;" Int J Cancer; 88(1); 2000 Oct. 1; pp.:12-20.

Couturier et al.; "Validation of 213Bi-alpha radioimmunotherapy for multiple myeloma;" Clinical Cancer Research 5(10 Suppl.); October 1999; pp.: 3165s-3170s.

Davies E J et al.; "Distribution and Clinical Significance of Heparan Sulfate Proteoglycans;" Ovarian Cancer Clin Cancer Res; 10(15); 2004; pp.: 5178-86.

DeGeorge et al.; "Regulatory considerations for preclinical development of anticancer drugs;" Cancer Chemother Pharmacol; 41(3); 1998; p.: 173-85.

Dmoszyńska A.; "Diagnosis and the current trends in multiple myeloma therapy;" Pol Arch Med Wewn; 118(10); October 2008; pp.: 563-6.

Dhodapkar et al.; "Syndecan-1 is a multifunctional regulator of myeloma pathobiology: control of tumor cell survival, growth, and bone cell differentiation;" Blood; 91; 1998; pp.: 2679-2688.

Dimopoulos et al.; "The role of novel drugs in multiple myeloma;" Annals of Oncology19 (Supplement 7); 2008; pp.: vii121-127.

Dore et al.; "Identification and location on syndecan-1 core protein of the epitopes of B-B2 and B-B4 monoclonal antibodies;" FEBS Lett; 26; 1998; pp.: 67-70.

Dowell et al.; "Pharmacokinetics of gemtuzumab ozogamicin, an antibody-targeted chemotherapy agent for the treatment of patients with acute myeloid leukemia in first relapse;" J Clin Pharmacol; 41; 2001; pp.: 1206-1214.

Durie et al.; "Myeloma management guidelines: a consensus report from the Scientific Advisors of the International Myeloma Foundation;" Hematol J, 4(6); 2003; pp.: 379-98.

Durie et al.; "International uniform response criteria for multiple myeloma;" Leukemia; 20(12); December 2006; pp.: 2220.

Eagan et al.; "Early clinical study of an intermittent schedule for maytansine (NSC-153858): brief communication;" J Natl Cancer Insti (Bethesda); 60; 1978; pp. 93-96.

Edinger et al.; "Noninvasive assessment of tumor cell proliferation in animal models;" Neoplasia; 1; 1999; pp.:303-310.

Facon et al.; "Superiority of melphalan-prednisone (MP)+ thalidomide (THAL) over MP and autologous stem cell transplantation in the treatment of newly diagnosed elderly patients with multiple myeloma;" J. Clin. Oncol.; 24(Suppl. 18); Abstract 1; 2006.

Fossella et al.; "Phase II Trial of BB-10901 (huN901-DM1) given weekly for four consecutive weeks every 6 weeks in patients with relapsed SCLC and CD56-positive small cell carcinoma;" J Clin Onco, ASCO Annual Meeting Proceedings; 23(16S), Part I of II; Jun. 1, 2005; 7159; Supplement.

Galsky et al.; "Phase I Trial of the Prostate-Specific Membrane Antigen-Directed Immunoconjugate MLN2704 in Patients With Progressive Metastatic Castration-Resistant Prostate Cancer;" Journal of Clinical Oncology; May 1, 2008; pp.: 2147-2154.

Gattei et al.; "Characterization of Anti-CD138 monoclonal antibodies as tools for investigating the molecular polymorphism of syndecan-1 in human lymphoma cells;" Br J. Haematol.; 104; 1999; pp.: 152-162.

Ghobrial et al.; "Emerging drugs in multiple myeloma;" Expert Opin Emerg Drugs; 12(1); March 2007; pp.: 155-63.

Giles et al.; "Phase I study of AVE9633, an AntiCD33-Maytansinoid Immunoconjugate, Administered as an Intravenous Infusion in Patients with Refractory/Relapsed CD33-Positive Acute Myeloid Leukemia (AML);" Blood; 108(11); Nov. 16, 2006.

Greipp et al.; "International staging system for multiple myeloma," J Clin Oncol; 23(15); Mary 20, 2005; pp.: 3412-20.

Greipp and Lust; "Pathogenetic relation between monoclonal gammopathies of undetermined significance and multiple myeloma;" Stem Cells. August 13 Suppl 2; 1995; pp.:10-21.

Gunaratnum et al.; "G-quadruplex compounds and cis-platin act synergistically to inhibit cancer cell growth in vitro and in vivo;" Biochemical Pharmacology; 78; 2009; pp.: 115-122.

Hamann et al.; "An anti-CD33 antibody-calicheamicin conjugate for treatment of acute myeloid leukemia;" Choice of linker; Bioconjug Chem; 13; 2002; pp.: 40-46.

Han et al.; "New insights into syndecan-2 expression and tumourigenic activity in colon carcinoma cells;" J Mol Histol; 35(3); 2004; pp.: 319-26.

Hashimoto et al.; "Colorectal Association of loss of epithelial syndecan-1 with stage and local metastasis of colorectal adenocarcinomas: an immunohistochemical study of clinically annotated tumors;" BMC Cancer 8; 2008; p. 185.

Helft et al.; "A phase I study of cantuzumab mertansine administered as a single intravenous infusion once weekly in patients with advanced solid tumors;" Clin Cancer Res; 10(13); 2004 Jul. 1; pp.: 4363-8.

Hideshima et al.; "Perifosine, an oral bioactive novel alkylphospholipid, inhibits Akt and induces in vitro and in vivo cytotoxicity in human multiple myeloma cells;" Blood; 107(10); 2006; pp.: 4053-62.

Hideshima et al.; "Understanding multiple myeloma pathogenesis in the bone marrow to identify new therapeutic targets;" Nat Rev Cancer; 7(8); 2007; pp.: 585-98.

Hiroshi et al.; "The Monoclonal Antibody nBT062 Conjugated to Cytotoxic Maytansinoids Has Potent and Selective Cytotoxicity against CD138 Positive Multiple Myeloma Cells in Vitro and in Vivo;" Blood; (ASH Annual Meeting Abstracts); 112; November 2008; p.: 1716.

Holden et al.; "A phase I study of weekly dosing of trastuzumab-DM1 (T-DM1) in patients (pts) with advanced HER2+ breast cancer (BC);" ASCO Meeting Abstracts; May 20, 2008; p..: 1029.

Horvathova et al.; In: al. SFSe, ed. Leucocyte Typing V.; Oxford: Oxford University Press; 1995; pp.: 713-714.

Huang et al.; "Validation and reduction of FACT/GOG-Ntx subscale for platinum/paclitaxel-induced neurologic symptoms: a gynecologic oncology group study;" Int J Gynecol Cancer; 17; 2007; pp.: 387-93.

Hwang et al.; "New Frontiers in the Treatment of Multiple Myeloma;" Scientific World Journal; 6; Dec. 6, 2006; pp.: 1475-503.

Ikeda et al.; "The monoclonal antibody nBT062 conjugated to maytansinoids has potent and selective cytotoxicity against CD138 positive multiple myeloma cells in vitro and in vivo;" Clin. Cancer Research; 15(12); 2009.

Ishitsuka et al.; "Targeting CD56 by the maytansinoid immunoconjugate IMGN901 (huN901-DM1): a potential therapeutic modality implication against natural killer/T cell malignancy;" Br. J. Haematol; 141(1); April 2008; pp.:129-31.

Issell et al.; "Maytansine;" Cancer Treat Rev; 5; 1978; pp.: 199-207.

Jemal et al.; "Cancer statistics;" CA Cancer J Clin; 58; 2008; pp.: 71-96.

Johnson et al.; "Novel and Targeted Agents for Small Cell Lung Cancer;" ASCO Educational Book; Jan. 1, 2008; pp.: 363-367.

Kovtun et al.; "Antibody-drug conjugates designed to eradicate tumors with homogeneous and heterogeneous expression of the target antigen;" Cancer Res; 66(6); 2006; pp.: 3214-21.

Kuesters et al.; "Correlation of ErbB2 Gene Status, mRNA and Protein Expression in a Panel of >100 Human Tumor Xenografts of Different Origin;" Onkologie; 29; 2006; pp:249-256

Krebs et al.; "High-throughput generation and engineering of recombinant human antibodies;" J. Immunol. Methods; 254; 2001; pp.: 67-84.

Krop et al.; "A Phase I Study of Trastuzumab-DM1, a First-in-Class HER2 Antibody-Drug Conjugate (ADC), in patients with HER2+ Metastatic Breast Cancer;" 14th European Cancer Conference (ECCO 14); Poster #2118; 2007.

Kupchan et al.; "Structural requirements for antileukemic activity among the naturally occurring and semisynthetic maytansinoids;" J Med Chem; 21; 1978; pp.:31-37.

Kyle; "Benign monoclonal gammopathy-after 20 to 35 years of follow-up;" Mayo Clin Proceedings 68(1); 1993; pp.: 26-36.

Kyle et al.; "Multiple myeloma;" N Engl J Med; 351(18); Oct. 28, 2004; pp.:1860-73.

Kyle et al.; "Criteria for diagnosis, staging, risk stratification do response assessment of multiple myeloma;" Leukemia; 23; 2009; pp.: 3-9.

Kyoizumi et al.; "Implantation and maintenance of functional human bone marrow in SCID-hu mice;" Blood; 79; 1992; pp.:1704-1711.

Kyoizumi et al.; "Preclinical analysis of cytokine therapy in the SCID-hu mouse;" Blood; 81; 1993; pp.:1479-1488.

Lambert J M; "Drug-conjugated monoclonal antibodies for the treatment of cancer;" Current Opinion in Pharmacology; 5; 2005; pp.: 543-549.

Langford et al.; "Multiple heparan sulfate chains are required for optimal syndecan-1 function;" J Biol Chem; 273(45); Nov. 6, 1998; pp.: 29965-71.

Legrand et al.; "An open label, dose escalation study of AVE9633 administered as a single agent by intravenous (IV) infusion weekly for 2 weeks in a 4-week cycle to patients with relapsed or refractory CD33-positive Acute Myeloid Leukemia (AML);" Blood; 118(11); Nov. 16, 2007.

Li et al.; "Clinicopathological significance of expression of paxillin, syndecan-1 and EMMPRIN in hepatocellular carcinoma;" World J. Gastroenterol. 11(10); 2005; pp.: 1445-51

Liu et al.; "Eradication of large colon tumor xenografts by targeted delivery of maytansinoids;" Proc Natl Acad Sci USA; 93; 1996; pp.:8618-8623.

Loussouarn et al.; "Prognostic impact of syndecan-1 expression in invasive ductal breast carcinomas;" Br J Cancer; 28; 2008; pp.: 1993-1998

Lorigan et al.; "Phase I trial of BB-10901 (huN901-DM1) given daily by IV infusion for three consecutive days every three weeks in patients with SCLC and other CD56-positive solid tumors;" European Journal of Cancer Supplements; 4(12); 2006; pp.: 195.

Ludwig et al.; "Supportive care in multiple myelom Best Practice & Research Clinical Haematology;" 20; Issue 4; 2007; pp.:817-835.

McCann et al.; "Phase II trial of huN901-DM1 in patients with relapsed small cell lung cancer (SCLC) and CD56-positive small cell carcinoma;" J Clin Onco; ASCO Annual Meeting Proceedings Part 1; 25(18S); 2007 Jun. 20; Supplement; p.:18084.

Mateos et al.; "Bortezomib plus melphalan and prednisone in elderly untreated patients with multiple myeloma: results of a multicenter phase 1/2 study;" Blood; 108; 2006; pp.: 2165-2172.

McCune et al.; "The SCID-hu mouse: murine model for the analysis of human hematolymphoid differentiation and function;" Science; 241; 1998; pp.: 1632-1639.

Mennerich et al.; "Shift of syndecan-1 expression from epithelial to stromal cells during progression of solid tumours;" Eur J Cancer; 40(9); June 2004; pp.: 1373-82.

Milowsky et al.; "Phase I/II trial of the prostate-specific membrane antigen (PSMA)-targeted immunoconjugate MLN2704 in patients (pts) with progressive metastatic castration resistant prostate cancer (CRPC);" J Clin Onco; ASCO Annual Meeting Proceedings Part I; 24(18S); 2006 p.: 4500.

Mita et al.; "A phase I study of a CanAg-targeted immunoconjugate, huC242-DM4, in subjects with CanAg-expressing solid tumors;" J Clin Onco; ASCO Annual Meeting Proceedings Part 1; 25(18S); 2007 Jun. 20; Supplement; p.: 3062.

Mitsogiannis et al; "Plasmacytoid transitional cell carcinoma of the urinary bladder;" Urology66(1); 2005; p. 194.

Morgan et al.; "Advances in oral therapy for multiple myeloma;" Lancet Oncol; 7(4); April 2006; pp.:316-25.

Mosmann T.; "Rapid colorimetric assay for cellular growth and survival: application to proliferation and cytotoxicity assays;" J Immunol Methods; 65; 1983 pp.:55-63.

Munshi et al.; "Plasma cell disorders;" In: Braunwald E, Fauci A S, Kasper D L, Hauser S L, Longo D L, Jameson J L, editors; Harrison's Principles of Internal Medicine; 16th ed; New York: McGraw-Hill Medical Publishing Division; 2008. pp.: 700-707.

Namikawa et al.; "Growth of human myeloid leukemias in the human marrow environment of SCID-hu mice;" Blood; 82; 1993; pp.:2526-2536.

NCCN Guidelines; "NCCN Clinical Practice Guidelines in Oncology;" Multiple Myeloma V.2.2009; National Comprehensive Cancer Network; Nov. 9, 2008; available at www.nccn.org.

Ning et al.; "Liposomal doxorubicin in combination with bortezomib for relapsed or refractory multiple myeloma;" Oncology (Williston Park); 21(12); November 277; pp.: 1503-8.

Numa et al.;"Syndecan-1 expression in cancer of the uterine cervix: association with lymph node metastasis;" Int J. Oncol. 20(1); pp.:2002 39-43.

Ocio et al., "New drugs in multiple myeloma: mechanisms of action and phase I/II clinical findings;" Lancelt Oncol: 9(12); December 2008; pp.:1157-65.

O'Connell et al.; "CD138 (Syndecan-1), a Plasma Cell Marker Immunohistochemical Profile in Hematopoietic and Nonhematopoietic Neoplasms;" Am J Clin Pathol; 121; 2004; pp.:254-263.

Ojima et al.; "Tumor-specific novel taxoid-monoclonal antibody conjugates;" J. Med. Chem.; 45; 2002; pp. 5620-5623.

Oken et al.; "Toxicity And Response Criteria Of The Eastern Cooperative Oncology Group;" Am J Clin Oncol; 5; 1982; pp.: 649-655.

Olafsen et al.; "Covalent disulfide-linked anti-CEA diabody allows site-specific conjugation and radiolabeling for tumor targeting applications;" Prot. Eng. Design & Selection 17; 1; 2004; pp.:21-27.

Orosz et al.; "Syndecan-1 expression in different soft tissue tumours;" Anticancer Res; 21(1 B); 2001; pp.:733-7.

Padlan, E A; "A possible procedure for reducing the immunogenicity of antibody variable domains while preserving their ligand-binding properties;" Mol. Immunol.; 28; 1991; pp.: 489-498.

Palacios et al.; "B-B4 monoclonal antibody and identification of human bone marrow plasma cells;" Br J Haematol; 96(3); March 1997; pp.:655-657.

Palumbo et al.; "Oral revlimid plus melphalan and prednisone (R-MP) for newly diagnosed multiple myeloma: results of a multicenter Phase I/II study;" Blood; 108; (ASH Annual Meeting Abstracts); Abstract 800; 2006.

Palumbo et al.; "Treatment of newly diagnosed myeloma;" Leukemia; 23; Nov. 13, 2008; pp.: 449-456.

Patriarca et al.; "Considerations in the treatment of multiple myeloma: a consensus statement from Italian experts;" Eur J Haematol; 82(2); February 2009; pp.:93-105.

Payne G.; "Progress in immunoconjugate cancer therapeutics;" Cancer Cell; 3; 2003; pp.:207-212.

Pegram et al.; "Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment;" J. Clin. Oncol.; 16; 1998; pp.: 2659-2671.

Podar et al.; "Bone marrow microenvironment and the identification of new targets for myeloma therapy;" Leukemia; 23(1); January 2009; pp.: 10-24.

Qin et al.; "The pharmacokinetics and pharmacodynamics of IMGN242 (huC242-DM4) in patients with CanAg-expressing solid tumors;" Journal of Clinical Oncology, 2008 ASCO Annual Meeting Proceedings (Post-Meeting Edition); 26(15S); May 20, 2008; Supplement; p.: 3066.

Quach et al.: "Mechanism of action of immunomodulatory drugs (ImiDS) in multiple myeloma," Leukemia; 24; 2010; pp.: 22-32.

Raje et al.; "Therapeutic use of immunomodulatory drugs in the treatment of multiple myeloma;" Expert Rev Anticancer Ther; 6(9); September 2006; pp.: 1239-47.

Rajkumar et al.; "Combination therapy with lenalidomide plus dexamethasone (Rev/Dex) for newly diagnosed myeloma;" Blood; Dec. 15, 2005; 106(13); pp.: 4050-4053.

Rajkumar et al.; "Phase III clinical trial of thalidomide plus dexamethasone compared with dexamethasone alone in newly diagnosed multiple myeloma: A clinical trial coordinated by the Eastern cooperative Oncology Group;" J Clin Oncol 2006; 24; pp.: 431-436.

Rajkumar et al.; "A Randomized Trial of Lenalidomide Plus High-Dose Dexamethasone (RD) Versus Lenalidomide Plus Low-Dose Dexamethasone (Rd) in Newly Diagnosed Multiple Myeloma (E4A03): A Trial Coordinated by the Eastern Cooperative Oncology Group;" Blood; 110; 2007; p.: 74.

Rawstron et al.; "Circulating plasma cells in multiple myeloma: characterization and correlation with disease stage;" Br J Haematol; 97; 1997; pp.: 46-55.

Remillard et al.; "Antimitotic activity of the potent tumor inhibitor maytansine;" Science; 198; 1975; pp.:1002-1005.

Richardson et al.; "New treatments for multiple myeloma;" Oncology (Williston Park); 19(14); December 2005; pp.: 1781-92.

Richardson et al.; "Lenalidomide in multiple myeloma;" Expert Rev Anticancer Ther, 6(8); August 2006; pp.:1165-73.

Richardson et al.; "New Drugs for Myeloma;" Oncologist June; 12(6); 2007; pp.:664-89.

Richardson et al.; "Lenalodomide, bortezomib, and dexamethasone as front-line-therapy for patients with multiple myeloma (MM): preliminary results of a phase I/II study;" Blood; 110; 2007; p.: 63a.

Riechelmann et al.; "Phase I trial with the CD44v6-targeting immunoconjugate bivatuzumab mertansine in head and neck squamous cell carcinoma;" Oral Oncol; 44(9); September 2008; pp.:823-9.

Roh et al.; "Syndecan-1 expression in gallbladder cancer and its prognostic significance;" Eur Surg Res. 41(2); 2008; pp.:245-50.

Roguska et al.; "Humanization of murine monoclonal antibodies through variable domain resurfacing;" Proc Natl Acad Sci USA; 91; 1994; pp.:969-973.

Ross et al.; "Prostate stem cell antigen as therapy target: tissue expression and in vivo efficacy of an immunoconjugate;" Cancer Res.; May 1, 2002; 62(9) pp.:2546-53.

Ross et al.; "Anticancer Antibodies;" Am J Clin Path; 119; Apr. 17, 2003; pp.: 472-485.

Rowinsky et al.; "SB-408075, a tumor-activated immunoconjugate targeting the C242 CanAg antigen with a potent maytansinoid payload: phase I, pharmacokinetic (PK), and biological studies;" Proc Am Soc Clin Oncol 21: Abstract #118; 2002.

Rupp et al.; "Safety and pharmacokinetics of bivatuzumab mertansine in patients with CD44v6-positive metastatic breast cancer: final results of a phase I study;" Anticancer Drugs; 18(4); April 2007; pp.:477-485.

Salfeld, "Isotype selection in antibody engineering", Nat. Biotechnol. 25 (12), 2007, pp. 1369-1372.

Sanderson et al.; "B lymphocytes express and lose syndecan at specific stages of differentiation;" Cell Regul.; 1989; 1; pp.:27-35.

Sandhu et al.; "Human hematopoiesis in SCID mice implanted with human adult cancellous bone;" Blood; 88; 1996; pp.:1973-1982.

Sankhala et al.; "A phase I and pharmacokinetic study of a CanAg-targeted immunoconjugate, HuC242-DM4, in patients with CanAg-expressing solid tumors;" AACR-NCI-EORTC "Molecular Targets and Cancer Therapeutics" International Conference; Abstract #B70; 2007.

Sasaki et al.; "Bisphosphonate risedronate reduces metastatic human breast cancer burden in bone in nude mice;" Cancer Res.; 55; 1995; pp.: 3551-3557.

Sauter et al.; "Pharmacokinetics, immunogenicity and safety of bivatuzumab mertansine, a novel CD44v6-targeting immunoconjugate, in patients with squamous cell carcinoma of the head and neck;" Int J. Oncol.; 30(4); April 2007; pp.: 927-35.

Schneider et al.; "Two subsets of peripheral blood plasma cells defined by differential expression of CD45 antigen;" Br J Haematol; 97; 1997; pp.: 56-64.

Schuurman, et al.; "Normal human immunoglobulin G4 is bispecific: it has two different antigen-combining sites;" Immunology; 97; 1999; pp.: 693-698.

Sebestyen et al.; "Syndecan-1 (CD138) expression in human non-Hodgkin lymphomas. Br J Haematol;" 104(2); 1999; pp.: 412-9.

Seftalioglu et al.; "Syndecan-1/CD138 expression in normal myeloid, acute lymphoblastic and myeloblastic leukemia cells;" Acta Histochem; 105; 2003; pp.:213-221.

Seftalioglu et al.; "Syndecan-1 (CD138) expression in acute myeloblastic leukemia cells—an immuno electron microscopic study;" Acta Oncol; 42; 2003; pp.:71-74.

Senter et al.; "Cures and regressions of established tumors with monoclonal antibody auristatin conjugates;" Abstract #2062, American Assoication for Cancer Res. (San Francisco, Calif.: American Association for Cancer Res.); 2007; p.: 414.

Shah et al.; "Expression of syndecan-1 and expression of epidermal growth factor receptor are associated with survival in patients with nonsmall cell lung carcinoma;" Cancer 101(7); 2004; pp.:1632-8.

Shields et al.; "High resolution mapping of the binding site on human IgG1 for Fc gamma RI, Fc gamma RII, Fc gamma RIII, and FcRn and design of IgG1 variants with improved binding to the Fc gamma R.;" J Biol Chem; 276(9); 2001; pp.:6591-604.

Sievers et al.; "Efficacy and safety of gemtuzumab ozogamicin in patients with CD33-positive acute myeloid leukemia in first relapse;" J. Clin. Oncol.; 19; 2001; pp. 3244-3254.

Sievers et al.; "Mylotarg: antibody-targeted chemotherapy comes of age;" Curr. Opin. Oncol.; 13; 2001; pp. 522-527.

Smith R.; "Single chain antibody variable region fragments;" available at www.stanford.edu/~smithr/science/scfv.html (last updated on May, 2001).

Strobeck M; "Multiple Myeloma therapies;" Nature Reviews Drug Discovery; 6(3); March 2007; pp.: 181-82.

Studnicka et al.; "Human-engineered monoclonal antibodies retain full specific binding activity by preserving non-CDR complementarity-modulating residues;" Protein Eng.; 7(6); 1994 pp.: 805-814.

Tai et al; "Immunomodulatory drug lenalidomide (CC-5013, IMiD3) augments anti-CD40 SGN-40-induced cytotoxicity in human multiple myeloma: clinical implications;" Cancer Res. 2005 Dec. 15; 65(24):11712-20.

Takimoto et al.; "Principles of oncologic pharmacotherapy;" Cancer Management: A multidisciplinary Approach; 11$^{th}$ Edition; Chapter 3; 2008; Apr. 15, 2009; available at http://www.cancernetwork.com/display/article/10165/1402628.

Tassone et al.; "Cytotoxic activity of the maytansinoid immunoconjugate B-B4-DM1 against CD138$^+$ multiple myeloma cells;" Blood; 104(12); 2004; pp.: 3688-3696.

Terpos et al.; "European Myeloma NetworkThe use of bisphosphonates in multiple myeloma: recommendations of an expert panel on behalf of the European Myeloma Network;" Ann Oncol. 20(8); 2009; pp.:1303-17.

Tijink et al.; "A phase I dose escalation study with anti-CD44v6 bivatuzumab mertansine in patients with incurable squamous cell carcinoma of the head and neck or esophagus;" Clin Cancer Res; 12(20 Pt 1); Oct. 15, 2006; pp.:6064-72.

Tolcher et al.; "A Phase I study of huC242-DM4 to assess the safety and pharmacokinetics of huC242-DM4 administered as a single intravenous infusion once every three weeks to subjects with solid tumors;" European Journal of Cancer Supplements;12(4); 2006 p.: 66.

Tolcher et al.; "Cantuzumab mertansine, a maytansinoid immunoconjugate directed to the CanAg antigen: a phase I, pharmacokinetic, and biologic correlative study;" J Clin Oncol; 21; 2003; pp.: 211-222.

Tomayko et al., "Determination of subcutaneous tumor size in athymic (nude) mice;" Cancer Chemother. Pharmacol, 24; 1989; pp.: 148.

Toyoshima et al.; "Expression of syndecan-1 is common in human lung cancers independent of expression of epidermal growth factor receptor;" Lung Cancer 31(2-3); 2001; pp.:193-202.

Udi, "In vitro analyse von Standard und innovativen anti-Multiplen Myelom (MM)-Therapien auf MM-Zelllinien und deren Interaktion mit dem Knochenmark (KM)-Milieu," Diss. Medical University Clinic and Polyclinic, Albert-Ludwigs-University Freiburg, Freiburg, Germany, 2010.

Urashima et al; "The development of a model for the homing of multiple myeloma cells to human bone marrow;" Blood; 90; 1997; pp.: 754-765.

Vogel, C W; "Preparation of immunoconjugates using antibody oligosaccharide moieties;" Methods in Molecular Biology: Bioconjugation protocols strategies and methods; 283; 2007 pp.: 87-108.

Vooijs et al; "Efficacy and toxicity of plasma-cell-reactive monoclonal antibodies B-B2 and B-B4 and their immunotoxins;" Cancer Immunol Immunother; 42; 1996; pp.: 319-328.

Wang et al.; "Targeted proteasome inhibition by Velcade induces apoptosis in human mesothelioma and breast cancer cell lines;" Cancer Chemother Pharmacol; Dec. 4, 2009.

Ward et al.; "Binding activities of a repertoire of single immunoglobin variable domains secreted from *Escherichia coli*;" Nature; 341; 1989; pp.:544-546.

Wargalla et al.; "Rate of internalization of an immunotoxin correlates with cytotoxic activity against human tumor cells;" Proc. Natl. Acad. Sci. USA; 86; 1989; pp.:5146-5150.

Weber et al.; "Lenalidomide plus high-dose dexamethasone provides improved overall survival compared to high-dose dexamethasone alone for relapsed or refractory multiple myeloma (MM): results of 2 Phase III studies (MM-009, MM-010) and subgroup analysis of patients with impaired renal function;" Blood; 108; (ASH Annual Meeting Abstracts); Abstract 3547; 2006.

Wiksten et al.; "Comparison of the prognostic value of a panel of tissue tumor markers and established clinico-pathological factors in patients with gastric cancer;" Gastric: Anticancer Res. 28(4C); 2008; pp.: 2279-87.

Wijdenes et al.; "A plasmocyte selective mAb (B-B4) recognizes syndecan-1;" Br J Haematol; 94(2) August 1996; pp.:318-23.

Wijdenes et al.; "CD138;" J Biol Regul Homeost Agents; 16(2) April-June 2002; pp.: 152-155.

Witzig et al; "Detection of myeloma cells in the peripheral blood by flow cytometry;" Cytometry; 26; 1996; pp.: 113-120.

Xie et al.; "Pharmacokinetics and biodistribution of the antitumor immunoconjugate, cantuzumab mertansine (huC242-DM1), and its two components in mice;" J Pharmacol Exp Ther.; 308(3); March 2004; pp.:1073-82.

Yang et al.; "Genetically fluorescent melanoma bone and organ metastasis models;" Clin Cancer Res; 5; 1999; pp.:3549-3559.

Yang et al.; "Whole-body optical imaging of green fluorescent protein-expressing tumors and metastases;" Proc Natl Acad Sci USA; 97; 200; pp.:1206-1211.

Yang et al.; "The syndecan-1 heparan sulfate proteoglycan is a viable target for myeloma therapy;" Blood; 110(6); Sep. 15, 2007 pp.: 2041-8.

Yasui et al.; "Recent advances in the treatment of Multiple Myeloma;" Curr Pharm Biotechnol; 7(5); October 2006; pp.:381-93.

Yoshitake et al.; "Conjugation of glucose oxidase from *Aspergillus niger* and rabbit antibodies using N-hydroxysuccinimide ester of N-(4-carboxycyclohexylmethyl)-maleimide;" Eur J Biochem; 101; 1979; pp.: 395-399.

Yu et al.; "Antitumor synergy of CV787, a prostate cancer-specific adenovirus, and paclitaxel and docetaxel;" Cancer Research; 61; Jan. 15, 2001; pp.: 517-525.

Zellweger et al.; "Tissue microarray analysis reveals prognostic significance of syndecan-1 expression in prostate cancer;" Prostate 55(1); 2003; pp.:20-9.

What is claimed is:

1. A method for treating a disease associated with target cells expressing CD138 comprising:
   administering to a subject in need thereof an immunoconjugate comprising at least one engineered targeting antibody targeting CD138 expressing cells, and
   at least one maytansinoid, wherein said engineered targeting antibody is functionally attached to said maytansinoid to form said immunoconjugate, wherein at least a part of the engineered targeting antibody confers IgG4 isotype properties, wherein
   the immunoconjugate is administered in intervals of less than 11.1 days within a period of 21 days constituting a multiple dose regimen, wherein the aggregate dose administered within an active treatment cycle is an aggregate maximum tolerable dose (AMTD) or a fraction of the AMTD and wherein said AMTD and/or said fraction exceeds the dose resulting in dose limiting toxicity (DLT) when the immunoconjugate is administered as a single dose, including as part of a multiple single dose regimen and/or exceeds the maximum tolerable dose (MTD) when the immunoconjugate is administered as a single dose, including as part of a multiple single dose regimen within said active treatment cycle, wherein the active treatment cycle includes the administering being performed at least once a week for at least three weeks and the active treatment cycle is followed by a resting period of at least one week, which together define a treatment cycle of at least 28 days, and wherein, after one, two or more treatment cycles, at least stable disease is achieved.

2. The method of claim 1, wherein the immunoconjugate is administered at least three times within said 21 days.

3. The method of claim 1, wherein the immunoconjugate is administered in equal doses.

4. The method of claim 1, wherein said multiple dose regimen lasts at least 3 weeks and is followed by a resting period.

5. The method of claim 4, wherein progression free survival or stable disease is maintained during the resting period.

6. The method of claim 5, wherein a level of said immunoconjugate in a body fluid of said subject, during said resting period is at least 0.5 μg/ml, at least 1 μg/ml, at least 2 μg/ml, at least 3 μg/ml, 4 μg/ml, 5 μg/ ml or 6 μg/ml and/or wherein more than 80%, more than 90%, more than 95% of the CD138 of isolated target cells are occupied by said immunoconjugate within four to twenty four hours after completion of administration of the immunoconjugate.

7. The method of claim 1 wherein the AMTD exceeds the dose of said DLT by at least 20%, at least 30%, at least 40%, at least 50%, at least 60%, at least 80%, at least 90%, at least 100% or at least 120% and said MTD by at least 30%, at least 40at least 50%, at least 60%, at least 80%, at least 90at least 100%, at least 120% or at least 140%.

8. The method of claim 1, wherein the AMTD is at least 240 mg/m$^2$, 300 mg/m$^2$, 360 mg/m$^2$, or 420 mg/m$^2$ and the dose resulting in said DLT is 200 mg/m$^2$ or the AMTD is at least 240 mg/m$^2$, 300 mg/m$^2$, 360 mg/m$^2$, or 420 mg/m$^2$ and said MTD is at least 160 mg/m$^2$ or at least 180 mg/m$^2$.

9. The method of claim 1, wherein at least stable disease is maintained during three, four, five, six, seven treatment cycles.

10. The method of claim 9, wherein after reaching at least stable disease, the immunoconjugate is administered as a maintenance therapy less than twice within said active treatment cycle as a repeated single dose of between 60 mg/m$^2$ and 280 mg/m$^2$, including about 70 mg/m$^2$, about 80 mg/m$^2$, about 90 mg/m$^2$, about 100 mg/m$^2$ , about 110 mg/m$^2$, about 120 mg/m$^2$, about 130 mg/m$^2$, about 140 mg/m$^2$, 150 mg/m$^2$, about 160 mg/m$^2$, about 170 mg/m$^2$, about 180 mg/m$^2$, about 190 mg/m$^2$, about 200 mg/m$^2$, about 210 mg/m$^2$, about 220 mg/m$^2$, about 230 mg/m$^2$, about 240 mg/m$^2$, about 250 mg/m$^2$, about 260 mg/m$^2$ and about 270 mg/m$^2$.

11. The method of claim 10, wherein the disease associated with target cells expressing CD138 is relapsed/refractory myeloma and wherein at least progression free survival, stable disease and or a minor response is obtained for more than 3 months during said maintenance therapy.

12. A method of claim 1, wherein administration of said immunoconjugate as a repeated multiple dose in said active treatment cycle, results in an aggregate effective amount and a first level of the immunoconjugate in a body fluid of the subject and wherein, an amount equivalent to said aggregate effective amount is administered as a single dose or repeated single dose in said active treatment cycle, results in a second level of the immunoconjugate in a body fluid of said subject, wherein the first level is equal or below the second level.

13. The method of claim 12, wherein the active treatment cycle lasts 21 days and/or the repeated multiple dose consists of 3 administrations of equal doses.

14. The method of claim 12, wherein said aggregate effective amount is more than 200 mg/m$^2$, about 220 mg/m$^2$, about 240 mg/m$^2$, about 260 mg/m$^2$, or about 280 mg/m$^2$.

15. The method of claim 1, wherein administration of said immunoconjugate as a multiple dose regime results, 0-2 hours after completion of administration in a mean plasma level of at least 7 μg/ml, 8, 9, 10, 11, 12, 13, 14, 15, 16, 17, 18, 19, 20, 21, 22, 23, 24, 25, 26, 27, 28, 29, 30, 40, 50, 60 or 70 μg/ml.

16. The method of claim 1, further comprising determining 0-2 hours following a completion of administering an individual dose of said immunoconjugate or a pharmaceutical composition comprising the same, a level of said immunoconjugate in a body fluid, determining whether the level of the immunoconjugate is below or above 7 μg/m$^2$, 8, 9, 10, 11, 12, 13, 14, 15, 16, 17, 18, 19, 20 μg/m$^2$,
increasing the individual dose in the next treatment cycle by at least 10 mg/m$^2$, 20 mg/m$^2$, about 30 mg/m$^2$, about 40 mg/m$^2$, about 50 mg/m$^2$, about 60 mg/m$^2$, 70 mg/m$^2$, about 80 mg/m$^2$, about 90 mg/m$^2$ or about 100 mg/m$^2$ if the level is below 7 μg/m$^2$, 8, 9, 10, 11, 12, 13, 14, 15, 16, 17, 18, 19, 20 μg/m$^2$, or
maintaining or decreasing by at least 10 mg/m$^2$, 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$ or about 100 mg/m$^2$, the individual dose in the next treatment cycle if the level is above 7 μg/m$^2$, 8, 9, 10, 11, 12, 13, 14, 15, 16, 17, 18, 19, 20 μg/m$^2$.

17. The method of claim 1, wherein the at least one maytansinoid is N$^{2'}$-(4-methyl-4-mercapto-1-oxopentyl)-maytansine (DM4) or N$^2$-deacetyl-N$^2$-(3-mercapto-1-oxopropyl)-maytansine (DM1).

18. The method of claim 17, wherein the at least one maytansinoid is DM4.

19. A method for treating a disease associated with target cells expressing CD138, comprising:
administering to a patient in need thereof a pharmaceutical composition comprising an immunoconjugate and a pharmaceutically acceptable carrier in an active treatment cycle which is optionally followed by a resting period, wherein the immunoconjugate comprises
at least one targeting agent targeting CD138 expressing cells, and at least one maytansinoid, wherein said targeting agent is functionally attached to said effector molecule to form said immunoconjugate, and wherein the dose of the immunoconjugate administered at least once a week is about 20 mg/m$^2$, about 30 mg/m$^2$, about 40 mg/m$^2$, about 50 mg/m$^2$, about 60 mg/m$^2$, 70 mg/m$^2$, about 80 mg/m$^2$, about 90 mg/m$^2$, about 100 mg/m$^2$, about 110 mg/m$^2$, about 120 mg/m$^2$, about 130 mg/m$^2$, about 140 mg/m$^2$, about 150 mg/m$^2$ or about 160 mg/m$^2$, about 170 mg/m$^2$, about 180 mg/m$^2$, about 190 mg/m$^2$, about 200 mg/m$^2$, about 210 mg/m$^2$, about 220 mg/m$^2$, about 230 mg/m$^2$, about 240 mg/m$^2$, about 250 mg/m$^2$, about 260 mg/m$^2$, about 270 mg/m$^2$ or about 280 mg/m$^2$ and the pharmaceutical composition is administered for at least three weeks alone or in combination with a cytotoxic agent.

20. The method of claim 19, wherein the active treatment cycle lasts at least 21 days and the immunoconjugate is administered once a week at a dose from about 40 mg/m$^2$ to about 140 mg/m$^2$.

21. A method for treating a disease associated with target cells expressing CD138 comprising:

administering to a subject in need thereof an immunoconjugate comprising at least one engineered targeting antibody targeting CD138 expressing cells, and at least one maytansinoid, wherein said engineered targeting antibody is functionally attached to said maytansinoid to form said immunoconjugate, wherein at least a part of the engineered targeting antibody confers IgG4 isotype properties, wherein the immunoconjugate is administered in intervals of less than 11.1 days within a period of 21 days constituting a multiple dose regimen, wherein the aggregate dose administered within an active treatment cycle is an aggregate maximum tolerable dose (AMTD) or a fraction of the AMTD and wherein said AMTD and/or said fraction exceeds the dose resulting in dose limiting toxicity (DLT) when the immunoconjugate is administered as a single dose, including as part of a multiple single dose regimen and/or exceeds the maximum tolerable dose (MTD) when the immunoconjugate is administered as a single dose, including as part of a multiple single dose regimen within said active treatment cycle, wherein said administration is followed, after at least two 21 day treatment cycles, each followed by a resting period, by a further administration of the immunoconjugate or a pharmaceutical composition comprising the immunoconjugate.

22. The method of claim 21, wherein the immunoconjugate or a pharmaceutical composition comprising the same is administered in said further administration (i) once every three to six weeks or (ii) at repeated multiple doses, wherein each individual dose of immunoconjugate is about 10 mg/m², about 20 mg/m², about 30 mg/m², about 40 mg/m², about 50 mg/m², about 60 mg/m², 70 mg/m², about 80 mg/m², about 90 mg/m² or about 100 mg/m² lower than the individual dose of a primary therapy and/or wherein individual doses are administered in intervals exceeding the interval of the individual doses.

23. The method of claim 21, wherein said effector is a maytansinoid and wherein a total amount of maytansinoid administered to said patient within said 21 days is more than 2 mg/m², more than 3 mg/m², more than 4 mg/m², more than 5 mg/m², more than 6 mg/m², more than 7 g/m², more than 8 mg/m², more than 9 mg/m² or more than 10 mg/m².

24. The method of claim 21, wherein said immunoconjugate is administered every $3^{rd}$ day, every $4^{th}$ day, every $5^{th}$ day or every $6^{th}$ day during said three weeks period.

25. A method for treating a disease associated with target cells expressing CD138 comprising:

administering to a subject in need thereof an immunoconjugate comprising at least one engineered targeting antibody targeting CD138 expressing cells, and at least one maytansinoid, wherein said engineered targeting antibody is functionally attached to said maytansinoid to form said immunoconjugate, wherein at least a part of the engineered targeting antibody confers IgG4 isotype properties, wherein the immunoconjugate is administered in intervals of less than 11.1 days within a period of 21 days constituting a multiple dose regimen, wherein the aggregate dose administered within an active treatment cycle is an aggregate maximum tolerable dose (AMTD) or a fraction of the AMTD and wherein said AMTD and/or said fraction exceeds the dose resulting in dose limiting toxicity (DLT) when the immunoconjugate is administered as a single dose, including as part of a multiple single dose regimen and/or exceeds the maximum tolerable dose (MTD) when the immunoconjugate is administered as a single dose, including as part of a multiple single dose regimen within said active treatment cycle, further comprising determining 0-4 hours, including at about 1, 2, or 3, following a completion of administering said immunoconjugate or a pharmaceutical composition comprising the same, a reference level (RL) of an said immunoconjugate or of an efficacy blood parameter in a body fluid of a patient, determining in a subsequent administration of said immunoconjugate, at 0-4 hours following a completion of said subsequent administration, a subsequent level (SL) of an said immunoconjugate or efficacy blood parameter, comparing the RL to the SL,
  (i) determining RL>SL, and increasing the aggregate dose in a treatment cycle following said subsequent administration by 5-100%, including 10-50% or 20-30%, and/or
  (ii) determining RL<SL, and decreasing the aggregate dose in a treatment cycle following said subsequent administration by 5-100%, including 10-50% or 20-30%.

26. A method for treating a disease associated with target cells expressing CD138 comprising:

administering to a subject in need thereof an immunoconjugate comprising at least one engineered targeting antibody targeting CD138 expressing cells, and at least one maytansinoid, wherein said engineered targeting antibody is functionally attached to said maytansinoid to form said immunoconjugate, wherein at least a part of the engineered targeting antibody confers IgG4 isotype properties, wherein the immunoconjugate is administered in intervals of less than 11.1 days within a period of 21 days constituting a multiple dose regimen, wherein the aggregate dose administered within an active treatment cycle is an aggregate maximum tolerable dose (AMTD) or a fraction of the AMTD and wherein said AMTD and/or said fraction exceeds the dose resulting in dose limiting toxicity (DLT) when the immunoconjugate is administered as a single dose, including as part of a multiple single dose regimen and/or exceeds the maximum tolerable dose (MTD) when the immunoconjugate is administered as a single dose, including as part of a multiple single dose regimen within said active treatment cycle, further comprising administering at least one cytotoxic agent, including two or three, at least once a week or once in a treatment cycle.

27. The method of claim 26, wherein said cytotoxic agent is lenalidomide and/or dexamethasone.

28. The method of claim 26, wherein said subject has not previously been exposed to an immunoconjugate comprising an antibody targeting CD138 expressing cells, to lenalidomide and/or to dexamethasone.

29. The method of claim 26, wherein said subject has previously been exposed to an immunoconjugate comprising an antibody targeting CD138 expressing cells, lenalidomide and/or dexamethasone.

30. The method of claim 29, wherein said subject responded to said exposure to an immunoconjugate comprising an antibody targeting CD138 expressing cells, lenalidomide and/or dexamethasone.

31. The method of claim 30, wherein said target cells expressing CD138 are refractory to exposure to an immunoconjugate comprising an antibody targeting CD138 expressing cells, lenalidomide and/or dexamethasone.

32. The method of claim 29, wherein said subject relapsed after said administration.

33. The method of claim 26, wherein lenalidomide is administered at a dose of 5 to 35 mg, or at a dose of less than 25, 20, 15 or 10 mg, orally once a day for 21 days and/or wherein dexamethasone is administered at a dose of 20 to 50 mg, or at a dose of less than 40 or 30 mg.

34. A method for treating a disease associated with target cells expressing CD138 comprising:
administering to a subject in need thereof an immunoconjugate comprising at least one engineered targeting antibody targeting CD138 expressing cells, and at least one maytansinoid, wherein said engineered targeting antibody is functionally attached to said maytansinoid to form said immunoconjugate, wherein at least a part of the engineered targeting antibody confers IgG4 isotype properties, wherein the immunoconjugate is administered in intervals of less than 11.1 days within a period of 21 days constituting a multiple dose regimen, wherein the aggregate dose administered within an active treatment cycle is an aggregate maximum tolerable dose (AMTD) or a fraction of the AMTD and wherein said AMTD and/or said fraction exceeds the dose resulting in dose limiting toxicity (DLT) when the immunoconjugate is administered as a single dose, including as part of a multiple single dose regimen and/or exceeds the maximum tolerable dose (MTD) when the immunoconjugate is administered as a single dose, including as part of a multiple single dose regimen within said active treatment cycle, wherein said subject suffers from a solid tumor comprising target cells which express CD138 and wherein said solid tumor is refractory to cancer hormone therapy or chemotherapy or the subject has relapsed after hormone therapy or chemotherapy, wherein said administration results in at least tumor growth delay or tumor stasis.

35. The method of claim 34, wherein said immunoconjugate is administered in a repeated multiple dose regime with individual doses of 20 mg/m$^2$ to 160 mg/m$^2$.

36. The method of claim 34, wherein said solid tumor is estrogen receptor negative and/or progesterone receptor negative and/or Her2/neu negative.

37. A method for treating a disease associated with target cells expressing CD138 comprising:
administering to a subject in need thereof an immunoconjugate comprising at least one engineered targeting antibody targeting CD138 expressing cells, and at least one maytansinoid, wherein said engineered targeting antibody is functionally attached to said maytansinoid to form said immunoconjugate, wherein at least a part of the engineered targeting antibody confers IgG4 isotype properties, wherein the immunoconjugate is administered in intervals of less than 11.1 days within a period of 21 days constituting a multiple dose regimen, wherein the aggregate dose administered within an active treatment cycle is an aggregate maximum tolerable dose (AMTD) or a fraction of the AMTD and wherein said AMTD and/or said fraction exceeds the dose resulting in dose limiting toxicity (DLT) when the immunoconjugate is administered as a single dose, including as part of a multiple single dose regimen and/or exceeds the maximum tolerable dose (MTD) when the immunoconjugate is administered as a single dose, including as part of a multiple single dose regimen within said active treatment cycle, wherein the administration of said immunoconjugate or pharmaceutical composition comprising the immunoconjugate is preceded by an administration of unconjugated antibody targeting CD138 expressing cells, wherein said immunoconjugate is administered 1-6 hours after completion of the administration of said unconjugated antibody.

38. The method of claim 37, wherein the unconjugated antibody is administered at a dose corresponding to a plasma level of 10 to 30 µg/ml immunoconjugate in a body fluid of the subject.

39. The method of claim 38, wherein the dose administered corresponds to about a difference between a theoretical and actual level of said immunoconjugate in a body fluid, 0-2 hours after completion of an administration of said immunoconjugate to said subject.

40. The method of claim 37, wherein said antibody is administered at a dose of 10 to 40 mg/m$^2$ or 20-30 mg/m$^2$.

41. The method of claim 37, wherein said immunoconjugate is administered at an individual dose that is up to 10 mg/m$^2$ to 30 mg/m$^2$ lower than the dose administered without said administration of said unconjugated antibody.

42. A method for treating a disease associated with target cells expressing CD138 comprising:
administering to a subject in need thereof an immunoconjugate comprising at least one engineered targeting antibody targeting CD138 expressing cells, and
at least one maytansinoid, wherein said engineered targeting antibody is functionally attached to said maytansinoid to form said immunoconjugate, wherein at least a part of the engineered targeting antibody confers IgG4 isotype properties, and
wherein the immunoconjugate is administered in a multiple dose regimen comprising
three doses within 21days, being administered once a week about 9.28 mg/m$^2$ or 11.4 mg/m$^2$ to about 25.7 mg/m$^2$, or more than three doses administered more than once a week and corresponding to a daily dose of about 9.28 mg/m$^2$ or 11.4 mg/m$^2$ to about 25.7 mg/m$^2$, followed by a resting period of about one week, which together define a treatment cycle of at least 28 days and administering at least one cytotoxic agent, including two or three, at least once a week or once in a treatment cycle.

43. The method for treating a disease associated with target cells expressing CD138 according to claim 42, wherein the immunoconjugate is administered in three doses within 21 days, being administered once a week and corresponding to a daily dose of about 14.28 mg/m$^2$ to about 25.7 mg/m$^2$.

44. The method of claim 42, wherein the immunoconjugate is BT062.

45. The method of claim 42, wherein said cytotoxic agent is lenalidomide and/or dexamethasone.

46. The method of claim 45, wherein lenalidomide is administered at a dose of 5 to 35 mg, or at a dose of less than 25, 20, 15 or 10 mg, orally once a day for 21 days and/or wherein dexamethasone is administered at a dose of 20 to 50 mg, or at a dose of less than 40 or 30 mg.

\* \* \* \* \*